United States Patent
Burmeister et al.

(10) Patent No.: US 7,579,450 B2
(45) Date of Patent: Aug. 25, 2009

(54) NUCLEIC ACID LIGANDS SPECIFIC TO IMMUNOGLOBULIN E AND THEIR USE AS ATOPIC DISEASE THERAPEUTICS

(75) Inventors: Paula Burmeister, Cambridge, MA (US); Sharon Cload, Cambridge, MA (US); John L. Diener, Cambridge, MA (US); Anthony Dominic Keefe, Cambridge, MA (US); Sara Chesworth Keene, Tewksbury, MA (US); Markus Kurz, Newton, MA (US); H. A. Daniel Lagassé, Somerville, MA (US); Harold Nicholas Marsh, Charlestown, MA (US); Pooja Sawhney, Arlington, MA (US); Chunhua Wang, Acton, MA (US)

(73) Assignee: Archemix Corp., Cambridge, MA (US)

( * ) Notice: Subject to any disclaimer, the term of this patent is extended or adjusted under 35 U.S.C. 154(b) by 1 day.

(21) Appl. No.: 11/115,780

(22) Filed: Apr. 26, 2005
(Under 37 CFR 1.47)

(65) Prior Publication Data
US 2007/0009907 A1    Jan. 11, 2007

Related U.S. Application Data

(60) Provisional application No. 60/565,601, filed on Apr. 26, 2004, provisional application No. 60/574,120, filed on May 24, 2004, provisional application No. 60/581,865, filed on Jun. 22, 2004, provisional application No. 60/660,204, filed on Mar. 7, 2005.

(51) Int. Cl.
C07H 21/04    (2006.01)
(52) U.S. Cl. .................................. 536/23.1
(58) Field of Classification Search .................. None
See application file for complete search history.

(56) References Cited

U.S. PATENT DOCUMENTS

| | | | |
|---|---|---|---|
| 3,710,795 A | 1/1973 | Higuchi et al. | |
| 4,683,195 A | 7/1987 | Mullis | |
| 4,935,363 A | 6/1990 | Brown et al. | |
| 4,959,309 A | 9/1990 | Dattagupta et al. | |
| 5,070,010 A | 12/1991 | Hsu | |
| 5,262,564 A | 11/1993 | Kun et al. | |
| 5,270,163 A | 12/1993 | Gold et al. | |
| 5,338,671 A | 8/1994 | Scalice et al. | |
| 5,459,015 A | 10/1995 | Janjic et al. | |
| 5,475,096 A | 12/1995 | Gold et al. | |
| 5,496,938 A | 3/1996 | Gold et al. | |
| 5,503,978 A | 4/1996 | Schneider et al. | |
| 5,567,588 A | 10/1996 | Gold et al. | |
| 5,580,737 A | 12/1996 | Polisky et al. | |
| 5,635,615 A | 6/1997 | Allen et al. | |
| 5,637,459 A | 6/1997 | Burke et al. | |
| 5,648,214 A | 7/1997 | Nieuwlandt et al. | |
| 5,654,151 A | 8/1997 | Allen et al. | |
| 5,660,985 A | 8/1997 | Pieken et al. | |
| 5,668,264 A | 9/1997 | Janjic et al. | |
| 5,672,695 A | 9/1997 | Eckstein et al. | |
| 5,674,685 A | 10/1997 | Janjic et al. | |
| 5,683,867 A | 11/1997 | Biesecker et al. | |
| 5,686,592 A | 11/1997 | Wiegand et al. | |
| 5,698,687 A | 12/1997 | Eckstein et al. | |
| 5,705,337 A | 1/1998 | Gold et al. | |
| 5,707,796 A | 1/1998 | Gold et al. | |
| 5,723,323 A | 3/1998 | Kauffman et al. | |
| 5,756,291 A | 5/1998 | Griffin et al. | 435/6 |
| 5,763,173 A | 6/1998 | Gold et al. | |
| 5,763,177 A | 6/1998 | Gold et al. | |
| 5,766,853 A | 6/1998 | Parma et al. | 435/6 |
| 5,789,157 A | 8/1998 | Jensen et al. | |
| 5,817,635 A | 10/1998 | Eckstein et al. | |
| 5,861,254 A | 1/1999 | Schneider et al. | |
| 5,958,691 A | 9/1999 | Pieken et al. | |
| 6,011,020 A | 1/2000 | Gold et al. | |
| 6,013,443 A | 1/2000 | Heilig et al. | |
| 6,020,130 A | 2/2000 | Gold et al. | |
| 6,051,698 A | 4/2000 | Janjic et al. | |
| 6,207,646 B1 | 3/2001 | Krieg et al. | |
| 6,207,816 B1 | 3/2001 | Gold et al. | |
| 6,214,806 B1 | 4/2001 | Krieg et al. | |
| 6,229,002 B1 | 5/2001 | Janjic et al. | |
| 6,239,116 B1 | 5/2001 | Krieg et al. | |
| 6,426,434 B1 | 7/2002 | Yoshida et al. | |
| 6,429,199 B1 | 8/2002 | Krieg et al. | |
| 6,498,148 B1 | 12/2002 | Raz et al. | |
| 6,514,948 B1 | 2/2003 | Raz et al. | |
| 6,653,292 B1 | 11/2003 | Krieg et al. | |
| 6,737,236 B1 * | 5/2004 | Pieken et al. | 435/6 |
| 2003/0229021 A1 | 12/2003 | Krah, III et al. | 514/13 |
| 2004/0018530 A1 | 1/2004 | Bowser et al. | 435/6 |
| 2004/0180360 A1 | 9/2004 | Wilson et al. | |
| 2006/0030535 A1 | 2/2006 | Healy et al. | |

FOREIGN PATENT DOCUMENTS

EP        059235        1/1996

(Continued)

OTHER PUBLICATIONS

King et al. (2002) Biochemistry. 41:9696-9706.*

(Continued)

*Primary Examiner*—Louis Wollenberger
(74) *Attorney, Agent, or Firm*—Ivor R. Elrifi; Mintz, Levin, Cohn, Ferris, Glovsky and Popeo, P.C.

(57) ABSTRACT

The invention discloses aptamers capable of binding to Immunoglobulin E ("IgE") useful as therapeutics in and diagnostics of atopic disease and/or other diseases or disorders in which IgE has been implicated. The invention further relates to materials and methods for the administration of aptamers capable of binding to IgE.

20 Claims, 19 Drawing Sheets

FOREIGN PATENT DOCUMENTS

| | | |
|---|---|---|
| GB | 2 183 661 A | 6/1987 |
| WO | WO89/06694 | 7/1989 |
| WO | WO91/14436 | 10/1991 |
| WO | WO 91/19813 | 12/1991 |
| WO | WO92/05285 | 4/1992 |
| WO | WO 92/07065 | 4/1992 |
| WO | WO92/14842 | 9/1992 |
| WO | WO92/14843 | 9/1992 |
| WO | WO 96/10576 | 4/1996 |
| WO | WO 98/18480 | 5/1998 |
| WO | WO 03/102212 A2 | 12/2003 |

OTHER PUBLICATIONS

Floege et al. (1999) Am. J. Pathology. 154:169-179.*
International Search Report for PCT/US05/14361, mailed Jun. 20, 2006.
Mendonsa et al., "In Vitro selection of high-affinity DNA ligands for human IgE using capillary electrophoresis", *Anal. Chem.*, 76: 5387-5392 (2004).
Wiegand et al., "High-affinity oligonucleotide ligands to human IgE inhibit binding to Fcε receptor I", *J. Immunol.*, 157: 221-230 (1996).
International Search Report for PCT/US05/43551, mailed Jun. 12, 2007.
Altschul et al., "Basic Local Alignment Search Tool", *J. Mol. Biol.* 215:403-410 (1990).
Altschul et al., "Gapped BLAST and PSI-BLAST: A new generation of protein database search programs", *Nuc. Acids Res.* 15:3389-3403 (1997).
Arthanari et al., "Fluoerescent dyes specific for quadruplex DNA", *Nuc. Acids Res.* 26(16):3724-3728 (1996).
Cotten et al., "2'-O-methyl, 2'-O-ethyl oligoribonucleotides and phosphorothioate oligodeoxyribonucleotides as inhibitors of the in vitro U7 snRNP-dependent mRNA processing event", *Nuc. Acids Res.* 19:2629-2635 (1991).
Froehler et al., "Deoxynucleoside H-Phosphonate Diester Intermediates in the Synthesis of Internucleotide Phosphate Analogues", *Tet. Lett.* 27:5575-5578 (1986).
Froehler et al., "Synthesis of DNA via deoxynucleoside H-phosphonate intermediates", *Nuc. Acids Res.* 14:5399-5407 (1986).
Green et al., "Nuclease-resistant nucleic acid ligands to vascular permeability factor/vascular endothelial growth factor", *Chem. Biol.* 2(1):683-695 (1995).
Greenwald et al., "Highly water soluble taxol derivatives: 7-polyethylene Glycol Carbamates and Carbonates", *J. Org. Chem.* 60:331-336 (1995).
Harris et al., "Effect of Pegylation on pharmaceuticals", *Nature* 2:214-221 (2003).
Hirose et al., "Rapid synthesis of Trideoxyribonucleotide blocks", *Tet. Lett.* 28:2449-2452 (1978).
Hobbs et al., "Polynucleotides containing 2'-amino-2'deoxyibose and 2'-azido-2'-deoxyribose", *Biochemistry* 12:5138-5145 (1973).
Joyce et al., "Detection of G-Quartet structure in a DNA aptamer stationary phase using a fluorescent dye", *Applied Spectroscopy* 58(7): 831-835 (2004).
Krieg, "CpG motifs in bacterial DNA and their immune effects", *Annu. Rev. Immunol.* 20:709-760 (2001).
Liu et al., "CpG directly induces T-bet expression and inhibits IgG1 and IgE switching in B cells", *Nat. Immunol.*, 4(7):687-93 (2003).
Macaya et al., "Thrombin-binding DNA aptamer forms a unimolecular quadruplex structure in solution", *Proc Natl. Acad. Sci.* 90:3745-3749 (1993).
Marathias et al., "Structures of the potassium-saturated, 2 :1, and intermediate, 1 :1, forms of a quadruplex DNA", *Nuc. Acids Res.* 28(9):1969-1977 (2000).
McGinnis et al., "BLAST : At the core of a powerful and diverse set of sequence analysis tools", *Nuc. Acids Res.* 32 :WO20-W25 (2004).
Needleman & Wunsch, "A general method applicable to the search for similarities in the amino acid sequence of two proteins",*J. Mol. Biol.* 48:443-453 (1970).

Padilla et al., "A Y639F/H784A T7 RNA polymerase double mutant displays superior properties for synthesizing RNAs with non-canonical NTPs", *Nuc. Acids Res.* 30:138 (2002).
Pearson & Lipman, "Improved tools for biological sequence comparison",*Proc. Natl. Acad. Sci.* 85:2444-2448 (1988).
Pietersz et al., "A 16-mer peptide (RQIKIWFQNRRMKWKK) from Antennapedia preferentially targets the Class I pathway", *Vaccine* 19(11-12):1397-1405 (2003).
Rothbard et al., "Arginine-Rich molecular transporters for drug delivery: Role of backbone spacing in cellular uptake", *J. Med. Chem.* 45(17):3612-3618 (2002).
Rothbard et al., "Conjugation of Arginine Oligomers to Cyclosporin A facilitates topical delivery and inhibition of inflammation", *Nat. Med.* 6(11):1253-1257 (2000).
Smith & Waterman, "Comparison of bio-sequences", *Adv. Appl. Math.* 2:482-489 (1981).
Sood et al., "A rapid and convenient synthesis of poly-thymidylic acid by the modified triester approach", *Nuc. Acids Res.* 4:2757-65 (1977).
Sproat et al., "New Synthetic Routes to synthons suitable for 2'-O-allyloligoribonucleotide assembly",*Nuc. Acids Res.* 19:733-738 (1991).
Tucker et al., "Detection and plasma pharmacokinetics of an anti-vascular endothelial growth factor oligonucleotide-aptamer (NX1838) in rhesus monkeys", *J. Chromatography Biomed. Sci. Appl.* 732(1):203-212 (Sep. 1999).
Vives et al., "A truncated HIV-1 Tat protein basic domain rapidly translocates through the plasma membrane and accumulates in the cell nucleus", *J. Biol. Chem.* 272(25): 16010-7 (1997).
Andrake et al., "DNA polymerase of bacteriophage T4 is an autogenous translational repressor", *Proc. Natl. Acad. Sci. USA* 85:7942-7946 (1988).
Carey et al., "Sequence-specific interaction of R17 coat protein with its ribonucleic acid binding site", *Biochem.* 22:2601-2610 (1983).
Chen et al., "Selection of high-affinity RNA ligands to reverse transcriptase: Inhibition of cDNA synthesis and Rnase H activity", *Biochem.* 33:8746-8756 (1994).
Cohen et al., "Interactions of hormonal steroids with nucleic acids: A specific requirement for guanine", *Proc. Natl. Acad. Sci. USA* 63:458-464 (1969).
Davis et al., "Identifying consensus patterns and secondary structure in SELEX sequence sets", *Methods in Enzymology* 267:302-314 (1996).
Dehouck et al., "Blood-brain barrier in vitro—rapid evaluation of strategies for achieving drug targeting to the central nervous system", *Biol. Physiology of the Blood Brain Barrier*, Couraud and Scherman eds. 23:143-146 (1996).
Ellington and Szostak, "Abstracts of papers presented at the 1990 meeting on RNA Processing", Cold Spring Harbor, NY, p. 84 (1990).
Fitzwater et al. "A SELEX primer", Methods in Enzymology 267:275-301 (1996).
Gath et al., "The blood-CSF barrier in vitro", *Biol. and Physiology of the Blood Brain Barrier*, Couraud and Scherman eds. 25:153-158 (1996).
Joyce and Inoue, "A novel technique for the rapid preparation of mutant RNAs", *Nuc. Acids Res.* 17:711-722 (1998).
Joyce, "Amplification, mutation and selection of catalytic RNA", RNA: Catalysis, Splicing, Evolution, Amsterdam pp. 83-87 (1989).
Kacian et al., "A replicating RNA molecule suitable for a detailed analysis of extracellular evolution and replication", Proc. Natl. Acad. Sci. USA 69:3038-3042 (1972).
Kadonaga et al., "Affinity purification of sequence-specific DNA binding proteins", *Proc. Natl. Acad. Sci. USA* 83:5889-5893 (1986).
Kellogg et al., "Taqstart antibody™: 'Hot start' PCR facilitated by a neutralizing monoclonal antibody directed against Taq DNA polymerase", *BioTechniques* 16:1134-1137 (1994).
Kinzler and Vogelstein, "Whole genome PCR: Application to the identification of sequences bound by gene regulatory proteins", *Nuc. Acids Res.* 17:3645-3653 (1989).
Kinzler and Vogelstein, "The *GLI* gene encodes a nuclear protein which binds specific sequences in the human genome", *Mol. Cell. Biol.* 10:634-642 (1989).

Kramer et al., "Evolution in vitro: Sequence and phenotype of a mutant RNA resistant to ethidium bromide", *J. Mol. Biol.* 89:719-736 (1974).

Lestienne et al., "Inhibition of human leucocyte elastase by polynucleotides", *Biochimie* 65:49-52 (1983).

Levisohn and Spiegelman, "The cloning of a self-replicating RNA molecule", *PNAS USA* 60:866-872 (1968).

Levisohn and Spiegelman, "Further extracellular Darwinian experiments with replicating RNA molecules: Diverse variants isolated under different selective conditions", *PNAS USA* 63:805-811 (1969).

Ma and Ptashne, "A new class of yeast transcriptional activators", *Cell* 51:113-119 (1987).

Maniatis et al., "Molecular Cloning: A Laboratory Manual", Cold Spring Harbor, NY p. 118 (1982).

Maniatis et al., "Regulation of inducible and tissue-specific gene expression", *Science* 236: 1237-1245 (1987).

Miele et al., "Autocatalytic replication of a recombinant RNA", *J. Mol. Biol.* 171:281-295 (1983).

Mills et al., "An extracellular Darwinian experiment with a self-duplicating nucleic acid molecule", *Proc. Natl. Acad. Sci. USA* 58:217-220 (1967).

Mills et al., "Complete nucleotide sequence of a replicating RNA molecule", *Science* 180:916-927 (1973).

Min et al., "Search for the optimal sequence of the ribosome binding site by random oligonucleotide-directed mutagenisis", *Nuc. Acids Res.* 16:5075-5088 (1988).

Muesing et al., "Nucleic acid structure and expression of the human AIDS/lymphadenopathy retrovirus", *Nature* 313:450-458 (1985).

Oliphant and Struhl, "The use of random-sequence oligonucleotides for determining consensus sequences", *Methods in Enzymology* 155:568-582 (1987).

Oliphant and Struhl, "Defining the consensus sequences of *E. coli* promoter elements by random selection", *Nuc. Acids Res.* 16:7673-7683 (1988).

Oliphant et al., "Cloning of random-sequence oligodeoxynucleotides", *Gene* 44:177-183 (1986).

Oliphant et al., "Defining the sequence specificity of DNA-binding proteins by selecting binding sites from random-sequence oligonucleotides: analysis of yeast GCN4 protein", *Mol. Cell. Biol*, 9:2944-2949 (1989).

Orgel, "Selection in vitro", *Proc. R. Soc. Lon.* B205:435-442 (1979).

Ou et al., "DNA amplification for direct detection of HIV-1 in DNA of peripheral blood mononuclear cells", *Science* 239:295-297 (1988).

Roberts et al., "Chemistry for peptide and protein PEGylation", *Advanced Drug Delivery Rev.* 54:459-476 (2002).

Robertson and Joyce, "Selection in vitro of an RNA enzyme that specifically cleaves single-stranded DNA", *Nature* 344:467-468 (1990).

Romaniuk et al., "RNA binding site of R17 coat protein", *Biochem.* 26:1563-1568 (1987).

Saffhill et al., "In vitro selection of bacteriophage Qβ ribonucleic acid variants resistant to ethidium bromide", *J. Mol. Biol.* 51:531-539 (1970).

Sambrook et al., "Molecular Cloning: A Laboratory Manual", Cold Spring Harbor, NY, pp. 8.9-8.10 (1989).

Singleton et al., "Dictionary of Microbiol. and Molecular Biology", Wiley & Sons, New York, NY, 2nd ed. p. 493.

Szostak, J.W., "Structure and Activity of Ribozymes, Redesigning the Molecules of Life", Springer-Verlag Berline Heidelberg, pp. 87-113 (1988).

Tanchou et al., "Monoclonal antibody-mediated inhibition of RNA binding and annealing activities of HIV type 1 nucleocapsid protein", *Aids Research and Human Retroviruses* 10:983-993 (1994).

Thiesen and Bach, "Target detection assay (TDA): A versatile procedure to determine DNA binding sites as demonstrated on SPI protein", *Nuc. Acids Res.* 18:3203-3209 (1990).

Uhlenbeck et al., "Interaction of R17 coat protein with its RNA binding site for translational repression", *J. Biomolecular Structure and Dynamics* 1:539-552 (1983).

Watson et al., "Molecular Biology of the Gene", Benjamin/Cummings Publishing Co., Inc. California, pp. 267, 295, 323, 361, 394, 396, 397 and 405 (1987).

German et al., "Aptamers as Ligands in Affinity Probe Capillary Electrophoresis," *Anal. Chem.*, 70(21):4540-4545 (1998).

* cited by examiner standard PEGylation multiple PEGylation

Binding Affinities

ARC445    4nM
ARC1384   0.5nM
ARC1572   0.3nM
ARC1573   0.4nM

| Group Number | Animals per Time Point | Test Article | Dosage Level (mg/kg) | Dose Concentrtion (mg/mL) | Dosing Regimen | Plasma Collection Time Points |
|---|---|---|---|---|---|---|
| 1 | 3 | ARC1785 | 10 | 2.5 | Intravenous bolus | t = pre-dose, 0.08, 0.5, 1, 2, 4, 8, 16, 24, 32, 48, 72 hr |
| 2 | 3 | ARC1787 | | | | |
| 3 | 3 | ARC1788 | | | | |
| 4 | 3 | ARC1790 | | | | |

Figure 18

| Group Number | Animals per Time Point | Test Article | Dosage Level (mg/kg) | Dose Concentration (mg/mL) | Dosing Regimen | Plasma Collection Time Points |
|---|---|---|---|---|---|---|
| 1 | 3 | ARC1785 | 10 | 2.5 | Subcutaneous bolus | t = pre-dose, 0.08, 0.5, 1, 2, 4, 8, 16, 24, 32, 48, 72 hr |
| 2 | 3 | ARC1787 | | | | |
| 3 | 3 | ARC1788 | | | | |
| 4 | 3 | ARC1790 | | | | |

Figure 20

| | | ARC1787 | ARC1788 | ARC1785 | ARC1790 |
|---|---|---|---|---|---|
| Parameters | Unit | 40 KDa branched PEG | 60 KDa branched PEG | 2x20 KDa PEG | 2x30 KDa PEG |
| IV administration | | | | | |
| $T_{1/2}$ | hr | 34.62* | 43.6* | 13.7* | 19.50 |
| $AUC_{0-last}$ | µM·hr | 794.55 | 986.35 | 166.13 | 2948.69 |
| $MRT_{last}$ | hr | 27.05 | 28.90 | 9.88 | 18.77 |
| | | | | | |
| SC administration | | | | | |
| $T_{1/2}$ | hr | 50.86 | 78.6* | 87.7* | 18.79 |
| $T_{max}$ | hr | 24.00 | 16.00 | 8.00 | 16.00 |
| $C_{max}$ | µM | 6.89 | 5.27 | 4.09 | 3.64 |
| $AUC_{0-last}$ | µM·hr | 553.31 | 274.25 | 243.20 | 115.84 |
| Partial $AUC_{0-t}$ | µM·hr | 389.45 | 274.25 | 102.16 | 115.84 |
| $MRT_{last}$ | hr | 53.13 | 34.90 | 48.09 | 27.60 |
| **Bioavailability (F) | % | 49.01 | 27.80 | 61.50 | 39.28 |

*Approximate half-life based on timepoints with extrapolated $AUC_{0-\infty}$ greater than 20%
** Bioavailability was based on Partial $AUC_{0-t}$ after SC administration which correspond to $AUC_{0-last}$ after IV administration

NUCLEIC ACID LIGANDS SPECIFIC TO IMMUNOGLOBULIN E AND THEIR USE AS ATOPIC DISEASE THERAPEUTICS

REFERENCE TO RELATED APPLICATIONS

This non-provisional patent application claims priority under 35 U.S.C. § 119(e) to the following provisional applications: U.S. Provisional Patent Application Ser. No. 60/565,601, filed Apr. 26, 2004, U.S. Provisional Patent Application Ser. No. 60/574,120, filed May 24, 2004, U.S. Provisional Patent Application Ser. No. 60/581,865, filed Jun. 22, 2004, and U.S. Provisional Patent Application Ser. No. 60/660,204, filed Mar. 7, 2005; each of which is herein incorporated by reference in its entirety.

FIELD OF INVENTION

The invention relates generally to the field of nucleic acids and more particularly to aptamers capable of binding to Immunoglobulin E ("IgE") useful as therapeutics in and diagnostics of atopic disease and/or other diseases or disorders in which IgE has been implicated. The invention further relates to materials and methods for the administration of aptamers capable of binding to IgE.

BACKGROUND OF THE INVENTION

Aptamers are nucleic acid molecules having specific binding affinity to molecules through interactions other than classic Watson-Crick base pairing.

Aptamers, like peptides generated by phage display or monoclonal antibodies ("mAbs"), are capable of specifically binding to selected targets and modulating the target's activity, e.g., through binding aptamers may block their target's ability to function. Created by an in vitro selection process from pools of random sequence oligonucleotides, aptamers have been generated for over 100 proteins including growth factors, transcription factors, enzymes, immunoglobulins, and receptors. A typical aptamer is 10-15 kDa in size (30-45 nucleotides), binds its target with sub-nanomolar affinity, and discriminates against closely related targets (e.g., aptamers will typically not bind other proteins from the same gene family). A series of structural studies have shown that aptamers are capable of using the same types of binding interactions (e.g., hydrogen bonding, electrostatic complementarities, hydrophobic contacts, steric exclusion) that drive affinity and specificity in antibody-antigen complexes.

Aptamers have a number of desirable characteristics for use as therapeutics and diagnostics including high specificity and affinity, biological efficacy, and excellent pharmacokinetic properties. In addition, they offer specific competitive advantages over antibodies and other protein biologics, for example:

1) Speed and control. Aptamers are produced by an entirely in vitro process, allowing for the rapid generation of initial leads, including therapeutic leads. In vitro selection allows the specificity and affinity of the aptamer to be tightly controlled and allows the generation of leads, including leads against both toxic and non-immunogenic targets.

2) Toxicity and Immunogenicity. Aptamers as a class have demonstrated little or no toxicity or immunogenicity. In chronic dosing of rats or woodchucks with high levels of aptamer (10 mg/kg daily for 90 days), no toxicity is observed by any clinical, cellular, or biochemical measure. Whereas the efficacy of many monoclonal antibodies can be severely limited by immune response to antibodies themselves, it is extremely difficult to elicit antibodies to aptamers most likely because aptamers cannot be presented by T-cells via the MHC and the immune response is generally trained not to recognize nucleic acid fragments.

3) Administration. Whereas most currently approved antibody therapeutics are administered by intravenous infusion (typically over 2-4 hours), aptamers can be administered by subcutaneous injection (aptamer bioavailability via subcutaneous administration is >80% in monkey studies (Tucker et al., J. Chromatography B. 732: 203-212, 1999)). This difference is primarily due to the comparatively low solubility and thus large volumes necessary for most therapeutic mAbs. With good solubility (>150 mg/mL) and comparatively low molecular weight (aptamer: 10-50 kDa; antibody: 150 kDa), a weekly dose of aptamer may be delivered by injection in a volume of less than 0.5 mL. In addition, the small size of aptamers allows them to penetrate into areas of conformational constrictions that do not allow for antibodies or antibody fragments to penetrate, presenting yet another advantage of aptamer-based therapeutics or prophylaxis.

4) Scalability and cost. Therapeutic aptamers are chemically synthesized and consequently can be readily scaled as needed to meet production demand. Whereas difficulties in scaling production are currently limiting the availability of some biologics and the capital cost of a large-scale protein production plant is enormous, a single large-scale oligonucleotide synthesizer can produce upwards of 100 kg/year and requires a relatively modest initial investment. The current cost of goods for aptamer synthesis at the kilogram scale is estimated at $500/g, comparable to that for highly optimized antibodies. Continuing improvements in process development are expected to lower the cost of goods to <$100/g in five years.

5) Stability. Therapeutic aptamers are chemically robust. They are intrinsically adapted to regain activity following exposure to factors such as heat and denaturants and can be stored for extended periods (>1 yr) at room temperature as lyophilized powders.

IgE and Atopic Disease

Atopy is the genetic predisposition to produce allergen-specific IgE and is one of the most important predisposing factors for the development of asthma and other allergic diseases. Atopic diseases such as allergic rhinitis (hayfever), asthma, and atopic dermatitis are prevalent among the U.S. population and are on the rise. Symptoms of allergic disease include vasodilation, smooth muscle contraction, local inflammation and vascular permeability. Increased production of IgE in response to common environmental allergens is the hallmark of atopic disease. Common allergens include dustmite feces, pollen, foods, animal dander and fungal spores. Mast cells are known to play a central role in the immediate phase reaction of allergic diseases through IgE-mediated release of a variety of chemical mediators like histamine, leukotrienes, and prostaglandins. T lymphocytes, basophils and eosinophils are thought to be responsible in inducing the late phase response. Immediate hypersensitivity caused by the stimulation of mast cells and basophils upon contact of allergy-specific IgE with antigen is a powerful mammalian immune effector system. These IgE-mediated reactions can cause diseases such as allergic rhinitis, atopic dermatitis, urticaria, food allergies, asthma, and in the most severe cases, anaphylactic shock which can result in death.

While not intending to be bound by any theory, the mechanism whereby IgE mediates allergic responses has been determined. In brief, IgE binds to the a chain of the high affinity IgE receptor, FcεRI, on mast cells and basophils. FcεRI on these cell types is tetrameric consisting of an a chain, a β chain and homodimeric γ chains. The β and γ chains are the signal transducing domains of FcεRI. Allergen cross-linking of IgE bound to mast cells results in stimulation of FcεRI and activation of a number of signal transduction pathways that lead to the release of a range of proinflammatory mediators and cytokines, including bronchoconstrictive and vasoactive substances, such as histamine, leukotrienes and various other cytokines (see FIG. 1). The role of IgE and Fc$_\epsilon$RI and mast cells has been confirmed in animal models of anaphylaxis: systemic delivery of IgE plus specific antigen (or treatment with anti-IgE alone) causes anaphylactic reactions in normal mice but fails to trigger immediate systemic responses in mast-cell-deficient or Fc$_\epsilon$RI-deficient mice.

Currently, there are therapeutic approaches under clinical evaluation that interfere with the immunological mechanisms underlying allergen-induced pathology, for example, an anti-IgE immunoglobulin, which directly targets IgE serum antibodies, thus inhibiting the central mechanism of immediate type hypersensitivity reactions. In addition, there has been interest in developing allergen-specific immunotherapy due to its potential to cure allergic diseases. However, both anti-IgE immunoglobulins and allergen-specific immunotherapy are limited by high costs and the necessity for permanent or every-season treatment.

In addition to the previously described advantages of aptamers as a novel class of therapeutics, because aptamers are nucleic acids, they can incorporate motifs that have an immuno-stimulatory effect desirable and beneficial in a therapeutic for atopic and other immune diseases. These motifs include the CpG motifs that have immunomodulatory effects, such as suppression of allergic responses mediated by type II T helper ($T_H2$) cells. CpG has been shown to rapidly induce expression of T-bet mRNA in purified B cells (Liu et al., 2003, Nature Immun. Vol 4, no. 7, p. 687-693).

Thus, it would be beneficial to have materials and methods to disrupt the biological function of IgE to treat disease in which it is implicated in pathogenesis. The present invention provides materials and methods to meet these and other needs.

SUMMARY OF THE INVENTION

The present invention provides materials and methods for the treatment, prevention and/or amelioration of atopic disease. In one embodiment, an aptamer comprising the following sequence: mAmGmCmCmUdGmGdG-s-dGmAmCmC-mCmAmU-s-dI-s-mGdI-s-dGdI-s-dGmCmU (SEQ ID NO 298) conjugated to a PEG moiety is provided. In some embodiments, the PEG moiety is selected from the group consisting of: a 60 kDa, a 40 kDa, a 30 kDa and a 20 kDa. In some embodiments, the PEG moiety is a branched while in other embodiments it is linear.

In a particular embodiment, the aptamer of the invention comprises the structure set forth below:

```
                              O
                              ‖   H
                      ─O─C─N~~ 5' Aptamer 3'
20 kDa mPEG ──O─┤
20 kDa mPEG ──O─┘
``` where,
~~~ indicates a linker

```
Aptamer =                                    (SEQ ID NO 216)
mAmGmCmCmUdGmGdG-s-dGmAmCmCmCmAmU-s-dI-s-mGdI-s-
dGdI-s-dGmCmU-3T
``` wherein mC, mG, mU and mA=2'-OMe C, 2'-OMe G, 2'-OMe U and 2'-OMe A respectively, dG=deoxy G, dI=deoxy inosine, s=a phosphorothioate backbone substitution, and 3T=3' inverted deoxy thymidine.

In some embodiments, the aptamer of the invention comprises the structure set forth below:

```
                              O
                              ‖   H
                      ─O─C─N~~ 5' Aptamer 3'
30 kDa mPEG ──O─┤
30 kDa mPEG ──O─┘
``` where,
~~~ indicates a linker

```
Aptamer =                                    (SEQ ID NO 216)
mAmGmCmCmUdGmGdG-s-dGmAmCmCmCmAmU-s-dI-s-mGdI-s-
dGdI-s-dGmCmU-3T
``` wherein mC, mG, mU and mA=2'-OMe C, 2'-OMe G, 2'-OMe U and 2'-OMe A respectively, dG=deoxy G, dI=deoxy inosine, s=a phosphorothioate backbone substitution, and 3T=3' inverted deoxy thymidine.

In some embodiments, the aptamer of the invention comprises the structure set forth below:

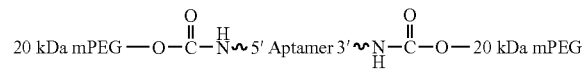

where,

⁓⁓⁓indicates a linker

```
Aptamer =                                    (SEQ ID NO 298)
mAmGmCmCmUdGmGdG-s-dGmAmCmCmCmAmU-s-dI-s-mGdI-s-
dGdI-s-dGmCmU
``` wherein mC, mG, mU and mA=2'-OMe C, 2'-OMe G, 2'-OMe U and 2'-OMe A respectively, dG=deoxy G, dI=deoxy inosine, s=a phosphorothioate backbone substitution, and 3T=3' inverted deoxy thymidine.

In some embodiments, the aptamer of the invention comprises the structure set forth below:

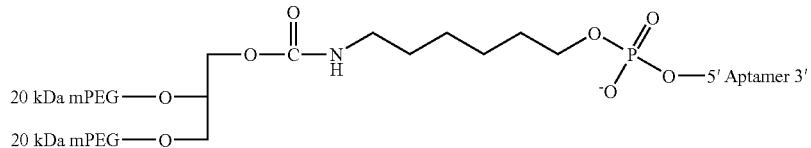

```
Aptamer =                                    (SEQ ID NO 216)
mAmGmCmCmUdGmGdG-s-dGmAmCmCmCmAmU-s-dI-s-mGdI-s-
dGdI-s-dGmCmU-3T
``` wherein mC, mG, mU and mA=2'-OMe C, 2'-OMe G, 2'-OMe U and 2'-OMe A respectively, dG=deoxy G, dI=deoxy inosine, s=a phosphorothioate backbone substitution, and 3T=3' inverted deoxy thymidine.

In some embodiments, the aptamer of the invention comprises the structure set forth below:

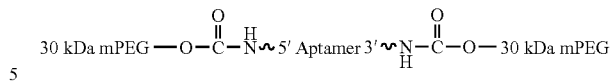

where,

⁓⁓⁓indicates a linker

```
Aptamer =                                    (SEQ ID NO 298)
mAmGmCmCmUdGmGdG-s-dGmAmCmCmCmAmU-s-dI-s-mGdI-s-
dGdI-s-dGmCmU
``` wherein mC, mG, mU and mA=2'-OMe C, 2'-OMe G, 2'-OMe U and 2'-OMe A respectively, dG=deoxy G, dI=deoxy inosine, s=a phosphorothioate backbone substitution, and 3T=3' inverted deoxy thymidine.

In some embodiments the aptamer of the invention comprises a non-alkyl linker. In some embodiments the aptamer of the invention comprises an alkyl linker. In some embodiments, the alkyl linker comprises 2 to 18 consecutive $CH_2$ group, particularly 2 to 12 consecutive $CH_2$ groups and more particularly 3 to 6 consecutive $CH_2$.

In some embodiments, the aptamer of the invention comprises the structure set forth below:

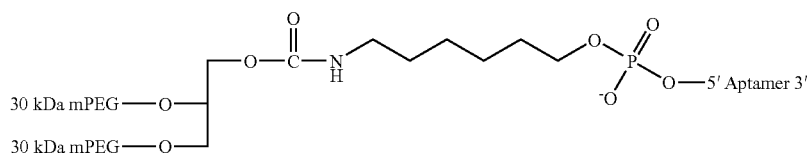

Aptamer = (SEQ ID NO 216)
mAmGmCmCmUdGmGdG-s-dGmAmCmCmCmAmU-s-dI-s-mGdI-s-
dGdI-s-dGmCmU-3T wherein mC, mG, mU and mA=2'-OMe C, 2'-OMe G, 2'-OMe U and 2'-OMe A respectively, dG=deoxy G, dI=deoxy inosine, s=a phosphorothioate backbone substitution, and 3T=3' inverted deoxy thymidine.

In some embodiments, the aptamer of the invention comprises the structure set forth below:

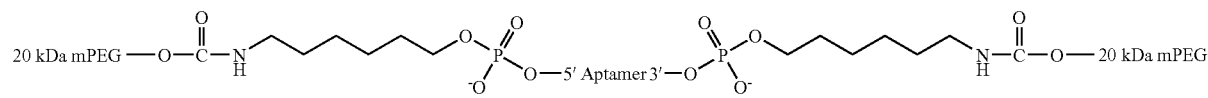

Aptamer = (SEQ ID NO 298)
mAmGmCmCmUdGmGdG-s-dGmAmCmCmCmAmU-s-dI-s-mGdI-s-
dGdI-s-dGmCmU wherein mC, mG, mU and mA=2'-OMe C, 2'-OMe G, 2'-OMe U and 2'-OMe A respectively, dG=deoxy G, dI=deoxy inosine, s=a phosphorothioate backbone substitution, and 3T=3' inverted deoxy thymidine.

In some embodiments, the aptamer of the invention comprises the structure set forth below:

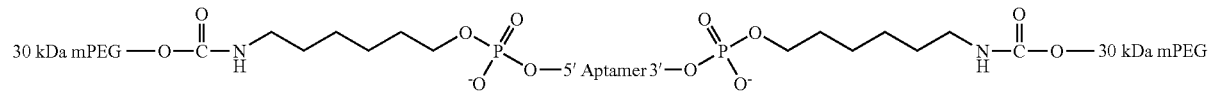

Aptamer = (SEQ ID NO 298)
mAmGmCmCmUdGmGdG-s-dGmAmCmCmCmAmU-s-dI-s-mGdI-s-
dGdI-s-dGmCmU wherein mC, mG, mU and mA=2'-OMe C, 2'-OMe G, 2'-OMe U and 2'-OMe A respectively, dG=deoxy G, dI=deoxy inosine, s=a phosphorothioate backbone substitution, and 3T=3' inverted deoxy thymidine.

In some embodiments, the aptamer of the invention modulates, particularly inhibits, a function of IgE or a variant thereof. In some embodiments, the aptamer inhibits a function of IgE or a variant thereof in vitro. In some embodiments, the aptamer inhibits a function of IgE or a variant thereof in vivo. In some embodiments, the aptamer of the invention prevents binding of IgE to its receptor. In some embodiments, a method of treating, preventing and/or ameliorating a disease mediated by IgE, comprising administering an aptamer of the invention or a salt thereof to a vertebrate, preferably a mammal, more preferably a human, is provided.

In some embodiments the invention provides a therapeutic composition comprising a therapeutically effective amount of any of the above described aptamers or a salt thereof. In some embodiments the therapeutic composition further comprises a pharmaceutically acceptable carrier or diluent.

In one embodiment, a method of treating a disease mediated by IgE, comprising administering the aptamer of the invention, particularly administering the therapeutic composition, to a vertebrate, preferably to a mammal, particularly to a human is provided. In some embodiments the disease to be treated is atopic disease. In particular embodiments the disease to be treated is selected from the group consisting of: allergic rhinitis, atopic dermatitis, asthma, acute urticaria, food allergies, peanut allergy, systemic anaphylaxis, allergic conjunctivitis, vernal keratoconjunctivitis, atopic keratoconjunctivitis, giant papillary conjunctivitis, and eosinophilic gastroenteritis. In a particular embodiment, the disease to be treated is asthma.

In some embodiments, the anti-IgE aptamer of the invention is administered to a subject, such as a vertebrate, preferably a mammal, more preferably a human, in conjunction with an immunostimulatory nucleic acid sequence, such as a second aptamer comprising a CpG motif.

In some embodiments the aptamer is administered to the subject via a route selected from the group consisting of subcutaneous administration, intravenous administration and intranasal administration. In a particular embodiment, the therapeutic composition is administered subcutaneously to a human subject having or at risk for atopic disease.

In some embodiments, a diagnostic method comprising contacting a PEG conjugated aptamer of the invention with a composition suspected of comprising IgE or a variant thereof and detecting the presence or absence of IgE or a variant thereof is provided. In some embodiments, an aptamer of the invention for use as an in vitro diagnostic is provided. While in other embodiments, an aptamer of the invention for use as an in vivo diagnostic is provided. In some embodiments an aptamer of the invention for use in the treatment, prevention and/or amelioration of disease in vivo is provided.

In some embodiments, an aptamer that specifically binds to IgE comprising a nucleic acid sequence at least 80% identical, particularly at least 90% identical to any one of the sequences selected from the group consisting of: SEQ ID NOS 11-15, 18, 19, 21, 29, 33, 41-44, 46, 50, 56-96, and 98-102.

In some embodiments, an aptamer that specifically binds to IgE comprising a nucleic acid sequence at least 80% identical, particularly at least 90% identical to the unique sequence region of any one of the sequences selected from the group consisting of: SEQ ID NOS SEQ ID NOS 11-15, 18, 19, 21, 29, 33, 41-44, 46, 50 and 56-89.

In some embodiments, an aptamer capable of binding IgE comprising a sequence of 30 contiguous nucleotides that are identical to a sequence of 30 contiguous nucleotides in any one of the aptamer acid sequences selected from the group of: SEQ ID NOS 11-15, 18, 19, 21, 29, 33, 41-44, 46, 50 and 56-96. In particular embodiments, an aptamer comprising 20 contiguous nucleotides that are identical to a sequence of 20 contiguous nucleotides in the unique sequence region of any one of the aptamer sequences selected from the group of: SEQ ID NOS 11-15, 18, 19, 21, 29, 33, 41-44, 46, 50, 56-96, 98-102 is provided. In even more particular embodiments, an aptamer comprising 8 contiguous nucleotides that are identical to a sequence of 8 contiguous nucleotides in the unique sequence region of any one of the aptamer sequences selected from the group consisting of: SEQ ID NOS 11-15, 18, 19, 21, 29, 33, 41-44, 46, 50, 56-96, 98-102 is provided. Preferably, the aptamer comprising 8 contiguous nucleotides identical to the unique sequence of an aptamer sequence selected from the group consisting of: SEQ ID NOS 11-15, 18, 19, 21, 29, 33, 41-44, 46, 50, 56-96, 98-102, specifically binds to IgE, preferably human IgE and in some embodiments modulates a function of IgE, preferably of human IgE. In some embodiments, an aptamer selected from the group consisting of: SEQ ID NOS 11-15, 18, 19, 21, 29, 33, 41-44, 46, 50, 56-96, 98-102, 119-124, 126-136, 139-157, 158-176, 178-190, 194-201, 206-243, 247, 249-259, 261-267, 269-290 and 292 is provided.

In some embodiments, the aptamer of the invention is a single stranded nucleic acid. In some embodiments, the aptamer of the invention is conjugated to a high molecular weight, non-immunogenic compound or a lipophilic compound. In some embodiments, the aptamer of the invention is conjugated to a polyalkylene glycol moiety, particularly a polyethylene glycol moiety. In some embodiments, the polyethylene glycol moiety is branched while in other embodiments it is linear.

In some embodiments, the aptamer of the invention comprises a chemical modification selected from the group consisting: of a chemical substitution at a sugar position; a chemical substitution at a phosphate position; a chemical substitution at a base position of the nucleic acid; 3' capping with an inverted nucleotide, and 5' capping with an inverted nucleotide. In some embodiments, the aptamer of the invention further comprises an immunostimulatory nucleic acid sequence, such as a CpG motif.

In some embodiments, the aptamer of the invention modulates, particularly inhibits, a function of IgE or a variant thereof. In some embodiments, the aptamer inhibits a function of IgE or a variant thereof in vitro. In some embodiments, the aptamer inhibits a function of IgE or a variant thereof in vivo. In some embodiments, the aptamer of the invention prevents binding of IgE to its receptor. In some embodiments, a method of treating, preventing and/or ameliorating a disease mediated by IgE, comprising administering an aptamer of the invention or a salt thereof to a vertebrate, preferably a mammal, more preferably a human, is provided.

In some embodiments, a therapeutic composition comprising a therapeutically effective amount of an aptamer of the invention or a salt thereof, and a pharmaceutically acceptable carrier or diluent is provided. In some embodiments, a method of treating, preventing and/or ameliorating a disease mediated by IgE, comprising administering an aptamer of the invention, preferably the therapeutic composition of the invention to a vertebrate, preferably a mammal, more preferably a human, is provided.

In some embodiments of the invention, the disease to be treated is an atopic disease, particularly a disease selected from the group consisting of: allergic rhinitis, atopic dermatitis, asthma, acute urticaria, food allergies, peanut allergy, systemic anaphylaxis, allergic conjunctivitis, vernal keratoconjunctivitis, atopic keratoconjunctivitis, giant papillary conjunctivitis, and eosinophilic gastroenteritis.

In some embodiments, the anti-IgE aptamer of the invention is administered to a subject, such as a vertebrate, preferably a mammal, more preferably a human, in conjunction with an immunostimulatory nucleic acid sequence, such as a second aptamer comprising a CpG motif. In some embodiments the immunostimulatory nucleic acid sequence is incorporated into or appended to the anti-IgE aptamer of the invention.

In some embodiments the aptamer of the invention is administered to a subject by a route selected from the group consisting of: subcutaneous administration, intravenous administration and intranasal administration.

In some embodiments, a diagnostic method comprising contacting an aptamer of the invention with a composition suspected of comprising IgE or a variant thereof and detecting the presence or absence of IgE or a variant thereof is provided. In some embodiments, an aptamer of the invention for use as an in vitro diagnostic is provided. While in other embodiments, an aptamer of the invention for use as an in vivo diagnostic is provided. In some embodiments an aptamer of the invention for use in the treatment, prevention and/or amelioration of disease in vivo is provided.

In another aspect of the invention, a method for increasing the binding affinity of an aptamer for a target, wherein the aptamer is capable of forming multimeric aggregates, is provided. In one embodiment, the method comprises the step of substituting a nucleotide in the aggregate forming aptamer with a nucleotide selected to prevent aggregate formation whereby the binding affinity of the resulting substituted aptamer for its target is increased relative the binding affinity a parent aptamer, the parent aptamer having the same nucleic acid sequence but lacking the nucleotide substitution. In some embodiments the nucleotide selected to prevent aggregate formation is a modified nucleotide. In some embodiments, the modified nucleotide is inosine.

In another aspect of the invention, a method for increasing the binding affinity of an aptamer for a target is provided, comprising the step of substituting an inosine for at least one nucleotide at a position that increases the binding affinity of the inosine substituted aptamer to the target relative to the binding affinity of the parent aptamer to the same target, the parent aptamer having the same nucleotide sequence but lacking the inosine modification. In one embodiment of the provided method, the substitution step comprises substituting no more than four, three or two inosines for four three or two nucleotides respectively, wherein the resulting aptamer comprises increased binding affinity to the target relative to that of the parent aptamer. In some embodiments, the inosine substituted nucleotide is a purine. In a particular embodiment, the inosine substituted purine is guanosine. In another embodiment, the method of the invention comprises a second chemical substitution step selected from the group consisting of: a chemical substitution at a sugar position; a chemical substitution at a phosphate position and chemical substitution at a base position of the nucleic acid. In a particular, embodiment further substituted aptamer comprises an increased binding affinity to the target relative to an aptamer identical to the further substituted aptamer except that it lacks the second chemical substitution.

In some embodiments, the substituting step comprises chemically synthesizing the aptamer with the desired substitution.

In some embodiments the binding affinity of the inosine substituted aptamer for the target is increased at least two, at least five, at least 10, at least 25, at least 50, at least 75, at least 85, at least 95, at least 100, at least 150, at least 200 fold relative to the parent aptamer. In some embodiments, the substituting step comprises chemically synthesizing the aptamer.

In one aspect of the invention, an aptamer having increased binding affinity for its target obtained by a substitution method of the invention is provided. In a particular embodiment the aptamer comprises increased binding affinity for IgE, particularly human IgE.

BRIEF DESCRIPTION OF THE FIGURES

FIG. 13(A) shows the rRfY clone according to SEQ ID NO 91, outlined residues are 2'-F; FIG. 13(B) shows ARC445 (SEQ ID NO 101), a dRmY clone, black residues are 2'-deoxy, grey residues are 2'-OMe; FIG. 13(C) shows ARC475 (SEQ ID NO 151), DNA clone, underlined residues are 2'-deoxy.

FIG. 18 is a table outlining the design of a pharmacokinetics study of PEGylated anti-IgE aptamers ARC1785 (SEQ ID NO 295), ARC1787 (SEQ ID NO 293), ARC1788 (SEQ ID NO 294), and ARC1790 (SEQ ID NO 296) administered sub-cutaneously to mice at 10 mg/kg.

FIG. 20 is a table summarizing the non-compartmental PK parameter estimates for PEGylated anti-IgE aptamers ARC1785 (SEQ ID NO 295), ARC1787 (SEQ ID NO 293), ARC1788 (SEQ ID NO 294) and ARC1790 (SEQ ID NO 296) after intravenous (IV) and subcutaneous (SC) administration to mice at 10 mg/kg.

DETAILED DESCRIPTION OF THE INVENTION

The details of one or more embodiments of the invention are set forth in the accompanying description below. Although any methods and materials similar or equivalent to those described herein can be used in the practice or testing of the present invention, the preferred methods and materials are now described. Other features, objects, and advantages of the invention will be apparent from the description. In the specification, the singular forms also include the plural unless the context clearly dictates otherwise. Unless defined otherwise, all technical and scientific terms used herein have the same meaning as commonly understood by one of ordinary skill in the art to which this invention belongs. In the case of conflict, the present Specification will control.

The SELEX™ Method

Figure 1:
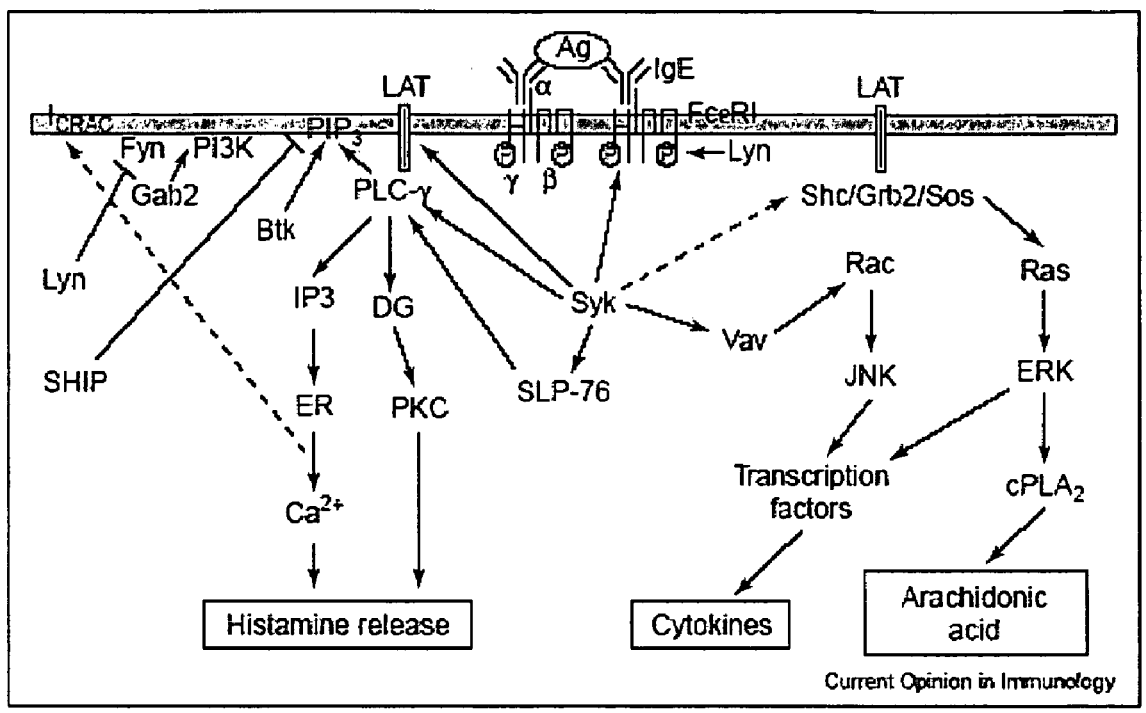
FIG. 1 is a schematic of IgE-mediated signal transduction events.
Figure 2:
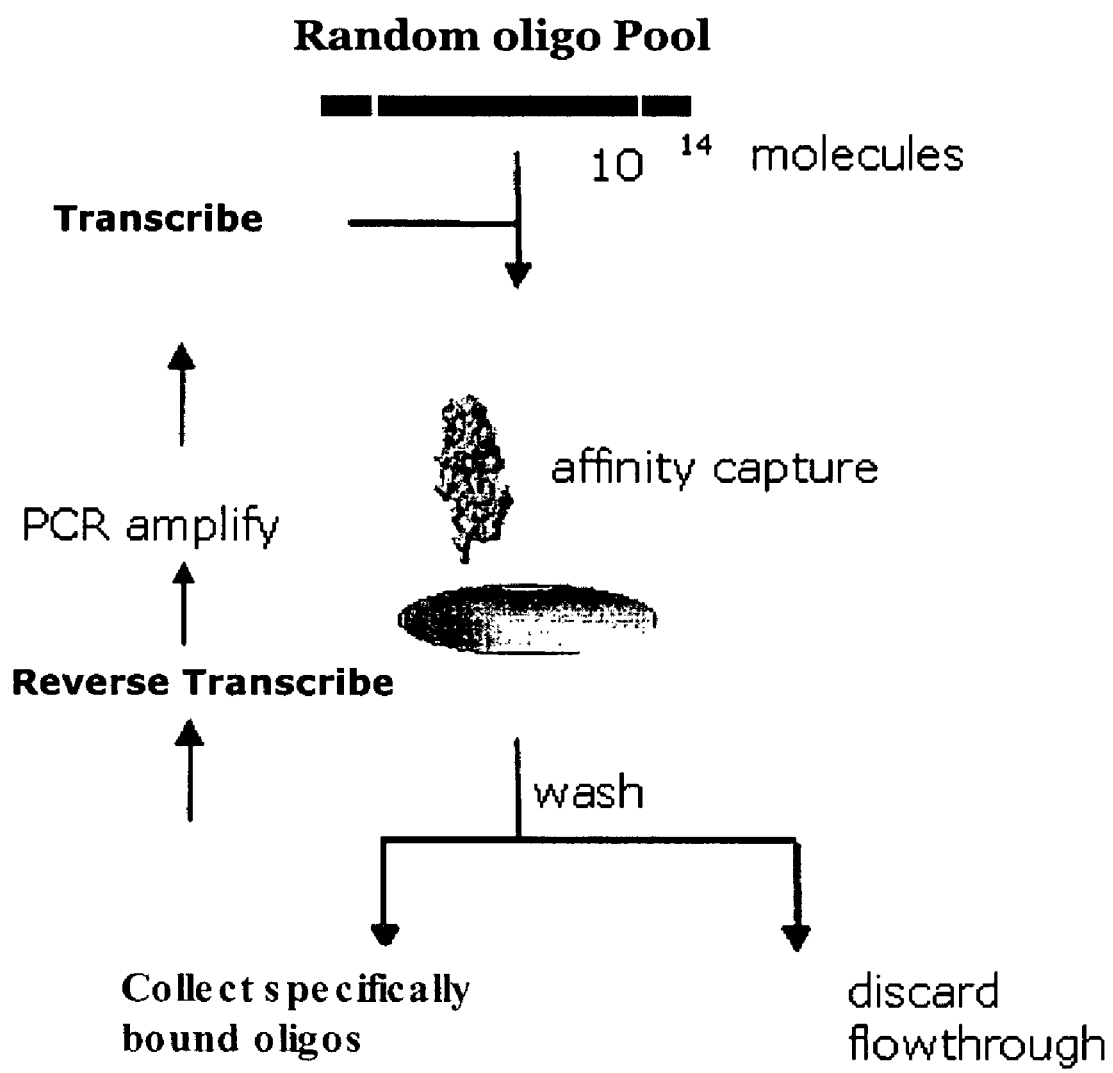
FIG. 2 is a schematic representation of the in vitro aptamer selection (SELEX™) process from pools of random sequence oligonucleotides comprised of ribonucleic acids. For the in vitro aptamer SELEX process using pools of random sequence oligonucleotides comprised of deoxyribonucleic acids, the reverse transcription and transcription steps are omitted.

A suitable method for generating an aptamer is with the process entitled "Systematic Evolution of Ligands by Exponential Enrichment" ("SELEX™") generally depicted for ribonucleic acid selections in FIG. 2 (For selections using a deoxyribonucleic acid pool, the reverse transcription and transcription steps depicted in FIG. 2 are omitted). The SELEX™ process is a method for the in vitro evolution of nucleic acid molecules with highly specific binding to target molecules and is described in, e.g., U.S. patent application Ser. No. 07/536,428, filed Jun. 11, 1990, now abandoned, U.S. Pat. No. 5,475,096 entitled "Nucleic Acid Ligands", and U.S. Pat. No. 5,270,163 (see also WO 91/19813) entitled "Nucleic Acid Ligands". Each SELEX™-identified nucleic acid ligand, i.e., each aptamer, is a specific ligand of a given target compound or molecule. The SELEX™ process is based on the unique insight that nucleic acids have sufficient capacity for forming a variety of two- and three-dimensional structures and sufficient chemical versatility available within their monomers to act as ligands (i.e., form specific binding pairs) with virtually any chemical compound, whether monomeric or polymeric. Molecules of any size or composition can serve as targets.

SELEX™ relies as a starting point upon a large library or pool of single stranded oligonucleotides comprising randomized sequences. The oligonucleotides can be modified or unmodified DNA, RNA, or DNA/RNA hybrids. In some examples, the pool comprises 100% random or partially random oligonucleotides. In other examples, the pool comprises random or partially random oligonucleotides containing at least one fixed sequence and/or conserved sequence incorporated within randomized sequence. In other examples, the pool comprises random or partially random oligonucleotides containing at least one fixed sequence and/or conserved sequence at its 5' and/or 3' end which may comprise a sequence shared by all the molecules of the oligonucleotide pool. Fixed sequences are sequences common to oligonucleotides in the pool which are incorporated for a preselected purpose such as, CpG motifs described further below, hybridization sites for PCR primers, promoter sequences for RNA polymerases (e.g., T3, T4, T7, and SP6), restriction sites, or homopolymeric sequences, such as poly A or poly T tracts, catalytic cores, sites for selective binding to affinity columns, and other sequences to facilitate cloning and/or sequencing of an oligonucleotide of interest. Conserved sequences are sequences, other than the previously described fixed sequences, shared by a number of aptamers that bind to the same target.

The oligonucleotides of the pool preferably include a randomized sequence portion as well as fixed sequences necessary for efficient amplification. Typically the oligonucleotides of the starting pool contain fixed 5' and 3' terminal sequences which flank an internal region of 30-50 random nucleotides. The randomized nucleotides can be produced in a number of ways including chemical synthesis and size selection from randomly cleaved cellular nucleic acids. Sequence variation in test nucleic acids can also be introduced or increased by mutagenesis before or during the selection/amplification iterations.

The random sequence portion of the oligonucleotide can be of any length and can comprise ribonucleotides and/or deoxyribonucleotides and can include modified or non-natural nucleotides or nucleotide analogs. See, e.g. U.S. Pat. No. 5,958,691; U.S. Pat. No. 5,660,985; U.S. Pat. No. 5,958,691; U.S. Pat. No. 5,698,687; U.S. Pat. No. 5,817,635; U.S. Pat. No. 5,672,695, and PCT Publication WO 92/07065. Random oligonucleotides can be synthesized from phosphodiester-linked nucleotides using solid phase oligonucleotide synthesis techniques well known in the art. See, e.g., Froehler et al., Nucl. Acid Res. 14:5399-5467 (1986) and Froehler et al., Tet. Lett. 27:5575-5578 (1986). Random oligonucleotides can also be synthesized using solution phase methods such as triester synthesis methods. See, e.g., Sood et al., Nucl. Acid Res. 4:2557 (1977) and Hirose et al., Tet. Lett., 28:2449 (1978). Typical syntheses carried out on automated DNA synthesis equipment yield $10^{14}$-$10^{16}$ individual molecules, a number sufficient for most SELEX™ experiments. Sufficiently large regions of random sequence in the sequence design increases the likelihood that each synthesized molecule is likely to represent a unique sequence.

The starting library of oligonucleotides may be generated by automated chemical synthesis on a DNA synthesizer. To synthesize randomized sequences, mixtures of all four nucleotides are added at each nucleotide addition step during the synthesis process, allowing for random incorporation of nucleotides. As stated above, in one embodiment, random oligonucleotides comprise entirely random sequences; however, in other embodiments, random oligonucleotides can comprise stretches of nonrandom or partially random sequences. Partially random sequences can be created by adding the four nucleotides in different molar ratios at each addition step.

The starting library of oligonucleotides may be, for example, RNA, DNA or RNA/DNA hybrid. In those instances where an RNA library is to be used as the starting library it is typically generated by transcribing a DNA library in vitro using T7 RNA polymerase or modified T7 RNA polymerases and purified. The RNA or DNA library is then mixed with the target under conditions favorable for binding and subjected to step-wise iterations of binding, partitioning and amplification, using the same general selection scheme, to achieve virtually any desired criterion of binding affinity and selectivity. More specifically, starting with a mixture containing the starting pool of nucleic acids, the SELEX™ method includes steps of: (a) contacting the mixture with the target under conditions favorable for binding; (b) partitioning unbound nucleic acids from those nucleic acids which have bound specifically to target molecules; (c) dissociating the nucleic acid-target complexes; (d) amplifying the nucleic acids dissociated from the nucleic acid-target complexes to yield a ligand-enriched mixture of nucleic acids; and (e) reiterating the steps of binding, partitioning, dissociating and amplifying through as many cycles as desired to yield highly specific, high affinity nucleic acid ligands to the target molecule. In those instances where RNA aptamers are being selected, the SELEX™ method further comprises the steps of: (i) reverse transcribing the nucleic acids dissociated from the nucleic acid-target complexes before amplification in step (d); and (ii) transcribing the amplified nucleic acids from step (d) before restarting the process.

Within a nucleic acid mixture containing a large number of possible sequences and structures, there is a wide range of binding affinities for a given target. A nucleic acid mixture comprising, for example, a 20 nucleotide randomized segment can have $4^{20}$ candidate possibilities. Those which have the higher affinity constants for the target are most likely to bind to the target. After partitioning, dissociation and amplification, a second nucleic acid mixture is generated, enriched for the higher binding affinity candidates. Additional rounds of selection progressively favor the best ligands until the resulting nucleic acid mixture is predominantly composed of only one or a few sequences. These can then be cloned, sequenced and individually tested for binding affinity as pure ligands or aptamers.

Cycles of selection and amplification are repeated until a desired goal is achieved. In the most general case, selection/amplification is continued until no significant improvement in binding strength is achieved on repetition of the cycle. The method is typically used to sample approximately $10^{14}$ different nucleic acid species but may be used to sample as many as about $10^{18}$ different nucleic acid species. Generally, nucleic acid aptamer molecules are selected in a 5 to 20 cycle procedure. In one embodiment, heterogeneity is introduced only in the initial selection stages and does not occur throughout the replicating process.

In one embodiment of SELEX™, the selection process is so efficient at isolating those nucleic acid ligands that bind most strongly to the selected target, that only one cycle of selection and amplification is required. Such an efficient selection may occur, for example, in a chromatographic-type process wherein the ability of nucleic acids to associate with targets bound on a column operates in such a manner that the column is sufficiently able to allow separation and isolation of the highest affinity nucleic acid ligands.

In many cases, it is not necessarily desirable to perform the iterative steps of SELEX™ until a single nucleic acid ligand is identified. The target-specific nucleic acid ligand solution may include a family of nucleic acid structures or motifs that have a number of conserved sequences and a number of sequences which can be substituted or added without significantly affecting the affinity of the nucleic acid ligands to the target. By terminating the SELEX™ process prior to completion, it is possible to determine the sequence of a number of members of the nucleic acid ligand solution family.

A variety of nucleic acid primary, secondary and tertiary structures are known to exist. The structures or motifs that have been shown most commonly to be involved in non-Watson-Crick type interactions are referred to as hairpin loops, symmetric and asymmetric bulges, pseudoknots and myriad combinations of the same. Almost all known cases of such motifs suggest that they can be formed in a nucleic acid sequence of no more than 30 nucleotides. For this reason, it is often preferred that SELEX™ procedures with contiguous randomized segments be initiated with nucleic acid sequences containing a randomized segment of between about 20 to about 50 nucleotides and in some embodiments, about 30 to about 40 nucleotides. In one example, the 5'-fixed:random:3'-fixed sequence comprises a random sequence of about 30 to about 50 nucleotides.

The core SELEX™ method has been modified to achieve a number of specific objectives. For example, U.S. Pat. No. 5,707,796 describes the use of SELEX™ in conjunction with gel electrophoresis to select nucleic acid molecules with specific structural characteristics, such as bent DNA. U.S. Pat. No. 5,763,177 describes SELEX™ based methods for selecting nucleic acid ligands containing photo reactive groups capable of binding and/or photo-crosslinking to and/or photo-inactivating a target molecule. U.S. Pat. No. 5,567,588 and U.S. Pat. No. 5,861,254 describe SELEX™ based methods which achieve highly efficient partitioning between oligonucleotides having high and low affinity for a target molecule. U.S. Pat. No. 5,496,938 describes methods for obtaining improved nucleic acid ligands after the SELEX™ process has been performed. U.S. Pat. No. 5,705,337 describes methods for covalently linking a ligand to its target.

SELEX™ can also be used to obtain nucleic acid ligands that bind to more than one site on the target molecule, and to obtain nucleic acid ligands that include non-nucleic acid species that bind to specific sites on the target. SELEX™ provides means for isolating and identifying nucleic acid ligands which bind to any envisionable target, including large and small biomolecules such as nucleic acid-binding proteins and proteins not known to bind nucleic acids as part of their biological function as well as cofactors and other small molecules. For example, U.S. Pat. No. 5,580,737 discloses nucleic acid sequences identified through SELEX™ which are capable of binding with high affinity to caffeine and the closely related analog, theophylline.

Counter-SELEX™ is a method for improving the specificity of nucleic acid ligands to a target molecule by eliminating nucleic acid ligand sequences with cross-reactivity to one or more non-target molecules. Counter-SELEX™ is comprised of the steps of: (a) preparing a candidate mixture of nucleic acids; (b) contacting the candidate mixture with the target, wherein nucleic acids having an increased affinity to the target relative to the candidate mixture may be partitioned from the remainder of the candidate mixture; (c) partitioning the increased affinity nucleic acids from the remainder of the candidate mixture; (d) dissociating the increased affinity nucleic acids from the target; (e) contacting the increased affinity nucleic acids with one or more non-target molecules such that nucleic acid ligands with specific affinity for the non-target molecule(s) are removed; and (f) amplifying the nucleic acids with specific affinity only to the target molecule to yield a mixture of nucleic acids enriched for nucleic acid sequences with a relatively higher affinity and specificity for binding to the target molecule. As described above for SELEX™, cycles of selection and amplification are repeated as necessary until a desired goal is achieved.

One potential problem encountered in the use of nucleic acids as therapeutics and vaccines is that oligonucleotides in their phosphodiester form may be quickly degraded in body fluids by intracellular and extracellular enzymes such as endonucleases and exonucleases before the desired effect is manifest. The SELEX™ method thus encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX™-identified nucleic acid ligands containing modified nucleotides are described, e.g., in U.S. Pat. No. 5,660,985, which describes oligonucleotides containing nucleotide derivatives chemically modified at the 2' position of ribose, 5 position of pyrimidines, and 8 position of purines, U.S. Pat. No. 5,756,703 which describes oligonucleotides containing various 2'-modified pyrimidines, and U.S. Pat. No. 5,580,737 which describes highly specific nucleic acid ligands containing one or more nucleotides modified with 2'-amino (2'-NH$_2$), 2'-fluoro (2'-F), and/or 2'-O-methyl (2'-OMe) substituents.

Modifications of the nucleic acid ligands contemplated in this invention include, but are not limited to, those which provide other chemical groups that incorporate additional charge, polarizability, hydrophobicity, hydrogen bonding, electrostatic interaction, and fluxionality to the nucleic acid ligand bases or to the nucleic acid ligand as a whole. Modifications to generate oligonucleotide populations which are resistant to nucleases can also include one or more substitute internucleotide linkages, altered sugars, altered bases, or combinations thereof. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, phosphorothioate or alkyl phosphate modifications, methylations, and unusual base-pairing combinations such as the isobases isocytidine and isoguanosine. Modifications can also include 3' and 5' modifications such as capping.

In one embodiment, oligonucleotides are provided in which the P(O)O group is replaced by P(O)S ("thioate"), P(S)S ("dithioate"), P(O)NR$_2$ ("amidate"), P(O)R, P(O)OR', CO or CH$_2$ ("formacetal") or 3'-amine (—NH—CH$_2$—CH$_2$—), wherein each R or R' is independently H or substituted or unsubstituted alkyl. Linkage groups can be attached to adjacent nucleotides through an —O—, —N—, or —S— linkage. Not all linkages in the oligonucleotide are required to be identical.

In further embodiments, the oligonucleotides comprise modified sugar groups, for example, one or more of the hydroxyl groups is replaced with halogen, aliphatic groups, or functionalized as ethers or amines. In one embodiment, the 2'-position of the furanose residue is substituted by any of an O-methyl, O-alkyl, O-allyl, S-alkyl, S-allyl, or halo group.

Methods of synthesis of 2'-modified sugars are described, e.g., in Sproat, et al., Nucl. Acid Res. 19:733-738 (1991); Cotten, et al., Nucl. Acid Res. 19:2629-2635 (1991); and Hobbs, et al., Biochemistry 12:5138-5145 (1973). Other modifications are known to one of ordinary skill in the art. Such modifications may be pre-SELEX™ process modifications or post-SELEX™ process modifications (modification of previously identified unmodified ligands) or may be made by incorporation into the SELEX™ process.

Pre-SELEX™ process modifications or those made by incorporation into the SELEX™ process yield nucleic acid ligands with both specificity for their SELEX™ target and improved stability, e.g., in vivo stability. Post-SELEX™ process modifications made to nucleic acid ligands may result in improved stability, e.g., in vivo stability without adversely affecting the binding capacity of the nucleic acid ligand.

The SELEX™ method encompasses combining selected oligonucleotides with other selected oligonucleotides and non-oligonucleotide functional units as described in U.S. Pat. No. 5,637,459 and U.S. Pat. No. 5,683,867. The SELEX™ method further encompasses combining selected nucleic acid ligands with lipophilic or non-immunogenic high molecular weight compounds in a diagnostic or therapeutic complex, as described, e.g., in U.S. Pat. No. 6,011,020, U.S. Pat. No. 6,051,698, and PCT Publication No. WO 98/18480. These patents and applications teach the combination of a broad array of shapes and other properties, with the efficient amplification and replication properties of oligonucleotides, and with the desirable properties of other molecules.

The identification of nucleic acid ligands to small, flexible peptides via the SELEX™ method has also been explored. Small peptides have flexible structures and usually exist in solution in an equilibrium of multiple conformers, and thus it was initially thought that binding affinities may be limited by the conformational entropy lost upon binding a flexible peptide. However, the feasibility of identifying nucleic acid ligands to small peptides in solution was demonstrated in U.S. Pat. No. 5,648,214. In this patent, high affinity RNA nucleic acid ligands to substance P, an 11 amino acid peptide, were identified.

The aptamers with specificity and binding affinity to the target(s) of the present invention are typically selected by the SELEX™ process as described herein. As part of the SELEX™ process, the sequences selected to bind to the target are then optionally minimized to determine the minimal sequence having the desired binding affinity. The selected sequences and/or the minimized sequences are optionally modified by performing random or directed mutagenesis of the sequence to increase binding affinity or alternatively to determine which positions in the sequence are essential for binding activity. Additionally, selections can be performed with sequences incorporating modified nucleotides to stabilize the aptamer molecules against degradation in vivo.

2' Modified SELEX™

In order for an aptamer to be suitable for use as a therapeutic, it is preferably inexpensive to synthesize, safe and stable in vivo. Wild-type RNA and DNA aptamers are typically not stable in vivo because of their susceptibility to degradation by nucleases. Resistance to nuclease degradation can be greatly increased by the incorporation of modifying groups at the 2'-position.

Fluoro and amino groups have been successfully incorporated into oligonucleotide pools from which aptamers have been subsequently selected. However, these modifications greatly increase the cost of synthesis of the resultant aptamer, and may introduce safety concerns in some cases because of the possibility that the modified nucleotides could be recycled into host DNA by degradation of the modified oligonucleotides and subsequent use of the nucleotides as substrates for DNA synthesis.

Aptamers that contain 2'-O-methyl ("2'-OMe") nucleotides, as provided herein, overcome many of these drawbacks. Oligonucleotides containing 2'-OMe nucleotides are nuclease-resistant and inexpensive to synthesize. Although 2'-OMe nucleotides are ubiquitous in biological systems, natural polymerases do not accept 2'-OMe NTPs as substrates under physiological conditions, thus there are no safety concerns over the recycling of 2'-OMe nucleotides into host DNA. The SELEX™ method used to generate 2'-modified aptamers is described, e.g., in U.S. Provisional Patent Application Ser. No. 60/430,761, filed Dec. 3, 2002, U.S. Provisional Patent Application Ser. No. 60/487,474, filed Jul. 15, 2003, U.S. Provisional Patent Application Ser. No. 60/517, 039, filed Nov. 4, 2003, U.S. patent application Ser. No. 10/729,581, filed Dec. 3, 2003, and U.S. patent application Ser. No. 10/873,856, filed Jun. 21, 2004, entitled "Method for in vitro Selection of 2'-O-methyl Substituted Nucleic Acids", each of which is herein incorporated by reference in its entirety.

The present invention includes aptamers that bind to and modulate the function of IgE which contain modified nucleotides (e.g., nucleotides which have a modification at the 2' position) to make the oligonucleotide more stable than the unmodified oligonucleotide to enzymatic and chemical degradation as well as thermal and physical degradation. Although there are several examples of 2'-OMe containing aptamers in the literature (see, e.g., Green et al., Current Biology 2, 683-695, 1995) these were generated by the in vitro selection of libraries of modified transcripts in which the C and U residues were 2'-fluoro (2'-F) substituted and the A and G residues were 2'-OH. Once functional sequences were identified then each A and G residue was tested for tolerance to 2'-OMe substitution, and the aptamer was re-synthesized having all A and G residues which tolerated 2'-OMe substitution as 2'-OMe residues. Most of the A and G residues of aptamers generated in this two-step fashion tolerate substitution with 2'-OMe residues, although, on average, approximately 20% do not. Consequently, aptamers generated using this method tend to contain from two to four 2'-OH residues, and stability and cost of synthesis are compromised as a result. By incorporating modified nucleotides into the transcription reaction which generate stabilized oligonucleotides used in oligonucleotide pools from which aptamers are selected and enriched by SELEX™ (and/or any of its variations and improvements, including those described herein), the methods of the present invention eliminate the need for stabilizing the selected aptamer oligonucleotides (e.g., by resynthesizing the aptamer oligonucleotides with modified nucleotides).

In one embodiment, the present invention provides aptamers comprising combinations of 2'-OH, 2'-F, 2'-deoxy, and 2'-OMe modifications of the ATP, GTP, CTP, TTP, and UTP nucleotides. In another embodiment, the present invention provides aptamers comprising combinations of 2'-OH, 2'-F, 2'-deoxy, 2'-OMe, 2'-NH$_2$, and 2'-methoxyethyl modifications of the ATP, GTP, CTP, TTP, and UTP nucleotides. In another embodiment, the present invention provides aptamers comprising $5^6$ combinations of 2'-OH, 2'-F, 2'-deoxy, 2'-OMe, 2'-NH$_2$, and 2'-methoxyethyl modifications of the ATP, GTP, CTP, TTP, and UTP nucleotides.

2' modified aptamers of the invention are created using modified polymerases, e.g., a modified T7 polymerase, having a rate of incorporation of modified nucleotides having bulky substituents at the furanose 2' position that is higher than that of wild-type polymerases. For example, a mutant T7 polymerase (Y639F) in which the tyrosine residue at position 639 has been changed to phenylalanine readily utilizes 2'deoxy, 2'amino-, and 2'fluoro-nucleotide triphosphates (NTPs) as substrates and has been widely used to synthesize modified RNAs for a variety of applications. However, this mutant T7 polymerase reportedly can not readily utilize (i.e., incorporate) NTPs with bulky 2'-substituents such as 2'-OMe or 2'-azido (2'-N$_3$) substituents. For incorporation of bulky 2' substituents, a T7 polymerase mutant (Y639F/H784A) having the histidine at position 784 changed to an alanine residue in addition to the Y639F mutation has been described and has been used in limited circumstances to incorporate modified pyrimidine NTPs. See Padilla, R. and Sousa, R., Nucleic Acids Res., 2002, 30(24): 138. A mutant T7 polymerase (H784A) having the histidine at position 784 changed to an alanine residue has also been described. Padilla et al., Nucleic Acids Research, 2002, 30: 138. In both the Y639F/H784A and H784A mutant T7 polymerases, the change to a smaller amino acid residue such as alanine allows for the incorporation of bulkier nucleotide substrates, e.g., 2'-OMe substituted nucleotides.

Generally, it has been found that under the conditions disclosed herein, the Y693F mutant can be used for the incorporation of all 2'-OMe substituted NTPs except GTP and the Y639F/H784A mutant can be used for the incorporation of all 2'-OMe substituted NTPs including GTP. It is expected that the H784A mutant possesses properties similar to the Y639F and the Y639F/H784A mutants when used under the conditions disclosed herein.

2'-modified oligonucleotides may be synthesized entirely of modified nucleotides, or with a subset of modified nucleotides. The modifications can be the same or different. All nucleotides may be modified, and all may contain the same modification. All nucleotides may be modified, but contain different modifications, e.g., all nucleotides containing the same base may have one type of modification, while nucleotides containing other bases may have different types of modification. All purine nucleotides may have one type of modification (or are unmodified), while all pyrimidine nucleotides have another, different type of modification (or are unmodified). In this way, transcripts, or pools of transcripts are generated using any combination of modifications, including for example, ribonucleotides (2'-OH), deoxyribonucleotides (2'-deoxy), 2'-F, and 2'-OMe nucleotides. A transcription mixture containing 2'-OMe C and U and 2'-OH A and G is referred to as an "rRmY" mixture and aptamers selected therefrom are referred to as "rRmY" aptamers. A transcription mixture containing deoxy A and G and 2'-OMe U and C is referred to as a "dRmY" mixture and aptamers selected therefrom are referred to as "dRmY" aptamers. A transcription mixture containing 2'-OMe A, C, and U, and 2'-OH G is referred to as a "rGmH" mixture and aptamers selected therefrom are referred to as "fGmH" aptamers. A transcription mixture alternately containing 2'-OMe A, C, U and G and 2'-OMe A, U and C and 2'-F G is referred to as an "alternating mixture" and aptamers selected therefrom are referred to as "alternating mixture" aptamers. A transcription mixture containing 2'-OMe A, U, C, and G, where up to 10% of the G's are ribonucleotides is referred to as a "r/mGmH" mixture and aptamers selected therefrom are referred to as "r/mGmH" aptamers. A transcription mixture containing 2'-OMe A, U, and C, and 2'-F G is referred to as a "fGmH" mixture and aptamers selected therefrom are referred to as "fGmH" aptamers. A transcription mixture containing 2'-OMe A, U, and C, and deoxy G is referred to as a "dGmH" mixture and aptamers selected therefrom are referred to as "fGmH" aptamers. A transcription mixture containing deoxy A, and 2'-OMe C, G and U is referred to as a "dAmB" mixture and aptamers selected therefrom are referred to as "dAmB" aptamers, and a transcription mixture containing all 2'-OH nucleotides is referred to as a "rN" mixture and aptamers selected therefrom are referred to as "rN" or "rRrY" aptamers. A "mRmY" aptamer is one containing all 2'-O-methyl nucleotides and is usually derived from a r/mGmH oligonucleotide by post-SELEX™ replacement, when possible, of any 2'-OH Gs with 2'-OMe Gs.

A preferred embodiment includes any combination of 2'-OH, 2'-deoxy and 2'-OMe nucleotides. A more preferred embodiment includes any combination of 2'-deoxy and 2'-OMe nucleotides. An even more preferred embodiment is with any combination of 2'-deoxy and 2'-OMe nucleotides in which the pyrimidines are 2'-OMe (such as dRmY, mRmY or dGmH).

Incorporation of modified nucleotides into the aptamers of the invention is accomplished before (pre-) the selection process (e.g., a pre-SELEX™ process modification). Optionally, aptamers of the invention in which modified nucleotides have been incorporated by pre-SELEX™ process modification can be further modified by post-SELEX™ process modification (i.e., a post-SELEX™ process modification after a pre-SELEX™ modification). Pre-SELEX™ process modifications yield modified nucleic acid ligands with specificity for the SELEX™ target and also improved in vivo stability. Post-SELEX™ process modifications, i.e., modification (e.g., truncation, deletion, substitution or additional nucleotide modifications of previously identified ligands having nucleotides incorporated by pre-SELEX™ process modification) can result in a further improvement of in vivo stability without adversely affecting the binding capacity of the nucleic acid ligand having nucleotides incorporated by pre-SELEX™ process modification.

To generate pools of 2'-modified (e.g., 2'-OMe) RNA transcripts in conditions under which a polymerase accepts 2'-modified NTPs the preferred polymerase is the Y693F/H784A mutant or the Y693F mutant. Other polymerases, particularly those that exhibit a high tolerance for bulky 2'-substituents, may also be used in the present invention. Such polymerases can be screened for this capability by assaying their ability to incorporate modified nucleotides under the transcription conditions disclosed herein.

A number of factors have been determined to be important for the transcription conditions useful in the methods disclosed herein. For example, increases in the yields of modified transcript are observed when a leader sequence is incorporated into the 5' end of a fixed sequence at the 5' end of the DNA transcription template, such that at least about the first 6 residues of the resultant transcript are all purines.

Another important factor in obtaining transcripts incorporating modified nucleotides is the presence or concentration of 2'-OH GTP. Transcription can be divided into two phases: the first phase is initiation, during which an NTP is added to the 3'-hydroxyl end of GTP (or another substituted guanosine) to yield a dinucleotide which is then extended by about 10-12 nucleotides; the second phase is elongation, during which transcription proceeds beyond the addition of the first about 10-12 nucleotides. It has been found that small amounts of 2'-OH GTP added to a transcription mixture containing an excess of 2'-OMe GTP are sufficient to enable the polymerase to initiate transcription using 2'-OH GTP, but once transcription enters the elongation phase the reduced discrimination between 2'-OMe and 2'-OH GTP, and the excess of 2'-OMe GTP over 2'-OH GTP allows the incorporation of principally the 2'-OMe GTP.

Another important factor in the incorporation of 2'-OMe substituted nucleotides into transcripts is the use of both divalent magnesium and manganese in the transcription mixture. Different combinations of concentrations of magnesium chloride and manganese chloride have been found to affect yields of 2'-O-methylated transcripts, the optimum concentration of the magnesium and manganese chloride being dependent on the concentration in the transcription reaction mixture of NTPs which complex divalent metal ions. To obtain the greatest yields of maximally 2' substituted O-methylated transcripts (i.e., all A, C, and U and about 90% of G nucleotides), concentrations of approximately 5 mM magnesium chloride and 1.5 mM manganese chloride are preferred when each NTP is present at a concentration of 0.5 mM. When the concentration of each NTP is 1.0 mM, concentrations of approximately 6.5 mM magnesium chloride and 2.0 mM manganese chloride are preferred. When the concentration of each NTP is 2.0 mM, concentrations of approximately 9.6 mM magnesium chloride and 2.9 mM manganese chloride are preferred. In any case, departures from these concentrations of up to two-fold still give significant amounts of modified transcripts.

Priming transcription with GMP or guanosine is also important. This effect results from the specificity of the polymerase for the initiating nucleotide. As a result, the 5'-terminal nucleotide of any transcript generated in this fashion is likely to be 2'-OH G. The preferred concentration of GMP (or guanosine) is 0.5 mM and even more preferably 1 mM. It has also been found that including PEG, preferably PEG-8000, in the transcription reaction is useful to maximize incorporation of modified nucleotides.

For maximum incorporation of 2'-OMe ATP (100%), UTP (100%), CTP (100%) and GTP (~90%) ("r/mGmH") into transcripts the following conditions are preferred: HEPES buffer 200 mM, DTT 40 mM, spermidine 2 mM, PEG-8000 10% (w/v), Triton X-100 0.01% (w/v), MgCl₂ 5 mM (6.5 mM where the concentration of each 2'-OMe NTP is 1.0 mM), MnCl₂ 1.5 mM (2.0 mM where the concentration of each 2'-OMe NTP is 1.0 mM), 2'-OMe NTP (each) 500 µM (more preferably, 1.0 mM), 2'-OH GTP 30 µM, 2'-OH GMP 500 µM, pH 7.5, Y639F/H784A T7 RNA Polymerase 15 units/mL, inorganic pyrophosphatase 5 units/mL, and an all-purine leader sequence of at least 8 nucleotides long. As used herein, one unit of the Y639F/H784A mutant T7 RNA polymerase (or any other mutant T7 RNA polymerase specified herein) is defined as the amount of enzyme required to incorporate 1 nmole of 2'-OMe NTPs into transcripts under the r/mGmH conditions. As used herein, one unit of inorganic pyrophosphatase is defined as the amount of enzyme that will liberate 1.0 mole of inorganic orthophosphate per minute at pH 7.2 and 25° C.

For maximum incorporation (100%) of 2'-OMe ATP, UTP and CTP ("rGmH") into transcripts the following conditions are preferred: HEPES buffer 200 mM, DTT 40 mM, spermidine 2 mM, PEG-8000 10% (w/v), Triton X-100 0.01% (w/v), MgCl₂ 5 mM (9.6 mM where the concentration of each 2'-OMe NTP is 2.0 mM), MnCl₂ 1.5 mM (2.9 mM where the concentration of each 2'-OMe NTP is 2.0 mM), 2'-OMe NTP (each) 500 µM (more preferably, 2.0 mM), pH 7.5, Y639F T7 RNA Polymerase 15 units/ml, inorganic pyrophosphatase 5 units/mL, and an all-purine leader sequence of at least 8 nucleotides long.

For maximum incorporation (100%) of 2'-OMe UTP and CTP ("rRmY") into transcripts the following conditions are preferred: HEPES buffer 200 mM, DTT 40 mM, spermidine 2 mM, PEG-8000 10% (w/v), Triton X-100 0.01% (w/v), MgCl₂ 5 mM (9.6 mM where the concentration of each 2'-OMe NTP is 2.0 mM), MnCl₂ 1.5 mM (2.9 mM where the concentration of each 2'-OMe NTP is 2.0 mM), 2'-OMe NTP (each) 500 µM (more preferably, 2.0 mM), pH 7.5, Y639F/H784A T7 RNA Polymerase 15 units/mL, inorganic pyrophosphatase 5 units/mL, and an all-purine leader sequence of at least 8 nucleotides long.

For maximum incorporation (100%) of deoxy ATP and GTP and 2'-OMe UTP and CTP ("dRmY") into transcripts the following conditions are preferred: HEPES buffer 200 mM, DTT 40 mM, spermine 2 mM, spermidine 2 mM, PEG-8000 10% (w/v), Triton X-100 0.01% (w/v), MgCl₂ 9.6 mM, MnCl₂ 2.9 mM, 2'-OMe NTP (each) 2.0 mM, pH 7.5, Y639F T7 RNA Polymerase 15 units/mL, inorganic pyrophosphatase 5 units/mL, and an all-purine leader sequence of at least 8 nucleotides long.

For maximum incorporation (100%) of 2'-OMe ATP, UTP and CTP and 2'-F GTP ("fGmH") into transcripts the following conditions are preferred: HEPES buffer 200 mM, DTT 40 mM, spermidine 2 mM, PEG-8000 10% (w/v), Triton X-100 0.01% (w/v), MgCl₂ 9.6 mM, MnCl₂ 2.9 mM, 2'-OMe NTP (each) 2.0 mM, pH 7.5, Y639F T7 RNA Polymerase 15 units/mL, inorganic pyrophosphatase 5 units/mL, and an all-purine leader sequence of at least 8 nucleotides long.

For maximum incorporation (100%) of deoxy ATP and 2'-OMe UTP, GTP and CTP ("dAmB") into transcripts the following conditions are preferred: HEPES buffer 200 mM, DTT 40 mM, spermidine 2 mM, PEG-8000 10% (w/v), Triton X-100 0.01% (w/v), MgCl₂ 9.6 mM, MnCl₂ 2.9 mM, 2'-OMe NTP (each) 2.0 mM, pH 7.5, Y639F T7 RNA Polymerase 15 units/mL, inorganic pyrophosphatase 5 units/mL, and an all-purine leader sequence of at least 8 nucleotides long.

For each of the above (a) transcription is preferably performed at a temperature of from about 20° C. to about 50° C., preferably from about 30° C. to 45° C., and more preferably at about 37° C. for a period of at least two hours and (b) 50-300 nM of a double stranded DNA transcription template is used (200 nM template is used in round 1 to increase diversity (300 nM template is used in dRmY transcriptions)), and for subsequent rounds approximately 50 nM, a 1/10 dilution of an optimized PCR reaction, using conditions described herein, is used). The preferred DNA transcription templates are described below (where ARC254 and ARC256 transcribe under all 2'-OMe conditions and ARC255 transcribes under rRmY conditions).

```
SEQ ID NO 1 ARC254
5'-CATCGATGCTAGTCGTAACGATCCNNNNNNNNNNNNNNNNNNNNNNNN
NNNNNNNNCGAGAACGTTCTCTCCTCTCCCTATAGTGAGTCGTATTA-3'

SEQ ID NO 2 ARC255
5'-CATGCATCGCGACTGACTAGCCGNNNNNNNNNNNNNNNNNNNNNNNN
NNNNNNGTAGAACGTTCTCTCCTCTCCCTATAGTGAGTCGTATTA-3'

SEQ ID NO 3 ARC256
5'-CATCGATCGATCGATCGACAGCGNNNNNNNNNNNNNNNNNNNNNNNN
NNNNNNGTAGAACGTTCTCTCCTCTCCCTATAGTGAGTCGTATTA-3'
```

Under rN transcription conditions of the present invention, the transcription reaction mixture comprises 2'-OH adenosine triphosphates (ATP), 2'-OH guanosine triphosphates (GTP), 2'-OH cytidine triphosphates (CTP), and 2'-OH uridine triphosphates (UTP). The modified oligonucleotides produced using the rN transcription mixtures of the present invention comprise substantially all 2'-OH adenosine, 2'-OH guanosine, 2'-OH cytidine, and 2'-OH uridine. In a preferred embodiment of rN transcription, the resulting modified oligonucleotides comprise a sequence where at least 80% of all adenosine nucleotides are 2'-OH adenosine, at least 80% of all guanosine nucleotides are 2'-OH guanosine, at least 80% of all cytidine nucleotides are 2'-OH cytidine, and at least 80% of all uridine nucleotides are 2'-OH uridine. In a more preferred embodiment of rN transcription, the resulting modified oligonucleotides of the present invention comprise a sequence where at least 90% of all adenosine nucleotides are 2'-OH adenosine, at least 90% of all guanosine nucleotides are 2'-OH guanosine, at least 90% of all cytidine nucleotides are 2'-OH cytidine, and at least 90% of all uridine nucleotides are 2'-OH uridine. In a most preferred embodiment of rN transcription, the modified oligonucleotides of the present invention comprise a sequence where 100% of all adenosine nucleotides are 2'-OH adenosine, 100% of all guanosine nucleotides are 2'-OH guanosine, 100% of all cytidine nucleotides are 2'-OH cytidine, and 100% of all uridine nucleotides are 2'-OH uridine.

Under rRmY transcription conditions of the present invention, the transcription reaction mixture comprises 2'-OH adenosine triphosphates, 2'-OH guanosine triphosphates, 2'-O-methyl cytidine triphosphates, and 2'-O-methyl uridine triphosphates. The modified oligonucleotides produced using the rRmY transcription mixtures of the present invention comprise substantially all 2'-OH adenosine, 2'-OH guanosine, 2'-O-methyl cytidine and 2'-O-methyl uridine. In a preferred embodiment, the resulting modified oligonucleotides comprise a sequence where at least 80% of all adenosine nucleotides are 2'-OH adenosine, at least 80% of all guanosine nucleotides are 2'-OH guanosine, at least 80% of all cytidine nucleotides are 2'-O-methyl cytidine and at least 80% of all uridine nucleotides are 2'-O-methyl uridine. In a more preferred embodiment, the resulting modified oligonucleotides comprise a sequence where at least 90% of all adenosine nucleotides are 2'-OH adenosine, at least 90% of all guanosine nucleotides are 2'-OH guanosine, at least 90% of all cytidine nucleotides are 2'-O-methyl cytidine and at least 90% of all uridine nucleotides are 2'-O-methyl uridine In a most preferred embodiment, the resulting modified oligonucleotides comprise a sequence where 100% of all adenosine nucleotides are 2'-OH adenosine, 100% of all guanosine nucleotides are 2'-OH guanosine, 100% of all cytidine nucleotides are 2'-O-methyl cytidine and 100% of all uridine nucleotides are 2'-O-methyl uridine.

Under dRmY transcription conditions of the present invention, the transcription reaction mixture comprises 2'-deoxy adenosine triphosphates, 2'-deoxy guanosine triphosphates, 2'-O-methyl cytidine triphosphates, and 2'-O-methyl uridine triphosphates. The modified oligonucleotides produced using the dRmY transcription conditions of the present invention comprise substantially all 2'-deoxy adenosine, 2'-deoxy guanosine, 2'-O-methyl cytidine, and 2'-O-methyl uridine. In a preferred embodiment, the resulting modified oligonucleotides of the present invention comprise a sequence where at least 80% of all adenosine nucleotides are 2'-deoxy adenosine, at least 80% of all guanosine nucleotides are 2'-deoxy guanosine, at least 80% of all cytidine nucleotides are 2'-O-methyl cytidine, and at least 80% of all uridine nucleotides are 2'-O-methyl uridine. In a more preferred embodiment, the resulting modified oligonucleotides of the present invention comprise a sequence where at least 90% of all adenosine nucleotides are 2'-deoxy adenosine, at least 90% of all guanosine nucleotides are 2'-deoxy guanosine, at least 90% of all cytidine nucleotides are 2'-O-methyl cytidine, and at least 90% of all uridine nucleotides are 2'-O-methyl uridine. In a most preferred embodiment, the resulting modified oligonucleotides of the present invention comprise a sequence where 100% of all adenosine nucleotides are 2'-deoxy adenosine, 100% of all guanosine nucleotides are 2'-deoxy guanosine, 100% of all cytidine nucleotides are 2'-O-methyl cytidine, and 100% of all uridine nucleotides are 2'-O-methyl uridine.

Under rGmH transcription conditions of the present invention, the transcription reaction mixture comprises 2'-OH guanosine triphosphates, 2'-O-methyl cytidine triphosphates, 2'-O-methyl uridine triphosphates, and 2'-O-methyl adenosine triphosphates. The modified oligonucleotides produced using the rGmH transcription mixtures of the present invention comprise substantially all 2'-OH guanosine, 2'-O-methyl cytidine, 2'-O-methyl uridine, and 2'-O-methyl adenosine. In a preferred embodiment, the resulting modified oligonucleotides comprise a sequence where at least 80% of all guanosine nucleotides are 2'-OH guanosine, at least 80% of all cytidine nucleotides are 2'-O-methyl cytidine, at least 80% of all uridine nucleotides are 2'-O-methyl uridine, and at least 80% of all adenosine nucleotides are 2'-O-methyl adenosine. In a more preferred embodiment, the resulting modified oligonucleotides comprise a sequence where at least 90% of all guanosine nucleotides are 2'-OH guanosine, at least 90% of all cytidine nucleotides are 2'-O-methyl cytidine, at least 90% of all uridine nucleotides are 2'-O-methyl uridine, and at least 90% of all adenosine nucleotides are 2'-O-methyl adenosine. In a most preferred embodiment, the resulting modified oligonucleotides comprise a sequence where 100% of all guanosine nucleotides are 2'-OH guanosine, 100% of all cytidine nucleotides are 2'-O-methyl cytidine, 100% of all uridine nucleotides are 2'-O-methyl uridine, and 100% of all adenosine nucleotides are 2'-O-methyl adenosine.

Under r/mGmH transcription conditions of the present invention, the transcription reaction mixture comprises 2'-O-methyl adenosine triphosphate, 2'-O-methyl cytidine triphosphate, 2'-O-methyl guanosine triphosphate, 2'-O-methyl uridine triphosphate and 2'-OH guanosine triphosphate. The resulting modified oligonucleotides produced using the r/mGmH transcription mixtures of the present invention comprise substantially all 2'-O-methyl adenosine, 2'-O-methyl cytidine, 2'-O-methyl guanosine, and 2'-O-methyl uridine, wherein the population of guanosine nucleotides has a maximum of about 10% 2'-OH guanosine. In a preferred embodiment, the resulting r/mGmH modified oligonucleotides of the present invention comprise a sequence where at least 80% of all adenosine nucleotides are 2'-O-methyl adenosine, at least 80% of all cytidine nucleotides are 2'-O-methyl cytidine, at least 80% of all guanosine nucleotides are 2'-O-methyl guanosine, at least 80% of all uridine nucleotides are 2'-O-methyl uridine, and no more than about 10% of all guanosine nucleotides are 2'-OH guanosine. In a more preferred embodiment, the resulting modified oligonucleotides comprise a sequence where at least 90% of all adenosine nucleotides are 2'-O-methyl adenosine, at least 90% of all cytidine nucleotides are 2'-O-methyl cytidine, at least 90% of all guanosine nucleotides are 2'-O-methyl guanosine, at least 90% of all uridine nucleotides are 2'-O-methyl uridine, and no more than about 10% of all guanosine nucleotides are 2'-OH guanosine. In a most preferred embodiment, the resulting modified oligonucleotides comprise a sequence where 100% of all adenosine nucleotides are 2'-O-methyl adenosine, 100% of all cytidine nucleotides are 2'-O-methyl cytidine, 90% of all guanosine nucleotides are 2'-O-methyl guanosine, and 100% of all uridine nucleotides are 2'-O-methyl uridine, and no more than about 10% of all guanosine nucleotides are 2'-OH guanosine.

Under fGmH transcription conditions of the present invention, the transcription reaction mixture comprises 2'-O-methyl adenosine triphosphates, 2'-O-methyl uridine triphosphates, 2'-O-methyl cytidine triphosphates, and 2'-F guanosine triphosphates. The modified oligonucleotides produced using the fGmH transcription conditions of the present invention comprise substantially all 2'-O-methyl adenosine, 2'-O-methyl uridine, 2'-O-methyl cytidine, and 2'-F guanosine. In a preferred embodiment, the resulting modified oligonucleotides comprise a sequence where at least 80% of all adenosine nucleotides are 2'-O-methyl adenosine, at least 80% of all uridine nucleotides are 2'-O-methyl uridine, at least 80% of all cytidine nucleotides are 2'-O-methyl cytidine, and at least 80% of all guanosine nucleotides are 2'-F guanosine. In a more preferred embodiment, the resulting modified oligonucleotides comprise a sequence where at least 90% of all adenosine nucleotides are 2'-O-methyl adenosine, at least 90% of all uridine nucleotides are 2'-O-methyl uridine, at least 90% of all cytidine nucleotides are 2'-O-methyl cytidine, and at least 90% of all guanosine nucleotides are 2'-F guanosine. In a most preferred embodiment, the resulting modified oligonucleotides comprise a sequence where 100% of all adenosine nucleotides are 2'-O-methyl adenosine, 100% of all uridine nucleotides are 2'-O-methyl uridine, 100% of all cytidine nucleotides are 2'-O-methyl cytidine, and 100% of all guanosine nucleotides are 2'-F guanosine.

Under dAmB transcription conditions of the present invention, the transcription reaction mixture comprises 2'-deoxy adenosine triphosphates, 2'-O-methyl cytidine triphosphates, 2'-O-methyl guanosine triphosphates, and 2'-O-methyl uridine triphosphates. The modified oligonucleotides produced using the dAmB transcription mixtures of the present invention comprise substantially all 2'-deoxy adenosine, 2'-O-methyl cytidine, 2'-O-methyl guanosine, and 2'-O-methyl uridine. In a preferred embodiment, the resulting modified oligonucleotides comprise a sequence where at least 80% of all adenosine nucleotides are 2'-deoxy adenosine, at least 80% of all cytidine nucleotides are 2'-O-methyl cytidine, at least 80% of all guanosine nucleotides are 2'-O-methyl guanosine, and at least 80% of all uridine nucleotides are 2'-O-methyl uridine. In a more preferred embodiment, the resulting modified oligonucleotides comprise a sequence where at least 90% of all adenosine nucleotides are 2'-deoxy adenosine, at least 90% of all cytidine nucleotides are 2'-O-methyl cytidine, at least 90% of all guanosine nucleotides are 2'-O-methyl guanosine, and at least 90% of all uridine nucleotides are 2'-O-methyl uridine. In a most preferred embodiment, the resulting modified oligonucleotides of the present invention comprise a sequence where 100% of all adenosine nucleotides are 2'-deoxy adenosine, 100% of all cytidine nucleotides are 2'-O-methyl cytidine, 100% of all guanosine nucleotides are 2'-O-methyl guanosine, and 100% of all uridine nucleotides are 2'-O-methyl uridine.

In each case, the transcription products can then be used as the library in the SELEX™ process to identify aptamers and/or to determine a conserved motif of sequences that have binding specificity to a given target. The resulting sequences are already partially stabilized, eliminating this step from the process to arrive at an modified aptamer sequence and giving a more highly stabilized aptamer as a result. Another advantage of the 2'-OMe SELEX™ process is that the resulting sequences are likely to have fewer 2'-OH nucleotides required in the sequence, possibly none. To the extent 2'-OH nucleotides remain they can be removed by performing post-SELEX™ modifications.

As described below, lower but still useful yields of transcripts fully incorporating 2' substituted nucleotides can be obtained under conditions other than the optimized conditions described above. For example, variations to the above transcription conditions include:

The HEPES buffer concentration can range from 0 to 1 M. The present invention also contemplates the use of other buffering agents having a pKa between 5 and 10 including, for example, Tris-hydroxymethyl-aminomethane.

The DTT concentration can range from 0 to 400 mM. The methods of the present invention also provide for the use of other reducing agents including, for example, mercaptoethanol.

The spermidine and/or spermine concentration can range from 0 to 20 mM.

The PEG-8000 concentration can range from 0 to 50% (w/v). The methods of the present invention also provide for the use of other hydrophilic polymer including, for example, other molecular weight PEG or other polyalkylene glycols.

The Triton X-100 concentration can range from 0 to 0.1% (w/v). The methods of the present invention also provide for the use of other non-ionic detergents including, for example, other detergents, including other Triton-X detergents.

The $MgCl_2$ concentration can range from 0.5 mM to 50 mM. The $MnCl_2$ concentration can range from 0.15 mM to 15 mM. Both $MgCl_2$ and $MnCl_2$ must be present within the ranges described and in a preferred embodiment are present in about a 10 to about 3 ratio of $MgCl_2:MnCl_2$, preferably, the ratio is about 3-5:1, more preferably, the ratio is about 3-4:1.

The 2'-OMe NTP concentration (each NTP) can range from 5 μM to 5 mM.

The 2'-OH GTP concentration can range from 0 μM to 300 μM.

The 2'-OH GMP concentration can range from 0 to 5 mM.

The pH can range from pH 6 to pH 9. The methods of the present invention can be practiced within the pH range of activity of most polymerases that incorporate modified nucleotides. In addition, the methods of the present invention provide for the optional use of chelating agents in the transcription reaction condition including, for example, EDTA, EGTA, and DTT.

Aptamer Medicinal Chemistry

Aptamer Medicinal Chemistry is an aptamer improvement technique in which sets of variant aptamers are chemically synthesized. These sets of variants typically differ from the parent aptamer by the introduction of a single substituent, and differ from each other by the location of this substituent. These variants are then compared to each other and to the parent. Improvements in characteristics may be profound enough that the inclusion of a single substituent may be all that is necessary to achieve a particular therapeutic criterion.

Alternatively the information gleaned from the set of single variants may be used to design further sets of variants in which more than one substituent is introduced simultaneously. In one design strategy, all of the single substituent variants are ranked, the top 4 are chosen and all possible double (6), triple (4) and quadruple (1) combinations of these 4 single substituent variants are synthesized and assayed. In a second design strategy, the best single substituent variant is considered to be the new parent and all possible double substituent variants that include this highest-ranked single substituent variant are synthesized and assayed. Other strategies may be used, and these strategies may be applied repeatedly such that the number of substituents is gradually increased while continuing to identify further-improved variants.

Aptamer Medicinal Chemistry may be used particularly to explore the local, rather than the global, introduction of substituents. Because aptamers are discovered within libraries that are generated by transcription, any substituents that are introduced during the SELEX™ process must be introduced globally. For example, if it is desired to introduce phosphorothioate linkages between nucleotides then they can only be introduced at every A (or every G, C, T, U etc.) (globally substituted). Aptamers which require phosphorothioates at some A's (or some G, C, T, U etc.) (locally substituted) but cannot tolerate it at other As cannot be readily discovered by this process.

The kinds of substituent that can be utilized by the Aptamer Medicinal Chemistry process are only limited by the ability to generate them as solid-phase synthesis reagents and introduce them into an oligomer synthesis scheme. The process is not limited to nucleotides alone. Aptamer Medicinal Chemistry schemes may include substituents that introduce steric bulk, hydrophobicity, hydrophilicity, lipophilicity, lipophobicity, positive charge, negative charge, neutral charge, zwitterions, polarizability, nuclease-resistance, conformational rigidity, conformational flexibility, protein-binding characteristics, mass etc. Aptamer Medicinal Chemistry schemes may include base-modifications, sugar-modifications or phosphodiester linkage-modifications.

When considering the kinds of substituents that are likely to be beneficial within the context of a therapeutic aptamer, it may be desirable to introduce substitutions that fall into one or more of the following categories:

Substituents already present in the body, e.g., 2'-deoxy, 2'-ribo, 2'-O-methyl purines or pyrimidines or 5-methyl cytosine.

Substituents already part of an approved therapeutic, e.g., phosphorothioate-linked oligonucleotides.

Substituents that hydrolyze or degrade to one of the above two categories, e.g., methylphosphonate-linked oligonucleotides.

The anti-IgE aptamers of the invention include aptamers developed through aptamer medicinal chemistry as described herein.

IgE Specific Binding Aptamers

The materials of the present invention comprise a series of nucleic acid aptamers of 20-50 nucleotides in length which bind specifically to IgE and which, in some embodiments, functionally modulate, e.g., block, the activity of IgE in in vivo and/or functional assays, such as cell based assays.

Aptamers capable of specifically binding and modulating IgE are set forth herein. These aptamers provide a low-toxicity, safe, and effective modality of treating and/or preventing atopic diseases or disorders such as allergic rhinitis (hay fever), atopic dermatitis, asthma, acute urticaria (Wheal-and-Flare), food allergies, and systemic anaphylaxis, which are known to be caused by or otherwise associated with IgE.

Examples of IgE specific binding aptamers for use as therapeutics and/or diagnostics include the following sequences: SEQ ID NOS 11 to 15, 18 to 19, 21, 29, 33, 41 to 44, 46, 50, 56 to 96, 98 to 102, 119 to 124, 126 to 136, 139 to 176, 178 to 190, 194 to 201, 206 to 243, 247, 249 to 259, 261 to 267, 269 to 290, 292 to 295 and 296; particularly selected from the group consisting of SEQ ID NOS 29, 33, 41 to 44, 46, 50, 98 to 102, 157 to 176, 178 to 190, 194 to 201, 206 to 219, 293 to 295 and 296; more particularly selected from group consisting of SEQ ID NOS 101, 157, 181, 216, 293 to 295 and 296 are provided.

Other aptamers that bind IgE are described below in Examples 1 to 4.

These aptamers may include modifications as described herein including, e.g., conjugation to lipophilic or high molecular weight compounds such as PEG, incorporation of a CpG motif, incorporation of a capping moiety, incorporation of modified nucleotides, substitutions in the phosphate backbone.

In one embodiment of the invention an isolated, non-naturally occurring aptamer that binds to IgE is provided. In some embodiments, the isolated, non-naturally occurring aptamer has a dissociation constant ("$K_D$") for IgE of less than 100 µM, less than 1 µM, less than 500 nM, less than 100 nM, less than 50 nM, less than 1 nM, less than 500 pM, less than 100 pM, less than 50 pM, or less than 1 pM. In some embodiments of the invention, the dissociation constant is determined by dot blot assay using a titration of human IgE under the conditions as described in Example 1 below. In a particular embodiment, the dissociation constant is determined by standard dot blot assay, using a titration of human IgE in Dulbecco's PBS (with $Mg^{++}$ and $Ca^{++}$) plus 0.1 mg/mL BSA at room temperature for 30 minutes.

In another embodiment, the aptamer of the invention modulates a function of IgE. In another embodiment, the aptamer of the invention inhibits an IgE function. In yet another embodiment of the invention, the aptamer binds and/or modulates a function of an IgE variant. An IgE variant as used herein encompasses variants that perform essentially the same function as an IgE function, preferably comprises substantially the same structure and in some embodiments comprises at least 70% sequence identity, preferably at least 80% sequence identity, more preferably at least 90% sequence identity, and more preferably at least 95% sequence identity to the amino acid sequence of IgE. In some embodiments of the invention, the sequence identity of target variants is determined using BLAST as described below.

The terms "sequence identity" or "% identity" in the context of two or more nucleic acid or protein sequences, refer to two or more sequences or subsequences that are the same or have a specified percentage of amino acid residues or nucleotides that are the same, when compared and aligned for maximum correspondence, as measured using one of the following sequence comparison algorithms or by visual inspection. For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters. Optimal alignment of sequences for comparison can be conducted, e.g., by the local homology algorithm of Smith & Waterman, Adv. Appl. Math. 2: 482 (1981), by the homology alignment algorithm of Needleman & Wunsch, J. Mol. Biol. 48: 443 (1970), by the search for similarity method of Pearson & Lipman, Proc. Nat'l. Acad. Sci. USA 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Ausubel et al., infra).

One example of an algorithm that is suitable for determining percent sequence identity is the algorithm used in the basic local alignment search tool (hereinafter "BLAST"), see, e.g. Altschul et al., J. Mol. Biol. 215: 403-410 (1990) and Altschul et al., Nucleic Acids Res., 15: 3389-3402 (1997). Software for performing BLAST analyses is publicly available through the National Center for Biotechnology Information (hereinafter "NCBI"). The default parameters used in determining sequence identity using the software available from NCBI, e.g., BLASTN (for nucleotide sequences) and BLASTP (for amino acid sequences) are described in McGinnis et al., Nucleic Acids Res., 32: W20-W25 (2004).

In another embodiment of the invention, the aptamer has substantially the same ability to bind IgE as that of an aptamer according to any one of SEQ ID NOS 11 to 15, 18 to 19, 21, 29, 33, 41 to 44, 46, 50, 56 to 96, 98 to 102, 119 to 124, 126 to 136, 139 to 176, 178 to 190, 194 to 201, 206 to 243, 247, 249 to 259, 261 to 267, 269 to 290, 292-295 and 296. In another embodiment of the invention, the aptamer has substantially the same structure and/or ability to bind IgE as that of an aptamer comprising any one of SEQ ID NOS of SEQ ID NOS 11 to 15, 18 to 19, 21, 29, 33, 41 to 44, 46, 50, 56 to 96, 98 to 102, 119 to 124, 126 to 136, 139 to 176, 178 to 190, 194 to 201, 206 to 243, 247, 249 to 259, 261 to 267, 269 to 290, 292 to 295 and 296. In another embodiment, the aptamers according to any one of SEQ ID NOS of SEQ ID NOS 11 to 15, 18 to 19, 21, 29, 33, 41 to 44, 46, 50, 56 to 96, 98 to 102, 119 to 124, 126 to 136, 139 to 176, 178 to 190, 194 to 201, 206 to 243, 247, 249 to 259, 261 to 267, 269 to 290, 292 to 295 and 296 are provided. In a particular embodiment an aptamer according to any one of SEQ ID NOS 101, 157, 181, 216, 293 to 295 and 296 are provided. In another embodiment, the aptamers of the invention are used as an active ingredient in pharmaceutical compositions. In another embodiment, the aptamers or compositions comprising the aptamers of the invention are used to treat atopic diseases or disorders such as allergic rhinitis (hay fever), atopic dermatitis, asthma, acute urticaria (Wheal-and-Flare), food allergies, peanut allergy, systemic anaphylaxis, allergic conjunctivitis, vernal keratoconjunctivitis, atopic keratoconjunctivitis, giant papillary conjunctivitis, and eosinophilic gastroenteritis.

In some embodiments aptamer therapeutics of the present invention have great affinity and specificity to their targets while reducing the deleterious side effects from non-naturally occurring nucleotide substitutions if the aptamer therapeutics break down in the body of patients or subjects. In some embodiments, the therapeutic compositions containing the aptamer therapeutics of the present invention are free of or have a reduced amount of fluorinated nucleotides.

The aptamers of the present invention can be synthesized using any oligonucleotide synthesis techniques known in the art including solid phase oligonucleotide synthesis techniques well known in the art (see, e.g., Froehler et al., Nucl. Acid Res. 14:5399-5467 (1986) and Froehler et al., Tet. Lett. 27:5575-5578 (1986)) and solution phase methods such as triester synthesis methods (see, e.g., Sood et al., Nucl. Acid Res. 4:2557 (1977) and Hirose et al., Tet. Lett., 28:2449 (1978)).

Aptamers Having Immunostimulatory Motifs

The present invention provides aptamers that bind to IgE and modulate their biological function. More specifically, the present invention provides aptamers that interfere with the binding of IgE to the IgE receptor, FcεRI, thereby preventing IgE mediated allergic reactions. The therapeutic potential of such aptamers can be further enhanced by selecting for aptamers which bind to IgE and contain immunostimulatory or immunomodulatory motifs, or by treating with aptamers which bind to IgE in conjunction with aptamers to a target known to bind immunostimulatory and/or immunomodulatory sequences.

Recognition of bacterial DNA by the vertebrate immune system is based on the recognition of unmethylated CG dinucleotides in particular sequence contexts ("CpG motifs"). One receptor that recognizes such a motif is Toll-like receptor 9 ("TLR 9"), a member of a family of Toll-like receptors (~10 members) that participate in the innate immune response by recognizing distinct microbial components. TLR 9 binds unmethylated oligodeoxynucleotide ("ODN") CpG sequences in a sequence-specific manner. The recognition of CpG motifs triggers defense mechanisms leading to innate and ultimately acquired immune responses. For example, activation of TLR 9 in mice induces activation of antigen presenting cells, up regulation of MHC class I and II molecules and expression of important co-stimulatory molecules and cytokines including IL-12 and IL-23. This activation both directly and indirectly enhances B and T cell responses, including robust up regulation of the TH1 cytokine IFN-gamma. Collectively, the response to CpG sequences leads to: protection against infectious diseases, improved immune response to vaccines, an effective response against asthma, and improved antibody-dependent cell-mediated cytotoxicity. Thus, CpG ODNs can provide protection against infectious diseases, function as immuno-adjuvants or cancer therapeutics (monotherapy or in combination with a mAb or other therapies), and can decrease asthma and allergic response.

Aptamers of the present invention comprising one or more CpG or other immunostimulatory sequences can be identified or generated by a variety of strategies using, e.g., the SELEX™ process described herein. In general the strategies can be divided into two groups. In group one, the strategies are directed to identifying or generating aptamers comprising both a CpG motif or other immunostimulatory sequence as well as a binding site for a target, where the target (hereinafter "non-CpG target") is a target other than one known to recognize CpG motifs or other immunostimulatory sequences and known to stimulates an immune response upon binding to a CpG motif. In some embodiments of the invention the non-CpG target is IgE. The first strategy of this group comprises performing SELEX™ to obtain an aptamer to a specific non-CpG target, preferably a target, e.g., IgE, where an immune response is relevant to disease development, using an oligonucleotide pool wherein a CpG motif has been incorporated into each member of the pool as, or as part of, a fixed region, e.g., in some embodiments the randomized region of the pool members comprises a fixed region having a CpG motif incorporated therein, and identifying an aptamer comprising a CpG motif. The second strategy of this group comprises performing SELEX™ to obtain an aptamer to a specific non-CpG target preferably a target, e.g., IgE, where an immune response is relevant to disease development, and following selection appending a CpG motif to the 5' and/or 3' end or engineering a CpG motif into a region, preferably a non-essential region, of the aptamer. The third strategy of this group comprises performing SELEX™ to obtain an aptamer to a specific non-CpG target, preferably a target, e.g., IgE, where an immune response is relevant to disease development, wherein during synthesis of the pool the molar ratio of the various nucleotides is biased in one or more nucleotide addition steps so that the randomized region of each member of the pool is enriched in CpG motifs, and identifying an aptamer comprising a CpG motif. The fourth strategy of this group comprises performing SELEX™ to obtain an aptamer to a specific non-CpG target, preferably a target, e.g., IgE, where an immune response is relevant to disease development, and identifying an aptamer comprising a CpG motif. The fifth strategy of this group comprises performing SELEX™ to obtain an aptamer to a specific non-CpG target, preferably a target, e.g., IgE, where a repressed immune response is relevant to disease development, and identifying an aptamer which, upon binding, stimulates an immune response but which does not comprise a CpG motif.

In group two, the strategies are directed to identifying or generating aptamers comprising a CpG motif and/or other sequences that are bound by the receptors for the CpG motifs (e.g., TLR9 or the other toll-like receptors) and upon binding stimulate an immune response. The first strategy of this group comprises performing SELEX™ to obtain an aptamer to a target known to bind to CpG motifs or other immunostimulatory sequences and upon binding stimulate an immune response using an oligonucleotide pool wherein a CpG motif has been incorporated into each member of the pool as, or as part of, a fixed region, e.g., in some embodiments the randomized region of the pool members comprise a fixed region having a CpG motif incorporated therein, and identifying an aptamer comprising a CpG motif. The second strategy of this group comprises performing SELEX™ to obtain an aptamer to a target known to bind to CpG motifs or other immunostimulatory sequences and upon binding stimulate an immune response and then appending a CpG motif to the 5' and/or 3' end or engineering a CpG motif into a region, preferably a non-essential region, of the aptamer. The third strategy of this group comprises performing SELEX™ to obtain an aptamer to a target known to bind to CpG motifs or other immunostimulatory sequences and upon binding stimulate an immune response wherein during synthesis of the pool, the molar ratio of the various nucleotides is biased in one or more nucleotide addition steps so that the randomized region of each member of the pool is enriched in CpG motifs, and identifying an aptamer comprising a CpG motif. The fourth strategy of this group comprises performing SELEX™ to obtain an aptamer to a target known to bind to CpG motifs or other immunostimulatory sequences and upon binding stimulate an immune response and identifying an aptamer comprising a CpG motif. The fifth strategy of this group comprises performing SELEX™ to obtain an aptamer to a target known to bind to CpG motifs or other immunostimulatory sequences, and identifying an aptamer which upon binding, stimulate an immune response but which does not comprise a CpG motif.

A variety of different classes of CpG motifs have been identified, each resulting upon recognition in a different cascade of events, release of cytokines and other molecules, and activation of certain cell types. See, e.g., CpG Motifs in Bacterial DNA and Their Immune Effects, Annu. Rev. Immunol. 2002, 20:709-760, incorporated herein by reference. Additional immunostimulatory motifs are disclosed in the following U.S. Patents, each of which is incorporated herein by reference: U.S. Pat. No. 6,207,646; U.S. Pat. No. 6,239,116; U.S. Pat. No. 6,429,199; U.S. Pat. No. 6,214,806; U.S. Pat. No. 6,653,292; U.S. Pat. No. 6,426,434; U.S. Pat. No. 6,514,948 and U.S. Pat. No. 6,498,148. Any of these CpG or other immunostimulatory motifs can be incorporated into an aptamer. The choice of aptamers is dependent on the disease or disorder to be treated. Preferred immunostimulatory motifs are as follows (shown 5' to 3' left to right) wherein "r" designates a purine, "y" designates a pyrimidine, and "X" designates any nucleotide: AACGTTCGAG (SEQ ID NO 4); AACGTT; ACGT; rCGy; rrCGyy, XCGX, XXCGXX, and $X_1X_2CGY_1Y_2$ wherein $X_1$ is G or A, $X_2$ is not C, $Y_1$ is not G and $Y_2$ is preferably T.

In those instances where a CpG motif is incorporated into an aptamer that binds to a specific target other than a target known to bind to CpG motifs and upon binding stimulate an immune response (a "non-CpG target"), the CpG is preferably located in a non-essential region of the aptamer. Non-essential regions of aptamers can be identified by site-directed mutagenesis, deletion analyses and/or substitution analyses. However, any location that does not significantly interfere with the ability of the aptamer to bind to the non-CpG target may be used. In addition to being embedded within the aptamer sequence, the CpG motif may be appended to either or both of the 5' and 3' ends or otherwise attached to the aptamer. Any location or means of attachment may be used so long as the ability of the aptamer to bind to the non-CpG target is not significantly interfered with.

As used herein, "stimulation of an immune response" can mean either (1) the induction of a specific response (e.g., induction of a Th1 response) or of the production of certain molecules or (2) the inhibition or suppression of a specific response (e.g., inhibition or suppression of the Th2 response) or of certain molecules.

Pharmaceutical Compositions

The invention also includes pharmaceutical compositions containing aptamer molecules that bind to IgE. In some embodiments, the compositions are suitable for internal use and include an effective amount of a pharmacologically active compound of the invention, alone or in combination, with one or more pharmaceutically acceptable carriers. The compounds are especially useful in that they have very low, if any toxicity.

Compositions of the invention can be used to treat, prevent and/or ameliorate a pathology, such as a disease or disorder, or alleviate the symptoms of such disease or disorder in a patient. For example, compositions of the present invention can be used to treat, prevent and/or ameliorate a pathology associated with atopic diseases or disorders such as allergic rhinitis (hay fever), atopic dermatitis, asthma, acute urticaria (Wheal-and-Flare), food allergies, and systemic anaphylaxis, which are known to be caused by or otherwise associated with IgE.

Compositions of the invention are useful for administration to a subject suffering from, or predisposed to, a disease or disorder which is related to or derived from a target to which the aptamers of the invention specifically bind. Compositions of the invention can be used in a method for treating a patient or subject having a pathology. The method involves administering to the patient or subject an aptamer or a composition comprising aptamers that bind IgE, so that binding of the aptamer to IgE alters the biological function of the target, thereby treating the pathology.

The patient or subject having a pathology, i.e., the patient or subject treated by the methods of this invention, can be a vertebrate, more particularly a mammal, or more particularly a human.

In practice, the aptamers or their pharmaceutically acceptable salts, are administered in amounts which will be sufficient to exert their desired biological activity, e.g., inhibiting the binding of the IgE aptamer to FceRI.

One aspect of the invention comprises an aptamer composition of the invention in combination with other treatments for IgE mediated disorders. The aptamer composition of the invention may contain, for example, more than one aptamer. In some examples, an aptamer composition of the invention, containing one or more compounds of the invention, is administered in combination with another useful composition such as an anti-inflammatory agent, an immunosuppressant, an antiviral agent, or the like. In general, the currently available dosage forms of the known therapeutic agents for use in such combinations will be suitable.

"Combination therapy" (or "co-therapy") includes the administration of an aptamer composition of the invention and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected).

"Combination therapy" may, but generally is not, intended to encompass the administration of two or more of these therapeutic agents as part of separate monotherapy regimens that incidentally and arbitrarily result in the combinations of the present invention. "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents.

Sequential or substantially simultaneous administration of each therapeutic agent can be effected by any appropriate route including, but not limited to, topical routes, oral routes, intravenous routes, intramuscular routes, and direct absorption through mucous membrane tissues. The therapeutic agents can be administered by the same route or by different routes. For example, a first therapeutic agent of the combination selected may be administered by injection while the other therapeutic agents of the combination may be administered topically.

Alternatively, for example, all therapeutic agents may be administered topically or all therapeutic agents may be administered by injection. The sequence in which the therapeutic agents are administered is not narrowly critical unless noted otherwise. "Combination therapy" also can embrace the administration of the therapeutic agents as described above in further combination with other biologically active ingredients. Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

Therapeutic or pharmacological compositions of the present invention will generally comprise an effective amount of the active component(s) of the therapy, dissolved or dispersed in a pharmaceutically acceptable medium. Pharmaceutically acceptable media or carriers include any and all solvents, dispersion media, coatings, antibacterial and antifungal agents, isotonic and absorption delaying agents and the like. The use of such media and agents for pharmaceutical active substances is well known in the art. Supplementary active ingredients can also be incorporated into the therapeutic compositions of the present invention.

The preparation of pharmaceutical or pharmacological compositions will be known to those of skill in the art in light of the present disclosure. Typically, such compositions may be prepared as injectables, either as liquid solutions or suspensions; solid forms suitable for solution in, or suspension in, liquid prior to injection; as tablets or other solids for oral administration; as time release capsules; or in any other form currently used, including eye drops, creams, lotions, salves, inhalants and the like. The use of sterile formulations, such as saline-based washes, by surgeons, physicians or health care workers to treat a particular area in the operating field may also be particularly useful. Compositions may also be delivered via microdevice, microparticle or sponge.

Upon formulation, therapeutics will be administered in a manner compatible with the dosage formulation, and in such amount as is pharmacologically effective. The formulations are easily administered in a variety of dosage forms, such as the type of injectable solutions described above, but drug release capsules and the like can also be employed.

In this context, the quantity of active ingredient and volume of composition to be administered depends on the host animal to be treated. Precise amounts of active compound required for administration depend on the judgment of the practitioner and are peculiar to each individual.

A minimal volume of a composition required to disperse the active compounds is typically utilized. Suitable regimes for administration are also variable, but would be typified by initially administering the compound and monitoring the results and then giving further controlled doses at further intervals.

For instance, for oral administration in the form of a tablet or capsule (e.g., a gelatin capsule), the active drug component can be combined with an oral, non-toxic, pharmaceutically acceptable inert carrier such as ethanol, glycerol, water and the like. Moreover, when desired or necessary, suitable binders, lubricants, disintegrating agents, and coloring agents can also be incorporated into the mixture. Suitable binders include starch, magnesium aluminum silicate, starch paste, gelatin, methylcellulose, sodium carboxymethylcellulose and/or polyvinylpyrrolidone, natural sugars such as glucose or beta-lactose, corn sweeteners, natural and synthetic gums such as acacia, tragacanth or sodium alginate, polyethylene glycol, waxes, and the like. Lubricants used in these dosage forms include sodium oleate, sodium stearate, magnesium stearate, sodium benzoate, sodium acetate, sodium chloride, silica, talcum, stearic acid, its magnesium or calcium salt and/or polyethyleneglycol, and the like. Disintegrators include, without limitation, starch, methyl cellulose, agar, bentonite, xanthan gum starches, agar, alginic acid or its sodium salt, or effervescent mixtures, and the like. Diluents, include, e.g., lactose, dextrose, sucrose, mannitol, sorbitol, cellulose and/or glycine.

The compounds of the invention can also be administered in such oral dosage forms as timed release and sustained release tablets or capsules, pills, powders, granules, elixirs, tinctures, suspensions, syrups and emulsions. Suppositories are advantageously prepared from fatty emulsions or suspensions.

The pharmaceutical compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating, or coating methods, and typically contain about 0.1% to 75%, preferably about 1% to 50%, of the active ingredient.

Liquid, particularly injectable compositions can, for example, be prepared by dissolving, dispersing, etc. The active compound is dissolved in or mixed with a pharmaceutically pure solvent such as, for example, water, saline, aqueous dextrose, glycerol, ethanol, and the like, to thereby form the injectable solution or suspension. Additionally, solid forms suitable for dissolving in liquid prior to injection can be formulated.

The compounds of the present invention can be administered in intravenous (both bolus and infusion), intraperitoneal, subcutaneous or intramuscular form, all using forms well known to those of ordinary skill in the pharmaceutical arts. Injectables can be prepared in conventional forms, either as liquid solutions or suspensions.

Parenteral injectable administration is generally used for subcutaneous, intramuscular or intravenous injections and infusions. Additionally, one approach for parenteral administration employs the implantation of a slow-release or sustained-released systems, which assures that a constant level of dosage is maintained, according to U.S. Pat. No. 3,710,795, incorporated herein by reference.

Furthermore, preferred compounds for the present invention can be administered in intranasal form via topical use of suitable intranasal vehicles, inhalants, or via transdermal routes, using those forms of transdernal skin patches well known to those of ordinary skill in that art. To be administered in the form of a transdermal delivery system, the dosage administration will, of course, be continuous rather than intermittent throughout the dosage regimen. Other preferred topical preparations include creams, ointments, lotions, aerosol sprays and gels, wherein the concentration of active ingredient would typically range from 0.01% to 15%, w/w or w/v.

For solid compositions, excipients include pharmaceutical grades of mannitol, lactose, starch, magnesium stearate, sodium saccharin, talcum, cellulose, glucose, sucrose, magnesium carbonate, and the like. The active compound defined above, may be also formulated as suppositories, using for example, polyalkylene glycols, for example, propylene glycol, as the carrier. In some embodiments, suppositories are advantageously prepared from fatty emulsions or suspensions.

The compounds of the present invention can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564. For example, the aptamer molecules described herein can be provided as a complex with a lipophilic compound or non-immunogenic, high molecular weight compound constructed using methods known in the art. An example of nucleic-acid associated complexes is provided in U.S. Pat. No. 6,011,020.

The compounds of the present invention may also be coupled with soluble polymers as targetable drug carriers. Such polymers can include polyvinylpyrrolidone, pyran copolymer, polyhydroxypropyl-methacrylamide-phenol, polyhydroxyethylaspanamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, poly-epsilon caprolactone, polyhydroxy butyric acid, polyorthoesters, polyacetals, polydihydropyrans, polycyanoacrylates and cross-linked or amphipathic block copolymers of hydrogels.

If desired, the pharmaceutical composition to be administered may also contain minor amounts of non-toxic auxiliary substances such as wetting or emulsifying agents, pH buffering agents, and other substances such as for example, sodium acetate, and triethanolamine oleate.

The dosage regimen utilizing the aptamers is selected in accordance with a variety of factors including type, species, age, weight, sex and medical condition of the patient; the severity of the condition to be treated; the route of administration; the renal and hepatic function of the patient; and the particular aptamer or salt thereof employed. An ordinarily skilled physician or veterinarian can readily determine and prescribe the effective amount of the drug required to treat, prevent, counter or arrest the progress of the condition.

Oral dosages of the present invention, when used for the indicated effects, will range between about 0.05 to 7500 mg/day orally. The compositions are preferably provided in the form of scored tablets containing 0.5, 1.0, 2.5, 5.0, 10.0, 15.0, 25.0, 50.0, 100.0, 250.0, 500.0 and 1000.0 mg of active ingredient. Infused dosages, intranasal dosages and transdermal dosages will range between 0.05 to 7500 mg/day. Subcutaneous, intravenous and intraperitoneal dosages will range between 0.05 to 3800 mg/day.

Effective plasma levels of the compounds of the present invention range from 0.002 mg/mL to 50 mg/mL.

Compounds of the present invention may be administered in a single daily dose, or the total daily dosage may be administered in divided doses of two, three or four times daily.

Modulation of Pharmacokinetics and Biodistribution of Aptamer Therapeutics

It is important that the pharmacokinetic properties for all oligonucleotide-based therapeutics, including aptamers, be tailored to match the desired pharmaceutical application. While aptamers directed against extracellular targets do not suffer from difficulties associated with intracellular delivery (as is the case with antisense and RNAi-based therapeutics), such aptamers must still be able to be distributed to target organs and tissues, and remain in the body (unmodified) for a period of time consistent with the desired dosing regimen.

Thus, the present invention provides materials and methods to affect the pharmacokinetics of aptamer compositions, and, in particular, the ability to tune aptamer pharmacokinetics. The tunability of (i.e., the ability to modulate) aptamer pharmacokinetics is achieved through conjugation of modifying moieties (e.g., PEG polymers) to the aptamer and/or the incorporation of modified nucleotides (e.g., 2'-fluoro or 2'-O-methyl) to alter the chemical composition of the nucleic acid. The ability to tune aptamer pharmacokinetics is used in the improvement of existing therapeutic applications, or alternatively, in the development of new therapeutic applications. For example, in some therapeutic applications, e.g., in antineoplastic or acute care settings where rapid drug clearance or turn-off may be desired, it is desirable to decrease the residence times of aptamers in the circulation. Alternatively, in other therapeutic applications, e.g., maintenance therapies where systemic circulation of a therapeutic is desired, it may be desirable to increase the residence times of aptamers in circulation.

In addition, the tunability of aptamer pharmacokinetics is used to modify the biodistribution of an aptamer therapeutic in a subject. For example, in some therapeutic applications, it may be desirable to alter the biodistribution of an aptamer therapeutic in an effort to target a particular type of tissue or a specific organ (or set of organs). In these applications, the aptamer therapeutic preferentially accumulates in a specific tissue or organ(s). In other therapeutic applications, it may be desirable to target tissues displaying a cellular marker or a symptom associated with a given disease, cellular injury or other abnormal pathology, such that the aptamer therapeutic preferentially accumulates in the affected tissue. For example, as described in the provisional application U.S. Ser. No. 60/550,790, filed on Mar. 5, 2004, and entitled "Controlled Modulation of the Pharmacokinetics and Biodistribution of Aptamer Therapeutics", and in the non-provisional application United States Serial No. 10/___,___, filed on Mar. 7, 2005, and entitled "Controlled Modulation of the Pharmacokinetics and Biodistribution of Aptamer Therapeutics", PEGylation of an aptamer therapeutic (e.g., PEGylation with a 20 kDa PEG polymer) is used to target inflamed tissues, such that the PEGylated aptamer therapeutic preferentially accumulates in inflamed tissue.

To determine the pharmacokinetic and biodistribution profiles of aptamer therapeutics (e.g., aptamer conjugates or aptamers having altered chemistries, such as modified nucleotides) a variety of parameters are monitored. Such parameters include, for example, the half-life ($t_{1/2}$), the plasma clearance (Cl), the volume of distribution (Vss), the area under the concentration-time curve (AUC), maximum observed serum or plasma concentration ($C_{max}$), and the mean residence time (MRT) of an aptamer composition. As used herein, the term "AUC" refers to the area under the plot of the plasma concentration of an aptamer therapeutic versus the time after aptamer administration. The AUC value is used to estimate the bioavailability (i.e., the percentage of administered aptamer therapeutic in the circulation after aptamer administration) and/or total clearance (Cl) (i.e., the rate at which the aptamer therapeutic is removed from circulation) of a given aptamer therapeutic. The volume of distribution relates the plasma concentration of an aptamer therapeutic to the amount of aptamer present in the body. The larger the Vss, the more an aptamer is found outside of the plasma (i.e., the more extravasation).

The present invention provides materials and methods to modulate, in a controlled manner, the pharmacokinetics and biodistribution of stabilized aptamer compositions in vivo by conjugating an aptamer to a modulating moiety such as a small molecule, peptide, or polymer terminal group, or by incorporating modified nucleotides into an aptamer. As described herein, conjugation of a modifying moiety and/or altering nucleotide(s) chemical composition alters fundamental aspects of aptamer residence time in circulation and distribution to tissues.

In addition to clearance by nucleases, oligonucleotide therapeutics are subject to elimination via renal filtration. As such, a nuclease-resistant oligonucleotide administered intravenously typically exhibits an in vivo half-life of <10 min, unless filtration can be blocked. This can be accomplished by either facilitating rapid distribution out of the blood stream into tissues or by increasing the apparent molecular weight of the oligonucleotide above the effective size cut-off for the glomerulus. Conjugation of small therapeutics to a PEG polymer (PEGylation), described below, can dramatically lengthen residence times of aptamers in circulation, thereby decreasing dosing frequency and enhancing effectiveness against vascular targets.

Aptamers can be conjugated to a variety of modifying moieties, such as high molecular weight polymers, e.g., PEG; peptides, e.g., Tat (a 13-amino acid fragment of the HIV Tat protein (Vives, et al. (1997), J. Biol. Chem. 272 (25): 16010-7)), Ant (a 16-amino acid sequence derived from the third helix of the Drosophila antennapedia homeotic protein (Pietersz, et al. (2001), Vaccine 19(11-12): 1397-405)) and Arg$_7$ (a short, positively charged cell-permeating peptides composed of polyarginine (Arg$_7$) (Rothbard, et al. (2000), Nat. Med. 6(11): 1253-7; Rothbard, J et al. (2002), J. Med. Chem. 45(17): 3612-8)); and small molecules, e.g., lipophilic compounds such as cholesterol. Among the various conjugates described herein, in vivo properties of aptamers are altered most profoundly by complexation with PEG groups. For example, complexation of a mixed 2'F and 2'-OMe modified aptamer therapeutic with a 20 kDa PEG polymer hinders renal filtration and promotes aptamer distribution to both healthy and inflamed tissues. Furthermore, the 20 kDa PEG polymer-aptamer conjugate proves nearly as effective as a 40 kDa PEG polymer in preventing renal filtration of aptamers. While one effect of PEGylation is on aptamer clearance, the prolonged systemic exposure afforded by presence of the 20 kDa moiety also facilitates distribution of aptamer to tissues, particularly those of highly perfused organs and those at the site of inflammation. The aptamer-20 kDa PEG polymer conjugate directs aptamer distribution to the site of inflammation, such that the PEGylated aptamer preferentially accumulates in inflamed tissue. In some instances, the 20 kDa PEGylated aptamer conjugate is able to access the interior of cells, such as, for example, kidney cells.

Modified nucleotides can also be used to modulate the plasma clearance of aptamers. For example, an unconjugated aptamer which incorporates both 2'-F and 2'-OMe stabilizing chemistries, which is typical of current generation aptamers as it exhibits a high degree of nuclease stability in vitro and in vivo, displays rapid loss from plasma (i.e., rapid plasma clearance) and a rapid distribution into tissues, primarily into the kidney, when compared to unmodified aptamer.

PEG-Derivatized Nucleic Acids

As described above, derivatization of nucleic acids with high molecular weight non-immunogenic polymers has the potential to alter the pharmacokinetic and pharmacodynamic properties of nucleic acids making them more effective therapeutic agents. Favorable changes in activity can include increased resistance to degradation by nucleases, decreased filtration through the kidneys, decreased exposure to the immune system, and altered distribution of the therapeutic through the body.

The aptamer compositions of the invention may be derivatized with polyalkylene glycol ("PAG") moieties. Examples of PAG-derivatized nucleic acids are found in U.S. patent application Ser. No. 10/718,833, filed on Nov. 21, 2003, which is herein incorporated by reference in its entirety. Typical polymers used in the invention include polyethylene glycol ("PEG"), also known as polyethylene oxide ("PEO") and polypropylene glycol (including poly isopropylene glycol). Additionally, random or block copolymers of different alkylene oxides (e.g., ethylene oxide and propylene oxide) can be used in many applications. In its most common form, a polyalkylene glycol, such as PEG, is a linear polymer terminated at each end with hydroxyl groups: HO—CH$_2$CH$_2$O—(CH$_2$CH$_2$O)$_n$—CH$_2$CH$_2$—OH. This polymer, alpha-, omega-dihydroxylpolyethylene glycol, can also be represented as HO-PEG-OH, where it is understood that the -PEG- symbol represents the following structural unit: —CH$_2$CH$_2$O—(CH$_2$CH$_2$O)$_n$—CH$_2$CH$_2$— where n typically ranges from about 4 to about 10,000.

As shown, the PEG molecule is di-functional and is sometimes referred to as "PEG diol." The terminal portions of the PEG molecule are relatively non-reactive hydroxyl moieties, the —OH groups, that can be activated, or converted to functional moieties, for attachment of the PEG to other compounds at reactive sites on the compound. Such activated PEG diols are referred to herein as bi-activated PEGs. For example, the terminal moieties of PEG diol have been functionalized as active carbonate ester for selective reaction with amino moieties by substitution of the relatively non-reactive hydroxyl moieties, —OH, with succinimidyl active ester moieties from N-hydroxy succinimide.

In many applications, it is desirable to cap the PEG molecule on one end with an essentially non-reactive moiety so that the PEG molecule is mono-functional (or mono-activated). In the case of protein therapeutics which generally display multiple reaction sites for activated PEGs, bi-functional activated PEGs lead to extensive cross-linking, yielding poorly functional aggregates. To generate mono-activated PEGs, one hydroxyl moiety on the terminus of the PEG diol molecule typically is substituted with non-reactive methoxy end moiety, —OCH$_3$. The other, un-capped terminus of the PEG molecule typically is converted to a reactive end moiety that can be activated for attachment at a reactive site on a surface or a molecule such as a protein.

PAGs are polymers which typically have the properties of solubility in water and in many organic solvents, lack of toxicity, and lack of immunogenicity. One use of PAGs is to covalently attach the polymer to insoluble molecules to make the resulting PAG-molecule "conjugate" soluble. For example, it has been shown that the water-insoluble drug paclitaxel, when coupled to PEG, becomes water-soluble. Greenwald, et al., *J. Org. Chem.*, 60:331-336 (1995). PAG conjugates are often used not only to enhance solubility and stability but also to prolong the blood circulation half-life of molecules.

Figure 3:
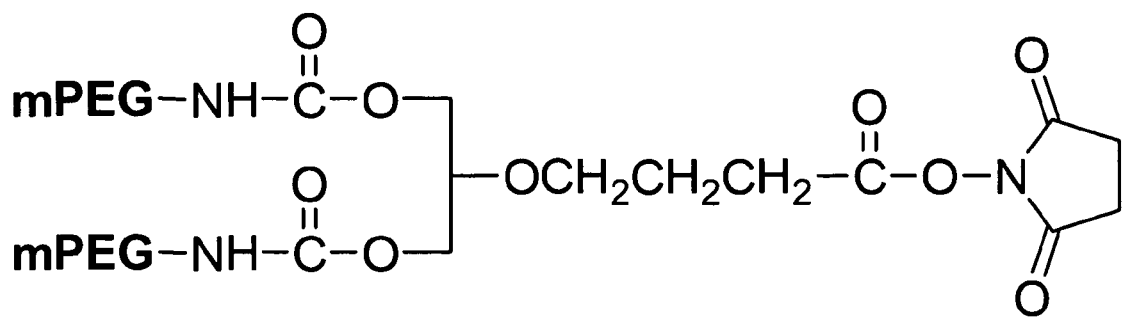
FIG. 3 is an illustration of a 40 kDa branched PEG.
Figure 4:
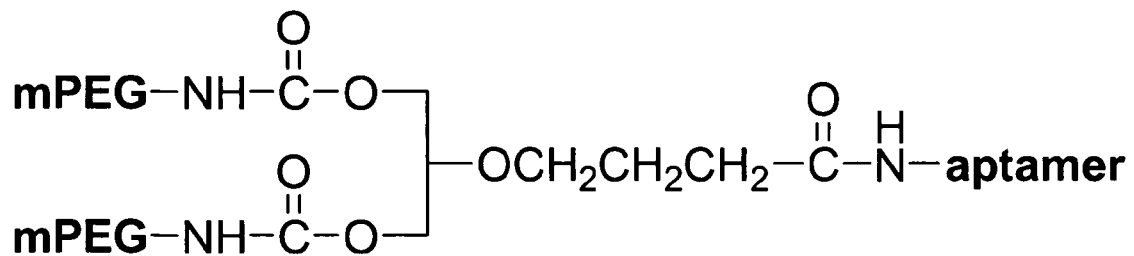
FIG. 4 is an illustration of a 40 kDa branched PEG attached to the 5'end of an aptamer.

Polyalkylated compounds of the invention are typically between 5 and 80 kDa in size however any size can be used, the choice dependent on the aptamer and application. Other PAG compounds of the invention are between 10 and 80 kDa in size. Still other PAG compounds of the invention are between 10 and 60 kDa in size. For example, a PAG polymer may be at least 10, 20, 30, 40, 50, 60, or 80 kDa in size. Such polymers can be linear or branched. In some embodiments the polymers are PEG. In some embodiment the polymers are branched PEG. In still other embodiments the polymers are 40 kDa branched PEG as depicted in FIG. 3. In some embodiments the 40 kDa branched PEG is attached to the 5' end of the aptamer as depicted in FIG. 4.

In contrast to biologically-expressed protein therapeutics, nucleic acid therapeutics are typically chemically synthesized from activated monomer nucleotides. PEG-nucleic acid conjugates may be prepared by incorporating the PEG using the same iterative monomer synthesis. For example, PEGs activated by conversion to a phosphoramidite form can be incorporated into solid-phase oligonucleotide synthesis. Alternatively, oligonucleotide synthesis can be completed with site-specific incorporation of a reactive PEG attachment site. Most commonly this has been accomplished by addition of a free primary amine at the 5'-terminus (incorporated using a modifier phosphoramidite in the last coupling step of solid phase synthesis). Using this approach, a reactive PEG (e.g., one which is activated so that it will react and form a bond with an amine) is combined with the purified oligonucleotide and the coupling reaction is carried out in solution.

The ability of PEG conjugation to alter the biodistribution of a therapeutic is related to a number of factors including the apparent size (e.g., as measured in terms of hydrodynamic radius) of the conjugate. Larger conjugates (>10 kDa) are known to more effectively block filtration via the kidney and to consequently increase the serum half-life of small macromolecules (e.g., peptides, antisense oligonucleotides). The ability of PEG conjugates to block filtration has been shown to increase with PEG size up to approximately 50 kDa (further increases have minimal beneficial effect as half life becomes defined by macrophage-mediated metabolism rather than elimination via the kidneys).

Production of high molecular weight PEGs (>10 kDa) can be difficult, inefficient, and expensive. As a route towards the synthesis of high molecular weight PEG-nucleic acid conjugates, previous work has been focused towards the generation of higher molecular weight activated PEGs. One method for generating such molecules involves the formation of a branched activated PEG in which two or more PEGs are attached to a central core carrying the activated group. The terminal portions of these higher molecular weight PEG molecules, i.e., the relatively non-reactive hydroxyl (—OH) moieties, can be activated, or converted to functional moieties, for attachment of one or more of the PEGs to other compounds at reactive sites on the compound. Branched activated PEGs will have more than two termini, and in cases where two or more termini have been activated, such activated higher molecular weight PEG molecules are referred to herein as, multi-activated PEGs. In some cases, not all termini in a branch PEG molecule are activated. In cases where any two termini of a branch PEG molecule are activated, such PEG molecules are referred to as bi-activated PEGs. In some cases where only one terminus in a branch PEG molecule is activated, such PEG molecules are referred to as mono-activated. As an example of this approach, activated PEG prepared by the attachment of two monomethoxy PEGs to a lysine core which is subsequently activated for reaction has been described (Harris et al., Nature, vol. 2: 214-221, 2003).

The present invention provides another cost effective route to the synthesis of high molecular weight PEG-nucleic acid (preferably, aptamer) conjugates including multiply PEGylated nucleic acids. The present invention also encompasses PEG-linked multimeric oligonucleotides, e.g., dimerized aptamers. The present invention also relates to high molecular weight compositions where a PEG stabilizing moiety is a linker which separates different portions of an aptamer, e.g., the PEG is conjugated within a single aptamer sequence, such that the linear arrangement of the high molecular weight aptamer composition is, e.g., nucleic acid-PEG-nucleic acid (-PEG-nucleic acid)$_n$ where n is greater than or equal to 1.

High molecular weight compositions of the invention include those having a molecular weight of at least 10 kDa. Compositions typically have a molecular weight between 10 and 80 kDa in size. High molecular weight compositions of the invention are at least 10, 20, 30, 40, 50, 60, or 80 kDa in size.

A stabilizing moiety is a molecule, or portion of a molecule, which improves pharmacokinetic and pharmacodynamic properties of the high molecular weight aptamer compositions of the invention. In some cases, a stabilizing moiety is a molecule or portion of a molecule which brings two or more aptamers, or aptamer domains, into proximity, or provides decreased overall rotational freedom of the high molecular weight aptamer compositions of the invention. A stabilizing moiety can be a polyalkylene glycol, such a polyethylene glycol, which can be linear or branched, a homopolymer or a heteropolymer. Other stabilizing moieties include polymers such as peptide nucleic acids (PNA). Oligonucleotides can also be stabilizing moieties; such oligonucleotides can include modified nucleotides, and/or modified linkages, such as phosphorothioates. A stabilizing moiety can be an integral part of an aptamer composition, i.e., it is covalently bonded to the aptamer.

Compositions of the invention include high molecular weight aptamer compositions in which two or more nucleic acid moieties are covalently conjugated to at least one polyalkylene glycol moiety. The polyalkylene glycol moieties serve as stabilizing moieties. In compositions where a polyalkylene glycol moiety is covalently bound at either end to an aptamer, such that the polyalkylene glycol joins the nucleic acid moieties together in one molecule, the polyalkylene glycol is said to be a linking moiety. In such compositions, the primary structure of the covalent molecule includes the linear arrangement nucleic acid-PAG-nucleic acid. One example is a composition having the primary structure nucleic acid-PEG-nucleic acid. Another example is a linear arrangement of: nucleic acid-PEG-nucleic acid-PEG-nucleic acid.

To produce the nucleic acid-PEG-nucleic acid conjugate, the nucleic acid is originally synthesized such that it bears a single reactive site (e.g., it is mono-activated). In a preferred embodiment, this reactive site is an amino group introduced at the 5'-terminus by addition of a modifier phosphoramidite as the last step in solid phase synthesis of the oligonucleotide. Following deprotection and purification of the modified oligonucleotide, it is reconstituted at high concentration in a solution that minimizes spontaneous hydrolysis of the activated PEG. In a preferred embodiment, the concentration of oligonucleotide is 1 mM and the reconstituted solution contains 200 mM NaHCO$_3$-buffer, pH 8.3. Synthesis of the conjugate is initiated by slow, step-wise addition of highly purified bi-functional PEG. In a preferred embodiment, the PEG diol is activated at both ends (bi-activated) by derivatization with succinimidyl propionate. Following reaction, the PEG-nucleic acid conjugate is purified by gel electrophoresis or liquid chromatography to separate fully-, partially-, and un-conjugated species. Multiple PAG molecules concatenated (e.g., as random or block copolymers) or smaller PAG chains can be linked to achieve various lengths (or molecular weights). Non-PAG linkers can be used between PAG chains of varying lengths.

The 2'-O-methyl, 2'-fluoro and other modified nucleotide modifications stabilize the aptamer against nucleases and increase its half life in vivo. The 3'-3'-dT cap also increases exonuclease resistance. See, e.g., U.S. Pat. Nos. 5,674,685; 5,668,264; 6,207,816; and 6,229,002, each of which is incorporated by reference herein in its entirety.

PAG-Derivatization of a Reactive Nucleic Acid

Figure 5:
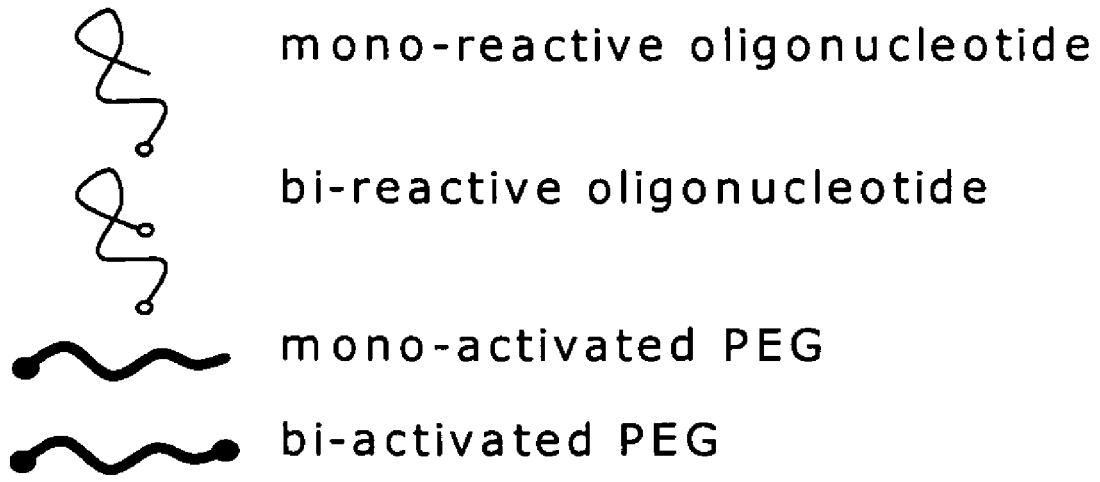
FIG. 5 is an illustration depicting various PEGylation strategies representing standard mono-PEGylation, multiple PEGylation, and dimerization via PEGylation.
Figure 5:
Figure 5:

High molecular weight PAG-nucleic acid-PAG conjugates can be prepared by reaction of a mono-functional activated PEG with a nucleic acid containing more than one reactive site. In one embodiment, the nucleic acid is bi-reactive, or bi-activated, and contains two reactive sites: a 5'-amino group and a 3'-amino group introduced into the oligonucleotide through conventional phosphoramidite synthesis, for example: 3'-5'-di-PEGylation as illustrated in FIG. 5. In alternative embodiments, reactive sites can be introduced at internal positions, using for example, the 5-position of pyrimidines, the 8-position of purines, or the 2'-position of ribose as sites for attachment of primary amines. In such embodiments, the nucleic acid can have several activated or reactive sites and is said to be multiply activated. Following synthesis and purification, the modified oligonucleotide is combined with the mono-activated PEG under conditions that promote selective reaction with the oligonucleotide reactive sites while minimizing spontaneous hydrolysis. In the preferred embodiment, monomethoxy-PEG is activated with succinimidyl propionate and the coupled reaction is carried out at pH 8.3. To drive synthesis of the bi-substituted PEG, stoichiometric excess PEG is provided relative to the oligonucleotide. Following reaction, the PEG-nucleic acid conjugate is purified by gel electrophoresis or liquid chromatography to separate fully, partially, and un-conjugated species.

The linking domains can also have one or more polyalkylene glycol moieties attached thereto. Such PAGs can be of varying lengths and may be used in appropriate combinations to achieve the desired molecular weight of the composition.

The effect of a particular linker can be influenced by both its chemical composition and length. A linker that is too long, too short, or forms unfavorable steric and/or ionic interactions with IgE will preclude the formation of complex between the aptamer and IgE. A linker, which is longer than necessary to span the distance between nucleic acids, may reduce binding stability by diminishing the effective concentration of the ligand. Thus, it is often necessary to optimize linker compositions and lengths in order to maximize the affinity of an aptamer to a target.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXAMPLES

Example 1

Aptamer Selection and Sequences

Example 1A h-IgE Selection of rRfY IgE Aptamers

Human IgE, purified from human myeloma plasma (hereinafter "h-IgE"), was purchased from Athens Research and Technology (Athens, Ga.). T7 RNA polymerase (Y639F) was expressed and purified. 2'-F pyrimidine nucleotides, and 2'-OMe purine and pyrimidine oligonucleotides were purchased from TriLink BioTechnologies (San Diego, Calif.). All other general reagents were purchased from commercial sources. One selection was performed to identify aptamers to h-IgE using a pool consisting of 2'-OH purine and 2'-F pyrimidine nucleotides (rRfY). A direct selection against h-IgE was performed and yielded high affinity aptamers specific for h-IgE.

Pool Preparation. A DNA template with the sequence 5'-GGGAAAAGCGAATCATACACAAGAN$_{40}$GCTC CGCCAGAGACCAACCGAGAA-3' (SEQ ID NO 5) was synthesized using an ABI EXPEDITE™ DNA synthesizer, and deprotected by standard methods. The templates were amplified with the primers 5' TAATACGACTCACTATAGG-GAAAAGCGAATCATACACAAGA 3' (SEQ ID NO 6) and 5' TTCTCGGTTGGTCTCTGGCGGAGC 3' (SEQ ID NO 7) and then used as a template for in vitro transcription with T7 RNA polymerase (Y639F). Transcriptions were done using 40 mM Tris, 40 mM DTT, 1 mM spermidine, 0.002% TritonX-100, 4% PEG-8000, 12 mM MgCl$_2$, 3 mM 2'-F-CTP, 3 mM 2'-F-UTP, 3 mM GTP, 3 mM ATP, 0.01 units/mL inorganic pyrophosphatase, and T7 polymerase (Y639F), and approximately 0.5 μM template DNA.

Selection. The selection was initiated by incubating of 2×10$^{14}$ molecules of 2'-F pyrimidine modified ARC212 pool (5' GGGAAAAGCGAAUCAUACACAAGA-N$_{40}$-GCUC-CGCCAGAGACCAACCGAGAA 3') (SEQ ID NO 8) with 100 pmoles of h-IgE protein in a final volume of 100 μL selection buffer (1×SHMCK: 20 mM Hepes, 120 mM NaCl, 5 mM KCl, 1 mM MgCl$_2$, 1 mM CaCl$_2$, pH 7.4) for 1 hour at room temperature. RNA-protein complexes and unbound RNA molecules were separated using a 0.45 micron nitrocellulose spin column (Schleicher & Schuell, Keene, N.H.). The column was pre-washed with 1 mL 1×SHMCK buffer, and then the solution containing pool:IgE complexes was added to the column and centrifuged at 1500×g for 2 min. The filter was washed twice with 400 μL 1×SCHMK to remove non-specific binders (Round 1, 2×400 μL 1×SHMCK; in later rounds, 2×500 μL 1×SCHMK). RNA was eluted by addition of 2×200 μL elution buffer (7 M urea, 100 mM sodium acetate, 3 mM EDTA, pre-heated to 95° C.). In later rounds, RNA was eluted with 2×100 μL elution buffer.

Eluted protein was extracted from the RNA mixture with phenol:choloroform, and the pool RNA was precipitated (2 μL glycogen, 1 volume isopropanol). The RNA was reverse transcribed with the ThermoScript RT-PCR™ system (Invitrogen, Carlsbad, Calif.) according to the manufacturer's instructions using the 3' primer according to SEQ ID NO 7. The cDNA was amplified by PCR (20 mM Tris pH 8.4, 50 mM KCl, 2 mM MgCl$_2$, 0.5 µM 5' primer (SEQ ID NO 6), 0.5 µM 3' primer (SEQ ID NO 7), 0.5 mM each dNTP, 0.05 units/mL Taq polymerase (New England Biolabs, Beverly, Mass.)). The PCR products were purified using the QIAquick PCR purification kit (Qiagen, Valencia, Calif.). Templates were transcribed using α$^{32}$P ATP body labeling overnight at 37° C. (4% PEG-8000, 40 mM Tris pH 8.0, 12 mM MgCl$_2$, 1 mM spermidine, 0.002% Triton x-100, 3 mM 2'OH purines, 3 mM 2'-F CTP and UTP, 25 mM DTT, inorganic pyrophosphatase, T7 RNA polymerase (Y639F) 5 µCi α$^{32}$P ATP). The reactions were desalted using Centrisep Spin columns (Princeton Separations, Adelphia, N.J.) according to the manufacturer's instructions and purified on a 1.5 mm denaturing polyacrylamide gel (8 M urea, 10% acrylamide; 19:1 acrylamide: bisacrylamide).

Subsequent rounds were repeated using the same method as for round 1, but with the addition of a negative selection step. Prior to incubation with protein target, the pool RNA was passed through a 0.45 micron nitrocellulose filter column to remove filter binding sequences, then the filtrate was carried on into the positive selection step.

In alternating rounds the pool RNA was gel purified. Transcription reactions were quenched with 50 mM EDTA and ethanol precipitated then purified on a 1.5 mm denaturing polyacrylamide gels. Pool RNA was removed from the gel by electroelution in an Elutrap® apparatus (Schleicher and Schuell, Keene, N.H.) at 225V for 1 hour in 1×TBE (90 mM Tris, 90 mM boric acid, 0.2 mM EDTA). The eluted material was precipitated by the addition of 300 mM sodium acetate and 2.5 volumes of ethanol.

The RNA concentration remained in excess of the h-IgE concentration throughout the selection. The protein concentration was 1 µM for the first 2 rounds, and then was dropped to lower concentrations during subsequent rounds (Table 1). Competitor tRNA was added to the binding reactions at 0.1 mg/mL beginning at Round 4. After 10 rounds of selection were completed, the pool was split into two. Round 11a was conducted with the positive selection having a 10:1 pool to h-IgE concentration ratio. In rounds 11b and 12b at 100:1 RNA to h-IgE concentration ratio was used. This was done to increase stringency in attempts to drive selection towards higher affinity binders. Table 1 contains the selection details including pool RNA concentration, protein concentration, and tRNA concentration used for each round, negative selections step(s) used (if any), and the number of PCR cyles required to obtain a PCR band on a 4% agarose E-Gel (Invitrogen, Carlsbad, Calif.) equal in intensity to the 100 bp marker lane of a 100 bp DNA ladder (~48 ng of DNA mass) when loaded according to the manufacturer's recommendations (New England Biolabs, Catalog # N3231L, Beverly, Mass.).

The progress of the selection was monitored via measuring the percentage of input pool RNA eluted from the nitrocellulose filter during the positive selection step.

TABLE 1

Conditions used each round of selection using (rRfY)

| Round # | RNA pool conc (µM) | protein type | protein conc (µM) | tRNA conc (mg/mL) | Negative Selection Step | % elution | PCR cycle # |
|---|---|---|---|---|---|---|---|
| 1 | 3.3 | h-IgE | 1 | 0 | none | 2.44 | 10 |
| 2 | ~1 | h-IgE | 1 | 0 | NC | 0.35 | 15 |
| 3 | 0.8 | h-IgE | 0.75 | 0 | NC | 1.02 | 13 |
| 4 | ~1 | h-IgE | 0.75 | 0.1 | NC | 0.05 | 15 |
| 5 | 1 | h-IgE | 0.75 | 0.1 | NC | 3.80 | 10 |
| 6 | ~1 | h-IgE | 0.5 | 0.1 | NC | 0.04 | 12 |
| 7 | 1 | h-IgE | 0.25 | 0.1 | NC | 3.27 | 8 |
| 8 | ~0.5 | h-IgE | 0.125 | 0.1 | NC | 0.13 | 11 |
| 9 | 0.5 | h-IgE | 0.05 | 0.1 | NC | 3.07 | 8 |
| 10 | ~0.5 | h-IgE | 0.05 | 0.1 | NC | 0.13 | 12 |
| 11a | 0.5 | h-IgE | 0.05 | 0.1 | NC | 7.24 | 8 |
| 11b | 0.5 | h-IgE | 0.005 | 0.1 | NC | 1.03 | 12 |
| 12b | ~0.5 | h-IgE | 0.005 | 0.1 | NC | 0.39 | 12 | h-IgE Binding Analysis. Dot blot binding assays were performed throughout the selections to monitor the protein binding affinity of the pools. Trace $^{32}$P-labeled pool RNA was combined with h-IgE and incubated at room temperature for 30 min in 1×SHMCK buffer plus 0.1 mg/mL tRNA in a final volume of 25 µL. The mixture was applied to a dot blot apparatus (Schleicher and Schuell Minifold-1 Dot Blot, Acrylic), assembled (from top to bottom) with nitrocellulose, nylon, and gel blot membranes. RNA that is bound to protein is captured on the nitrocellulose filter; whereas the non-protein bound RNA is captured on the nylon filter. When a significant positive ratio of binding of RNA in the presence of h-IgE versus in the absence of h-IgE was seen, the pools were cloned using the TOPO TA cloning kit (Invitrogen, Carlsbad, Calif.) according to the manufacturer's instructions. Round 11a pool templates were cloned and sequenced, and 8 unique clones were assayed in a 1-point dot blot screen (+/−20 nM h-IgE). Round 12b pool was cloned and sequenced, and 4 unique clones were assayed for protein binding in a 1-point dot blot screen (+/−20 nM h-IgE). The percent bound (signal over background) at 20 nM h-IgE for each of clone screened is listed in the far right column in Table 2 below. The sequences for these 12 clones are listed below in Table 3. Based on the 1-point dot blot screen, several clones were selected for $K_D$ determination. Clone transcripts were 5'end labeled with γ-$^{32}$P ATP. Binding reactions were prepared under the same conditions used to screen pool affinity as described above: trace $^{32}$P labeled clones were combined with a titration of h-IgE and incubated at room temperature for 30 minutes in 1×SCHMCK buffer plus 0.1 mg/mL tRNA in a final volume of 25 µL. $K_D$ values were determined using the dot blot assay for all unique sequences with +/−h-IgE binding ratios >2 in the initial screens by fitting the equation (ampl.1/(1+$K_{D1}$/[h-IgE])+ampl.2/(1+$K_{D2}$/[h-IgE]))+background; in which ampl.1 and ampl.2 represent the plateau values for two phases of a biphasic saturation plot and $K_{D1}$ and $K_{D2}$ represent the dissociation constants for each interaction to the resulting data (Kaleidagraph). Results of protein binding characterization are tabulated in Table 2.

TABLE 2

Clone binding activity

| SEQ ID NO | h-IgE $K_{D1}$ (nM) | h-IgE $K_{D2}$ (nM) | 1-pt Screen Data % Bound +/− h-IgE 20 nM |
|---|---|---|---|
| 11 | 0.144 | 12.5 | 4.08 |
| 12 | 0.057 | 9.85 | 4.70 |
| 13 | 0.139 | 14.6 | 5.67 |
| 14 | 1.08 | 99.5 | 2.57 |
| 15 | 0.115 | 19.0 | 3.89 |
| 16 | N.T. | | 1.11 |
| 17 | N.T. | | 0.76 |
| 18 | 1.14 | 27.3 | 4.31 |
| 22 | N.B. | | 0.80 |
| 20 | N.T. | | 1.36 |
| 21 | 0.183 | 27.1 | 2.64 |
| 19 | 0.095 | 17.4 | 3.55 |

N.T. = not tested
N.B. = no significant binding observed

The nucleic acid sequences of the rRfY aptamers characterized in Table 3 are given below. The unique sequence of each aptamer begins at nucleotide 25, immediately following the sequence GGGAAAAGCGAAUCAUACACAAGA (SEQ ID NO 9), and runs until it meets the 3'fixed nucleic acid sequence GCUCCGCCAGAGACCAACCGAGAA (SEQ ID NO 10).

Unless noted otherwise, individual sequences listed below are represented in the 5' to 3' orientation and were selected under rRfY SELEX™ conditions wherein the purines (A and G) are 2'-OH and the pyrimidines (U and C) are 2'-fluoro. In some embodiments, the invention comprises aptamers with a nucleic acid sequences as described in Table 3 below. In other embodiments, the nucleic acid sequences of the aptamers described in Table 3 additionally comprise a 3' cap (e.g., a 3' inverted dT (3T)), and/or a 5' amine ($NH_2$) modification to facilitate chemical coupling, and/or conjugation to a high molecular weight, non-immunogenic compound (e.g., PEG).

TABLE 3

Sequence Information for rRfY aptamers h-IgE Selection (Round 11a)

SEQ ID NO 11
GGGAAAAGCGAAUCAUACACAAGACGUCGCCAGAUUGAGUGUCGUGGUUC
GGGUUGAGGCGGAAGCUCCGCCAGAGACCAACCGAGAA

SEQ ID NO 12
GGAAAAGCGAAUCAUACACAAGAGUCGCGAUAGAUUGCUUGUGAAUGGUU
UUGGUGGAAGCGGGCUCCGCCAGAGACCAACCGAGAA

SEQ ID NO 13
GGGAAAAGCGAAUCAUACACAAGAGUCGCUAGAUUGCUAGUGUAUGGUUU
AUCUAAAGGCGGCCGCUCCGCCAGAGACCAACCGAGAA

SEQ ID NO 14
GGGAAAAGCGAAUCAUACACAAGAGGUCUUUACAGAUCCUGUGUAGUGGUU
CGAUACAUGCGGGGCUCCGCCAGAGACCAACCGAGAA.

SEQ ID NO 15
GGGAAAAGCGAAUCAUACACAAGACGUGAGCAUAUCAUUGAGUGUAGUGG
UUCCGGAGUAAGUCGCUCCGCCAGAGACCAACCGAGAA

SEQ ID NO 16
GGGAAAAGCGAAUCAUACACAAGAGCACCUUGACUGUGAUUCGCGGGUGU
GAGUCGUGCGAAGGCUCCGCCAGAGACCAACCGAGAA

TABLE 3-continued

Sequence Information for rRfY aptamers

SEQ ID NO 17
GGGAAAAGCGAAUCAUACACAAGAGUGCAAGAAGUGCAUUGCUGUGUCUG
GUUCUUGGCGAUGUGCUCCGCCAGAGACCAACCGAGAA

SEQ ID NO 18
GGGAAAAGCGAAUCAUACACAAGAUCCGAGGGUGGGCAAUAGGCUCACAA
GGGUUUCGCGUGAUGCUCCGCCAGAGACCAACCGAGAA h-IgE selection (round 12b)

SEQ ID NO 19
GGGAAAAGCGAAUCAUACACAAGAGUGCCGAGGCAUUGCUUGGUAUGGUU
CCGGUCUUGUCGGGGCUCCGCCAGAGACCAACCGAGAA

SEQ ID NO 20
GGGAAAAGCGAAUCAUACACAAGACGUCGCCAGAUUGAGUGUGGUGGUUC
GGGUUGAGGCGGAAGCUCCGCCAGAGACCAACCGAGAA

SEQ ID NO 21
GGGAAAAGCGAAUCAUACACAAGACGUCAGUAAGAUUGAGUGUAUGGUUC
CUGGUGGACAAUAAUGGCUCCGCCAGAGACCAACCGAGAA

SEQ ID NO 22
GGGAAAAGCGAAUCAUACACAAGAGAGUGGAGGAGGUAUGUAUGGUUUGU
GCGUCUGGUGCGGUGCUCCGCCAGAGACCAACCGAGAA

Example 1B

Selection of dRmY IgE Aptamers

A selection was performed to identify IgE aptamers containing deoxy-A, G and 2'O-Methyl C, U residues (dRmY composition). This was a direct selection against h-IgE which had been immobilized on a hydrophobic plate. This selection yielded a pool significantly enriched for h-IgE binding versus naïve, unselected pool.

Pool Preparation. A DNA template with the sequence 5'-GGGAGAGGAGAGAACGTTCTACN$_{30}$CGCTGTCG ATCGATCGATCGATG-3' (SEQ ID NO 23) was synthesized using an ABI EXPEDITE™ DNA synthesizer, and deprotected by standard methods. The templates were amplified with 5' primer 5'-GGGAGAGGAGAGAACGTTCTAC-3' (SEQ ID NO 24) and 3'-primer 5'-CATCGATCGATCGATC-GACAGC-3' (SEQ ID NO 25) and then used as a template for in vitro transcription with T7 RNA polymerase (Y639F). Transcriptions were done using 200 mM Hepes, 40 mM DTT, 2 mM spermidine, 0.01% TritonX-100, 10% PEG-8000, 9.6 mM $MgCl_2$, 2.9 mM $MnCl_2$, 30 μM GTP, 2 mM mCTP, 2 mM mUTP, 2 mM dGTP, 2 mM dATP, 2 mM GMP, 2 mM spermine, 0.01 units/ul inorganic pyrophosphatase, and T7 polymerase (Y639F).

Selection. Each round of selection was initiated by immobilizing 20 pmoles of h-IgE to the surface of a Nunc Maxisorp (Rochester, N.Y.) hydrophobic plate for 1 hour at room temperature in 100 μL of 1×PBS. The supernatant was then removed and the wells were washed 5 times with 120 μL wash buffer (1×PBS, 0.1 mg/mL tRNA and 0.1 mg/mL ssDNA). In round one, 100 pmoles of pool RNA ($6 \times 10^{13}$ unique molecules) were incubated in 100 μL binding buffer (1×PBS, 0.1 mg/mL tRNA and 0.1 mg/mL ssDNA) in the wells with immobilized protein target for 1 hour at room temperature.

The supernatant was then removed and the wells were washed 5 times with 120 μL wash buffer. In subsequent rounds a negative selection step was included; the pool RNA was also incubated for 1 hour at room temperature in empty wells to remove any plastic binding sequences from the pool before the positive selection step. Starting at round 3, a second negative selection step was introduced to further select against non specific binders; the pool was incubated for 1 hour in a well that had been previously blocked with 100 μl blocking buffer (1×PBS, 0.1 mg/mL tRNA, 0.1 mg/mL ssDNA and 0.1 mg/mL BSA). From round 3 forward, the target-immobilized wells were blocked for 1 hour at room temperature in 100 μl blocking buffer (1×PBS, 0.1 mg/mL tRNA, 0.1 mg/mL ssDNA and 0.1 mg/mL BSA) before the positive selection step. In all cases, the pool RNA bound to immobilized h-IgE was reverse transcribed directly in the selection plate after by the addition of RT mix (3' primer, (SEQ ID NO 25), and Thermoscript RT, Invitrogen) followed by incubation at 65° C. for 1 hour. The resulting cDNA was used as a template for PCR (Taq polymerase, New England Biolabs). "Hot start" PCR conditions coupled with a 68° C. annealing temperature were used to minimize primer-dimer formation. PCR amplification was carried out for the number of cycles (reported in the last column of Table 4 below) required to obtain a PCR band on a 4% agarose E-Gel (Invitrogen, Carlsbad, Calif.) equal in intensity to the 100 bp marker lane of a 100 bp DNA ladder when loaded according to the manufacturer's recommendations (~48 ng of DNA mass) (New England Biolabs, Catalog # N3231L, Beverly, Mass.). Amplified pool template DNA was desalted with a Micro Bio-Spin column (Bio-Rad, Hercules, Calif.) according to the manufacturer's recommended conditions and used to program transcription of the pool RNA for the next round of selection. The transcribed pool was gel purified using a 10% polyacrylamide gel in each round. Table 4 below shows the conditions used for each round of dRmY aptamer selection.

TABLE 4

Conditions used in each round of selection using dRmY composition

| Round # | RNA pool conc (μM) | protein type | protein conc (μM) | tRNA, ssDNA conc (mg/mL) | Negative Selection Step | PCR cycle # |
|---|---|---|---|---|---|---|
| 1 | 1 | h-IgE | 0.2 | 0.1 | none | 18 |
| 2 | 1 | h-IgE | 0.2 | 0.1 | plate | 18 |
| 3 | 1 | h-IgE | 0.2 | 0.1 | plate, blocking buffer | 20 |
| 4 | 1 | h-IgE | 0.2 | 0.1 | plate, blocking buffer | 17 |
| 5 | 1 | h-IgE | 0.2 | 0.1 | plate, blocking buffer | 17 |
| 6 | 1 | h-IgE | 0.2 | 0.1 | plate, blocking buffer | 15 |
| 7 | 1 | h-IgE | 0.2 | 0.1 | plate, blocking buffer | 16 | h-IgE Binding Analysis: The selection progress was monitored using a sandwich filter binding assay. The 5'-$^{32}$P-labeled pool RNA (trace concentration) was incubated with h-IgE, 1×PBS plus 0.1 mg/mL tRNA, 0.1 mg/mL ssDNA and 0.1 mg/mL BSA for 30 minutes at room temperature and then applied to a nitrocellulose and nylon filter sandwich in a dot blot apparatus (Schleicher and Schuell). The percentage of pool RNA bound to the nitrocellulose was calculated after round 6 and 7 with a seven point screen (0.25 nM, 0.5 nM, 1 nM, 4 nM, 16 nM, 64 nM and 128 nM h-IgE, also a no-target control was run). Pool $K_D$ measurements were measured using a titration of protein and the dot blot apparatus as described above.

Figure 6:
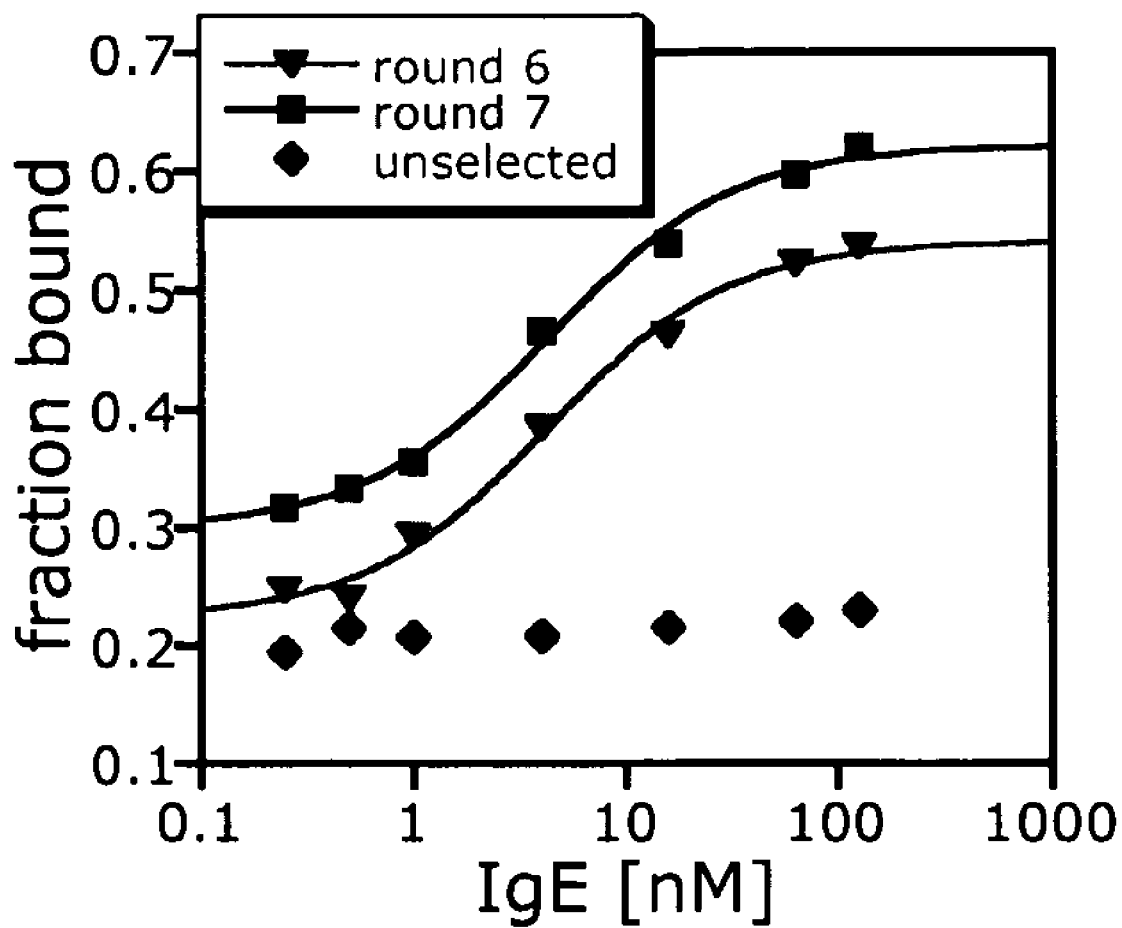
FIG. 6 is a plot of pool binding activity to h-IgE after rounds 6 and 7 of dRmY clone selection.

The dRmY h-IgE selection was enriched for h-IgE binding vs. the naïve pool after 6 rounds of selection. At round 6 and round 7 the pool $K_D$ was approximately 4 nM. The round 6 pool was cloned using TOPO TA cloning kit (Invitrogen) and 31 individual sequences were generated. There were two dominant clones, represented by 8 and 3 of the 31 sequences, and 21 singletons. FIG. 6 shows a plot of fraction bound versus h-IgE concentration for the round 6 and 7 pools.

Clone screening. For $K_D$ determination, clone transcripts of each of the 23 unique sequences were 5'end labeled with γ-$^{32}$P ATP. $K_D$ values were determined using an 8 point screen in the dot blot assay (0-300 nM h-IgE, 3 fold serial dilutions), and buffer conditions of 1× Dulbecco's PBS; 1.0 mg/mL tRNA; 0.1 mg/mL sheared salmon sperm DNA; and 0.1 mg/mL BSA. Dissociation constants ($K_DS$) were estimated fitting the data to the equation: fraction RNA bound=amplitude/(1+$K_D$/[h-IgE])+background. Under these binding assay conditions, 20 out of the 23 unique sequences did not show significant binding. Clones according to SEQ ID NO 43 and SEQ ID NO 46 exhibited dissociation constants of 87.7 nM and 109.7 nM respectively.

Each of the 23 unique clones were subsequently re-tested for binding to h-IgE under different assay conditions. Clones were made synthetically using standard chemical synthesis and deprotection methods. Clones were then purified by gel electrophoresis. Trace 5'-$^{32}$P labeled aptamers were combined with 7 decreasing concentrations of human IgE starting with 300 nM (3 fold dilutions) and a no protein sample, and incubated at room temperature for 30 minutes in dPBS (contains $Mg^{++}$ and $Ca^{++}$) and 0.1 mg/mL BSA. $K_D$ values were determined using the dot blot assay as previously described. The assay was repeated 3 times for each clone. The average percent bound was calculated for each protein concentration and the equilibrium dissociation constants were calculated using the equation:

$((A+P+K)-sqrt((A+P+K)^2-4A*P))/2A+B$; where
 $A$=[aptamer]$_{total}$, $P$=[protein]$_{total}$ and
 $B$=background signal.

Under these assay conditions, the clones with nucleic acid sequences according to SEQ ID NO 43 and SEQ ID NO 46 showed remarkably improved binding to h-IgE, and six additional clones out of the 23 unique sequences exhibited high affinity binding to h-IgE in the low nanomolar range. Results of protein binding characterization are tabulated in Table 5A, and the sequences for all 22 clones generated are listed below in Table 5B.

TABLE 5A dRmY Clone Binding Activity in dPBS (with Ca++ and Mg++), 0.1 mg/mL BSA:

| SEQ ID NO | Aptamer | $K_D$ (nM) | Error (nM) |
|---|---|---|---|
| 43 | ARC1991 | 2 | 2 |
| 50 | ARC1992 | 10 | 8 |
| 42 | ARC1993 | 9 | 4 |
| 46 | ARC1994 | 5 | 5 |
| 41 | ARC1995 | 4 | 2 |
| 33 | ARC2001 | 18.0 | 0.1 |
| 44 | ARC2002 | 8 | 6 |
| 29 | ARC2005 | 5 | 3 |

The unique sequence of each aptamer in Table 5B begins at nucleotide 23, immediately following the sequence GGGAGAGGAGAGAACGUUCUAC (SEQ ID NO 26), and runs until it meets the 3' fixed nucleic acid sequence CGCUGUCGAUCGAUCGAUCGAUG (SEQ ID NO 27).

Unless noted otherwise, individual sequences listed below are represented in the 5' to 3' orientation and were selected under dRmY SELEX™ conditions wherein the purines (A and G) are deoxy and the pyrimidines (U and C) are 2'-OMe. In some embodiments, the invention comprises aptamers with a nucleic acid sequences as described in Table 5B below. In other embodiments, the nucleic acid sequences of the aptamers described in Table 5B additionally comprise a 3' cap (e.g., a 3' inverted dT (3T)), and/or a 5' amine ($NH_2$) modification to facilitate chemical coupling, and/or conjugation to a high molecular weight, non-immunogenic compound (e.g., PEG).

TABLE 5B

Unique sequences from Round 6 pool (all are dRmY composition):

SEQ ID NO 28
GGGAGAGGAGAGAACGUUCUACGAUUAGCAGGGAGGGAGAGUGCGAAGAG
GACGCUGUCGAUCGAUCGAUCAUG

SEQ ID NO 29
GGGAGAGGAGAGAACGUUCUACACUCUGGGGACCCGUGGGGGAGUGCAGC
AACGCUGUCGAUCGAUCGAUCGAUG

SEQ ID NO 30
GGGAGAGGAGAGAACGUUCUACGAGGUGAGGGUCUACAAUGGAGGGAUGG
UCGCUGUCGAUCGAUCGAUCGAUG

SEQ ID NO 31
GGGAGAGGAGAGAACGUUCUACCCGCAGCAUAGCCUGNGGACCCAUGNGG
GGCGCUGUCGAUCGAUCGAUCGAUG

SEQ ID NO 32
GGGAGAGGAGAGAACGUUCUACUGGGGGGCGUGUUCAUUAGCAGCGUCGU
GUCGCUGUCGAUCGAUCGAUCGAUG

SEQ ID NO 33
GGGAGAGGAGAGAACGUUCUACGCAGCGCAUCUGGGGACCCAAGAGGGGA
UUCGCUGUCGAUCGAUCGAUCGAUG

SEQ ID NO 34
GGGAGAGGAGAGAACGUUCUACGGGAUGGGUAGUUGGAUGGAAAUGGGAA
CGCUGUCGAUCGAUCGAUCGAUG

SEQ ID NO 35
GGGAGAGGAGAGAACGUUCUACGAGGUGUAGGGAUAGAGGGGUGUAGGUA
ACGCUGUCGAUCGAUCGAUCGAUG

TABLE 5B-continued

Unique sequences from Round 6 pool (all are dRmY composition):

SEQ ID NO 36
GGGAGAGGAGAGAACGUUCUACAGGGAGUGGAGCUACAGAGAGGGUUAGGG
GUCGCUGUCGAUCGAUCGAUCGAUG

SEQ ID NO 37
GGGAGAGGAGAGAACGUUCUACGGAUGUUGGGAGUGAUAGAAGGAAGGGG
AGCGCUGUCGAUCGAUCGAUCGAUG

SEQ ID NO 38
GGGAGAGGAGAGAACGUUCUACUUGGGGUGGAAGGAGUAAGGGAGGUGCU
GAUCGCUGUCGAUCGAUCGAUCGAUG

SEQ ID NO 39
GGGAGAGGAGAGAACGUUCUACGUAUUAGGGGGGAAGGGGAGGAAUAGAU
CACGCUGUCGAUCGAUCGAUCGAUG

SEQ ID NO 40
GGGAGAGGAGAGAACGUUCUACAGGGAGAGAGUGUUGAGUGAAGAGGAGG
AGUCGCUGUCGAUCGAUCGAUCGAUG

SEQ ID NO 41
GGGAGAGGAGAGAACGUUCUACAUUGUGCUCCUGGGGCCCAGUGGGGAGC
CACGCUGUCGAUCGAUCGAUCGAUG

SEQ ID NO 42
GGGAGAGGAGAGAACGUUCUACGAGCAGCCCUGGGGCCCGGAGGGGGAUG
GUCGCUGUCGAUCGAUCGAUCGAUG

SEQ ID NO 43
GGGAGAGGAGAGAACGUUCUACAGGCAGUUCUGGGGACCCAUGGGGAAG
UGCGCUGUCGAUCGAUCGAUCGAUG

SEQ ID NO 44
GGGAGAGGAGAGAACGUUCUACCAACGGCAUCCUGGGCCCCACAGGGGAU
GUCGCUGUCGAUCGAUCGAUCGAUG

SEQ ID NO 45
GGGAGAGGAGAGAACGUUCUACGAGUGGAUAGGGAAGAAGGGGAGUAGUC
ACGCUGUCGAUCGAUCGAUCGAUG

SEQ ID NO 46
GGGAGAGGAGAGAACGUUCUACCCGCAGCAUAGCCUGGGGACCCAUGGGG
GGCGCUGUCGAUCGAUCGAUCGAUG

SEQ ID NO 47
GGGAGAGGAGAGAACGUUCUACGGUCGCGUGUGGGGACGGAUGGGUAUU
GGUCGCUGUCNAUCGAUCGAUCGAUG

SEQ ID NO 48
GGGAGAGGAGAGAACGUUCUACGGGGUUACGUCGCACGAUACAUGCAUUC
AUCGCUGUCGAUCGAUCGAUCGAUG

SEQ ID NO 49
GGGAGAGGAGAGAACGUUCUACUAGCGAGGAGGGGUUUUCUAUUUUUGCG
AUCGCUGUCGAUCGAUCGAUCGAUG

SEQ ID NO 50
GGGAGAGGAGAGAACGUUCUACAAGCAGUUCUGGGGACCCAUGGGGAAG
UGCGCUGUCGAUCGAUCGAUCGAUG

Example 1C

Selection of rRmY h-IgE Aptamers

A selection was performed to identify h-IgE aptamers containing 2'-ribo G and A and 2'-OMethyl C and U residues (rRmY composition). This was a direct selection against h-IgE which had been immobilized on a hydrophobic plate. This selection yielded a pool significantly enriched for h-IgE binding versus naïve, unselected pool.

Pool Preparation. A DNA template with the sequence 5'-GGGAGAGGAGAGAACGTTCTACN$_{30}$CGCTGT CATCGATCGATCGATG-3' (SEQ ID NO 51) was synthesized using an ABI EXPEDITE™ DNA synthesizer, and deprotected by standard methods. The templates were amplified with 5' primer 5'-GGGAGAGGAGAGAACGTTCTAC-3' (SEQ ID NO 52) and 3' primer 5'-CATCGATCGATC-GATCGACAGC-3' (SEQ ID NO 53) and then used as a template for in vitro transcription with T7 RNA polymerase (Y639F). Transcriptions were done using 200 mM Hepes, 40 mM DTT, 2 mM spermidine, 0.01% TritonX-100, 10% PEG-8000, 5 mM MgCl$_2$, 1.5 mM MnCl$_2$, 500 μM rGTP, 500 μM rATP, 500 μM mCTP, 500 μM mUTP, 500 μM GMP, 0.01 units/μL inorganic pyrophosphatase, and T7 polymerase (Y639F).

Selection. Each round of selection was initiated by immobilizing 20 pmoles of h-IgE to the surface Nunc Maxisorp hydrophobic plates for 2 hours at room temperature in 100 μL of 1× Dulbecco's PBS. The supernatant was then removed and the wells were washed 4 times with 120 μL wash buffer (1×DPBS, 0.2% BSA, and 0.05% Tween-20). Pool RNA was heated to 90° C. for 3 minutes and cooled to room temperature for 10 minutes to refold. In round 1, a positive selection step was conducted. Briefly, 1×10$^{14}$ molecules (0.2 nmoles) of pool RNA were incubated in 100 μL binding buffer (1×DPBS and 0.05% Tween-20) in the wells with immobilized protein target for 1 hour at room temperature. The supernatant was then removed and the wells were washed 4× with 120 μL wash buffer. In subsequent rounds a negative selection step was included. The pool RNA was also incubated for 30 minutes at room temperature in empty wells to remove any plastic binding sequences from the pool before the positive selection step. The number of washes was increased by 2 additional 120 μl washes (total of 6×120 μl washes) after round 4 to increase stringency. In all cases, the pool RNA bound to immobilized h-IgE was reverse transcribed directly in the selection plate after by the addition of RT mix (3' primer, (SEQ ID NO 53) and Thermoscript RT, Invitrogen)) followed by incubation at 65° C. for 1 hour. The resulting cDNA was used as a template for PCR (Taq polymerase, New England Biolabs) "Hot start" PCR conditions coupled with a 60° C. annealing temperature were used to minimize primer-dimer formation. Amplified pool template DNA was desalted with a Centrisep column (Princeton Separations) according to the manufacturer's recommended conditions and used to program transcription of the pool RNA for the next round of selection. The transcribed pool was gel purified on a 10% polyacrylamide gel every round. Table 6 below shows the rRmY selection pool h-IgE usage per round.

TABLE 6 rRmY Pool and h-IgE usage per round.

| Round | pmoles of pool used | pmoles of h-IgE used |
|---|---|---|
| 1 | 200 | 20 |
| 2 | 140 | 20 |
| 3 | 115 | 20 |
| 4 | 40 | 20 |
| 5 | 130 | 20 |
| 6 | 80 | 20 |
| 7 | 90 | 20 |

The selection progress was monitored using a sandwich filter binding assay. The 5'-$^{32}$P-labeled pool RNA was refolded at 90° C. for 3 minutes and cooled to room temperature for 10 minutes. Next, pool RNA (trace concentration) was incubated with h-IgE in 1×DPBS plus 0.1 mg/mL tRNA for 30 minutes at room temperature and then applied to a nitrocellulose and nylon filter sandwich in a dot blot apparatus (Schleicher and Schuell). The percentage of pool RNA bound to the nitrocellulose was calculated and monitored approximately every 3 rounds with a single point screen (+/− 250 nM h-IgE). Pool K$_D$ measurements were measured using a titration of protein and the dot blot apparatus as described above.

The selection was enriched after 4 rounds over the naïve pool. The selection stringency was increased by 2 additional 120 μl washes and the selection was continued for 2 more rounds. At round 6 the pool K$_D$ was approximately 500 nM. The pools were cloned using TOPO TA cloning kit (Invitrogen) and individual clones sequences were obtained. The round 6 pool contained one dominant clone with a nucleic acid sequence according to SEQ ID NO 56, which made up 71% of the 24 clones sequenced. The dominant clone, as well as three clones that appeared in duplicate, were tested for binding to h-IgE using a 12 point screen (0-250 nM h-IgE in 2 fold serial dilutions). The three duplicate clones showed a higher extent of binding than the dominant clone, however, all of the K$_D$S were approximately 500 nM. An additional set of 96 sequences was obtained, and the dominant clone with a nucleic acid sequence according to SEQ ID NO 56 made up 40% of the 96 clones, along with eight other sequence families which were not evident in the first sequence set. A single point screen was performed on the additional unique sequences (+/−200 nM h-IgE). Based on the single point screen, K$_D$S were determined for an additional 24 K$_D$S sequences using a 12 point screen (0-400 nM h-IgE, 2 fold serial dilutions). The K$_D$S for each of these clones were in excess of 100 nM and further efforts on these clones were terminated. Table 7 below shows the nucleotide sequences of rRmy clones selected.

The unique sequence of each aptamer begins at nucleotide 22, immediately following the sequence GGGAGAG-GAGAGAACGUUCUA (SEQ ID NO 54), and runs until it meets the 3'fixed nucleic acid sequence CGCUGUCGAUC-GAUCGAUG (SEQ ID NO 55).

Unless noted otherwise, individual sequences listed below are represented in the 5' to 3' orientation and were selected under rRmY SELEX™ conditions wherein the purines (A and G) are 2'-OH and the pyrimidines (U and C) are 2'-OMe. In some embodiments, the invention comprises aptamers with a nucleic acid sequences as described in Table 7 below. In other embodiments, the nucleic acid sequences of the aptamers described in Table 7 additionally comprise a 3' cap (e.g., a 3' inverted dT (3T)), and/or a 5' amine (NH$_2$) modification to facilitate chemical coupling, and/or conjugation to a high molecular weight, non-immunogenic compound (e.g., PEG).

TABLE 7

| rRmY Unique Clone Sequence Information |
| --- |
| SEQ ID NO 56<br>GGGAGAGGAGAGAACGUUCUACGAUCUGGGCGAGCCAGUCUGACUGAGGA<br>AGCGCUGUCGAUCGAUCGAUCGAUGAAGGGCG |
| SEQ ID NO 57<br>GGGAGAGGAGAGAACGUUCUACGCGGUCGGGUGUGUGGAGGAAGUAGUUC<br>GUCGCUGUCGAUCGAUCGAUCGAUGAAGGGCG |
| SEQ ID NO 58<br>GGGAGAGGAGAGAACGUUCUACGACGUUAAUGCAGCGGCUAGGGAUGGGC<br>AGCGCUGUCGAUCGAUCGAUCGAUGAAGGGCG |
| SEQ ID NO 59<br>GGGAGAGGAGAGAACGUUCUACAGGCGUGUUGGUAGGGUACGACGAGGCA<br>UGCGCUGUCGAUCGAUCGAUCGAUGAAGGGCG |
| SEQ ID NO 60<br>GGGAGAGGAGAGAACGUUCUACUGAGGGAUAAUACGGGUGGGAUUGUCUU<br>CCCGCUGUCGAUCGAUCGAUCGAUGAAGGGCG |
| SEQ ID NO 61<br>GGGAGAGGAGAGAACGUUCUACGAAAAAGAUAUGAGAGAAAGGAUUAAGA<br>GACGCUGUCGAUCGAUCGAUCGAUGAAGGGCG |
| SEQ ID NO 62<br>GGGAGAGGAGAGAACGUUCUACGAAGAAGAUAUGAGAGAAAGGAUUAAGA<br>GACGCUGUCGAUCGAUCGAUCGAUGAAGGGCG |
| SEQ ID NO 63<br>GGGAGAGGAGAGAACGUUCUACGAAAAAGAUAUGAGAGAAAGGAUUAAGA<br>GACGCUGUCGAUCGAUCGAUCGAUGAAGGGCG |
| SEQ ID NO 64<br>GGGAGAGGAGAGAACGUUCUACGAAAAAGAUAUGAGAGAAAGGAUUAAGA<br>GGCGCUGUCGAUCGAUCGAUCGAUGAAGGGCG |
| SEQ ID NO 65<br>GGGAGAGGAGAGAACGUUCUACGAAAAAGACAUGAGAGAAAGGAUUAAGA<br>GACGCUGUCGAUCGAUCGAUCGAUGAAGGGCG |
| SEQ ID NO 66<br>GGGAGAGGAGAGAACGUUCUACNAAAAAGUAUAUGAGAGAAAGGAUUAAN<br>AGACGCUGUCGAUCGAUCGAUCGAUGAAGGGCG |
| SEQ ID NO 67<br>GGGAGAGGAGAGAACGUUCUACGAAAAAGAUAUGAGAGAAAAGGAUUGAG<br>AGAUGCUGUCGAUCGAUCGAUCGAUGAAGGGCG |
| SEQ ID NO 68<br>GGGAGAGGAGAGCACGUUCUACGAAAAAGAUAUGGAGAGAAAGGAUUAAG<br>AGACGCUGUCGAUCGAUCGAUCGAUGAAGGGCG |
| SEQ ID NO 69<br>GGGAGAGGAGAGAACGUUCUACGAAAAAGAUAUGAGAGAAAGGAUUAAAA<br>GAGACGCUGUCGAUCGAUCGAUCGAUGAAGGGCG |
| SEQ ID NO 70<br>GGGAGAGGAGAGAACGUUCUACGAANAAGAUACAUAGUAGAAAGGAUUAA<br>UAAGACGCUGUCGAUCGAUCGAUCGAUGAAGGGCG |
| SEQ ID NO 71<br>GGGAGAGGAGAGAACGUUCUACAGGCGUGUUGGUAGGGUACGACGAGGCA<br>UGCGCUGUCGAUCGAUCGAUCGAUGAAGGGCG |
| SEQ ID NO 72<br>GGGAGAGGAGAGAACGUUCUACGCAAAAAUGUGAUGCGAGGUAAUGGAAC<br>GCCGCUGUCGAUCGAUCGAUCGAUGAAGGGCG |
| SEQ ID NO 73<br>GGGAGAGGAGAGAACGUUCUACGGACCUCAGCGAUAGGGGUUGAAACCGA<br>CACGCUGUCGAUCGAUCGAUCGAUGAAGGGCG |
| SEQ ID NO 74<br>GGGAGAGGAGAGAACGUUCUACAUGGUCGGAUGCUGGGGAGUAGGCAAGG<br>UUCGCUGUCGAUCGAUCGAUCGAUGAAGGGCG |

TABLE 7-continued

| rRmY Unique Clone Sequence Information |
| --- |
| SEQ ID NO 75<br>GGGAGAGGAGAGAACGUUCUACGUAUCGGCGAGCGAAGCAUCCGGGAGCG<br>UUCGCUGUCGAUCGAUCGAUCGAUGAAGGGCG |
| SEQ ID NO 76<br>GGGAGAGGAGAGAACGUUCUACGUAUUGGCGCGCGAAGCAUCCGGGAGCG<br>UUCGCUGUCGAUCGAUCGAUCGAUGAAGGGCG |
| SEQ ID NO 77<br>GGGAGAGGAGAGAACGUUCUACUUAUACCUGACGGCCGGAGGCGCAUAGG<br>UGCGCUGUCGAUCGAUCGAUCGAUGAAGGGCG |
| SEQ ID NO 78<br>GGGAGAGGAGAGAACGUUCUACAUGGUCGGAUGCUGGGGAGUAGGCAAGG<br>UUCGCUGUCGAUCGAUCGAUCGAUGAAGGGCG |
| SEQ ID NO 79<br>GGGAGAGGAGAGAACGUUCUACACGAGAGUACUGAGGCGCUUGGUACAGA<br>GUCGCUGUCGAUCGAUCGAUCGAUGAAGGGCG |
| SEQ ID NO 80<br>GGGAGAGGAGAGAACGUUCUACAGAAGGUAGAAAAAGGAUAGCUGUGAGA<br>AGCGCUGUCGAUCGAUCGAUCGAUGAAGGGCG |
| SEQ ID NO 81<br>GGGAGAGGAGAGAACGUUCUACUGAGGGAUAAUACGGGUGGGAUUGUCUU<br>CCCGCUGUCGAUCGAUCGAUCGAUGAAGGGCG |
| SEQ ID NO 82<br>GGGAGAGGAGAGAACGUUCUACAUUGAGCGUUGAAGUUGGGGAAGCUCCG<br>AGGCCGCUGUCGAUCGAUCGAUCGAUGAAGGGCG |
| SEQ ID NO 83<br>GGGAGAGGAGAGAACGUUCUACGCGGAGAUAUACAGCGAGGUAAUGGAAC<br>GCCGCUGUCGAUCGAUCGAUCGAUGAAGGGCG |
| SEQ ID NO 84<br>GGGAGAGGAGAGAACGUUCUACGAAGACAGCCCAAUAGCGGCACGGAACU<br>UGCGCUGUCGAUCGAUCGAUCGAUGAAGGGCG |
| SEQ ID NO 85<br>GGGAGAGGAGAGAACGUUCUACCGGUUGAGGGCUCGCGUGGAAGGCCAAC<br>ACGCGCUGUCGAUCGAUCGAUCGAUGAAGGGCG |
| SEQ ID NO 86<br>GGGAGAGGAGAGAACGUUCUACAUAUCAAUAGACUCUUGACGUUUGGGUU<br>UGCGCUGUCGAUCGAUCGAUCGAUGAAGGGCG |
| SEQ ID NO 87<br>GGGAGAGGAGAGAACGUUCUACAGUGAAGGAAAAGUAAGUGAAGGUGUGC<br>GCUGUCGAUCGAUCGAUCGAUGAAGGGCG |
| SEQ ID NO 88<br>GGGAGAGGAGAGAACGUUCUACGGAUGAAAUGAGUGUCUGCGAUAGGUUA<br>AGCGCUGUCGAUCGAUCGAUCGAUGAAGGGCG |
| SEQ ID NO 89<br>GGGAGAGGAGAGAACGUUCUACGGAAGGAAUGUGUGUCUGCGAUAGGUUA<br>AGCGCUGUCGAUCGAUCGAUCGAUGAAGGGCG |

Example 2

Aptamer Modification

Example 2A rRfY IgE Clone Minimization

Efforts were taken to minimize the IgE aptamers described above in Example 1A while maintaining, preferably improving, binding affinity. In order to identify the core structural elements required for h-IgE binding, the 3'-boundaries of several of the high affinity h-IgE binders were determined.

RNA transcripts were labeled at the 5'-end with γ-$^{32}$P ATP and T4 polynucleotide kinase. Radiolabeled ligands were subjected to partial alkaline hydrolysis and then selectively bound in solution to h-IgE at 500 nM before being partitioned over nitrocellulose filters. Retained oligonucleotides were resolved on 8% denaturing polyacrylamide gels. The smallest oligonucleotide bound to h-IgE defined the 3'-boundary. The 3'-boundaries of selected clones are described in Table 8. On the basis of the boundary experiments as well as visual inspection of predicted folds, truncated constructs were prepared and oligos were ordered from Integrated DNA Technologies (Coralville, Iowa). Minimized versions of the parent clones with nucleic acid sequences according to SEQ ID NO 11, SEQ ID NO 18, and SEQ ID NO 21 showed significant protein binding, measured by the sandwich filter binding assay previously described. Minimer binding data are shown in Table 8, while the corresponding sequences are shown in Table 9.

TABLE 8

Minimer binding activity

| Minimized Clone | Parent Clone | 3'-boundary of parent | h-IgE $K_{D1}$ (nM) | h-IgE $K_{D2}$ (nM) |
|---|---|---|---|---|
| SEQ ID NO 90 | SEQ ID NO 11 | U49 | 0.33 | 28.2 |
| SEQ ID NO 91 | SEQ ID NO 11 | | 0.56 | 36.9 |
| SEQ ID NO 92 | SEQ ID NO 11 | | 0.25 | 22.0 |
| SEQ ID NO 93 | SEQ ID NO 18 | U55 | 0.65 | 17.1 |
| SEQ ID NO 94 | SEQ ID NO 18 | | 1.01 | 26.5 |
| SEQ ID NO 95 | SEQ ID NO 21 | G47 | 4.5 | 117.2 |
| SEQ ID NO 96 | SEQ ID NO 21 | | 0.365 | 39.7 |

*All measurements were done in 1× SHMCK buffer plus 0.1 mg/mL tRNA.

Unless noted otherwise, individual sequences listed below are represented in the 5' to 3' orientation and were selected under rRfY SELEX™ wherein all purines (A and G) are 2'-OH, and all pyrimidines (C and U) are 2'-fluoro. In some embodiments, the invention comprises aptamers with a nucleic acid sequences as described in Table 9 below. In other embodiments, the nucleic acid sequences of the aptamers described in Table 9 additionally comprise a 3' cap (e.g., a 3' inverted dT (3T)), and/or a 5' amine (NH$_2$) modification to facilitate chemical coupling, and/or conjugation to a high molecular weight, non-immunogenic compound (e.g., PEG).

TABLE 9

Sequences of rRfY minimized aptamers.

SEQ ID NO 90
GGGAAAAGCGAAUCAUACACAAGACGUCGCCAGAUUGAGUGUCGUGGUU

SEQ ID NO 91
GGAAUCAUACACAAGACGUCGCCAGAUUGAGUGUCGUGGUUCC

SEQ ID NO 92
GGAAUCAUACACAAGACGUCGCCAGAUUGAGUGUCGUGGUU

SEQ ID NO 93
GGAGAUCCGAGGGUGGGCAAUAGGCUCACAAGGGUUU

SEQ ID NO 94
GGAUCCGAGGGUGGGCAAUAGGCUCACAAGGGUCC

TABLE 9-continued

Sequences of rRfY minimized aptamers.

SEQ ID NO 95
GGAAUCAUACACAAGACGUCAGUAAGAUUGAGUGUAUGGUUCC

SEQ ID NO 96
GGAAUCAUACACAAGACGUCAGUAAGAUUGAGUGUAUGGUU

Example 2B dRmY IgE Clone Minimization

Efforts were taken to minimize the dRmY IgE aptamers described above in Example 1B while maintaining, preferably improving, binding affinity. On the basis of the inspection of predicted folds for clones with nucleic acid sequences according to SEQ ID NO 43 and SEQ ID NO 46, a panel of minimized sequences was designed. The highest affinity molecule, ARC445 (SEQ ID NO 101) is 23 nucleotides in length and binds h-IgE with a $K_D$ of 22 nM. The data are summarized in Table 10. Table 11 shows the nucleotide sequences of ARC441 to ARC447 (SEQ ID NOs 97-103), the truncants derived from the clones with nucleic acid sequences according to SEQ ID NO 43 and SEQ ID NO 46.

TABLE 10

Minimized dRmY h-IgE binders

| Minimer SEQ ID NO | ARC reference number for minimer | SEQ ID NO Parent clone | $K_D$ h-IgE (nM) |
|---|---|---|---|
| 97 | ARC441 | SEQ ID NO 43 | N.B. |
| 98 | ARC442 | SEQ ID NO 43 | 174 |
| 99 | ARC443 | SEQ ID NO 43 | 55 |
| 100 | ARC444 | SEQ ID NO 46 | 73 |
| 101 | ARC445 | SEQ ID NO 46 | 22 |
| 102 | ARC446 | SEQ ID NO 46 | 43 |
| 103 | ARC447 | SEQ ID NO 46 | N.B. |

$K_D$ measurements were performed in 1×PBS in the presence of 0.1 mg/mL BSA, 1 mg/mL tRNA and 0.1 mg/mL ssDNA at 25° C. for 30 minutes.

Unless noted otherwise, individual sequences listed below are represented in the 5' to 3' orientation and were selected under dRmY SELEX™ wherein all purines (A and G) are deoxy, and all pyrimidines (C and U) are 2'-O-methyl. In some embodiments, the invention comprises aptamers with a nucleic acid sequences as described in Table 11 below. In other embodiments, the nucleic acid sequences of the aptamers described in Table 11 additionally comprise a 3' cap (e.g., a 3' inverted dT (3T)), and/or a 5' amine (NH$_2$) modification to facilitate chemical coupling, and/or conjugation to a high molecular weight, non-immunogenic compound (e.g., PEG).

TABLE 11

Truncants of clones with nucleic acid sequences according to SEQ ID NO 43 and SEQ ID NO 46

SEQ ID NO 97 (ARC 441)
UUCUGGGGACCCAUGGGGAA

TABLE 11-continued

Truncants of clones with nucleic acid sequences according to SEQ ID NO 43 and SEQ ID NO 46

SEQ ID NO 98 (ARC 442)
GUUCUGGGGACCCAUGGGGGAAC

SEQ ID NO 99 (ARC 443)
AGUUCUGGGGACCCAUGGGGGAACU

SEQ ID NO 100 (ARC 444)
GCCUGGGGACCCAUGGGGGGC

SEQ ID NO 101 (ARC 445)
AGCCUGGGGACCCAUGGGGGGCU

SEQ ID NO 102 (ARC 446)
UAGCCUGGGGACCCAUGGGGGGCUA

SEQ ID NO 103 (ARC 447)
GCCUGGGGAACCAUGGGGGGC

Example 2C

Doped Reselection: ARC445

Doped reselections are used to explore the sequence requirements within an active clone or minimer. During doped reselection, selections are carried out with a synthetic, degenerate pool that has been designed based on a single sequence. The level of degeneracy usually varies from 70% to 85% wild type nucleotide. In general, neutral mutations are observed but in some cases sequence changes can result in improvements in affinity. The composite sequence information can then be used to identify the minimal binding motif and aid in aptamer medicinal chemistry efforts.

A selection using a doped pool based on the minimized h-IgE binding sequence ARC445 (SEQ ID NO 101) (described in Example 2B) was performed in order to identify higher affinity binders. The selection was against h-IgE immobilized to the surface of a hydrophobic plate and utilized techniques designed to drive selection toward higher affinity aptamers such as combinations of multiple longer washes (e.g. 30 minutes, 60 minutes, overnight).

Pool preparation. A DNA template with the sequence 5'-GGGAGAGGAGAGAACGTTCTACAGC-CTGGGGACCCATGGGGGGCTGGTCG ATCGATCGAT-CATCGATG-3' (SEQ ID NO 104) was synthesized using an ABI EXPEDITE™ DNA synthesizer, and deprotected by standard methods. The nucleotides in bold had an 85% chance of being the indicated residue and a 5% chance of being one of the other 3 nucleotides. The templates were amplified with 5'primer 5'-GGGAGAGGAGAGAACGTTC-TAC-3' (SEQ ID NO 52) and 3' primer 5'-CATCGATGATC-GATCGATCGACC-3' (SEQ ID NO 105) and then used as a template for in vitro transcription with T7 RNA polymerase (Y639F). Transcriptions were done using 200 mM Hepes, 40 mM DTT, 2 mM spermidine, 0.01% TritonX-100, 10% PEG-8000, 9.6 mM MgCl$_2$, 2.9 mM MnCl$_2$, 30 µM GTP, 2 mM mCTP, 2 mM mUTP, 2 mM dGTP, 2 mM dATP, 2 mM GMP, 2 mM spermine, 0.01 units/µl inorganic pyrophosphatase, and T7 polymerase (Y639F).

Selection. Each round of selection was initiated by immobilizing 20 pmoles of h-IgE to the surface of a Nunc Maxisorp hydrophobic plate for 1 hour at room temperature in 100 µL 1× Dulbecco's PBS (DPBS). The supernatant was then removed and the wells were washed 2 times with 120 µL 1× Dulbecco's PBS. The wells were blocked by adding 100 µL blocking buffer (1× Dulbecco's PBS, 0.1 mg/mL tRNA, 0.1 mg/mL salmon sperm DNA, and 0.1 mg/mL BSA) and incubating 1 hour at room temperature. The supernatant was removed and the wells were washed 2 times with 120 µL wash buffer. Starting at round 2, a negative binding incubation for one hour to an empty well, and a negative binding incubation to a well blocked with BSA were both conducted for the RNA pools. The positive selection was conducted by adding 100 pmoles of pool RNA in 100 µL 1× Dulbecco's PBS to the target well. 0.1 mg/mL tRNA and 0.1 mg/mL salmon sperm DNA was also added to the positive selection. After incubation for 1 hour at room temperature the supernatant was removed and the wells were washed five times with 120 µL wash buffer (1×DPBS) as outlined in Table 12 below. Additional selections were added by branching off the selected pool at round 3 and round 4. These were conducted with longer washes to increase selection stringency.

The RNA was reverse transcribed with the ThermoScript RT-PCR™ system (Invitrogen) in a 100 µl reaction volume at 65 degrees for 30 minutes, using the 3' primer sequence according to SEQ ID NO 5. The cDNA was amplified by PCR (20 mM Tris pH 8.4, 50 mM KCl, 2 mM MgCl$_2$, 0.5 µM 5' primer (SEQ ID NO 52), 0.5 µM 3' primer (SEQ ID NO 105), 0.5 mM each dNTP, 0.05 units/µL Taq polymerase (New England Biolabs) using the number of PCR cycles (last column, Table 12) required to obtain a PCR band on a 4% agarose E-Gel (Invitrogen, Carlsbad, Calif.) equal in intensity to the 100 bp marker lane of a 100 bp DNA ladder when loaded according to the manufacturer's recommendations (~48 ng of DNA mass) (New England Biolabs, Catalog # N3231L, Beverly, Mass.). The PCR products were then desalted using Centrisep Spin columns (Princeton Separations). Templates were transcribed overnight at 37 degrees using 200 mM Hepes, 40 mM DTT, 2 mM spermidine, 0.01% TritonX-100, 10% PEG-8000, 9.6 mM MgCl$_2$, 2.9 mM MnCl$_2$, 30 µM GTP, 2 mM mCTP, 2 mM mUTP, 2 mM dGTP, 2 mM dATP, 2 mM GMP, 2 mM spermine, 0.01 units/µl inorganic pyrophosphatase, and T7 polymerase (Y639F). RNA for subsequent rounds was purified on a 10% polyacrylamide gel. Table 12 below shows a summary of the doped reselection profile for ARC445 (SEQ ID NO 101).

TABLE 12

| ARC445 doped reselection profile | | | | |
|---|---|---|---|---|
| Round | RNA (pmol) | Negative steps | target (pmol) | washes | PCR cycles |
| Regular conditions | | | | | |
| 1 | 100 | none | 20 | 120 µl/quick | 19 |
| 2 | 100 | well, BSA | 20 | 120 µl/quick | 10 |
| 3a | 100 | well, BSA | 20 | 120 µl/quick | 10 |
| 4a | 80.64 | well, BSA | 20 | 120 µl/quick | 10 |

TABLE 12-continued

ARC445 doped reselection profile

| Round | RNA (pmol) | Negative steps | target (pmol) | washes | PCR cycles |
|---|---|---|---|---|---|
| 5a | 100 | well, BSA | 20 | 120 µl/quick | 10 |
| LONG WASHES starting at round 3 (split from regular round 3 template) | | | | | |
| 1 | 100 | none | 20 | 120 µl/quick | 19 |
| 2 | 100 | well, BSA | 20 | 120 µl/quick | 10 |
| 3b | 30.67 | well, BSA | 20 | 120 µl/30 min | 10 |
| 4b | 100 | well, BSA | 20 | 120 µl/ON | 12 |
| LONG WASHES starting at round 4 (split from regular round 4 template) | | | | | |
| 1 | 100 | none | 20 | 120 µl/quick | 19 |
| 2 | 100 | well, BSA | 20 | 120 µl/quick | 10 |
| 3a | 100 | well, BSA | 20 | 120 µl/quick | 10 |
| 4c | 80.64 | well, BSA | 20 | 120 µl/30 min | 10 |
| 5c | 100 | well, BSA | 20 | 120 µl/ON | 12 |

DNA from the final selection rounds from all wash conditions and from round 2 and 3 from the non-stringent selection were cloned using TOPO TA cloning kit (Invitrogen, Carlsbad Calif.). Seven sequences were selected to be synthesized and tested for specific binding to h-IgE using the dot blot assay and conditions previously described in Example 1B above. None of the seven clones tested showed any significant binding to h-IgE. Table 13 below shows the sequences of clones from the ARC445 doped reselection.

Unless noted otherwise, individual sequences listed below are represented in the 5' to 3' orientation and were selected under dRmY SELEX™ wherein all purines (A and G) are deoxy, and all pyrimidines (C and U) are 2'-O-methyl. In some embodiments, the invention comprises aptamers with a nucleic acid sequences as described in Table 13 below. In other embodiments, the nucleic acid sequences of the aptamers described in Table 13 additionally comprise a 3' cap (e.g., a 3' inverted dT (3T)), and/or a 5' amine (NH$_2$) modification to facilitate chemical coupling, and/or conjugation to a high molecular weight, non-immunogenic compound (e.g., PEG).

TABLE 13

Sequences of clones from the ARC445 doped reselection

SEQ ID NO 106 ARC664
AGCCUGGGGACCCAUGGGGGCU

SEQ ID NO 107 ARC665
CGCCUGGGGACCCAGGGGGGCU

SEQ ID NO 108 ARC666
AGCCUGGUGGCCCAUGGGGUGCU

SEQ ID NO 109 ARC667
AGCCUGGGGACCCAUGGGGGGUGGU

SEQ ID NO 110 ARC668
AGUCUGGGGACAGAUGGAUGGCU

TABLE 13-continued

Sequences of clones from the ARC445 doped reselection

SEQ ID NO 111 ARC669
AGCUGUGGAGUCGUGUGGGGCU

SEQ ID NO 112 ARC670
AAGCCUGGGGACCCAUGGGGGGGCU

Example 2D

Doped Re-selection of DNA IgE Aptamers

A selection using a doped pool based on the h-IgE binding sequence D17.4 5'-GGGGCACGTTTATCCGTCCCTC-CTAGTGGCGTGCCCC-3' (SEQ ID NO 113), (U.S. Pat. No. 5,686,592 incorporated herein by reference in its entirety) was performed in order to identify higher affinity binders. The selection was against h-IgE immobilized to the surface of a hydrophobic plate and utilized techniques designed to drive selection toward higher affinity aptamers such as combinations of multiple longer washes (e.g. 30 minutes, 60 minutes, overnight). The experiment yielded a number of D17.4 derivatives with increased affinity for h-IgE.

Pool preparation. The DNA template (ARC 273) with the sequence 5'gatcccttgttcagtccGGGGCACGTT-TATCCGTCCCTCCTAGTGGCGT GCCCCttaagccacag-gactccaaa-3' (SEQ ID NO 114) in which the primer binding sites are represented in lower case and the nucleotides in bold had an 85% chance of being the indicated residue and a 5% chance of being one of the other 3 nucleotides. The template was synthesized on an ABI EXPEDITE™ DNA synthesizer, and deprotected by standard methods. The pool was amplified with the 5' primer 5'-GATCCCTTGTTCAGTCCG-3' (SEQ ID NO 115) and 3' primer 5'-GGAGTCCTGTGGCTTArA-3' (SEQ ID NO 116) (where rA stands for ribo adenosine which enabled primer cleavage post-PCR, allowing template and pool bands to be separated by gel) using standard conditions. The product was subjected to alkaline hydrolysis (200 mM NaOH, 90° C., 15 min) followed by precipitation with isopropanol. The strands were separated on an 8% denaturing polyacrylamide gel and the ssDNA pool, which migrated with a lower mobility, was excised from the gel.

Each round of selection was initiated by immobilizing 20 pmoles of h-IgE to the surface of a Nunc Maxisorp hydrophobic plate for 1 hour at room temperature in 100 µL selection buffer (1×SCHMK; see Example 1A). The supernatant was then removed and the wells were washed 4 times with 120 µL wash buffer (1×SCHMK, 0.2% BSA and 0.5% Tween-20). The wells were blocked by adding 100 µL blocking buffer (1×SHMCK, 1% BSA, 0.5% Tween-20) and incubating 1 hour at room temperature. The supernatant was removed and the wells were washed 4 times with 120 µL wash buffer. In round one, 80 pmoles of pool DNA (1.5×10$^{13}$ unique molecules) in 100 µL selection buffer was incubated in a blank well for 1 hour at room temperature as a negative selection step to eliminate non-specific binders. The supernatant was then removed, 12 µL of 9.1 mg/mL salmon sperm DNA in 1×SCHMK was added, and the mixture was transferred to the well containing target protein. After incubation 1 hour at room temperature the supernatant was removed and the wells were washed multiple times with 120 μL wash buffer. Table 14 below shows the selection conditions for the doped reselection.

TABLE 14

Selection stringency as a function of round and washing

| Round # | # initial washes | # washes with 15 minute incubation in buffer | # washes with an overnight incubation in buffer | # washes post buffer incubation |
|---------|------------------|----------------------------------------------|-------------------------------------------------|---------------------------------|
| 1 | 6 | — | — | — |
| 2 | 6 | — | — | — |
| 3 | 6 | — | — | — |
| 4 | 6 | 2 | — | — |
| 5 | 6 | 2 | 1 | 1 |

In all cases, the pool DNA bound to immobilized h-IgE was eluted with 2×150 μL washes of hot elution buffer (7 M Urea, 100 mM NaOAc pH 5, 3 mM EDTA), precipitated by the addition of isopropanol, then amplified by PCR. DNA eluted after round one of selection was amplified and purified as described above for the initial DNA doped pool amplification using the 5' and 3' primers according to SEQ ID NO 115 and SEQ ID NO 116 using standard conditions. For rounds 2-4, eluted DNA was amplified using the 5' and 3' primers according to SEQ ID NO 115 and 5'-(5-biotin-T)(5-biotin-T)(5-biotin-T)GGAGTCCTGTGGCTTAA-3' (SEQ ID NO 117). The PCR product was then extracted with phenol and precipitated with ethanol. DNA was then re-suspended in 5-10 μl of 1×SCHMK buffer with addition of 300 pmoles of neutravidin (Pierce, Rockford, Ill.), incubated for 30 min. at room temperature, followed by addition of 10 μl of formamide loading dye and separation on an 8% denaturing polyacrylamide gel. The biotin-neutravidin complex remains intact through denaturation, significantly reducing the mobility of the anti-sense DNA strand relative to the sense DNA strand. Thus the strands were separated and the desired ssDNA pool members, which migrate with a higher mobility, were excised from the gel and carried into the next round of selection.

After selection rounds 3 and 5, the pool templates re-amplified using the 5' and 3' primers according to SEQ ID NO 115 and 5'-GGAGTCCTGTGGCTTAA-3' (SEQ ID NO 118) (which is completely unmodified DNA) and were cloned using TOPO TA cloning kit (Invitrogen). 84 individual sequences were generated. Individual clones were prepared without the primer binding sequences and screened for h-IgE binding at 5 and 50 nM using the dot blot assay set up and conditions previously described in Example 1A. Three clones with nucleic acid sequences according to the following SEQ ID NOs in this initial screen did not show any binding to h-IgE: SEQ ID NO 125, SEQ ID NO 137, and SEQ ID NO 138. $K_D$S were determined for the best binders identified in the initial screen, using a titration of h-IgE (30 μM to 30 μM, 3 fold dilutions) (Table 15). Several clones showed improved binding versus the parent sequence, D17.4 (SEQ ID NO 113). The clone with a nucleic acid sequence according to SEQ ID NO 140 showed among the most significant improvements in affinity relative to the parent sequence D17.4 (SEQ ID NO 113). Interestingly, the differences between the clone with a nucleic acid sequence according to SEQ ID NO 140 and clone D17.4 (SEQ ID NO 113) were quite subtle involving changes only in the proposed Watson/Crick stem directly adjacent to the loop region of the D17.4 aptamer (SEQ ID NO 113). Nearly all of the unique clones from the re-selection (including the clone with a nucleic acid sequence according to SEQ ID NO 140) had acquired mutations in the G8-C30 base pair of D17.4 to become either A8-T30 or C8-G30 effectively switching the functional groups presented in the major groove of the helix at that pairing position from a 5'-strand-carbonyl/3'-strand-amino in the case of G8-C30 to a 5'-strand-amino/3'-strand carbonyl in the cases of both A8-T30 and C8-G30. The highest affinity clones (other than that of the clone according to SEQ ID NO 140) were then redesigned with their own loop sequences (residues 9-29) and an optimized stem sequence based on the stem of the clone with a nucleic acid sequence according to SEQ ID NO 140 (residues 1-8 and 30-37). The C4-C34 mispairing was reverted to G4-C34 in the optimized SEQ ID NO 140 stem. Table 15 below shows nucleotide sequence lengths and affinities of selected DNA aptamers. Table 16 shows the nucleotide sequences of DNA aptamers selected.

TABLE 15

Lengths and binding affinities of selected DNA aptamers

| SEQ ID NO/ | Length | $K_D$ (nM) |
|------------|--------|-----------|
| 113 | 37 | 0.5-2 |
| 132 | 37 | 0.4 |
| 119 | 37 | 0.6 |
| 139 | 36 | 0.4 |
| 133 | 37 | 0.7 |
| 147 | 37 | 0.5 |
| 128 | 37 | 0.5 |
| 140 | 36 | 0.2 |
| 149 | 38 | 0.8 |
| 131 | 37 | 0.3 |
| 150 | 37 | 0.7 |
| 151 | 37 | 0.5 |
| 152 | 37 | 0.2 |
| 153 | 37 | 0.6 |
| 154 | 37 | 0.4 |
| 155 | 37 | 0.4 |
| 156 | 37 | 0.2 |

For the DNA aptamers described below all the nucleotides (A, T, C and G) are deoxy. Unless noted otherwise, the individual sequences are represented in the 5' to 3' orientation. In some embodiments, the invention comprises aptamers with a nucleic acid sequences as described in Table 16 below. In other embodiments, the nucleic acid sequences of the aptamers described in Table 16 additionally comprise a 3' cap (e.g., a 3' inverted dT (3T)), and/or a 5' amine ($NH_2$) modification to facilitate chemical coupling, and/or conjugation to a high molecular weight, non-immunogenic compound (e.g., PEG).

TABLE 16

DNA h-IgE Doped re-selection aptamer sequence information (Clone sequences are listed without the primer regions)

SEQ ID NO 113 D17.4
GGGGCACGTTTATCCGTCCCTCCTAGTGGCGTGCCCC

TABLE 16-continued

DNA h-IgE Doped re-selection aptamer sequence information (Clone sequences are listed without the primer regions)

SEQ ID NO 119
GGGGCACATTTATCCGTCCCTCCTAGTGGTGTGCCCC

SEQ ID NO 120
GGGGTACCTTTATCCGTCCCTCCTAGTGGGGTGCCCC

SEQ ID NO 121
GGGGTACCTTTATCCGTCCCTCCTAGTGGGGTACCCC

SEQ ID NO 122
GGGGCAAATTTATCCGTCCCTCCTAGTGGTTTGCCCC

SEQ ID NO 123
GGGGCATATTTATCCGTCCCTCCTAGTGGTATGCCCC

SEQ ID NO 124
GGGGCACATTTATCCGTTCCTCCTAGTGGTGTGCCCC

SEQ ID NO 125
GGGGTACATTTATCCGTCCCTCCTAGTGGCATGCCCC

SEQ ID NO 126
GGGGCATGTTTATCCGTCCCTCCTAGTGGCATGCCCC

SEQ ID NO 127
GGGGCAACTTTATCCGTTCCTCCTAGTGGGTTGCCC

SEQ ID NO 128
GGGGCACATTCATCCGTCCCTCCTAGTGGTGTGCTCC

SEQ ID NO 129
GGGGTACCTTGATCCGTCCCTCCTAGTGGGGTGCCCC

SEQ ID NO 130
GGGGCATGTTTATCCGTTCCTCCTAGTGGCATGCCCC

SEQ ID NO 131
GGGGCAGCTTTATCCGTTCCTCCTAGTGGGCTGCCTC

SEQ ID NO 132
GGGGTACCTTTATCCGTTTCTCCTAGTGGGGTGCCCC

SEQ ID NO 133
GGGGTATGTTGATCCGTCCCTCCTAGTGGCATGCCCC

SEQ ID NO 134
GGGGCATGTTCATCCGTTCCTCCTAGTGGCGTGCCCC

SEQ ID NO 135
GGGACACATTTATCCGTTACTCTTAGTGGTGTGCCCC

SEQ ID NO 136
GGGGCACATTTATCCGTTACTCTTAGTGGTGTGCCCC

SEQ ID NO 137
GGGGCACGTTTACAGTCCCTCCTTATCGCCTCCC

SEQ ID NO 138
GGGGCACGTTTACAGTCCCTCCTTATCGCCTCCC

SEQ ID NO 139
GGGCAACTTTATCCGTTCCTCTTAGTGGGTTGCCCC

SEQ ID NO 140
GGGCTACTTTATCCGTCCCTCCTAGTGGGTAGCCCC

SEQ ID NO 141
GGCACCTTTATCCGTCCCTCCTAGTGGGGTGCCCC

SEQ ID NO 142
GGGGCACCTTTATCCGTCCCTCCTAGTGGGGTGCCCC

SEQ ID NO 143
GGGCACATTCATCCGTTCCTCCTAGTGGTGTGCCCC

TABLE 16-continued

DNA h-IgE Doped re-selection aptamer sequence information (Clone sequences are listed without the primer regions)

SEQ ID NO 144
GGCACCTTTATCCGTTCCTTCTAGTGGGGTGCCC

SEQ ID NO 145
CGGCACCTTTATCCGTTACTCTTAGTGNGGTGCCCC

SEQ ID NO 146
GGCACCTTGATCCGTTCCTCCTAGTGGGGTGCCCC

SEQ ID NO 147
GCGGGCAAATTCATCCCGTCCCTCCTAGTGGTTTGCCC

SEQ ID NO 148
GGGCACTTTATCCGTTCCTTCTAGTGGGTGTCCC

SEQ ID NO 149
GGCGGCAGCTTTATCCGTACCTCCCAGTGGGCTGCTCC

SEQ ID NO 150 ARC474
GGGGCAGCTTTATCCGTACCTCCCAGTGGGCTGCCCC

SEQ ID NO 151 ARC475
GGGGCTACTTTATCCGTCCCTCCTAGTGGGTAGCCCC

SEQ ID NO 152 ARC476
GGGGCTACTTTATCCGTACCTCCCAGTGGGTAGCCCC

SEQ ID NO 153 ARC477
GGGGCTACTTGATCCGTCCCTCCTAGTGGGTAGCCCC

SEQ ID NO 154 ARC478
GGGGCTACTTCATCCGTCCCTCCTAGTGGGTAGCCCC

SEQ ID NO 155 ARC479
GGGGCTACTTTATCCGTTCCTCTTAGTGGGTAGCCCC

SEQ ID NO 156 ARC480
GGGGCTACTTTATCCGTTCCTCCTAGTGGGTAGCCCC

SEQ ID NO 157 ARC656
GGGGCTACTTTATCCGTTCCTCCTAGTGGGTAGCCCC-3T

Example 2

Aptamer Medicinal Chemistry of ARC445 for Increased Plasma Stability and Increased In Vitro Affinity A highly stable and potent variant of ARC445 (SEQ ID NO 101) was identified through a systematic synthetic approach involving multiple phases of aptamer synthesis, purification and assaying for binding activity. Modifications, such as systematic replacement of the 2'-deoxy containing residues with 2'-O methyl containing residues was the basic approach used to achieve a significant increase in plasma nuclease resistance and overall stability.

During the processes of clone screening and minimization that led to ARC445 (SEQ ID NO 101), there was excellent agreement among the relative potency of aptamers in binding (as measured by dot-blot assay previously described), ELISA, FACS and histamine release assays (described in Example 3 below). Accordingly, the majority of test variants were tested for h-IgE binding affinity in dot-blot binding assays as an indicator of relative potency. For $K_D$ determination, chemically synthesized aptamers were purified using denaturing polyacrylamide gel electrophoresis, 5'end labeled with γ-$^{32}$P ATP and were tested for direct binding to full human h-IgE. An 8 point protein titration was used in the previously described dot blot binding assay (either {100 nM, 30 nM, 10 nM, 3 nM, 1 nM, 300 pM, 100 pM, 0 pM} or {10 nM, 3 nM, 1 nM, 300 pM, 100 pM, 30 pM, 10 pM, 0 pM}) in Dulbecco's PBS (with Mg$^{++}$ and Ca$^{++}$) with 0.1 mg/mL BSA at room temperature, for 30 minutes. $K_D$ values were calculated by fitting the equation y=(max/(1+K/protein))+yint using KaleidaGraph (KaleidaGraph v. 3.51, Synergy Software). Sequences of the ARC445 derivatives synthesized, purified and assayed for binding to h-IgE as well as the results of the protein binding characterization are tabulated below in Table 17.

The first step in the process of replacing deoxy containing residues with 2'-O methyl containing residues was the synthesis and assay for binding activity of ARC1250-ARC1264 (SEQ ID NOs 158-172) each of which is equivalent to ARC445 with the addition of a 3'-inverted-dT (3T) and the replacement of a single 2'-deoxy residue with a 2'-O methyl residue. As can be seen from the binding data in Table 17, some positions readily tolerate substitution of a deoxy residue for a 2'-O methyl residue, while others do not. Interestingly, replacement of a 2'-deoxy residue with a 2'-O methyl residue conferred a significant improvement in affinity at position 10 (ARC1256) (SEQ ID NO 164).

Based upon the structure activity relationship (SAR) results from Phase 1 of the aptamer medicinal chemistry process, a second series of aptamers were designed, synthesized, purified and tested for binding to h-IgE. For these and all subsequent molecules, molecules that retained an affinity ($K_D$) of <1 nM or better where used in arriving at further aptamer design strategies. In Phase 2 which resulted in ARC1332-ARC1337 (SEQ ID NOs 173-178), the data from phase 1 was used to design more highly modified composite molecules using exclusively 2'-O methyl substitutions. The addition of stabilizing phosphorothioate containing linkages were also tested. The best of these in terms of simple binding affinity was ARC1335 (SEQ ID NO 176).

Figure 7:
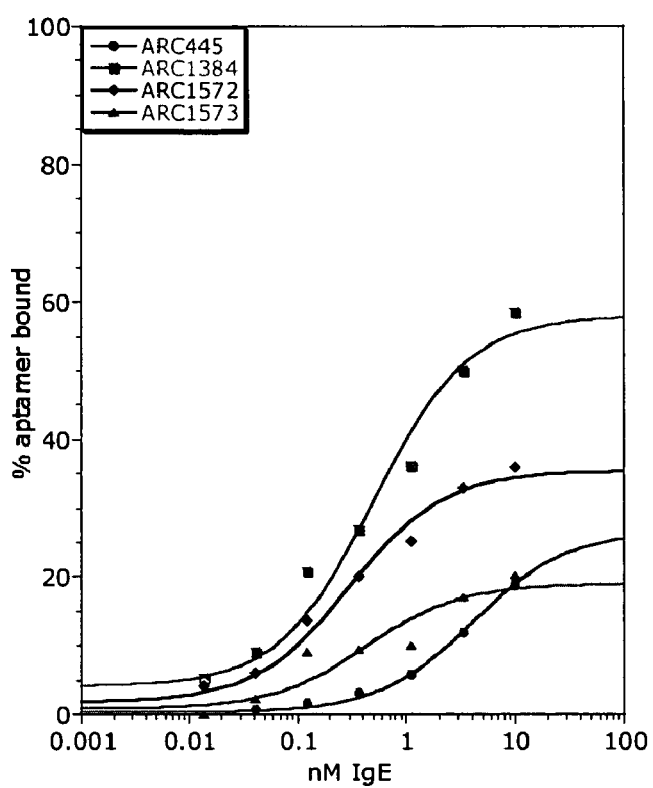
FIG. 7 shows the direct binding curves and binding affinities for ARC445 (SEQ ID NO 101) and derivatives thereof, depicting that modification yielded increased proportion binding to h-IgE.

In Phases 3 (ARC1382-ARC1384, SEQ ID NOs 179-181) and Phase 4 of aptamer medicinal chemistry process (ARC1572-1573, SEQ ID NOs 182-183) the effects of further phosphorothioate modifications in the ARC1335 (SEQ ID NO 176) context were tested. The molecule from these limited series that seemed to strike the best balance between an intermediate number of phosphorothioates and highest affinity was ARC1384 (SEQ ID NO 181) (see FIG. 7).

Figure 8:
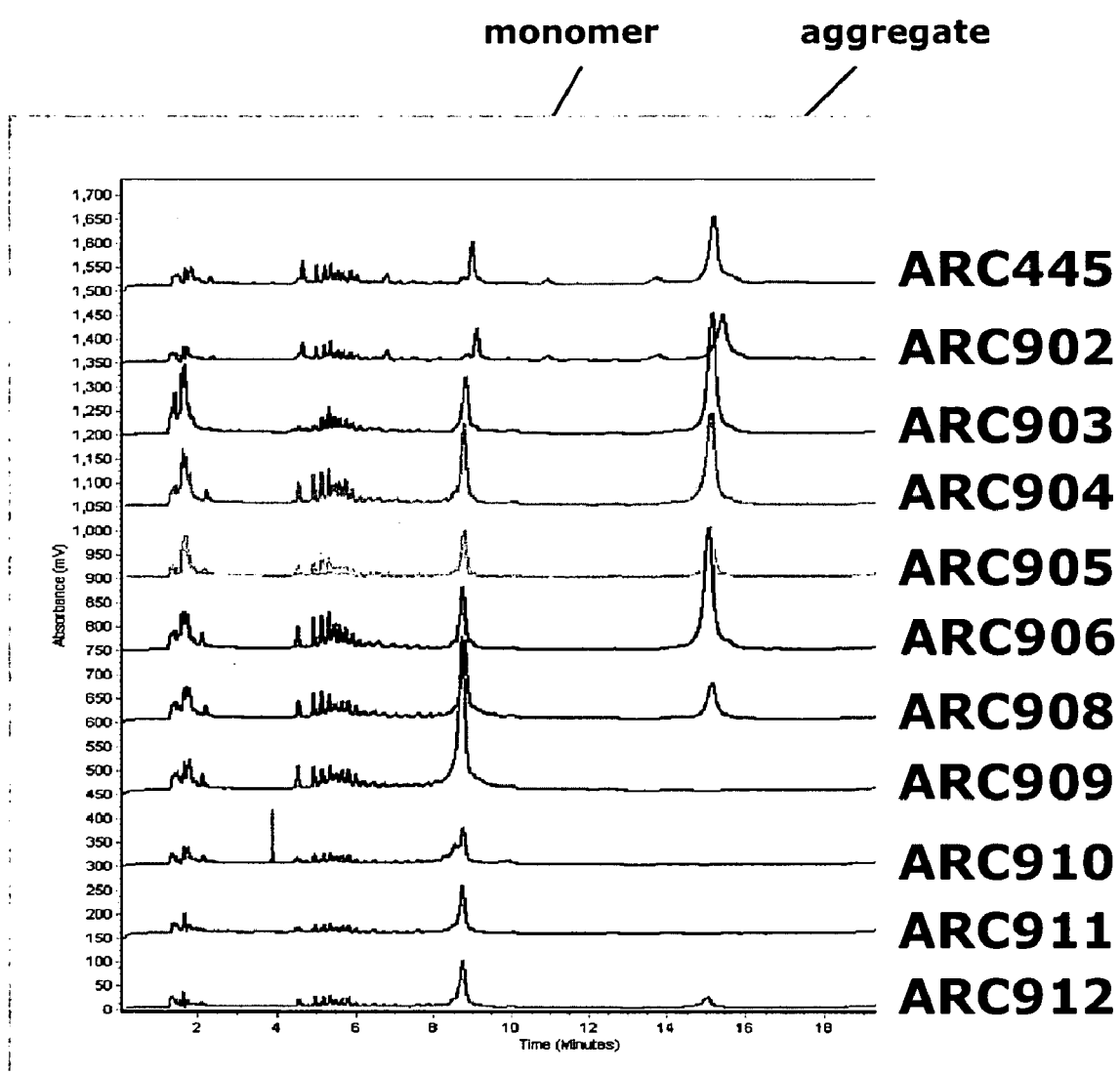
FIG. 8 depicts the ion exchange HPLC trace analysis of anti-IgE aptamer ARC445 (SEQ ID NO 101) and several derivatives thereof.
Figure 9:
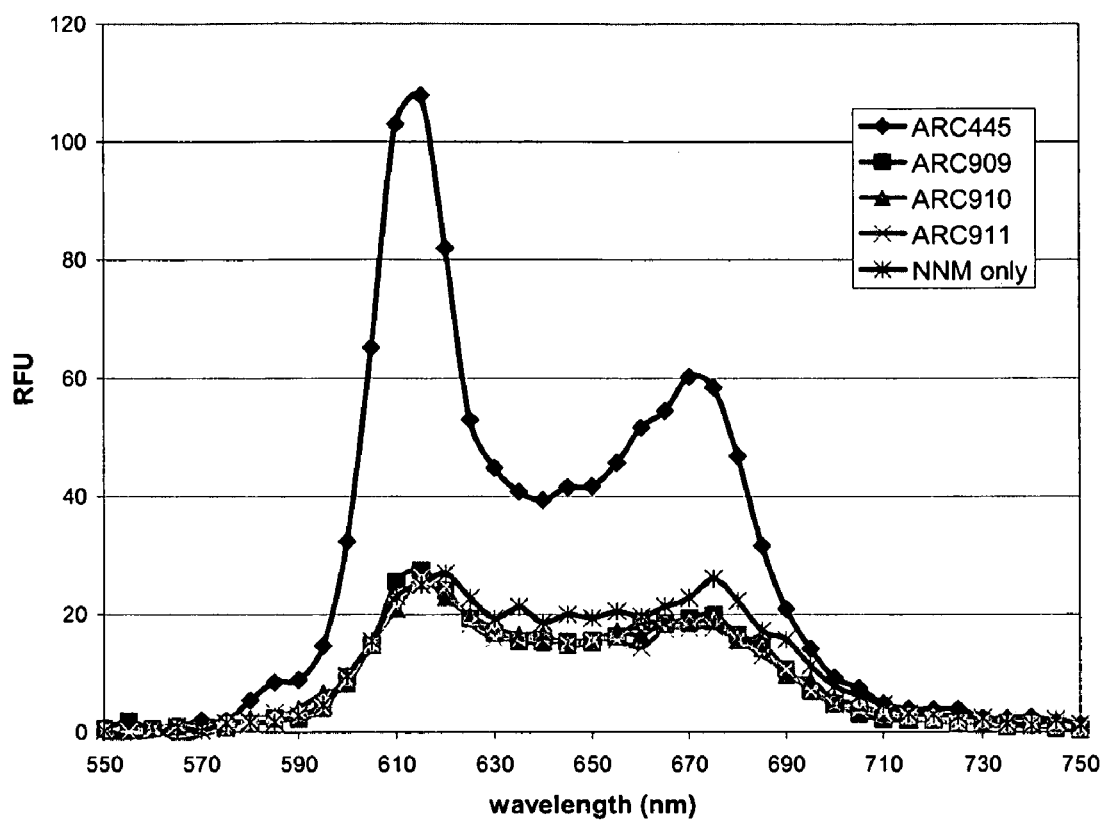
FIG. 9 is a graph showing an increase of NMM fluorescence in ARC445 (SEQ ID NO 101), and a decrease in NMM fluorescence in ARC445 derivatives, ARC909-911 (SEQ ID NOs 191-193), which contain 7-deaza-G substitutions for dG.
Figure 10:
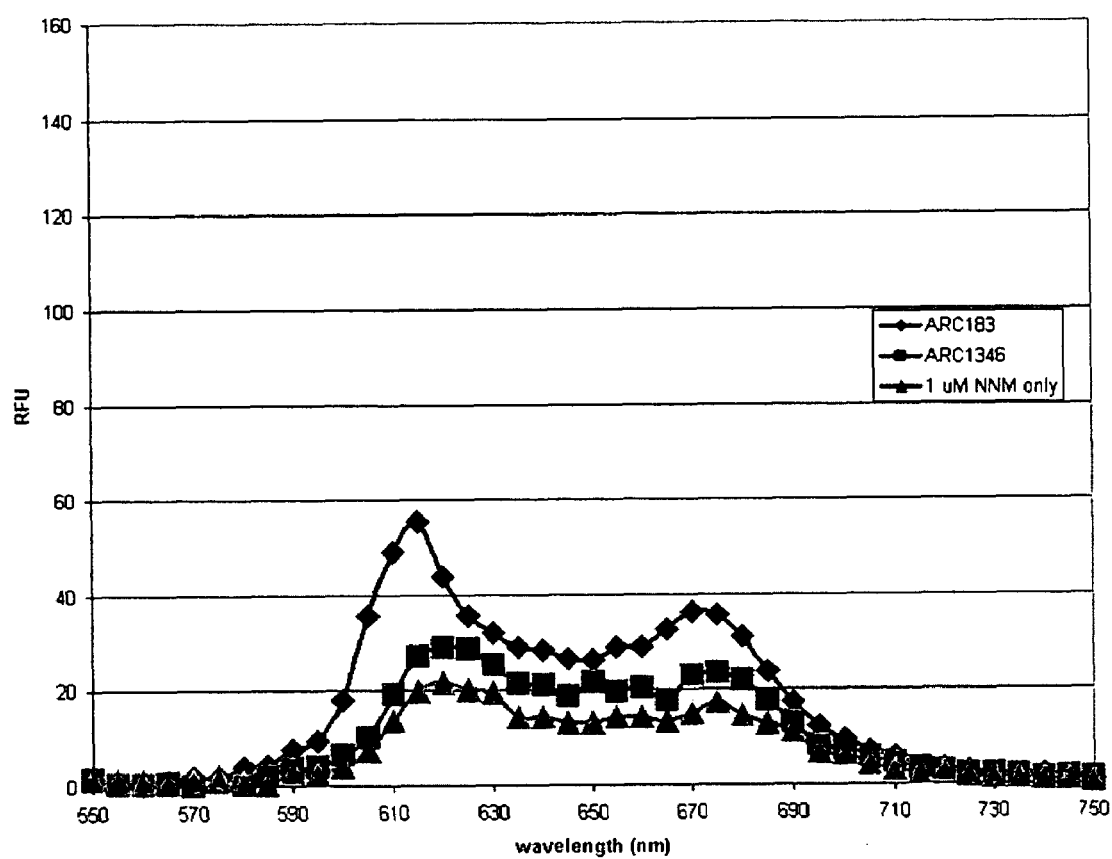
FIG. 10 is a graph showing an increase of NMM fluorescence in ARC183, (positive experimental control) and a decrease in NMM fluorescence in ARC1346 (negative experimental control).

During the synthesis of ARC445 and its derivatives, peaks were observed on ion exchange HPLC that appeared to correspond to multimeric aggregates of ARC445. FIG. 8 is an example of the HPLC trace analysis of ARC445 and several derivatives which shows the multiple peaks due to aptamer aggregation. ARC445 contains 2 runs of guanosine residues at positions 6-9 and 16-21. While not intending to be bound by theory, either or both of these runs may be the cause of aptamer aggregation. It has been reported that in much the same way that ethidium bromide fluorescence is increased upon binding to duplex RNA and DNA, that N-methylmesoporphyrin IX (NMM) fluorescence is increased upon binding to G-quartet structures (Arthanari et al., Nucleic Acids Research, 26(16): 3724 (1996); Marathais et al., Nucleic Acids Research, 28(9): 1969 (2000); Joyce et al., Applied Spectroscopy, 58(7): 831 (2004)). Thus as shown in FIG. 9, we used NMM fluorescence to establish that ARC445 does in fact adopt a G-quartet structure. According to the literature protocols, 100 microliter reactions containing ~1 micromolar NMM and ~2 micromolar aptamer in Dulbecco's PBS containing magnesium and calcium were analyzed using a SpectraMax Gemini XS fluorescence plate reader. Fluorescence emission spectra were collected from 550 to 750 nm with and excitation wavelength of 405 nm. The G-quartet structure of the anti-thrombin DNA aptamer ARC183 has long been established in the literature (Macaya et al., Proc. Natl. Acad. Sci., 90: 3745 (1993)) and thus it was used as a positive control in this experiment (FIG. 10). ARC1346 shown in FIG. 10 is an aptamer of a similar size and nucleotide composition as ARC445 that is not predicted to have a G-quartet structure and is therefore a negative control in the experiment (FIG. 10). As can be seen FIGS. 9 and 10, ARC183 and ARC445 show a significant increase in NMM fluorescence relative to NMM alone while the negative control, ARC1346 does not.

Figure 11:
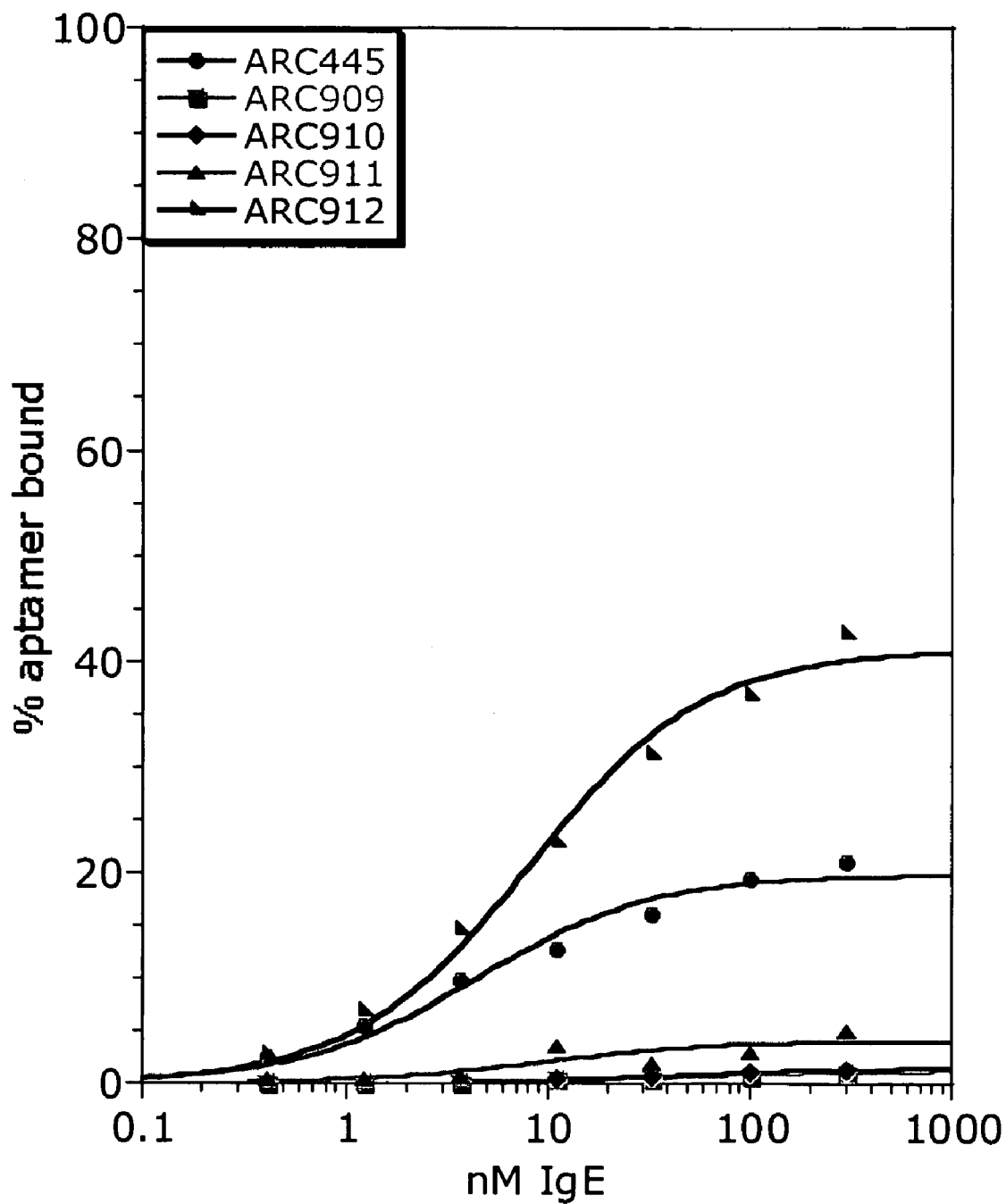
FIG. 11 shows the direct binding curves for ARC445 (SEQ ID NO 101) compared to derivatives thereof, depicting that substituting dG with 7-deaza-G (as in ARC909-911 (SEQ ID NOs 191-193)) significantly reduces proportion binding to h-IgE.

In addition to substituting dG with dG analogs and screening for minimization of the "G-quartet" signal in the NMM fluorescence assay, aptamers were screened for binding using the dot blot assay and the binding reaction conditions previously described (Dulbeccos PBS (with Ca$^{++}$ and Mg$^{++}$) plus 0.1 mg/mL BSA, room temperature for 30 minutes) to test whether dG analogs improved affinity for and thus potency against h-IgE. The first analog tested was deoxy-7-deaza G. With the nitrogen at position 7 on the purine base replaced by carbon, the hydrogen bond acceptor required for the G:G pairing in a G-quartet is effectively removed. In Phase 5.1 (SEQ ID NOs 184-201) each individual G in ARC445 is replaced by 7-deaza G. As can be seen in FIG. 8 and FIG. 9, removal of the G N-7 at positions 18-20 (ARC909-911, SEQ ID NOs 191-193) completely removed the aptamer aggregation observed by HPLC and NMM fluorescence. However these substitutions also completely remove binding to h-IgE, as demonstrated by the binding curves depicted in FIG. 11 (see also $K_D$ values reported in Table 17). ARC912 (SEQ ID NO 194) also showed significant reduction in HPLC aggregation and retained some binding to h-IgE. Based upon the binding results and HPLC for ARC912 (SEQ ID NO 194), the mC:dG pair at position 3:21 was substituted for another Watson/Crick pairing that did not have a dG at position 21, in attempts to reduce multimeric aggregation. This was done in ARC1244-ARC1249 (SEQ ID NOs 195-200) but did not yield any aptamers with affinities even comparable to ARC445 (SEQ ID NO 101) and was thus dropped as an option for modification of ARC445.

While not wishing to be bound by any theory, substitution of dG with 7-deaza-G in provided the insight that it is the longer G-run from positions 16 to 21 that is the likely cause of the aggregation phenomenon and that the N-7 position in many of the residues tested may be required for high affinity binding to h-IgE either through direct hydrogen bonding interactions or through interactions with other residues in the aptamer itself that promote functional folding of the aptamer.

In phase 5.2 of the aptamer medicinal chemistry process (SEQ ID NOs 201-211), dG was substituted with deoxy inosine in the context of ARC1335 (SEQ ID NO 176). Since deoxy inosine lacks the exocyclic amine found in deoxy guanosine, a single amino to N7 hydrogen bond is removed from a potential G-quartet for each dG to dI substitution. Binding assays for ARCs 1548, 1552-1555, and 1562-1567 (SEQ ID NOs 201-211 respectively) revealed an SAR relationship for dG to dI substitution almost completely reversed from that of the dG to 7-deaza-G substitutions. In the dI series, substitutions were not tolerated at positions 6-9 while they were tolerated from moderately to very well at positions 16-21.

Figure 12:
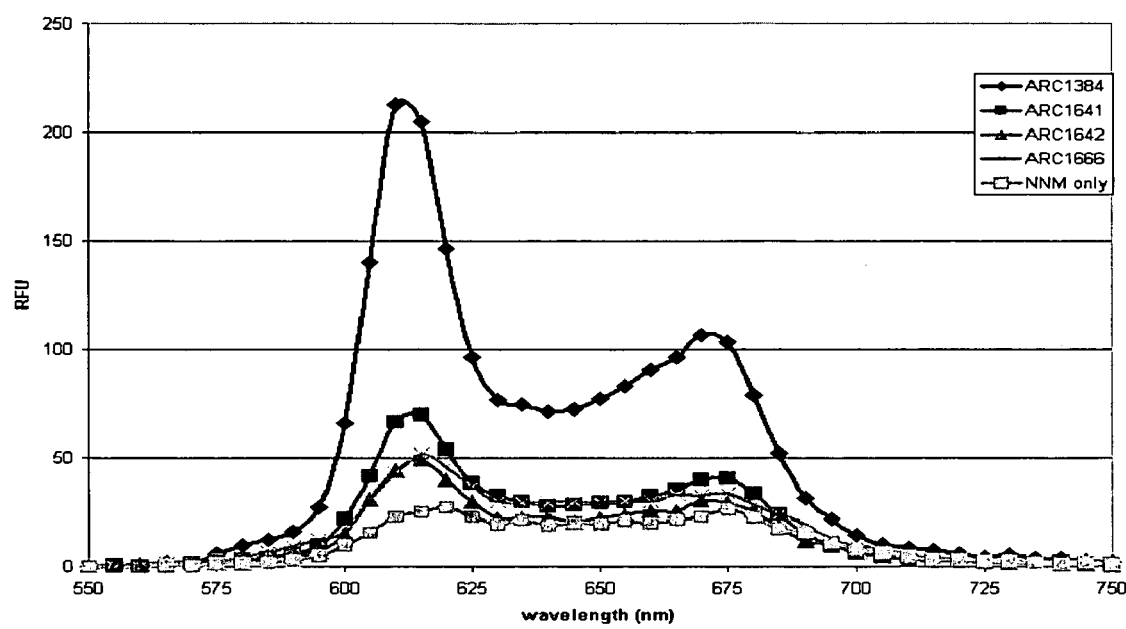
FIG. 12 is a graph showing a decrease in NMM fluorescence in ARC445 derivatives ARC1641, 1642, and 1666 (SEQ ID NOs 212, 213, and 216 respectively), which contain inosine substitutions for dG, as compared to ARC1384 (SEQ ID NO 181), an ARC445 derivative containing 2'-O-methyl and phosphorothioate substitutions but no inosine substitutions for dG. (SEQ ID NO 101).

The results from phase 5.2 led to the design of composite molecules containing multiple dG to dI substitutions in the ARC1384 context. The results from phase 5.3 (SEQ ID NOs 212-219) yielded a number of aptamers with greatly improved affinity relative to ARC445 (SEQ ID NO 101) and ARC1384 (SEQ ID NO 181). For example, ARC1666 (SEQ ID NO 216) also showed significantly reduced G-quartet formation as assayed by NMM fluorescence, as depicted in FIG. 12.

In some embodiments, the invention comprises aptamers with a nucleic acid sequences as described in Table 17 below. In some embodiments, the nucleic acid sequences of the aptamers described in Table 17, where lacking, additionally comprise a 3' cap (e.g., an inverted dT cap (3T)), and/or 5' amine ($NH_2$) modification to facilitate chemical coupling, and/or conjugation to a high molecular weight, non-immunogenic compound (e.g., PEG). In other embodiments, the nucleic acid sequences described in Table 17 lack the indicated 3' cap (e.g., a 3' inverted dT cap (3T)). Lower case letters "f", "m", and "d" denote 2'-fluoro, 2-O-methyl, and deoxy modifications respectively, "s" denotes an internucleotide phosphorothioate substitution, and "I" denotes an inosine substitution for guanosine.

TABLE 17

Sequences and Binding Affinities of ARC445 Modified Derivatives

| SEQ ID NO | ARC # | Sequences (5'→3'), (3T = inv dT), (T = dT), (s = phosphorothioate), (mN = 2'-O Methyl containing residue) (dI = deoxy) inosine containing residue) (X = 7-deaza guanosine containing residue) | $K_D$ (nM) |
|---|---|---|---|
| 101 | ARC445 | dAdGmCmCmUdGdGdGdGdAmCmCmCdAmUd GdGdGdGdGdGmCmU | 3 |
| 158 | ARC1250 | mAdGmCmCmUdGdGdGdGdAmCmCmCdAmUd GdGdGdGdGdGmCmU-3T | 11 |
| 159 | ARC1251 | dAmGmCmCmUdGdGdGdGdAmCmCmCdAmUd GdGdGdGdGdGmCmU-3T | 7 |
| 160 | ARC1252 | dAdGmCmCmUmGdGdGdGdAmCmCmCdAmUd GdGdGdGdGdGmCmU-3T | 98 |
| 161 | ARC1253 | dAdGmCmCmUdGmGdGdGdAmCmCmCdAmUd GdGdGdGdGdGmCmU-3T | 2 |
| 162 | ARC1254 | dAdGmCmCmUdGdGmGdGdAmCmCmCdAmUd GdGdGdGdGdGmCmU-3T | 24 |
| 163 | ARC1255 | dAdGmCmCmUdGdGdGmGdAmCmCmCdAmUd GdGdGdGdGdGmCmU-3T | 8 |

TABLE 17-continued

Sequences and Binding Affinities of ARC445 Modified Derivatives

| SEQ ID NO | ARC # | Sequences (5'→3'), (3T = inv dT), (T = dT), (s = phosphorothioate), (mN = 2'-O Methyl containing residue) (dI = deoxy) inosine containing residue) (X = 7-deaza guanosine containing residue) | $K_D$ (nM) |
|---|---|---|---|
| 164 | ARC1256 | dAdGmCmCmUdGdGdGdGdAmCmCmCdAmUd GdGdGdGdGdGmCmU-3T | 0.4 |
| 165 | ARC1257 | dAdGmCmCmUdGdGdGdGdAmCmCmCmAmUd GdGdGdGdGdGmCmU-3T | 6 |
| 166 | ARC1258 | dAdGmCmCmUdGdGdGdGdAmCmCmCdAmUm GdGdGdGdGdGmCmU-3T | 15 |
| 167 | ARC1259 | dAdGmCmCmUdGdGdGdGdAmCmCmCdAmUd GmGdGdGdGdGmCmU-3T | 5 |
| 168 | ARC1260 | dAdGmCmCmUdGdGdGdGdAmCmCmCdAmUd GdGmGdGdGdGmCmU-3T | 102 |
| 169 | ARC1261 | dAdGmCmCmUdGdGdGdGdAmCmCmCdAmUd GdGdGmGdGdGmCmU-3T | 63 |
| 170 | ARC1262 | dAdGmCmCmUdGdGdGdGdAmCmCmCdAmUd GdGdGdGmGdGmCmU-3T | 32 |
| 171 | ARC1263 | dAdGmCmCmUdGdGdGdGdAmCmCmCdAmUd GdGdGdGdGmGmCmU-3T | 64 |
| 172 | ARC1264 | mAmGmCmCmUdGdGdGdGdAmCmCmCdAmUd GdGdGdGmGmGmCmU-3T | 47 |
| 173 | ARC1332 | dAmGmCmCmUdGdGdGdGmAmCmCmCmAmUd GdGdGdGdGmGmCmU-3T | 0.5 |
| 174 | ARC1333 | dAmGmCmCmUdGmGdGdGdAmCmCmCdAmUd GmGdGdGdGdGmCmU-3T | 1.5 |
| 175 | ARC1334 | dAmGmCmCmUdGmGdGdGmAmCmCmCmAmUd GmGdGdGdGdGmCmU-3T | 0.3 |
| 176 | ARC1335 | mAmGmCmCmUdGmGdGdGmAmCmCmCmAmUd GmGdGdGdGdGmCmU-3T | 0.3 |
| 177 | ARC1336 | dA-s-mGmCmCmUdGmGdGdGmAmCmCmCmA mU-s-dG-s-mGdGdGdG-s-dGmCmU-3T | No Binding |
| 178 | ARC1337 | dA-s-mGmCmCmUdGmGdGdG-s-mAmCmCm CmAmU-s-dG-s-mGdG-s-dGdG-s-dGmCmU-3T | 0.2 |
| 179 | ARC1382 | mAmGmCmCmUdGmGdG-s-dGmAmCmCmCmA mUdGmGdG-s-dGdG-s-dGmCmU-3T | 1.1 |
| 180 | ARC1383 | mAmGmCmCmUdGmGdG-s-dGmAmCmCmCmA mU-s-dGmGdG-s-dGdG-s-dGmCmU-3T | 1 |
| 181 | ARC1384 | mAmGmCmCmUdGmGdG-s-dGmAmCmCmCmA mU-s-dG-s-mGdG-s-dGdG-s-dGmCmU-3T | 0.5 |
| 182 | ARC1572 | mAmGmCmCmU-s-dGmG-s-dG-s-dGmAmC mCmCmAmU-s-dGmG-s-dG-s-dG-s-dG-s-dGmCmU-3T | 0.3 |
| 183 | ARC1573 | mAmGmCmCmU-s-dG-s-dG-s-mG-s-dG-s-dGm AmCmCmAmU-s-dG-s-mG-s-dG-s-d G-s-dG-s-dG-s-mCmU-3T | 0.4 |

TABLE 17-continued

Sequences and Binding Affinities of ARC445 Modified Derivatives

Sequences (5'→3'), (3T = inv dT),(T = dT), (s = phosphorothioate), (mN = 2'-O Methyl containing residue) (dI = deoxy inosine containing residue)(X = 7-deaza guanosine containing residue)

| SEQ ID NO | ARC # | Sequence | $K_D$ (nM) |
|---|---|---|---|
| 184 | ARC902 | dAXmCmCmUdGdGdGdGdAmCmCmCdAmUdGdGdGdGdGdGmCmU | 9 |
| 185 | ARC903 | dAdGmCmCmUXdGdGdGdAmCmCmCdAmUdGdGdGdGdGdGmCmU | 14 |
| 186 | ARC904 | dAdGmCmCmUdGXdGdGdAmCmCmCdAmUdGdGdGdGdGdGmCmU | 8 |
| 187 | ARC905 | dAdGmCmCmUdGdGXdGdAmCmCmCdAmUdGdGdGdGdGdGmCmU | 9 |
| 188 | ARC906 | dAdGmCmCmUdGdGdGXdAmCmCmCdAmUdGdGdGdGdGdGmCmU | 88 |
| 189 | ARC907 | dAdGmCmCmUdGdGdGdGdAmCmCmCdAmUXdGdGdGdGdGmCmU | 22 |
| 190 | ARC908 | dAdGmCmCmUdGdGdGdGdAmCmCmCdAmUdGXdGdGdGdGmCmU | 3 |
| 191 | ARC909 | dAdGmCmCmUdGdGdGdGdAmCmCmCdAmUdGdGXdGdGdGmCmU | No Binding |
| 192 | ARC910 | dAdGmCmCmUdGdGdGdGdAmCmCmCdAmUdGdGdGXdGdGmCmU | No Binding |
| 193 | ARC911 | dAdGmCmCmUdGdGdGdGdAmCmCmCdAmUdGdGdGdGXdGmCmU | No Binding |
| 194 | ARC912 | dAdGmCmCmUdGdGdGdGdAmCmCmCdAmUdGdGdGdGdGXmCmU | 9 |
| 195 | ARC1244 | dAdGdGmCmUdGdGdGdGdAmCmCmCdAmUdGdGdGdGdGmCmCmU | 450 |
| 196 | ARC1245 | dAdGdGmCmUdGdGdGdGdAmCmCmCdAmUdGdGdGdGdGmCmCmU | 198 |
| 197 | ARC1246 | dAdGmUmCmUdGdGdGdGdAmCmCmCdAmUdGdGdGdGdGdAmCmU | 34 |
| 198 | ARC1247 | dAdGmUmCmUdGdGdGdGdAmCmCmCdAmUdGdGdGdGdGmAmCmU | 192 |
| 199 | ARC1248 | dAdGdAmCmUdGdGdGdGdAmCmCmCdAmUdGdGdGdGdGmUmCmU | 38 |
| 200 | ARC1249 | dAdGdAmAmCmUdGdGdGdGdAmCmCmCdAmUdGdGdGdGdGmUmCmU | 130 |
| 201 | ARC1548 | mAdImCmCmUdGmGdGdGdGmAmCmCmCmAmUdGmGdGdGdGmCmU-3T | 3.3 |
| 202 | ARC1552 | mAXmCmCmUdGdImGdGdGmAmCmCmCmAmUdGmGdGdGdGmCmU-3T | No Binding |
| 203 | ARC1553 | mAmGmCmCmUdGdIdGdGmAmCmCmCmAmUdGmGdGdGdGmCmU-3T | No Binding |
| 204 | ARC1554 | mAmGmCmCmUdGmGdIdGdGmAmCmCmCmAmUdGmGdGdGdGmCmU-3T | No Binding |
| 205 | ARC1555 | mAmGmCmCmUdGmGdGdIdGmAmCmCmCmAmUdGmGdGdGdGmCmU-3T | No Binding |
| 206 | ARC1562 | mAmGmCmCmUdGmGdGdGmAmCmCmCmAmUdImGdGdGdGdGmCmU-3T | 0.6 |
| 207 | ARC1563 | mAmGmCmCmUdGmGdGdGmAmCmCmCmAmUdGdIdGdGdGdGmCmU-3T | 2.2 |
| 208 | ARC1564 | mAmGmCmCmUdGmGdGdGmAmCmCmCmAmUdGmGdIdGdGdGmCmU-3T | 0.5 |
| 209 | ARC1565 | mAmGmCmCmUdGmGdGdGmAmCmCmCmAmUdGmGdGdIdGdGmCmU-3T | 1.4 |
| 210 | ARC1566 | mAmGmCmCmUdGmGdGdGmAmCmCmCmAmUdGmGdGdGdIdGmCmU-3T | 0.1 |
| 211 | ARC1567 | mAmGmCmCmUdGmGdGdGmAmCmCmCmAmUdGmGdGdGdGdImCmU-3T | 3.5 |
| 212 | ARC1641 | mAmGmCmCmUdGmGdG-s-dGmAmCmCmAmU-s-dG-s-mGdG-s-dGdI-s-dGmCmU-3T | 0.4 |
| 213 | ARC1642 | mAmGmCmCmUdGmGdG-s-dGmAmCmCmAmU-s-dI-s-mGdG-s-dGdI-s-dGmCmU-3T | 0.4 |
| 214 | ARC1643 | mAmGmCmCmU-s-dGmG-s-dG-s-dGmAmCmCmAmU-s-dGmG-s-dG-s-dG-s-dI-s-dGmCmU-3T | 1.1 |
| 215 | ARC1644 | mAmGmCmCmU-s-dGmG-s-dG-s-dGmAmCmCmAmU-s-dImG-s-dG-s-dG-s-dI-s-dGmCmU-3T | 1.7 |
| 216 | ARC1666 | mAmGmCmCmUdGmGdG-s-dGmAmCmCmAmU-s-dI-s-mGdI-s-dGdI-s-dGmCmU-3T | 0.035 |
| 217 | ARC1667 | mAmGmCmCmUdGmGdG-s-dGmAmCmCmAmU-s-dG-s-mGdI-s-dGdI-s-dGmCmU-3T | 0.4 |
| 218 | ARC1728 | mAmGmCmCmU-s-dGmG-s-dG-s-dGmAmCmCmAmU-s-dGmG-s-dI-s-dG-s-dI-s-dGmCmU-3T | 2.3 |
| 219 | ARC1729 | mAmGmCmCmU-s-dGmG-s-dG-s-dGmAmCmCmAmU-s-dImG-s-dI-s-dG-s-dI-s-dGmCmU-3T | 1 |

Example 2F

ARC656 Aptamer Medicinal Chemistry

A highly stable and potent variant of ARC656 (SEQ ID NO 157) (described in Example 2D) was identified through a systematic synthetic approach involving multiple phases of aptamer synthesis, purification and assay for binding activity. Systematic replacement of the 2'-deoxy containing residues with 2'-O methyl containing residues was the basic approach used, in order to achieve a significant increase in plasma nuclease resistance and overall stability.

During the processes of clone screening and minimization that led to ARC656 (SEQ ID NO 157), there was excellent agreement among the relative potency of aptamers in binding (as measured by dot-blot assay previously described), ELISA, FACS and histamine release assays (described in Example 3 below). Accordingly the test variant binding affinity for h-IgE measured in a dot-blot assay binding assay was used to characterize the relative potency of the majority of the aptamers synthesized. For $K_D$ determination, chemically synthesized aptamers were purified using denaturing polyacrylamide gel electrophoresis, 5'end labeled with $\gamma$-$^{32}$P ATP and were tested for direct binding to full human IgE. An 8 point protein titration was used in the dot blot binding assay {30 nM, 10 nM, 3 nM, 1 nM, 300 pM, 100 pM, 30 pM 0 pM} using Dulbecco's PBS (with Mg$^{++}$ and Ca$^{++}$) with 0.1 mg/mL BSA. $K_D$ values were calculated by fitting the equation y=(max/(1+K/protein))+yint using KaleidaGraph (Kaleida-Graph v. 3.51, Synergy Software). Sequences of the ARC656 derivatives synthesized, purified and assayed for binding to h-IgE as well as the results of the protein binding characterization are tabulated below in Table 18.

The first step in the process of replacing deoxy containing residues with 2'-O methyl containing residues was the synthesis and assay for binding activity of ARC1265-ARC1306 (SEQ ID NOs 220-261), each of which is equivalent to ARC656 with the replacement of a single 2'-deoxy residue with a 2'-O methyl residue. As can be seen from the binding data in Table 18, some positions readily tolerate substitution of a deoxy residue for a 2'-O methyl residue, while others do not. The proposed stem region of ARC656 best tolerated substitution of deoxy containing residues with 2'-O methyl residues. In addition, phase one included some block substitutions of deoxy to 2'-O methyl in the stem region of the aptamer.

Based upon the structure activity relationship (SAR) results from Phase 1 of the aptamer medicinal chemisty design, a second series of aptamers were designed, synthesized, purified and tested for binding to h-IgE. The addition of stabilizing phosphorothioate containing linkages (ARC1391 (SEQ ID NO 266) & ARC1417 (SEQ ID NO 292)) were also tested. The best of these in terms of simple binding affinity was ARC1410 (SEQ ID NO 285). While it is clear that many of the constructs tested retain relatively high affinity binding for h-IgE, few of them retain affinity equal to the parent compound ARC656 (SEQ ID NO 157).

In some embodiments, the invention comprises aptamers with a nucleic acid sequences as described in Table 18 below. In some embodiments, the nucleic acid sequences of the aptamers described in Table 18, where lacking, additionally comprise a 3' cap (e.g., an inverted dT cap (3T)), and/or 5' amine (NH$_2$) modification to facilitate chemical coupling, and/or conjugation to a high molecular weight, non-immunogenic compound (e.g., PEG). In other embodiments, the nucleic acid sequences described in Table 18 lack the indicated 3' cap (e.g., a 3' inverted dT cap (3T)). Lower case letters "f", "m", and "d" preceding nucleotide abbreviations A, C, G, or T denote 2'-fluoro, 2-O-methyl, and deoxy modifications respectively, and "s" denotes an internucleotide phosphorothioate substitution.

TABLE 18

Sequences and Binding Affinities of ARC656 Modified Derivatives

| ARC # | Sequences (5'→3'), (3T = inv dT), (T = dT), (s = phosphorothioate), (mN = 2'-O Methyl containing residue) (dI = deoxy inosine containing residue) (X = 7-deaza guanosine containing residue) | $K_D$ (nM) |
|---|---|---|
| 157 ARC656 | dGdGdGdGdCTdAdCTTTdATdCdCdGTTd CdCTdCdCTdAdGTdGdGdGTdAdGdCdCd CdC-3T | 0.2 |
| 220 ARC1265 | mGdGdGdGdCTdAdCTTTdATdCdCdGTTd CdCTdCdCTdAdGTdGdGdGTdAdGdCdCd CdC-3T | 0.2 |
| 221 ARC1266 | dGmGdGdGdCTdAdCTTTdATdCdCdGTTd CdCTdCdCTdAdGTdGdGdGTdAdGdCdCd CdC-3T | 0.2 |
| 222 ARC1267 | dGdGmGdGdCTdAdCTTTdATdCdCdGTTd CdCTdCdCTdAdGTdGdGdGTdAdGdCdCd CdC-3T | 0.1 |
| 223 ARC1268 | dGdGdGmGdCTdAdCTTTdATdCdCdGTTd CdCTdCdCTdAdGTdGdGdGTdAdGdCdCd CdC-3T | 0.2 |

TABLE 18-continued

Sequences and Binding Affinities of ARC656 Modified Derivatives

| | ARC # | Sequences (5'→3'), (3T = inv dT),(T = dT), (s = phosphorothioate), (mN = 2'-O Methyl containing residue) (dI = deoxy inosine containing residue)(X = 7-deaza guanosine containing residue) | $K_D$ (nM) |
|---|---|---|---|
| 224 | ARC1269 | dGdGdGdGmCTdAdCTTTdATdCdCdGTTdCdCTdCdCTdAdGTdGdGdGTdAdGdCdCdC-3T | 0.3 |
| 225 | ARC1270 | dGdGdGdGdCmUdAdCTTTdATdCdCdGTTdCdCTdCdCTdAdGTdGdGdGTdAdGdCdCdC-3T | 0.2 |
| 226 | ARC1271 | dGdGdGdGdCTmAdCTTTdATdCdCdGTTdCdCTdCdCTdAdGTdGdGdGTdAdGdCdCdC-3T | 0.2 |
| 227 | ARC1272 | dGdGdGdGdCTdAmCTTTdATdCdCdGTTdCdCTdCdCTdAdGTdGdGdGTdAdGdCdCdC-3T | 0.2 |
| 228 | ARC1273 | dGdGdGdGdCTdAdCmUTTdATdCdCdGTTdCdCTdCdCTdAdGTdGdGdGTdAdGdCdCdC-3T | 3 |
| 229 | ARC1274 | dGdGdGdGdCTdAdCTmUTdATdCdCdGTTdCdCTdCdCTdAdGTdGdGdGTdAdGdCdCdC-3T | 2 |
| 230 | ARC1275 | dGdGdGdGdCTdAdCTTmUdATdCdCdGTTdCdCTdCdCTdAdGTdGdGdGTdAdGdCdCdC-3T | 0.3 |
| 231 | ARC1276 | dGdGdGdGdCTdAdCTTTmAdTdCdCdGTTdCdCTdCdCTdAdGTdGdGdGTdAdGdCdCdC-3T | 3 |
| 232 | ARC1277 | dGdGdGdGdCTdAdCTTTdAmUdCdCdGTTdCdCTdCdCTdAdGTdGdGdGTdAdGdCdCdC-3T | 6 |
| 233 | ARC1278 | dGdGdGdGdCTdAdCTTTdATmCdCdGTTdCdCTdCdCTdAdGTdGdGdGTdAdGdCdCdC-3T | 2 |
| 234 | ARC1279 | dGdGdGdGdCTdAdCTTTdATdCmCdGTTdCdCTdCdCTdAdGTdGdGdGTdAdGdCdCdC-3T | 0.8 |
| 235 | ARC1280 | dGdGdGdGdCTdAdCTTTdATdCdCmGTTdCdCTdCdCTdAdGTdGdGdGTdAdGdCdCdC-3T | 0.6 |
| 236 | ARC1281 | dGdGdGdGdCTdAdCTTTdATdCdCdGmUTdCdCTdCdCTdAdGTdGdGdGTdAdGdCdCdC-3T | 0.1 |
| 237 | ARC1282 | dGdGdGdGdCTdAdCTTTdATdCdCdGTmUdCdCTdCdCTdAdGTdGdGdGTdAdGdCdCdC-3T | 0.2 |
| 238 | ARC1283 | dGdGdGdGdCTdAdCTTTdATdCdCdGTTmCdCTdCdCTdAdGTdGdGdGTdAdGdCdCdC-3T | 0.6 |
| 239 | ARC1284 | dGdGdGdGdCTdAdCTTTdATdCdCdGTTdCmCTdCdCTdAdGTdGdGdGTdAdGdCdCdC-3T | 0.1 |

TABLE 18-continued

Sequences and Binding Affinities of
ARC656 Modified Derivatives

| ARC # | Sequences (5'→3'), (3T = inv dT),(T = dT), (s = phosphorothioate), (mN = 2'-O Methyl containing residue) (dI = deoxy inosine containing residue)(X = 7-deaza guanosine containing residue) | $K_D$ (nM) |
|---|---|---|
| 240 ARC1285 | dGdGdGdGdCTdAdCTTTdATdCdCdGTTd CdCmUdCdCTdAdGTdGdGdGdTdAdGdCdC dCdC-3T | 0.8 |
| 241 ARC1286 | dGdGdGdGdCTdAdCTTTdATdCdCdGTTd CdCTmCdCTdAdGTdGdGdGdTdAdGdCdCd CdC-3T | 7 |
| 242 ARC1287 | dGdGdGdGdCTdAdCTTTdATdCdCdGTTd CdCTdCmCTdAdGTdGdGdGdTdAdGdCdCd CdC-3T | 1.0 |
| 243 ARC1288 | dGdGdGdGdCTdAdCTTTdATdCdCdGTTd CdCTdCdCmUdAdGTdGdGdGdTdAdGdCdC dCdC-3T | 2 |
| 244 ARC1289 | dGdGdGdGdCTdAdCTTTdATdCdCdGTTd CdCTdCdCTmAdGTdGdGdGdTdAdGdCdCd CdC-3T | No Binding |
| 245 ARC1290 | dGdGdGdGdCTdAdCTTTdATdCdCdGTTd CdCTdCdCTdAmGTdGdGdGdTdAdGdCdCd CdC-3T | No Binding |
| 246 ARC1291 | dGdGdGdGdCTdAdCTTTdATdCdCdGTTd CdCTdCdCTdAdGmUdGdGdGdTdAdGdCdC dCdC-3T | No Binding |
| 247 ARC1292 | dGdGdGdGdCTdAdCTTTdATdCdCdGTTd CdCTdCdCTdAdGTmGdGdGdTdAdGdCdCd CdC-3T | 22 |
| 248 ARC1293 | dGdGdGdGdCTdAdCTTTdATdCdCdGTTd CdCTdCdCTdAdGTdGmGdGdTdAdGdCdCd CdC-3T | No Binding |
| 249 ARC1294 | dGdGdGdGdCTdAdCTTTdATdCdCdGTTd CdCTdCdCTdAdGTdGdGmTdAdGdCdCd CdC-3T | 8 |
| 250 ARC1295 | dGdGdGdGdCTdAdCTTTdATdCdCdGTTd CdCTdCdCTdAdGTdGdGdGmUdAdGdCdC dCdC-3T | 3 |
| 251 ARC1296 | dGdGdGdGdCTdAdCTTTdATdCdCdGTTd CdCTdCdCTdAdGTdGdGdGdTmAdGdCdCd CdC-3T | 1.2 |
| 252 ARC1297 | dGdGdGdGdCTdAdCTTTdATdCdCdGTTd CdCTdCdCTdAdGTdGdGdGdTdAmGdCdCd CdC-3T | 0.8 |
| 253 ARC1298 | dGdGdGdGdCTdAdCTTTdATdCdCdGTTd CdCTdCdCTdAdGTdGdGdGdTdAdGmCdCd CdC-3T | 0.4 |
| 254 ARC1299 | dGdGdGdGdCTdAdCTTTdATdCdCdGTTd CdCTdCdCTdAdGTdGdGdGdTdAdGdCmCd CdC-3T | 0.5 |
| 255 ARC1300 | dGdGdGdGdCTdAdCTTTdATdCdCdGTTd CdCTdCdCTdAdGTdGdGdGdTdAdGdCdCm CdC-3T | 0.7 |

TABLE 18-continued

Sequences and Binding Affinities of ARC656 Modified Derivatives

| | ARC # | Sequences (5'→3'), (3T = inv dT), (T = dT), (s = phosphorothioate), (mN = 2'-O Methyl containing residue) (dI = deoxy inosine containing residue)(X = 7-deaza guanosine containing residue) | $K_D$ (nM) |
|---|---|---|---|
| 256 | ARC1301 | dGdGdGdGdCTdAdCTTTdATdCdCdGTTdCdCTdCdCTdAdGTdGdGdGTdAdGdCdCdCmC-3T | 0.5 |
| 257 | ARC1302 | mGmGmGmGdCTmAdCTTTdATdCdCdGTTdCdCTdCdCTdAdGTdGdGmGTmAmGdCdCdCdC-3T | 19 |
| 258 | ARC1303 | dGdGdGdGmCmUdAmCTTTdATdCdCdGTTdCdCTdCdCTdAdGTdGdGdGmUdAdGmCmCmCmC-3T | 1.3 |
| 259 | ARC1304 | mGmGmGmGdCTdAdCTTTdATdCdCdGTTdCdCTdCdCTdAdGTdGdGdGTdAdGmCmCmCmC-3T | 0.6 |
| 260 | ARC1305 | mGmGmGmGmCTdAdCTTTdATdCdCdGTTdCdCTdCdCTdAdGTdGdGdGTdAmGmCmCmCmC-3T | No Binding |
| 261 | ARC1306 | mGmGmGmCTdAdCTTTdATdCdCdGTTdCdCTdCdCTdAdGTdGdGdGTdAmGmCmCmC-3T | 14 |
| 262 | ARC1387 | mGmGmGmGdCTmAdCTTTdATdCdCdGTTdCdCTdCdCTdAdGTdGdGdGTdAmGmCmCmCmC-3T | 2.4 |
| 263 | ARC1388 | mGmGmGmGmCmUmAmCTTTdATdCdCdGTTdCdCTdCdCTdAdGTdGdGdGTdAmGmCmCmCmC-3T | 4.4 |
| 264 | ARC1389 | mGmGmGmGdCTmAdCTTmUdATdCdCdGmUmUdCmCTdCdCTdAdGTdGdGdGTdAmGmCmCmCmC-3T | 5.4 |
| 265 | ARC1390 | mGmGmGmGmCmUmAmCTTmUdATdCdCdGmUmUdCmCTdCdCTdAdGTdGdGdGTdAmGmCmCmCmC-3T | 17 |
| 266 | ARC1391 | mGmGmGmGdCTmAdC-s-TTTdATdCdCdGTTdCdCTdCdCTdAdGTdGdGdGTdAmGmCmCmCmC-3T | 4.4 |
| 267 | ARC1392 | mGmGmGmGdCTmAdCT-s-TTdATdCdCdGTTdCdCTdCdCTdAdGTdGdGdGTdAmGmCmCmCmC-3T | 3 |
| 268 | ARC1393 | mGmGmGmGdCTmAdCTT-s-TdATdCdCdGTTdCdCTdCdCTdAdGTdGdGdGTdAmGmCmCmCmC-3T | No Binding |
| 269 | ARC1394 | mGmGmGmGdCTmAdCTTT-s-dATdCdCdGTTdCdCTdCdCTdAdGTdGdGdGTdAmGmCmCmCmC-3T | 8.1 |
| 270 | ARC1395 | mGmGmGmGdCTmAdCTTTdA-s-TdCdCdGTTdCdCTdCdCTdAdGTdGdGdGTdAmGmCmCmCmC-3T | 5.7 |
| 271 | ARC1396 | mGmGmGmGdCTmAdCTTTdAT-s-dCdCdGTTdCdCTdCdCTdAdGTdGdGdGTdAmGmCmCmCmC-3T | 2 |

TABLE 18-continued

Sequences and Binding Affinities of
ARC656 Modified Derivatives

| ARC # | Sequences (5'→3'), (3T = inv dT),(T = dT), (s = phosphorothioate), (mN = 2'-O Methyl containing residue) (dI = deoxy inosine containing residue)(X = 7-deaza guanosine containing residue) | $K_D$ (nM) |
|---|---|---|
| 272 ARC1397 | mGmGmGmGdCTmAdCTTTdATdC-s-dCdG TTdCdTdCdCTdAdGTdGdGdGTdAmGmC mCmCmC-3T | 1.8 |
| 273 ARC1398 | mGmGmGmGdCTmAdCTTTdATdCdC-s-dG TTdCdTdCdCTdAdGTdGdGdGTdAmGmC mCmCmC-3T | 2.7 |
| 274 ARC1399 | mGmGmGmGdCTmAdCTTTdATdCdCdG-s- TTdCdTdCdCTdAdGTdGdGdGTdAmGmC mCmCmC-3T | 1.8 |
| 275 ARC1400 | mGmGmGmGdCTmAdCTTTdATdCdCdGT- s-TdCdCTdCdCTdAdGTdGdGdGTdAmGm CmCmCmC-3T | 2.4 |
| 276 ARC1401 | mGmGmGmGdCTmAdCTTTdATdCdCdGTT- s-dCdCTdCdCTdAdGTdGdGdGTdAmGmC mCmCmC-3T | 2 |
| 277 ARC1402 | mGmGmGmGdCTmAdCTTTdATdCdCdGTTd C-s-dCTdCdCTdAdGTdGdGdGTdAmGmC mCmCmC-3T | 2.1 |
| 278 ARC1403 | mGmGmGmGdCTmAdCTTTdATdCdCdGTTd CdC-s-TdCdCTdAdGTdGdGdGTdAmGmC mCmCmC-3T | Not Done |
| 279 ARC1404 | mGmGmGmGdCTmAdCTTTdATdCdCdGTTd CdCT-s-dCdCTdAdGTdGdGdGTdAmGmC mCmCmC-3T | 1.8 |
| 280 ARC1405 | mGmGmGmGdCTmAdCTTTdATdCdCdGTTd CdCTdC-s-dCTdAdGTdGdGdGTdAmGmC mCmCmC-3T | 2.5 |
| 281 ARC1406 | mGmGmGmGdCTmAdCTTTdATdCdCdGTTd CdCTdCdC-s-TdAdGTdGdGdGTdAmGmC mCmCmC-3T | 3.2 |
| 282 ARC1407 | mGmGmGmGdCTmAdCTTTdATdCdCdGTTd CdCTdCdCT-s-dAdGTdGdGdGTdAmGmC mCmCmC-3T | 1.8 |
| 283 ARC1408 | mGmGmGmGdCTmAdCTTTdATdCdCdGTTd CdCTdCdCTdA-s-dGTdGdGdGTdAmGmC mCmCmC-3T | 1 |
| 284 ARC1409 | mGmGmGmGdCTmAdCTTTdATdCdCdGTTd CdCTdCdCTdAdG-s-TdGdGdGTdAmGmC mCmCmC-3T | Not Done |
| 285 ARC1410 | mGmGmGmGdCTmAdCTTTdATdCdCdGTTd CdCTdCdCTdAdGT-s-dGdGdGTdAmGmC mCmCmC-3T | 0.7 |
| 286 ARC1411 | mGmGmGmGdCTmAdCTTTdATdCdCdGTTd CdCTdCdCTdAdGTdG-s-dGdGTdAmGmC mCmCmC-3T | 5.4 |
| 287 ARC1412 | mGmGmGmGdCTmAdCTTTdATdCdCdGTTd CdCTdCdCTdAdGTdGdG-s-dGTdAmGmC mCmCmC-3T | 2.5 |

TABLE 18-continued

Sequences and Binding Affinities of
ARC656 Modified Derivatives

Sequences (5'→3'),
(3T = inv dT), (T = dT),
(s = phosphorothioate),
(mN = 2'-O Methyl
containing residue)
(dI = deoxy
inosine containing
residue) (X =
7-deaza guanosine

| | ARC # | containing residue) | $K_D$ (nM) |
|---|---|---|---|
| 288 | ARC1413 | mGmGmGmGdCTmAdCTTTdATdCdCdGTTd CdCTdCdCTdAdGTdGdGdG-s-TdAmGmC mCmCmC-3T | 3.3 |
| 289 | ARC1414 | mGmGmGmGdCTmAdCTTTdATdCdCdGTTd CdCTdCdCTdAdGTdGdGdGT-s-dAmGmC mCmCmC-3T | 2.9 |
| 290 | ARC1415 | mGmGmGmGdCTmAdCT-s-TTdA-s-TdC- s-dCdGTT-s-dCdCT-s-dCdCT-s-dAd GT-s-dGdGdG-s-TdAmGmCmCmCmC-3T | 1.2 |
| 291 | ARC1416 | mGmGmGmGmCmUmAmCT-s-TTdA-s-Td C-s-dCdGTT-s-dCdCT-s-dCdCT-s-d AdGT-s-dGdGdG-s-TdAmGmCmCmCmC- 3T | No Binding |
| 292 | ARC1417 | mGmGmGmGmCmUmAmCT-s-TmUdA-s-Td C-s-dCdGmUmUdCmCT-s-dCdCT-s-dA dGT-s-dGdGdG-s-TdAmGmCmCmCmC-3 T | 27 |

Example 2G

Synthesis of Aptamer-5'-PEG Conjugates

The oligonucleotide 5' NH₂ mA mG mC mC mU dG mG dG-s-dG mA mC mC mC mA mU-s-dI-s-mG dI-s-dG dI-s-dG mC mU-idT 3' (ARC1666, SEQ ID NO 216) was synthesized on an AKTA OligoPilot 100 synthesizer (GE Healthcare, Uppsala, Sweden) according to the recommended manufacturer's procedures using standard commercially available 2'-OMe RNA, deoxyinosine and DNA phosphoramidites (Glen Research, Sterling, Va.) and a inverted deoxythymidine CPG support. A terminal amine functions was attached with a 5'-amino-modifier C6-TFA (Glen Research, Sterling, Va.). After deprotection, the oligonucleotide was purified by ion exchange chromatography on Super Q 5PW (30) resin (Tosoh Biosciences) and ethanol precipitated.

Aliquots of the 5'-amine-modified aptamer were conjugated to different PEG moieties post-synthetically (e.g., 40 kDa, 60 kDa PEG moieties). Aptamers were dissolved in a water/DMSO (1:1) solution to a concentration between 1.5 and 3 mM. Sodium carbonate buffer, pH 8.5, was added to a final concentration of 100 mM, and the oligo was reacted overnight with a 1.7-3 fold molar excess of the desired PEG reagent (e.g. 40 kDa Sunbright GL2-400NP p-nitrophenyl carbonate ester [NOF Corp, Japan], 40 kDa or 60 kDa mPEG2-NHS ester [Nektar, Huntsville Ala.]) dissolved in an equal volume of acetonitrile. The resulting 40 kDa or 60 kDa PEGylated products were purified by ion exchange chromatography on Super Q 5PW (30) resin (Tosoh Biosciences), and desalted using reverse phase chromatography performed on Amberchrom CG300-S resin (Rohm and Haas), and lyophilized.

The resulting PEGylated aptamer sequences are listed in Table 19 below. Lower case letters "f", "m", and "d" denote 2'-fluoro, 2-O-methyl, and deoxy modifications respectively, "s" denotes an internucleotide phopshorothioate substitution, "I" denotes an inosine substitution for guanosine, "NH" denotes an amine to facilitate chemical coupling, and "3T" denotes a 3' inverted dT.

TABLE 19

5' PEG conjugates of anti-IgE aptamer ARC1666

ARC1787 (SEQ ID NO 293)
40K-NH-mAmGmCmCmUdGmGdG-s-dGmAmCmCmCmAmU-s-dI-s-mGdI-s-dGdI-s-dGmCmU-3T

ARC1788 (SEQ ID NO 294)
60K-NH--mAmGmCmCmUdGmGdG-s-dGmAmCmCmCmAmU-s-dI-s-mGdI-s-dGdI-s-dGmCmU-3T

5' PEGylation had little to no effect on aptamer function, measured by a cell based assay described in Example 3 below.

Example 2H

Synthesis of Aptamer-3'-5'-PEG Conjugates

The oligonucleotide 5' NH₂ mA mG mC mC mU dG mG dG-s-dG mA mC mC mC mA mU-s-dI-s-mG dI-s-dG dI-s-dG mC mU-NH₂ 3' (ARC1784, SEQ ID NO 297) was synthesized on an AKTA OligoPilot 100 synthesizer (GE Healthcare Uppsala, Sweden) according to the recommended manufacturer's procedures using standard commercially available 2'-OMe RNA, deoxyinosine and DNA phosphoramidites (Glen Research, Sterling, Va.) and a 3'-phthalimide-amino-modifier C6 CPG support (Glen Research, Sterling, Va.). A terminal amine functions was attached with a 5'-amino-modifier C6-TFA (Glen Research, Sterling, Va.). After deprotection, the oligonucleotides was purified by ion exchange chromatography on Super Q 5PW (30) resin (Tosoh Biosciences) and ethanol precipitated.

Aliquots of the 3'-5'-diamine-modified aptamer were conjugated to different PEG moieties post-synthetically (e.g., 20 kDa and 30 kDa PEG moieties). Aptamers were dissolved in a water/DMSO (1:1) solution to a concentration between 1.5 and 3 mM. Sodium carbonate buffer, pH 8.5, was added to a final concentration of 100 mM, and the oligo was reacted overnight with a 2.7-3.5 fold molar excess of the desired PEG reagent (e.g., 20 kDa or 30 kDa Sunbright GL2-400NP p-nitrophenyl carbonate ester [NOF Corp, Japan]) dissolved in an equal volume of acetonitrile. The resulting 2×20 kDa or 2×30 kDa PEGylated products were purified by ion exchange chromatography on Super Q 5PW (30) resin (Tosoh Biosciences), and desalted using reverse phase chromatography performed on Amberchrom CG300-S resin (Rohm and Haas), and lyophilized.

The resulting bi-PEGylated aptamer sequences are listed in Table 20 below. Lower case letters "f", "m", and "d" denote 2'-fluoro, 2-O-methyl, and deoxy modifications respectively, "s" denotes an internucleotide phopshorothioate substitution, "I" denotes an inosine substitution for guanosine, and "NH" denotes an amine to facilitate chemical coupling.

TABLE 20

3'-5'-PEG Conjugates of anti-IgE aptamer ARC1666

ARC1785 (SEQ ID NO 295)
PEG20K-NH-mAmGmCmCmUdGmGdG-s-dGmAmCmCmAmU-s-dI-s-mGdI-s-dGdI-s-dGmCmU-NH-PEG20K

ARC1790 (SEQ ID NO 296)
PEG30K-NH-mAmGmCmCmUdGmGdG-s-dGmAmCmCmAmU-s-dI-s-mGdI-s-dGdI-s-dGmCmU-NH-PEG30K

3'-5' PEGylation had little to no effect on aptamer function as measured by a cell based assay described in Example 3 below.

Example 3

Functional Cell Assays

Example 3A

Receptor (FcεR1) Binding Inhibition ELISA

A panel of the rRfY IgE aptamers (described above in Example 1A) were tested for the ability to inhibit complex formation between h-IgE and soluble, monomeric FcεR1$_\alpha$ (purified in-house) using an ELISA assay. FcεR1 (100 μL, 10 μg/mL) in 1×PBS was incubated in the wells of a Nunc Maxisorb 96 well plate overnight at 4° C. to coat the surface of the wells. The supernatants were removed, the wells were washed 3 times with 120 μl 1×PBS, and the wells were blocked with 300 mL 1×PBS plus 0.2% Tween-20 at 4° C. for two hours. After blocking, the wells were washed three times with 1×PBS. Various concentrations of aptamer were next incubated with 0.5 nM h-IgE in 100 μL PBS plus 0.05% Tween-20 at room temperature for 30 minutes, and then the mixtures were added to the assay well and incubated at room temperature for 1 hour. The wells were then washed 5 times with 120 μL 1×PBS. Bound h-IgE was detected by the addition of HRP-labeled anti-h-IgE polyclonal antibody (Goat anti-human IgE-HRP (074-1004) (KPL, Gaithersburg, Md.)). Quantablue substrate (Pierce, Rockford, Ill.) was used to detect peroxidase activity. 100 μl of Quantablue substrate was added to each well and incubated at room temperature for 15 minutes. Next, 100 μl of the provided stop solution was added to each well, and the plates were read on a SpectraMax 96 well plate reader at excitation/emission of 325 nm and 420 nm respectively. The relative fluorescence units (RFU) of each well were used to calculate IC50's. Table 21 below shows the IC$_{50}$s calculated for FcεRI$_\alpha$ receptor inhibition with various aptamers from the rRfY selection.

TABLE 21

Receptor (FcεR1) binding inhibition - rRfY aptamers

| SEQ ID NO | IC50 (nM) |
|---|---|
| 11 | 2.6 |
| 12 | 5.0 |
| 13 | 4.3 |
| 14 | 26.8 |
| 18 | 51.3 |
| 21 | 3.7 |
| 19 | 7.4 |

Example 3B

Receptor (FcεR1) Binding Inhibition by FACS

A panel of aptamers representing rRfY, dRmY and DNA compositions was tested for the ability to inhibit h-IgE binding to FcεR1 expressed on the surface of rat basophilic leukemia (RBL) cells. SX38 cells, an RBL cell line (Harvard University, Cambridge, Mass.), stably expressing the human α, β, and γ chains of the h-IgE receptor, were used in a flow cytometry h-IgE binding assay. The cells were cultured in Eagle's Minimal Essential Medium (MEM) with 16% fetal bovine serum (FBS) and 1 mg/mL G418 (Invitrogen) at 37° C., 5% $CO_2$. One million SX38 cells in 1×DPBS with 1% BSA (Sigma, St. Louis, Mo.) and 0.03% NaAzide (FACs buffer) (VWR, West Chester, Pa.) were aliquotted into an appropriate number of wells in a 96 well plate and incubated on ice for 30 minutes. For each aptamer concentration, a 2× mixture of aptamer plus h-IgE (Athens Research and Technology, Athens, Ga.) was incubated on ice for 30 minutes. The aptamer and h-IgE mixture was added to the SX38 cells to obtain a final 1× concentration and incubated on ice for an additional 30 minutes. Final aptamer concentrations ranging from 0-1 μM were screened against 3 μg/mL h-IgE (15 nM). The cells were then washed 3× with FACs buffer to remove any h-IgE that did not bind to the receptor. To detect h-IgE binding, an anti-h-IgE-FITC antibody (QED Biosciences, San Diego, Calif.) was added to the cells and incubated for 30 minutes on ice. After the incubation, the cells were washed 3× with FACs buffer to remove any unbound antibody. The cells were resuspended in FACs buffer and were analyzed using FACSCAN (BD Biosciences, San Jose, Calif.). h-IgE alone and h-IgE versus the naïve pool were included as positive and negative controls, respectively. h-IgE aptamer activity was measured by percent inhibition of h-IgE binding to the cells. Mean fluorescence intensity values were used to calculate percent inhibition. Table 22 shows the $IC_{50}$ for various rRfY, dRmY, and DNA clones selected as calculated by FACS assay.

TABLE 22 rRfY, dRmY, DNA clones: Receptor (FceR1) binding inhibition by FACS assay

| SEQ ID NO | ARC# | Composition | $IC_{50}$ (nM) |
|---|---|---|---|
| 12 | | rRfY | 7.1 |
| 11 | | rRfY | 14 |
| 21 | | rRfY | 14.4 |
| 18 | | rRfY | 35 |
| 13 | | rRfY | 10.3 |
| 19 | | rRfY | 9.9 |
| 14 | | rRfY | 17.3 |
| 91 | | rRfY | 3.8 |
| 93 | | rRfY | 12.5 |
| 98 | ARC442 | dRmY | 58.9 |
| 99 | ARC443 | dRmY | 30.2 |
| 100 | ARC444 | dRmY | 52.4 |
| 102 | ARC445 | dRmY | 22.6 |
| 102 | ARC446 | dRmY | 33.8 |
| 149 | | DNA | 55.9 |
| 149 (with 3' idT) | | DNA | 35.8 |
| 152 | | DNA | 17.4 |
| 151 | | DNA | 17.1 |
| 151(with 3' idT) | | DNA | 10.6 |
| 155 | | DNA | 14.4 |
| 156 | | DNA | 9.7 |

*idT: same sequence with inverted dT residue at the 3'-end
N.D.: not determined

Several of the modified derivatives of ARC445 (SEQ ID NO 101) (described in Example 2E) as ARC656 (SEQ ID NO 157) (described in Example 2D) were also tested for h-IgE receptor (FceR1) binding inhibition using the FACS assay described above with the following modifications: for each aptamer concentration, a 2× mixture of aptamer plus h-IgE (Athens Research and Technology, Athens, Ga.) was incubated on ice for 30 minutes; the aptamer and h-IgE mixture was added to the SX38 cells to obtain a final 1× concentration and incubated on ice for an additional 2 hours; and final aptamer concentrations ranging from 0-1 µM were screened against 0.5 µg/mL h-IgE (2.5 nM. The calculated $IC_{50}$ values are summarized in Table 23.

TABLE 23

ARC445 modified Derivatives; ARC656: Receptor (FceR1) binding inhibition by FACS assay

| SEQ ID NO | ARC # | FACs IC50 (nM) |
|---|---|---|
| 101 | ARC445 | 10.8 |
| 176 | ARC1335 | 7.3 |
| 178 | ARC1337 | 4.7 |
| 179 | ARC1382 | 6.9 |
| 180 | ARC1383 | 7.5 |

TABLE 23-continued

ARC445 modified Derivatives; ARC656: Receptor (FceR1) binding inhibition by FACS assay

| SEQ ID NO | ARC # | FACs IC50 (nM) |
|---|---|---|
| 181 | ARC1384 | 4.4 |
| 182 | ARC1572 | 22.8 |
| 183 | ARC1573 | 69.4 |
| 212 | ARC1641 | 1.8 |
| 213 | ARC1642 | 1.8 |
| 214 | ARC1643 | 8.0 |
| 215 | ARC1644 | 5.2 |
| 216 | ARC1666 | 1.7 |
| 217 | ARC1667 | 2.3 |
| 218 | ARC1728 | 13.2 |
| 219 | ARC1729 | 2.9 |
| 157 | ARC656 | 21.2 |

The PEG-conjugated aptamers described in Examples 2G and 2H were all active in the FACS assay, under the conditions described directly above. The calculated $IC_{50}$ values are summarized in Table 24 below. As can be seen from the data in Table 24, various types of PEG conjugation had little effect on aptamer function.

TABLE 24

| SEQ ID NO | PEG | ARC # | FACS $IC_{50}$ (nM) |
|---|---|---|---|
| 295 | 2 × 20 kDa (linear) | ARC1785 | 2.0 |
| 296 | 2 × 30 kDa (linear) | ARC1790 | 0.89 |
| 293 | 40 kDa branched | ARC1787 | 1.2 |
| 294 | 60 kDa branched | ARC1788 | 1.2 |

Example 3C

Aptamer Cross Reactivity with Cynomolgous Monkey IgE

Aptamers were tested for the ability to inhibit complex formation between cynomolgous monkey IgE and FceR1$_\alpha$-Fc using an ELISA assay. FceR1$_\alpha$-Fc (100 mL, 5 µm/mL) in PBS was incubated in the wells of a Nunc Maxisorb 96 well plate overnight at 4° C. to coat the surface of the wells. The supernatants were removed, the wells were washed 3 times with 120 µl 1×PBS, and the wells were blocked with 300 µL PBS plus 0.2% Tween-20 at 4° C. for 2 hours. The wells were washed 3 times with 120 µL 1×PBS. Various concentrations of aptamer were next incubated with 0.5 ng h-IgE in 100 µL PBS (or cynomolgous monkey serum (Sigma) diluted to 10% with same) at room temperature for 30 minutes, and then the mixtures were added to the assay well and incubated at room temperature for 1 hour. The wells were then washed 5 times with 120 µL PBS. Bound IgE (both monkey and human) was detected by the addition of HRP-labeled anti-IgE polyclonal antibody (Goat anti-human IgE-HRP (074-1004) (KPL, Gaithersburg, Md.)). Quantablue substrate (Pierce, Rockford, Ill.) was used to detect peroxidase activity. 100 µl of Quantablue substrate was added to each well and incubated at room temperature for 15 minutes. Next, 100 µl of the provided stop solution was added to each well, and the plates were read on a SpectraMax 96 well plate reader at excitation/emission of 325 μm and 420 nm respectively. The relative fluorescence units (RFU) of each well were used to calculate $IC_{50}$'s.).

The presence of the following DNA aptamers with nucleic acid sequences according to SEQ ID NO 149 (with a 3'inverted deoxy thymidine) and SEQ ID NO 151 (with a 3' inverted deoxy thymidine), or the rRfY aptamers with nucleic acid sequences according to SEQ ID NO 90 and SEQ ID NO 93, at concentrations up to 250 nM and 1 μM respectively, did not inhibit monkey binding to FcεR1-Fc, while the dRmY aptamers ARC445 (SEQ ID NO 101) and ARC1666 (SEQ ID NO 216) were quite potent at blocking the interaction (ARC445, $IC_{50}$monkey=161 nM; $IC_{50}$human=63 nM; ARC1666, $IC_{50}$monkey=8 nM; $IC_{50}$human=5 nM), indicating this molecule is cross reactive with cynomolgous monkey IgE and human IgE. Additional control experiments showed that ARC445 did not inhibit detection of monkey IgE in this assay format.

Figure 13:
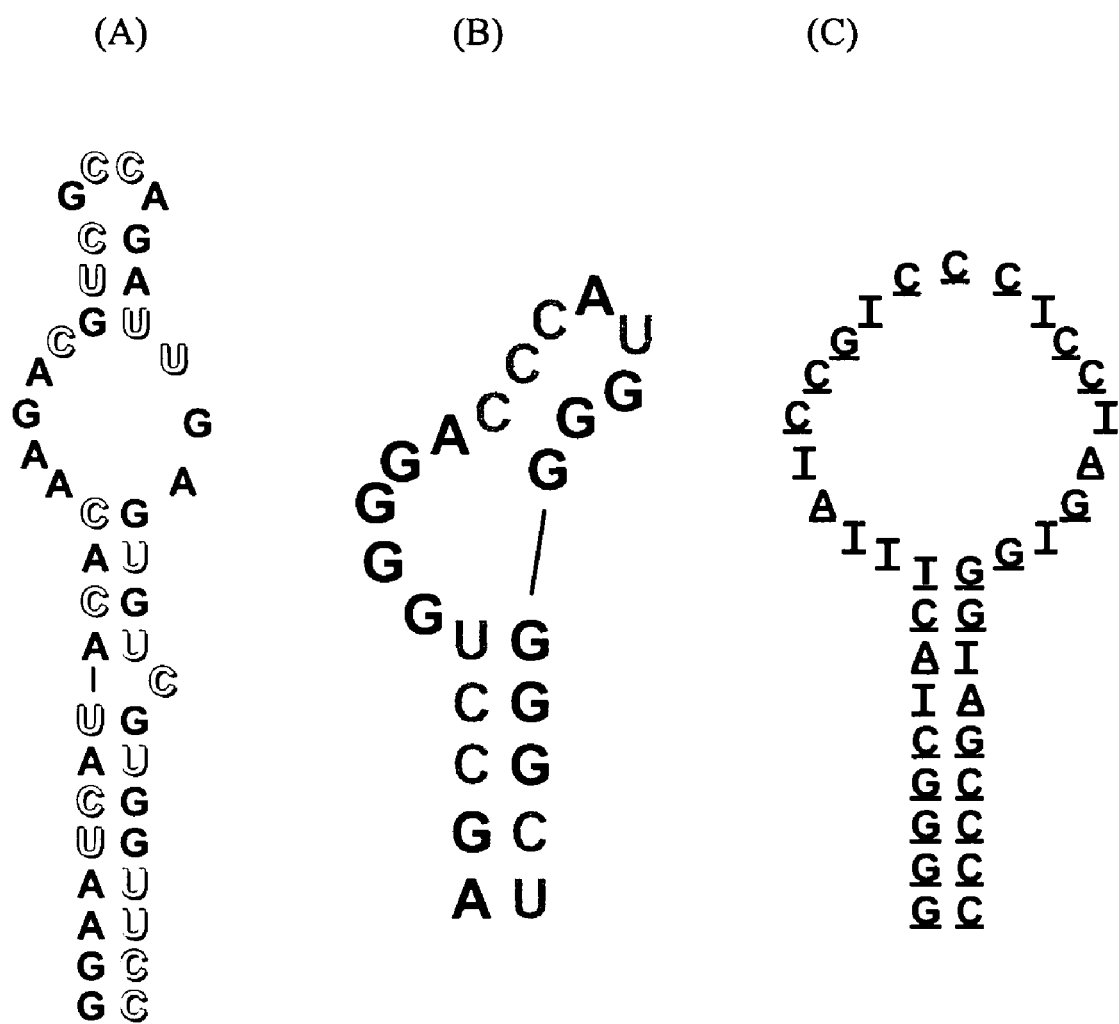
FIG. 13 is a schematic of predicted secondary structures for rRfY, dRmY and DNA minimized aptamers showing highest potency in IgE:FcεR1 binding inhibition by FACS.

FIG. 13 shows possible secondary structures for rRfY, dRmY and DNA minimized aptamers showing highest potency in IgE:FcεR1 binding inhibition by FACS. Left: SEQ ID NO 91 (rRfY), outlined residues are 2'-F; middle: ARC445 (SEQ ID NO 101) (dRmY), underlined residues are 2'-deoxy, outlined residues are 2'-OMe; right ARC475 (SEQ ID NO 151) (DNA), underlined residues are 2'-deoxy.

Example 3D

Inhibition of Histamine Release

IgE aptamer cell based activity was measured using a histamine release assay using SX38 cells (Dana Farber Cancer Institute, Boston, Mass.), an RBL cell line stably expressing the human α, β, and γ chains of the h-IgE receptor. Because supernatants of SX38 cells in the presence of h-IgE and an anti-h-IgE cross linking antibody contain more histamine than aptamer blocked cells, a competitive histamine ELISA (Immuno-Biological Laboratories, Minneapolis, Minn.) was used to quantify the levels of histamine released into the supernatants of SX38 cells treated with h-IgE and h-IgE cross linking antibody +/− IgE aptamer.

Figure 14:
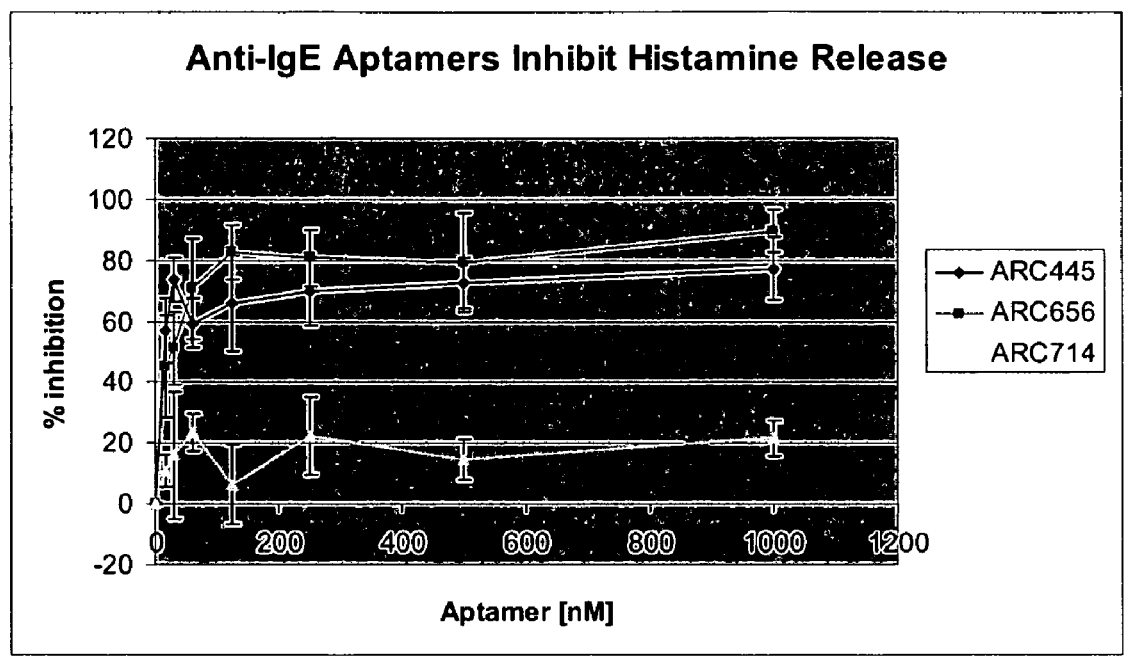
FIG. 14 is a plot showing ARC445 (SEQ ID NO 101) and ARC656 (SEQ ID NO 157) blocking of h-IgE-induced histamine release in SX38 cells.

Two hundred thousand (200,000) SX38 cells per well were plated in MEM plus 16% FBS in a 24 well plate one day prior to the experiment. The next day, appropriate concentrations of aptamer (8 point titration of 2-fold serial dilutions beginning with 1 μM) plus 3 ug/mL of h-IgE (Athens Research and Technology, Athens, Ga.) were incubated together for 30 minutes in MEM plus 16% FBS. The mixture was then added to the SX38 cells and incubated at 37° C., 5% $CO_2$ for 30 minutes. Each concentration was tested in quadruplicate. The cells were washed three times with MEM plus 16% FBS, then incubated for an additional 5.5 hours in MEM plus 16% FBS. An h-IgE cross-linking antibody (QED Biosciences, San Diego, Calif.) was added to the media on the cells at a concentration of 1 ug/mL and incubated for an additional 2 hours. The supernatants were collected and frozen at −20° C. until use in the histamine ELISA. The histamine ELISA was used according to manufacturer's recommendations. h-IgE alone and h-IgE versus the naïve pool were included as positive and negative controls, respectively. IgE aptamer activity was measured by percent inhibition of histamine release into the supernatants as shown in FIG. 14 (wherein ARC445 is SEQ ID NO 101, ARC656 is SEQ ID NO 157 and ARC714 is a non-binding negative control).

Several modified derivatives of ARC445 (SEQ ID NO 101) (described in Example 2E), along with the DNA aptamer, ARC656 (SEQ ID NO 157) (described in Example 2D) were also tested for their ability to inhibit histamine release in SX38 cells as described above. The calculated $IC_{50}$s for the ARC445 derivatives tested are summarized in Table 25.

TABLE 25

ARC445 Modified Derivatives; ARC656: Inhibition of Histamine Release in SX38 cells

| SEQ ID NO | ARC # | Histamine Release $IC_{50}$ (nM) |
|---|---|---|
| 101 | ARC445 | 31.28 |
| 176 | ARC1335 | 33.69 |
| 181 | ARC1384 | 59.0 |
| 216 | ARC1666 | 19.4 |
| 157 | ARC656 | 16.9 |

Example 4

PK Studies

In Examples 4, all mass based concentration data in this example refers only to the molecular weight of the oligonucleotide portion of the aptamer, irrespective of the mass conferred by PEG conjugation.

Example 4A

Plasma Stability of Anti-IgE Atamers

A subset of the aptamers identified in the aptamer medicinal chemistry process was assayed for nuclease stability in both human and rat plasma. Plasma nuclease degradation was measured on denaturing polyacrylamide gel electrophoresis as described below. Briefly, for plasma stability determination, chemically synthesized aptamers were purified using denaturing polyacrylamide gel electrophoresis, 5'end labeled with γ-$^{32}$P ATP and then gel purified again. Trace $^{32}$-P labeled aptamer was incubated in the presence of 100 nM unlabeled aptamer in 95% human plasma (or 95% rat plasma) in a 200 microliter binding reaction. The reaction for the time zero point was made separately with the same components except that the plasma was replaced with PBS. This insured that the amount or radioactivity loaded on gels was consistent across an experiment. Reactions were incubated at 37° C. in a thermocycler for the 1, 3, 10, 30 and 100 hours unless otherwise specified. At each time point, 20 microliters of the reaction was removed, combined with 200 microliters of formamide loading dye and flash frozen in liquid nitrogen and stored at −20° C. After the last time point was taken, frozen samples were thawed and 20 microliters was removed from each time point. SDS was then added to the small samples to a final concentration of 0.1%. The samples were then incubated at 90° C. for 10-15 minutes and loaded directly onto a 15% denaturing PAGE gel and run at 12 W for 35 minutes. Radioactivity on the gels was quantified using a Storm 860 phosphoroimager system (Amersham Biosciences, Piscataway, N.J.). The percentage of full length aptamer at each time point was determined by quantifying the full length aptamer band and dividing by the total counts in the lane. The fraction of full length aptamer at each time-point was then normalized to the percentage full length aptamer of the 0 hour time-point. The fraction of full length aptamer as a function of time was fit to the equation:

$$m1*e^{(-m2*m0)}$$

where m1 is the maximum % full length aptamer (m1=100); and m2 is the rate of degradation.

The half-life of the aptamer ($T_{1/2}$) is equal to the (ln 2)/m2.

Figure 15A:
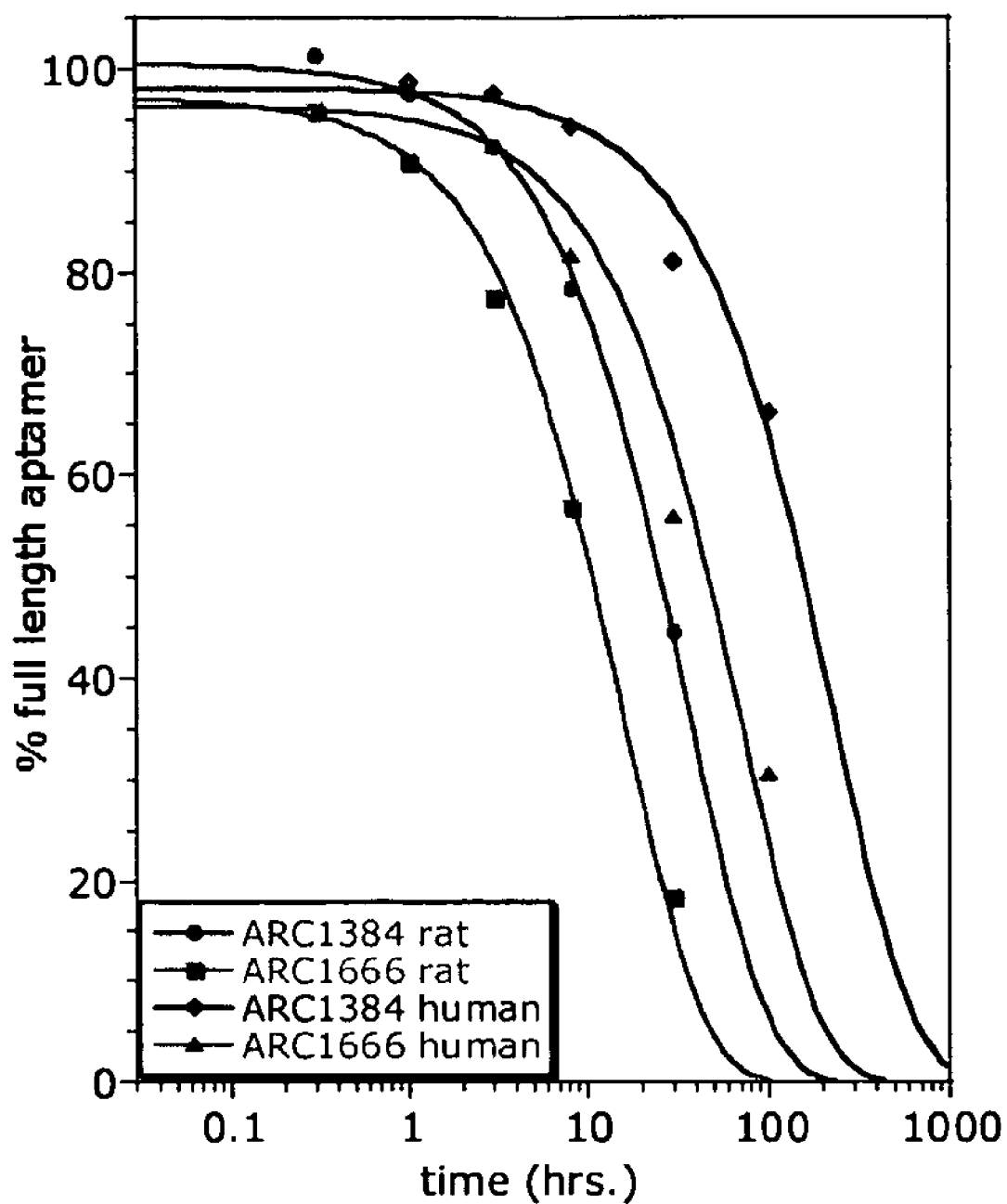
FIG. 15A is a graph depicting the % full length ARC1384 and ARC1666 present in human and rat plasma as a function of incubation time.
Figure 15:
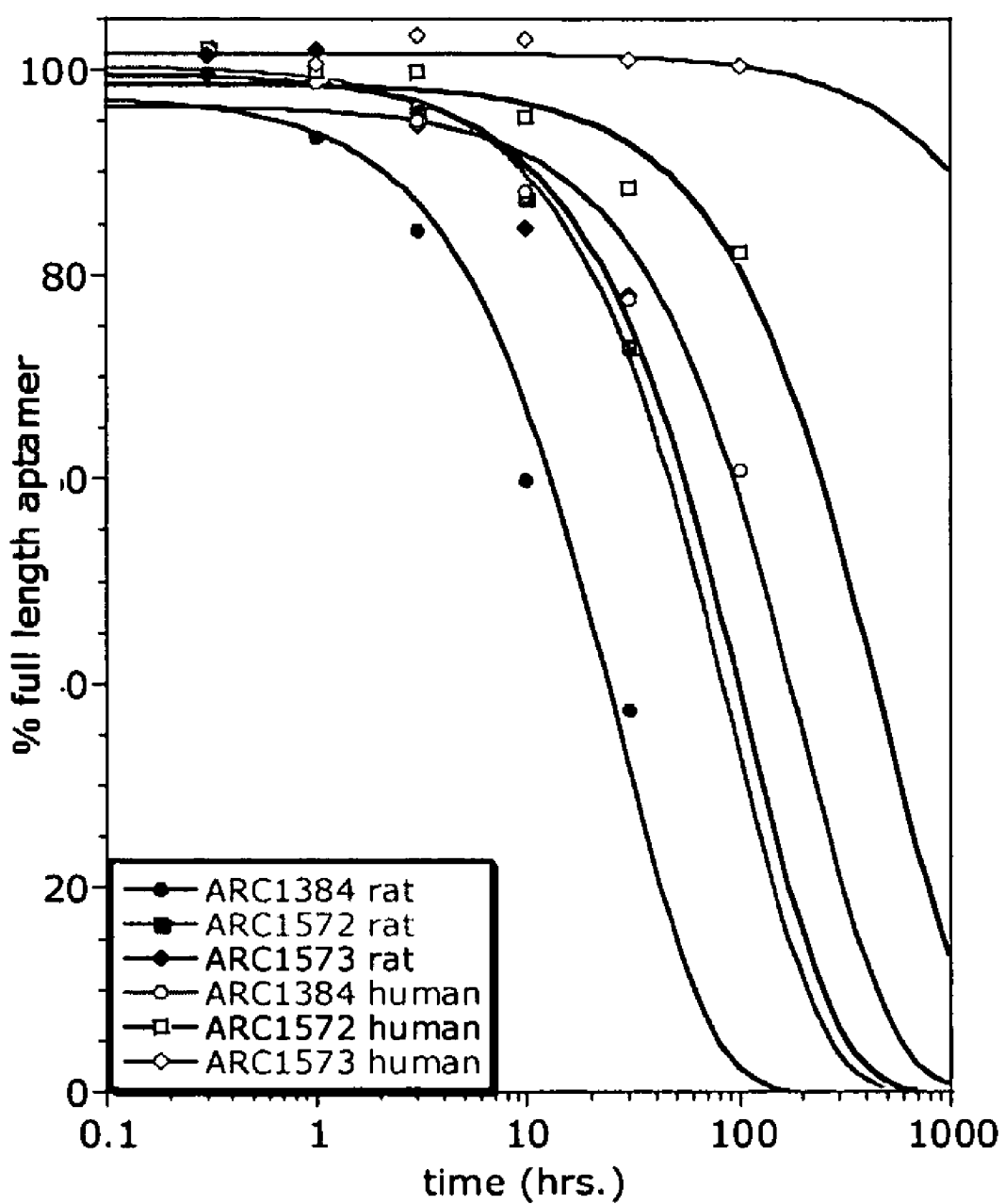
FIG. 15B is a graph depicting the % full length ARC1384, ARC1572 and ARC1573 present in human and rat plasma a function of incubation time.

Sample data is shown in FIGS. 15a and 15b and the results for the aptamers tested are summarized in Table 26. Consistent with our expectations, aptamers are more stable in human plasma than in rat plasma and increasing the number of stabilizing modifications to the sugar-phosphate backbone correlates with increasing plasma stability.

TABLE 26

Plasma stability of ARC445 and ARC656 derivatives

| SEQ ID NO | ARC # | ~T½ in rat plasma (hrs) | ~T½ in human plasma (hrs) |
|---|---|---|---|
| 101 | ARC445 | 2.2 | Not done |
| 176 | ARC1335 | 16 | Not done |
| 178 | ARC1337 | 29 | Not done |
| 179 | ARC1382 | 16 | Not done |
| 180 | ARC1383 | 26 | Not done |
| 181 | ARC1384 | 22 | 149 |
| 182 | ARC1572 | 62 | 339 |
| 183 | ARC1573 | 74 | >500 |
| 216 | ARC1666 | 11 | 49 |
| 219 | ARC1729 | 42 | 180 |
| 157 | ARC656 | Not done | 6 |
| 285 | ARC1410 | Not done | 9 |

Example 4B

Figures 16, 17:
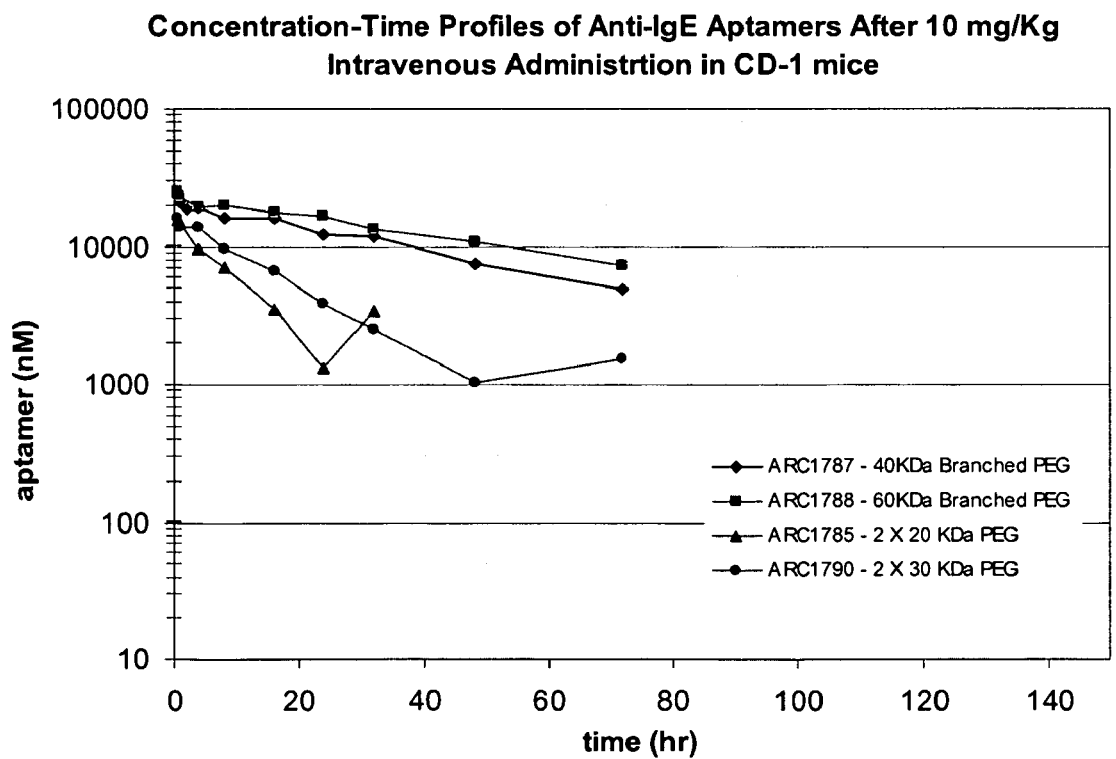
FIG. 16 is a table outlining the design of a pharmacokinetics study of PEGylated anti-IgE aptamers ARC1785 (SEQ ID NO 295), ARC1787 (SEQ ID NO 293), ARC1788 (SEQ ID NO 294), and ARC1790 (SEQ ID NO 296) administered intravenously to mice at 10 mg/kg.
FIG. 17 is a graph showing the pharmacokinetic profile of PEGylated anti-IgE aptamers ARC1785 (SEQ ID NO 295), ARC1787 (SEQ ID NO 293), ARC1788 (SEQ ID NO 294), ARC1790 (SEQ ID NO 296) after intravenous (IV) administration to mice at 10 mg/kg.

Pharmacokinetics of Anti-IgE Atamers Versus PEGylation: ARC1785, ARC1787, ARC1788, and ARC1790 After IV Administration to Mice at 10 mg/kg The design for the murine pharmacokinetic study of ARC1785, ARC1787, ARC1788, and ARC1790 via intravenous (IV) administration is shown in FIG. 16. Briefly, the study consisted of 3 groups (33 animals total). At each sample collection time point, 3 animals were terminally sacrificed and 0.5 mL of whole blood collected via cardiac puncture for harvesting of plasma. The aptamer was formulated for injection from a lyophilized powder to a final concentration of 10 mg/mL (oligo weight) in standard 0.9% saline and sterile-filtered (0.2 μm) prior to dosing. The route of administration used was a single intravenous bolus injection at a dose of 10 mg/kg. At specified time points, t=pre-dose, 0.08, 0.5, 1, 2, 4, 8, 16, 24, 32, 48, and 72 hours, whole blood samples were obtained, transferred directly to K2EDTA-coated tubes, mixed by inversion, and placed on wet ice.

Plasma was harvested by centrifugation of blood-EDTA tubes at 3500 rpm for 5 minutes. Plasma samples were transferred to fresh labeled 1.5 mL tubes and stored at −80° C. until the time of analysis. Analysis of plasma samples for aptamer concentration was accomplished using a homogeneous assay format utilizing the direct addition of plasma aliquots to assay wells containing the commercially available fluorescent nucleic acid detection reagent Oligreen™ (Molecular Probes, Eugene, Oreg.). After a brief incubation period (5 min) at room temperature, protected from light, the assay plates were read by a fluorescence plate reader. The fluorescence signal from each well was proportional to the concentration of aptamer in the well, and sample concentrations were calculated by interpolation of fluorescence values from a fluorescence-concentration standard curve (mean values from duplicate curves). Mean plasma concentrations were obtained at each time point from the three animals in each group, and are plotted versus time post-dose in FIG. 17.

Plasma concentration versus time data appeared was subjected to noncompartmental analysis (NCA) using the industry standard pharmacokinetic modeling software WinNonLin™ v.4.0 (Pharsight Corp., Mountain View, Calif.). Estimates were obtained for the following primary pharmacokinetic parameters: maximum plasma concentration, Cmax; area under the concentration-time curve, AUC; terminal half-life, t½; terminal clearance, Cl; and volume of distribution at steady state, Vss. Noncompartmental analysis (NCA) of the data using WinNonLin™ v.4.0 (Pharsight Corp., Mountain View, Calif.)., yielded the estimates for the primary pharmacokinetic parameters listed in FIG. 20.

Example 4C

Pharmacokinetics and Bioavailability of Anti-IgE Aptamers Versus PEGylation: ARC1785, ARC1787. ARC1788 and ARC1790 After SC Administration to Mice at 10 mg/kg The design for the murine pharmacokinetic study of the bioavailability of ARC1785, ARC1787, ARC1788, and ARC1790 via subcutaneous routes of administration is shown in FIG. 18. Briefly, the study consisted of 3 groups (33 animals total). At each sample collection time point, 3 animals were terminally sacrificed and 0.5 mL of whole blood collected via cardiac puncture for harvesting of plasma. The aptamer was formulated for injection from a lyophilized powder to a final concentration of 10 mg/mL (oligo weight) in standard 0.9% saline and sterile-filtered (0.2 μm) prior to dosing. The route of administration used was a single subcutaneous bolus injection at a dose of 10 mg/kg. At specified time points, t=pre-dose, 0.08, 0.5, 1, 2, 4, 8, 16, 24, 32, 48, and 72 hours, whole blood samples were obtained, transferred directly to K2EDTA-coated tubes, mixed by inversion, and placed on wet ice.

Figure 19:
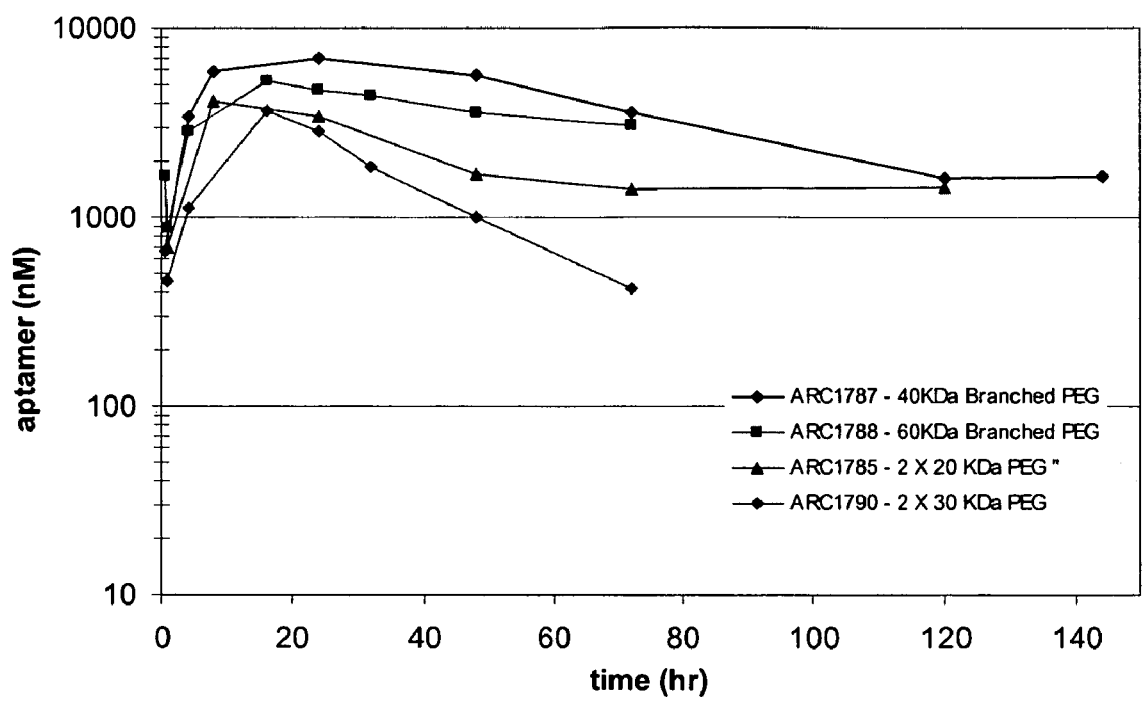
FIG. 19 is a graph showing the pharmacokinetic profile of PEGylated anti-IgE aptamers ARC1785 (SEQ ID NO 295), ARC1787 (SEQ ID NO 293), ARC1788 (SEQ ID NO 294) and ARC1790 (SEQ ID NO 296) after subcutaneous (SC) administration to mice at 10 mg/kg.

Plasma was harvested by centrifugation of blood-EDTA tubes at 3500 rpm for 5 minutes. Plasma samples were transferred to fresh labeled 1.5 mL tubes and stored at −80° C. until the time of analysis. Analysis of plasma samples for aptamer concentration was accomplished using a homogeneous assay format utilizing the direct addition of plasma aliquots to assay wells containing the commercially available fluorescent nucleic acid detection reagent Oligreen™ (Molecular Probes, Eugene, Oreg.). After a brief incubation period (5 min) at room temperature, protected from light, the assay plates were read by a fluorescence plate reader. The fluorescence signal from each well was proportional to the concentration of aptamer in the well, and sample concentrations were calculated by interpolation of fluorescence values from a fluorescence-concentration standard curve (mean values from duplicate curves). Mean plasma concentrations were obtained at each time point from the three animals in each group, and are plotted versus time post-dose in FIG. 19.

Plasma concentration versus time data appeared was subjected to noncompartmental analysis (NCA) using the industry standard pharmacokinetic modeling software WinNonLin™ v.4.0. Estimates were obtained for the following primary pharmacokinetic parameters: maximum plasma concentration, Cmax; area under the concentration-time curve, AUC; terminal half-life, $t\frac{1}{2}$; terminal clearance, Cl; and volume of distribution at steady state, Vss. Noncompartmental analysis (NCA) of the data using WinNonLin™ v.4.0 (Pharsight Corp., Mountain View, Calif.), yielded the estimates for the primary pharmacokinetic parameters listed in FIG. 20. As can be seen from the table of FIG. 20 all of the PEG conjugated aptamers tested exhibited subcutaneous bioavailability.

The invention having now been described by way of written description and example, those of skill in the art will recognize that the invention can be practiced in a variety of embodiments and that the description and examples above are for purposes of illustration and not limitation of the following claims.

What is claimed is:

1. An aptamer comprising the following sequence: mAmGmCmCmUdGmGdG-s-dGmAmCmCmCmAmU-s-dI-s-mGdI-s-dGdI-s-dGmCmU (SEQ ID NO:298), wherein mC, mG, mU and mA=2'-OMe C, 2'-OMe G, 2'-OMe U and 2'-OMe A respectively, dG=deoxy G, dI=deoxy inosine, and s=a phosphorothioate backbone substitution.

2. The aptamer of claim 1, wherein the aptamer is conjugated to a PEG moiety, wherein the PEG moiety comprises a molecular weight selected from the group consisting of: 60 kDa, 40 kDa, 30 kDa and 20 kDa.

3. The aptamer of claim 2, wherein the PEG moiety is a branched PEG.

4. The aptamer of claim 3, having the structure set forth below:

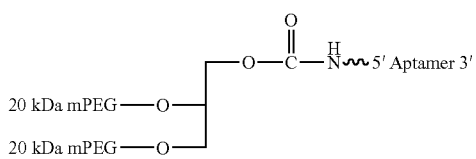

where,

∿∿∿ indicates a linker

Aptamer =                                    (SEQ ID NO 216)
mAmGmCmCmUdGmGdG-s-dGmAmCmCmCmAmU-s-dI-s-mGdI-s-
dGdI-s-dGmCmU-3T wherein mC, mG, mU and mA=2'-OMe C, 2'-OMe G, 2'-OMe U and 2'-OMe A respectively, dG=deoxy G, dI=deoxy inosine, s=a phosphorothioate backbone substitution, and 3T=3' inverted deoxy thymidine.

5. The aptamer of claim 4, wherein the linker is an alkyl linker.

6. The aptamer of claim 5, wherein the alkyl linker comprises 2 to 18 consecutive $CH_2$ groups.

7. An aptamer, having the structure set forth below:

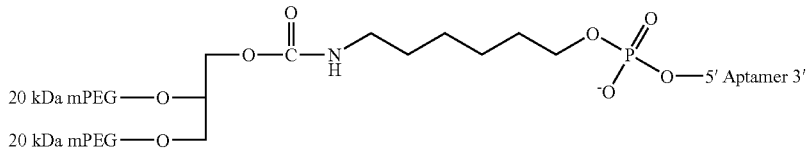

```
Aptamer =                                     (SEQ ID NO 216)
mAmGmCmCmUdGmGdG-s-dGmAmCmCmCmAmU-s-dI-s-mGdI-s-
dGdI-s-dGmCmU-3T
``` wherein mC, mG, mU and mA=2'-OMe C, 2'-OMe G, 2'-OMe U and 2'-OMe A respectively, dG=deoxy G, dI=deoxy inosine, s=a phosphorothioate backbone substitution, and 3T=3' inverted deoxy thymidine.

8. The aptamer of claim 3, having the structure set forth below:

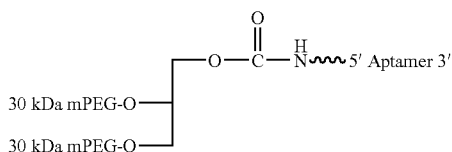

where,
~~~ indicates a linker

```
Aptamer =                                     (SEQ ID NO 216)
mAmGmCmCmUdGmGdG-s-dGmAmCmCmCmAmU-s-dI-s-mGdI-s-
dGdI-s-dGmCmU-3T
``` wherein mC, mG, mU and mA=2'-OMe C, 2'-OMe G, 2'-OMe U and 2'-OMe A respectively, dG=deoxy G, dI=deoxy inosine, s=a phosphorothioate backbone substitution, and 3T=3' inverted deoxy thymidine.

9. The aptamer of claim 8, wherein the linker is an alkyl linker.

10. The aptamer of claim 9, wherein the alkyl linker comprises 2 to 18 consecutive $CH_2$ groups.

11. An aptamer, having the structure set forth below:

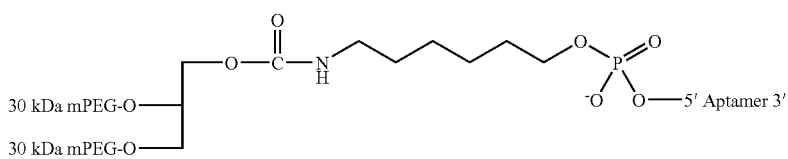

```
Aptamer =                                     (SEQ ID NO 216)
mAmGmCmCmUdGmGdG-s-dGmAmCmCmCmAmU-s-dI-s-mGdI-s-
dGdI-s-dGmCmU-3T
``` wherein mC, mG, mU and mA=2'-OMe C, 2'-OMe G, 2'-OMe U and 2'-OMe A respectively, dG=deoxy G, dI=deoxy inosine, s=a phosphorothioate backbone substitution, and 3T=3' inverted deoxy thymidine.

12. The aptamer of claim 2, having the structure set forth below:

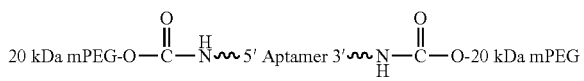

where,
~~~ indicates a linker

```
Aptamer =                                     (SEQ ID NO 298)
mAmGmCmCmUdGmGdG-s-dGmAmCmCmCmAmU-s-dI-s-mGdI-s-
dGdI-s-dGmCmU
``` wherein mC, mG, mU and mA=2'-OMe C, 2'-OMe G, 2'-OMe U and 2'-OMe A respectively, dG=deoxy G, dI=deoxy inosine, s=a phosphorothioate backbone substitution, and 3T=3' inverted deoxy thymidine.

13. The aptamer of claim 12, wherein the linker is an alkyl linker.

14. The aptamer of claim 13, wherein the alkyl linker comprises 2 to 18 consecutive $CH_2$ groups.

15. The aptamer of claim 13, having the structure set forth below:

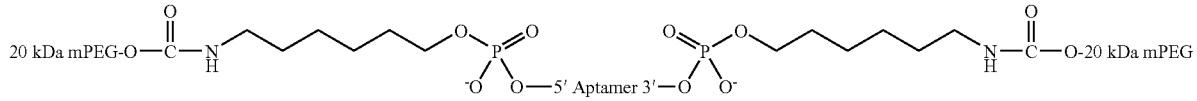

Aptamer = (SEQ ID NO 298)
mAmGmCmCmUdGmGdG-s-dGmAmCmCmCmAmU-s-dI-s-mGdI-s-dGdI-s-dGmCmU wherein mC, mG, mU and mA=2'-OMe C, 2'-OMe G, 2'-OMe U and 2'-OMe A dG=deoxy G, dI=deoxy inosine, and s=a phosphorothioate backbone substitution.

16. The aptamer of claim 2, having the structure set forth below:

30 kDa mPEG-O—C(=O)—N(H)~~~ 5' Aptamer 3' ~~~N(H)—C(=O)—O-30 kDa mPEG where,

~~~ indicates a linker

Aptamer = (SEQ ID NO 298)
mAmGmCmCmUdGmGdG-s-dGmAmCmCmCmAmU-s-dI-s-mGdI-s-dGdI-s-dGmCmU wherein mC, mG, mU and mA=2'-OMe C, 2'-OMe G, 2'-OMe U and 2'-OMe A respectively, dG=deoxy G, dI=deoxy inosine, and s=a phosphorothioate backbone substitution.

17. The aptamer of claim 16, wherein the linker is an alkyl linker.

18. The aptamer of claim 17, wherein the alkyl linker comprises 2 to 18 consecutive $CH_2$ groups.

19. An aptamer, having the structure set forth below:

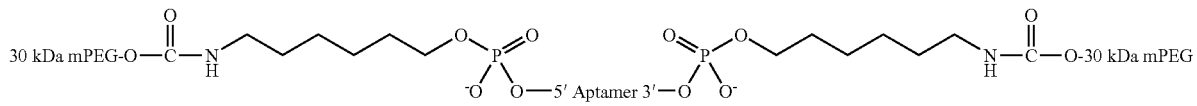

Aptamer = (SEQ ID NO 298)
mAmGmCmCmUdGmGdG-s-dGmAmCmCmCmAmU-s-dI-s-mGdI-s-dGdI-s-dGmCmU wherein mC, mG, mU and mA=2'-OMe C, 2'-OMe G, 2'-OMe U and 2'-OMe A respectively, dG=deoxy G, dI=deoxy inosine, and s=a phosphorothioate backbone substitution.

20. A composition comprising an aptamer of any one of claims 1, 4, 7, 8, 11, 12, 15, 16, and 19 or a salt thereof and a pharmaceutically acceptable carrier or diluent.

* * * * *

```
                         SEQUENCE LISTING

<160> NUMBER OF SEQ ID NOS: 298

<210> SEQ ID NO 1
<211> LENGTH: 93
<212> TYPE: DNA
<213> ORGANISM: artificial
<220> FEATURE:
<223> OTHER INFORMATION: synthetic template
<220> FEATURE:
<221> NAME/KEY: misc_feature
<222> LOCATION: (25)..(54)
<223> OTHER INFORMATION: n is a, t, c, or g

<400> SEQUENCE: 1
catcgatgct agtcgtaacg atccnnnnnn nnnnnnnnnn nnnnnnnnnn nnnncgagaa      60
cgttctctcc tctccctata gtgagtcgta tta                                  93

<210> SEQ ID NO 2
<211> LENGTH: 92
<212> TYPE: DNA
<213> ORGANISM: artificial
<220> FEATURE:
<223> OTHER INFORMATION: synthetic template
<220> FEATURE:
<221> NAME/KEY: misc_feature
<222> LOCATION: (24)..(53)
<223> OTHER INFORMATION: n is a, t, c, or g

<400> SEQUENCE: 2
catgcatcgc gactgactag ccgnnnnnnn nnnnnnnnnn nnnnnnnnnn nnngtagaac      60
gttctctcct ctccctatag tgagtcgtat ta                                   92

<210> SEQ ID NO 3
<211> LENGTH: 92
<212> TYPE: DNA
<213> ORGANISM: artificial
<220> FEATURE:
<223> OTHER INFORMATION: synthetic template
<220> FEATURE:
<221> NAME/KEY: misc_feature
<222> LOCATION: (24)..(53)
<223> OTHER INFORMATION: n is a, t, c, or g

<400> SEQUENCE: 3
catcgatcga tcgatcgaca gcgnnnnnnn nnnnnnnnnn nnnnnnnnnn nnngtagaac      60
gttctctcct ctccctatag tgagtcgtat ta                                   92
```

-continued

<210> SEQ ID NO 4
<211> LENGTH: 10
<212> TYPE: DNA
<213> ORGANISM: artificial
<220> FEATURE:
<223> OTHER INFORMATION: synthetic immunostimulatory motif

<400> SEQUENCE: 4
aacgttcgag                                                          10

<210> SEQ ID NO 5
<211> LENGTH: 88
<212> TYPE: DNA
<213> ORGANISM: artificial
<220> FEATURE:
<223> OTHER INFORMATION: synthetic template
<220> FEATURE:
<221> NAME/KEY: misc_feature
<222> LOCATION: (25)..(64)
<223> OTHER INFORMATION: n is a, t, c, or g

<400> SEQUENCE: 5
gggaaaagcg aatcatacac aagannnnnn nnnnnnnnnn nnnnnnnnnn nnnnnnnnnn     60
nnnngctccg ccagagacca accgagaa                                        88

<210> SEQ ID NO 6
<211> LENGTH: 41
<212> TYPE: DNA
<213> ORGANISM: artificial
<220> FEATURE:
<223> OTHER INFORMATION: synthetic primer

<400> SEQUENCE: 6
taatacgact cactataggg aaaagcgaat catacacaag a                         41

<210> SEQ ID NO 7
<211> LENGTH: 24
<212> TYPE: DNA
<213> ORGANISM: artificial
<220> FEATURE:
<223> OTHER INFORMATION: synthetic primer

<400> SEQUENCE: 7
ttctcggttg gtctctggcg gagc                                            24

<210> SEQ ID NO 8
<211> LENGTH: 88
<212> TYPE: RNA
<213> ORGANISM: artificial
<220> FEATURE:
<223> OTHER INFORMATION: synthetic template
<220> FEATURE:
<221> NAME/KEY: misc_feature
<222> LOCATION: (25)..(64)
<223> OTHER INFORMATION: n is a c, u, or g

<400> SEQUENCE: 8
gggaaaagcg aaucauacac aagannnnnn nnnnnnnnnn nnnnnnnnnn nnnnnnnnnn     60
nnnngcuccg ccagagacca accgagaa                                        88

<210> SEQ ID NO 9
<211> LENGTH: 24
<212> TYPE: RNA
<213> ORGANISM: artificial
<220> FEATURE:

```
<223> OTHER INFORMATION: synthetic fixed region

<400> SEQUENCE: 9
gggaaaagcg aaucauacac aaga                                              24

<210> SEQ ID NO 10
<211> LENGTH: 24
<212> TYPE: RNA
<213> ORGANISM: artificial
<220> FEATURE:
<223> OTHER INFORMATION: synthetic fixed region

<400> SEQUENCE: 10
gcuccgccag agaccaaccg agaa                                              24

<210> SEQ ID NO 11
<211> LENGTH: 88
<212> TYPE: RNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(88)
<223> OTHER INFORMATION: all purines (A and G) are 2'-OH, all
      pyrimidines (C and U) are 2'-fluoro

<400> SEQUENCE: 11
gggaaaagcg aaucauacac aagacgucgc cagauugagu gucguggttuc ggguugaggc      60 ggaagcuccg ccagagacca accgagaa                                          88

<210> SEQ ID NO 12
<211> LENGTH: 87
<212> TYPE: RNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(87)
<223> OTHER INFORMATION: all purines (A and G) are 2'-OH, all
      pyrimidines (C and U) are 2'-fluoro

<400> SEQUENCE: 12
ggaaaagcga aucauacaca agagucgcga uagauugcuu gugaauggutu uuggtuggaag     60 cgggcuccgc cagagaccaa ccgagaa                                           87

<210> SEQ ID NO 13
<211> LENGTH: 88
<212> TYPE: RNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(88)
<223> OTHER INFORMATION: all purines (A and G) are 2'-OH, all
      pyrimidines (C and U) are 2'-fluoro

<400> SEQUENCE: 13
gggaaaagcg aaucauacac aagagucgcu agauugcuag uguauggtuuu aucuaaaggc      60 ggccgcuccg ccagagacca accgagaa                                          88

<210> SEQ ID NO 14
<211> LENGTH: 87
<212> TYPE: RNA
```

```
<213> ORGANISM: artificial
<220> FEATURE:
<223> OTHER INFORMATION: synthetic aptamer
<220> FEATURE:
<221> NAME/KEY: modified_base
<222> LOCATION: (1)..(87)
<223> OTHER INFORMATION: all purines (A and G) are 2'-OH, all
      pyrimidines (C and U) are 2'-fluoro

<400> SEQUENCE: 14
gggaaaagcg aaucauacac aagaggucuu acagauccug uguagugguu cgauacaugc      60
ggggcuccgc cagagaccaa ccgagaa                                          87

<210> SEQ ID NO 15
<211> LENGTH: 88
<212> TYPE: RNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(88)
<223> OTHER INFORMATION: all purines (A and G) are 2'-OH, all
      pyrimidines (C and U) are 2'-fluoro

<400> SEQUENCE: 15
gggaaaagcg aaucauacac aagacgugag cauaucauug aguguagugg uuccggagua      60
agucgcuccg ccagagacca accgagaa                                         88

<210> SEQ ID NO 16
<211> LENGTH: 87
<212> TYPE: RNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(87)
<223> OTHER INFORMATION: all purines (A and G) are 2'-OH, all
      pyrimidines (C and U) are 2'-fluoro

<400> SEQUENCE: 16
gggaaaagcg aaucauacac aagagcaccu ugacugugau ucgcgggugu gagucgugcg      60
aaggcuccgc cagagaccaa ccgagaa                                          87

<210> SEQ ID NO 17
<211> LENGTH: 88
<212> TYPE: RNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(88)
<223> OTHER INFORMATION: all purines (A and G) are 2'-OH, all
      pyrimidines (C and U) are 2'-fluoro

<400> SEQUENCE: 17
gggaaaagcg aaucauacac aagagugcaa gaagugcauu gcugugucug guucuuggcg      60
augugcuccg ccagagacca accgagaa                                         88

<210> SEQ ID NO 18
<211> LENGTH: 88
<212> TYPE: RNA
<213> ORGANISM: artificial
<220> FEATURE:
<223> OTHER INFORMATION: synthetic aptamer
```

```
<220> FEATURE:
<221> NAME/KEY: modified_base
<222> LOCATION: (1)..(88)
<223> OTHER INFORMATION: all purines (A and G) are 2'-OH, all
      pyrimidines (C and U) are 2'-fluoro

<400> SEQUENCE: 18
gggaaaagcg aaucauacac aagauccgag ggugggcaau aggcucacaa ggguuucgcg      60
ugaugcuccg ccagagacca accgagaa                                        88

<210> SEQ ID NO 19
<211> LENGTH: 88
<212> TYPE: RNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(88)
<223> OTHER INFORMATION: all purines (A and G) are 2'-OH, all
      pyrimidines (C and U) are 2'-fluoro

<400> SEQUENCE: 19
gggaaaagcg aaucauacac aagagugccg aggcauugcu gguaugguu ccggucuugu       60 cggggcuccg ccagagacca accgagaa                                        88

<210> SEQ ID NO 20
<211> LENGTH: 88
<212> TYPE: RNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(88)
<223> OTHER INFORMATION: all purines (A and G) are 2'-OH, all
      pyrimidines (C and U) are 2'-fluoro

<400> SEQUENCE: 20
gggaaaagcg aaucauacac aagacgucgc cagauugagu guggugguuc ggguugaggc      60
ggaagcuccg ccagagacca accgagaa                                        88

<210> SEQ ID NO 21
<211> LENGTH: 90
<212> TYPE: RNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(90)
<223> OTHER INFORMATION: all purines (A and G) are 2'-OH, all
      pyrimidines (C and U) are 2'-fluoro

<400> SEQUENCE: 21
gggaaaagcg aaucauacac aagacgucag uaagauugag uguaugguuc cuggguggaca     60 auaauggcuc cgccagagac caaccgagaa                                      90

<210> SEQ ID NO 22
<211> LENGTH: 88
<212> TYPE: RNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(88)
```

<223> OTHER INFORMATION: all purines (A and G) are 2'-OH, all
      pyrimidines (C and U) are 2'-fluoro

<400> SEQUENCE: 22
gggaaaagcg aaucauacac aagagagugg aggagguaug uaugguuugu gcgucuggug    60
cggugcuccg ccagagacca accgagaa                                      88

<210> SEQ ID NO 23
<211> LENGTH: 75
<212> TYPE: DNA
<213> ORGANISM: artificial
<220> FEATURE:
<223> OTHER INFORMATION: synthetic template
<220> FEATURE:
<221> NAME/KEY: misc_feature
<222> LOCATION: (23)..(52)
<223> OTHER INFORMATION: n is a, t, c, or g

<400> SEQUENCE: 23
gggagaggag agaacgttct acnnnnnnnn nnnnnnnnnn nnnnnnnnnn nncgctgtcg    60
atcgatcgat cgatg                                                    75

<210> SEQ ID NO 24
<211> LENGTH: 22
<212> TYPE: DNA
<213> ORGANISM: artificial
<220> FEATURE:
<223> OTHER INFORMATION: synthetic primer

<400> SEQUENCE: 24
gggagaggag agaacgttct ac                                            22

<210> SEQ ID NO 25
<211> LENGTH: 22
<212> TYPE: DNA
<213> ORGANISM: artificial
<220> FEATURE:
<223> OTHER INFORMATION: synthetic primer

<400> SEQUENCE: 25
catcgatcga tcgatcgaca gc                                            22

<210> SEQ ID NO 26
<211> LENGTH: 22
<212> TYPE: RNA
<213> ORGANISM: artificial
<220> FEATURE:
<223> OTHER INFORMATION: synthetic fixed region

<400> SEQUENCE: 26
gggagaggag agaacguucu ac                                            22

<210> SEQ ID NO 27
<211> LENGTH: 23
<212> TYPE: RNA
<213> ORGANISM: artificial
<220> FEATURE:
<223> OTHER INFORMATION: synthetic fixed region

<400> SEQUENCE: 27
cgcugucgau cgaucgaucg aug                                           23

<210> SEQ ID NO 28
<211> LENGTH: 75
<212> TYPE: DNA

```
<213> ORGANISM: artificial
<220> FEATURE:
<223> OTHER INFORMATION: synthetic aptamer
<220> FEATURE:
<221> NAME/KEY: modified_base
<222> LOCATION: (1)..(75)
<223> OTHER INFORMATION: all purines (A and G) are deoxy, all
      pyrimidines (C and U) are 2'-O-methyl

<400> SEQUENCE: 28
gggagaggag agaacguucu acgauuagca gggagggaga gugcgaagag gacgcugucg    60
aucgaucgau cgaug                                                    75

<210> SEQ ID NO 29
<211> LENGTH: 75
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(75)
<223> OTHER INFORMATION: all purines (A and G) are deoxy, all
      pyrimidines (C and U) are 2'-O-methyl

<400> SEQUENCE: 29
gggagaggag agaacguucu acacucuggg gacccguggg ggagugcagc aacgcugucg    60
aucgaucgau cgaug                                                    75

<210> SEQ ID NO 30
<211> LENGTH: 74
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(74)
<223> OTHER INFORMATION: all purines (A and G) are deoxy, all
      pyrimidines (C and U) are 2'-O-methyl

<400> SEQUENCE: 30
gggagaggag agaacguucu acgaggugag ggucuacaau ggagggaugg ucgcugucga    60
ucgaucgauc gaug                                                     74

<210> SEQ ID NO 31
<211> LENGTH: 75
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(75)
<223> OTHER INFORMATION: all purines (A and G) are deoxy, all
      pyrimidines (C and U) are 2'-O-methyl
<220> FEATURE:
<221> NAME/KEY: misc_feature
<222> LOCATION: (38)..(38)
<223> OTHER INFORMATION: n is a, c, u, or g
<220> FEATURE:
<221> NAME/KEY: misc_feature
<222> LOCATION: (48)..(48)
<223> OTHER INFORMATION: n is a, c, u, or g

<400> SEQUENCE: 31
gggagaggag agaacguucu acccgcagca uagccugngg acccaugngg ggcgcugucg    60
aucgaucgau cgaug                                                    75
```

<210> SEQ ID NO 32
<211> LENGTH: 75
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(75)
<223> OTHER INFORMATION: all purines (A and G) are deoxy, all
      pyrimidines (C and U) are 2'-O-methyl

<400> SEQUENCE: 32
gggagaggag agaacguucu acugggggc guguucauua gcagcgucgu gucgcugucg    60
aucgaucgau cgaug                                                   75

<210> SEQ ID NO 33
<211> LENGTH: 75
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(75)
<223> OTHER INFORMATION: all purines (A and G) are deoxy, all
      pyrimidines (C and U) are 2'-O-methyl

<400> SEQUENCE: 33
gggagaggag agaacguucu acgcagcgca ucuggggacc caagagggga uucgcugucg    60
aucgaucgau cgaug                                                    75

<210> SEQ ID NO 34
<211> LENGTH: 73
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(73)
<223> OTHER INFORMATION: all purines (A and G) are deoxy, all
      pyrimidines (C and U) are 2'-O-methyl

<400> SEQUENCE: 34
gggagaggag agaacguucu acgggauggg uaguuggaug gaaaugggaa cgcugucgau    60
cgaucgaucg aug                                                      73

<210> SEQ ID NO 35
<211> LENGTH: 74
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(74)
<223> OTHER INFORMATION: all purines (A and G) are deoxy, all
      pyrimidines (C and U) are 2'-O-methyl

<400> SEQUENCE: 35
gggagaggag agaacguucu acgaggugua gggauagagg gguguaggua acgcugucga    60
ucgaucgauc gaug                                                     74

<210> SEQ ID NO 36

```
<211> LENGTH: 75
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(75)
<223> OTHER INFORMATION: all purines (A and G) are deoxy, all
      pyrimidines (C and U) are 2'-O-methyl

<400> SEQUENCE: 36
gggagaggag agaacguucu acaggagugg agcuacagag aggguuaggg gucgcugucg    60
aucgaucgau cgaug                                                    75

<210> SEQ ID NO 37
<211> LENGTH: 75
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(75)
<223> OTHER INFORMATION: all purines (A and G) are deoxy, all
      pyrimidines (C and U) are 2'-O-methyl

<400> SEQUENCE: 37
gggagaggag agaacguucu acggauguug ggagugauag aaggaagggg agcgcugucg    60
aucgaucgau cgaug                                                    75

<210> SEQ ID NO 38
<211> LENGTH: 76
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(76)
<223> OTHER INFORMATION: all purines (A and G) are deoxy, all
      pyrimidines (C and U) are 2'-O-methyl

<400> SEQUENCE: 38
gggagaggag agaacguucu acuuggggug gaaggaguaa gggaggugcu gaucgcuguc    60
gaucgaucga ucgaug                                                   76

<210> SEQ ID NO 39
<211> LENGTH: 75
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(75)
<223> OTHER INFORMATION: all purines (A and G) are deoxy, all
      pyrimidines (C and U) are 2'-O-methyl

<400> SEQUENCE: 39
gggagaggag agaacguucu acguauuagg ggggaagggg aggaauagau cacgcugucg    60
aucgaucgau cgaug                                                    75

<210> SEQ ID NO 40
<211> LENGTH: 76
<212> TYPE: DNA
<213> ORGANISM: artificial
```

```
<220> FEATURE:
<223> OTHER INFORMATION: synthetic aptamer
<220> FEATURE:
<221> NAME/KEY: modified_base
<222> LOCATION: (1)..(76)
<223> OTHER INFORMATION: all purines (A and G) are deoxy, all
      pyrimidines (C and U) are 2'-O-methyl

<400> SEQUENCE: 40
gggagaggag agaacguucu acagggagag aguguugagu gaagaggagg agucgcuguc      60
gaucgaucga ucgaug                                                     76

<210> SEQ ID NO 41
<211> LENGTH: 75
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(75)
<223> OTHER INFORMATION: all purines (A and G) are deoxy, all
      pyrimidines (C and U) are 2'-O-methyl

<400> SEQUENCE: 41
gggagaggag agaacguucu acauugugcu ccugggccc agugggagc cacgcugucg       60 aucgaucgau cgaug                                                      75

<210> SEQ ID NO 42
<211> LENGTH: 75
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(75)
<223> OTHER INFORMATION: all purines (A and G) are deoxy, all
      pyrimidines (C and U) are 2'-O-methyl

<400> SEQUENCE: 42
gggagaggag agaacguucu acgagcagcc cugggggcccg gaggggaug gucgcugucg     60 aucgaucgau cgaug                                                      75

<210> SEQ ID NO 43
<211> LENGTH: 75
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(75)
<223> OTHER INFORMATION: all purines (A and G) are deoxy, all
      pyrimidines (C and U) are 2'-O-methyl

<400> SEQUENCE: 43
gggagaggag agaacguucu acaggcaguu cugggaccc auggggaag ugcgcugucg      60 aucgaucgau cgaug                                                      75

<210> SEQ ID NO 44
<211> LENGTH: 75
<212> TYPE: DNA
<213> ORGANISM: artificial
<220> FEATURE:
<223> OTHER INFORMATION: synthetic aptamer
<220> FEATURE:
```

```
<221> NAME/KEY: modified_base
<222> LOCATION: (1)..(75)
<223> OTHER INFORMATION: all purines (A and G) are deoxy, all
      pyrimidines (C and U) are 2'-O-methyl

<400> SEQUENCE: 44
gggagaggag agaacguucu accaacggca uccugggccc cacaggggau gucgcugucg      60
aucgaucgau cgaug                                                      75

<210> SEQ ID NO 45
<211> LENGTH: 74
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(74)
<223> OTHER INFORMATION: all purines (A and G) are deoxy, all
      pyrimidines (C and U) are 2'-O-methyl

<400> SEQUENCE: 45
gggagaggag agaacguucu acgaguggau agggaagaag gggaguaguc acgcugucga      60
ucgaucgauc gaug                                                       74

<210> SEQ ID NO 46
<211> LENGTH: 75
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(75)
<223> OTHER INFORMATION: all purines (A and G) are deoxy, all
      pyrimidines (C and U) are 2'-O-methyl

<400> SEQUENCE: 46
gggagaggag agaacguucu acccgcagca uagccugggg acccaugggg ggcgcugucg      60
aucgaucgau cgaug                                                      75

<210> SEQ ID NO 47
<211> LENGTH: 76
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(76)
<223> OTHER INFORMATION: all purines (A and G) are deoxy, all
      pyrimidines (C and U) are 2'-O-methyl
<220> FEATURE:
<221> NAME/KEY: misc_feature
<222> LOCATION: (61)..(61)
<223> OTHER INFORMATION: n is a, c, u, or g

<400> SEQUENCE: 47
gggagaggag agaacguucu acggucgcgu guggggacg gaugggauauu ggucgcuguc      60 naucgaucga ucgaug                                                     76

<210> SEQ ID NO 48
<211> LENGTH: 75
<212> TYPE: DNA
<213> ORGANISM: artificial
<220> FEATURE:
<223> OTHER INFORMATION: synthetic aptamer
```

```
<220> FEATURE:
<221> NAME/KEY: modified_base
<222> LOCATION: (1)..(75)
<223> OTHER INFORMATION: all purines (A and G) are deoxy, all
      pyrimidines (C and U) are 2'-O-methyl

<400> SEQUENCE: 48
gggagaggag agaacguucu acggggguuac gucgcacgau acaugcauuc aucgcugucg    60
aucgaucgau cgaug                                                     75

<210> SEQ ID NO 49
<211> LENGTH: 75
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(75)
<223> OTHER INFORMATION: all purines (A and G) are deoxy, all
      pyrimidines (C and U) are 2'-O-methyl

<400> SEQUENCE: 49
gggagaggag agaacguucu acuagcgagg aggggguuuuc uauuuuugcg aucgcugucg   60
aucgaucgau cgaug                                                    75

<210> SEQ ID NO 50
<211> LENGTH: 75
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(75)
<223> OTHER INFORMATION: all purines (A and G) are deoxy, all
      pyrimidines (C and U) are 2'-O-methyl

<400> SEQUENCE: 50
gggagaggag agaacguucu acaagcaguu cugggaccc auggggggaag ugcgcugucg    60 aucgaucgau cgaug                                                    75

<210> SEQ ID NO 51
<211> LENGTH: 75
<212> TYPE: DNA
<213> ORGANISM: artificial
<220> FEATURE:
<223> OTHER INFORMATION: synthetic template
<220> FEATURE:
<221> NAME/KEY: misc_feature
<222> LOCATION: (23)..(52)
<223> OTHER INFORMATION: n is a, t, c, or g

<400> SEQUENCE: 51
gggagaggag agaacgttct acnnnnnnnn nnnnnnnnnn nnnnnnnnnn nncgctgtcg    60
atcgatcgat cgatg                                                    75

<210> SEQ ID NO 52
<211> LENGTH: 22
<212> TYPE: DNA
<213> ORGANISM: artificial
<220> FEATURE:
<223> OTHER INFORMATION: synthetic primer

<400> SEQUENCE: 52
gggagaggag agaacgttct ac                                             22
```

```
<210> SEQ ID NO 53
<211> LENGTH: 22
<212> TYPE: DNA
<213> ORGANISM: artificial
<220> FEATURE:
<223> OTHER INFORMATION: synthetic primer

<400> SEQUENCE: 53
catcgatcga tcgatcgaca gc                                              22

<210> SEQ ID NO 54
<211> LENGTH: 21
<212> TYPE: RNA
<213> ORGANISM: artificial
<220> FEATURE:
<223> OTHER INFORMATION: synthetic fixed region

<400> SEQUENCE: 54
gggagaggag agaacguucu a                                               21

<210> SEQ ID NO 55
<211> LENGTH: 23
<212> TYPE: RNA
<213> ORGANISM: artificial
<220> FEATURE:
<223> OTHER INFORMATION: synthetic fixed region

<400> SEQUENCE: 55
cgcugucgau cgaucgaucg aug                                             23

<210> SEQ ID NO 56
<211> LENGTH: 82
<212> TYPE: RNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(82)
<223> OTHER INFORMATION: all purines (A and G) are 2'-OH, all
      pyrimidines (C and U) are 2'-O-methyl

<400> SEQUENCE: 56
gggagaggag agaacguucu acgaucuggg cgagccaguc ugacugagga agcgcugucg     60
aucgaucgau cgaugaaggg cg                                              82

<210> SEQ ID NO 57
<211> LENGTH: 82
<212> TYPE: RNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(82)
<223> OTHER INFORMATION: all purines (A and G) are 2'-OH, all
      pyrimidines (C and U) are 2'-O-methyl

<400> SEQUENCE: 57
gggagaggag agaacguucu acgcggucgg guguguggag gaaguaguuc gucgcugucg     60
aucgaucgau cgaugaaggg cg                                              82

<210> SEQ ID NO 58
<211> LENGTH: 82
<212> TYPE: RNA
```

<213> ORGANISM: artificial
<220> FEATURE:
<223> OTHER INFORMATION: synthetic aptamer
<220> FEATURE:
<221> NAME/KEY: modified_base
<222> LOCATION: (1)..(82)
<223> OTHER INFORMATION: all purines (A and G) are 2'-OH, all
      pyrimidines (C and U) are 2'-O-methyl

<400> SEQUENCE: 58
gggagaggag agaacguucu acgacguuaa ugcagcggcu agggaugggc agcgcugucg    60
aucgaucgau cgaugaaggg cg                                            82

<210> SEQ ID NO 59
<211> LENGTH: 82
<212> TYPE: RNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(82)
<223> OTHER INFORMATION: all purines (A and G) are 2'-OH, all
      pyrimidines (C and U) are 2'-O-methyl

<400> SEQUENCE: 59
gggagaggag agaacguucu acaggcgugu ugguagggua cgacgaggca ugcgcugucg    60
aucgaucgau cgaugaaggg cg                                            82

<210> SEQ ID NO 60
<211> LENGTH: 82
<212> TYPE: RNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(82)
<223> OTHER INFORMATION: all purines (A and G) are 2'-OH, all
      pyrimidines (C and U) are 2'-O-methyl

<400> SEQUENCE: 60
gggagaggag agaacguucu acugagggau aauacgggug ggauugucuu cccgcugucg    60
aucgaucgau cgaugaaggg cg                                            82

<210> SEQ ID NO 61
<211> LENGTH: 82
<212> TYPE: RNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(82)
<223> OTHER INFORMATION: all purines (A and G) are 2'-OH, all
      pyrimidines (C and U) are 2'-O-methyl

<400> SEQUENCE: 61
gggagaggag agaacguucu acgaaaaaga uaugagagaa aggauuaaga gacgcugucg    60
aucgaucgau cgaugaaggg cg                                            82

<210> SEQ ID NO 62
<211> LENGTH: 82
<212> TYPE: RNA
<213> ORGANISM: artificial
<220> FEATURE:
<223> OTHER INFORMATION: synthetic aptamer

```
<220> FEATURE:
<221> NAME/KEY: modified_base
<222> LOCATION: (1)..(82)
<223> OTHER INFORMATION: all purines (A and G) are 2'-OH, all
      pyrimidines (C and U) are 2'-O-methyl

<400> SEQUENCE: 62
gggagaggag agaacguucu acgaagaaga uaugagagaa aggauuaaga gacgcugucg    60
aucgaucgau cgaugaaggg cg                                            82

<210> SEQ ID NO 63
<211> LENGTH: 82
<212> TYPE: RNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(82)
<223> OTHER INFORMATION: all purines (A and G) are 2'-OH, all
      pyrimidines (C and U) are 2'-O-methyl

<400> SEQUENCE: 63
gggagaggag agaacguucu acgaaaaaga uaugagagaa aggauuaaga gacgcugucg    60
aucgaucgau cgaugaaggg cg                                            82

<210> SEQ ID NO 64
<211> LENGTH: 82
<212> TYPE: RNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(82)
<223> OTHER INFORMATION: all purines (A and G) are 2'-OH, all
      pyrimidines (C and U) are 2'-O-methyl

<400> SEQUENCE: 64
gggagaggag agaacguucu acgaaaaaga uaugagagaa aggauuaaga ggcgcugucg    60
aucgaucgau cgaugaaggg cg                                            82

<210> SEQ ID NO 65
<211> LENGTH: 82
<212> TYPE: RNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(82)
<223> OTHER INFORMATION: all purines (A and G) are 2'-OH, all
      pyrimidines (C and U) are 2'-O-methyl

<400> SEQUENCE: 65
gggagaggag agaacguucu acgaaaaaga caugagagaa aggauuaaga gacgcugucg    60
aucgaucgau cgaugaaggg cg                                            82

<210> SEQ ID NO 66
<211> LENGTH: 83
<212> TYPE: RNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(83)
```

```
<223> OTHER INFORMATION: all purines (A and G) are 2'-OH, all
      pyrimidines (C and U) are 2'-O-methyl
<220> FEATURE:
<221> NAME/KEY: misc_feature
<222> LOCATION: (23)..(23)
<223> OTHER INFORMATION: n is a, c, u, or g
<220> FEATURE:
<221> NAME/KEY: misc_feature
<222> LOCATION: (50)..(50)
<223> OTHER INFORMATION: n is a, c, u, or g

<400> SEQUENCE: 66
gggagaggag agaacguucu acnaaaaagu auaugagaga aaggauuaan agacgcuguc      60
gaucgaucga ucgaugaagg gcg                                             83

<210> SEQ ID NO 67
<211> LENGTH: 83
<212> TYPE: RNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(83)
<223> OTHER INFORMATION: all purines (A and G) are 2'-OH, all
      pyrimidines (C and U) are 2'-O-methyl

<400> SEQUENCE: 67
gggagaggag agaacguucu acgaaaaaga uaugagagaa aaggauugag agaugcuguc      60
gaucgaucga ucgaugaagg gcg                                             83

<210> SEQ ID NO 68
<211> LENGTH: 83
<212> TYPE: RNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(83)
<223> OTHER INFORMATION: all purines (A and G) are 2'-OH, all
      pyrimidines (C and U) are 2'-O-methyl

<400> SEQUENCE: 68
gggagaggag agcacguucu acgaaaaaga uauggagaga aaggauuaag agacgcuguc      60
gaucgaucga ucgaugaagg gcg                                             83

<210> SEQ ID NO 69
<211> LENGTH: 84
<212> TYPE: RNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(84)
<223> OTHER INFORMATION: all purines (A and G) are 2'-OH, all
      pyrimidines (C and U) are 2'-O-methyl

<400> SEQUENCE: 69
gggagaggag agaacguucu acgaaaaaga uaugagagaa aggauuaaaa gagacgcugu      60
cgaucgaucg aucgaugaag ggcg                                            84

<210> SEQ ID NO 70
<211> LENGTH: 85
<212> TYPE: RNA
<213> ORGANISM: artificial
```

```
<220> FEATURE:
<223> OTHER INFORMATION: synthetic aptamer
<220> FEATURE:
<221> NAME/KEY: modified_base
<222> LOCATION: (1)..(85)
<223> OTHER INFORMATION: all purines (A and G) are 2'-OH, all
      pyrimidines (C and U) are 2'-O-methyl
<220> FEATURE:
<221> NAME/KEY: misc_feature
<222> LOCATION: (26)..(26)
<223> OTHER INFORMATION: n is a, c, u, or g

<400> SEQUENCE: 70
gggagaggag agaacguucu acgaanaaga uacauaguag aaaggauuaa uaagacgcug        60
ucgaucgauc gaucgaugaa gggcg                                             85

<210> SEQ ID NO 71
<211> LENGTH: 82
<212> TYPE: RNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(82)
<223> OTHER INFORMATION: all purines (A and G) are 2'-OH, all
      pyrimidines (C and U) are 2'-O-methyl

<400> SEQUENCE: 71
gggagaggag agaacguucu acaggcgugu ugguagggua cgacgaggca ugcgcugucg        60
aucgaucgau cgaugaaggg cg                                                82

<210> SEQ ID NO 72
<211> LENGTH: 82
<212> TYPE: RNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(82)
<223> OTHER INFORMATION: all purines (A and G) are 2'-OH, all
      pyrimidines (C and U) are 2'-O-methyl

<400> SEQUENCE: 72
gggagaggag agaacguucu acgcaaaaau gugaugcgag guaauggaac gccgcugucg        60
aucgaucgau cgaugaaggg cg                                                82

<210> SEQ ID NO 73
<211> LENGTH: 82
<212> TYPE: RNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(82)
<223> OTHER INFORMATION: all purines (A and G) are 2'-OH, all
      pyrimidines (C and U) are 2'-O-methyl

<400> SEQUENCE: 73
gggagaggag agaacguucu acggaccuca gcgauagggg uugaaaccga cacgcugucg        60
aucgaucgau cgaugaaggg cg                                                82

<210> SEQ ID NO 74
<211> LENGTH: 82
<212> TYPE: RNA
```

<213> ORGANISM: artificial
<220> FEATURE:
<223> OTHER INFORMATION: synthetic aptamer
<220> FEATURE:
<221> NAME/KEY: modified_base
<222> LOCATION: (1)..(82)
<223> OTHER INFORMATION: all purines (A and G) are 2'-OH, all
      pyrimidines (C and U) are 2'-O-methyl

<400> SEQUENCE: 74
gggagaggag agaacguucu acauggucgg augcugggga guaggcaagg uucgcugucg    60
aucgaucgau cgaugaaggg cg                                             82

<210> SEQ ID NO 75
<211> LENGTH: 82
<212> TYPE: RNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(82)
<223> OTHER INFORMATION: all purines (A and G) are 2'-OH, all
      pyrimidines (C and U) a 2'-O-methyl

<400> SEQUENCE: 75
gggagaggag agaacguucu acguaucggc gagcgaagca uccgggagcg uucgcugucg    60
aucgaucgau cgaugaaggg cg                                             82

<210> SEQ ID NO 76
<211> LENGTH: 82
<212> TYPE: RNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(82)
<223> OTHER INFORMATION: all purines (A and G) are 2'-OH, all
      pyrimidines (C and U) are 2'-O-methyl

<400> SEQUENCE: 76
gggagaggag agaacguucu acguauuggc gcgcgaagca uccgggagcg uucgcugucg    60
aucgaucgau cgaugaaggg cg                                             82

<210> SEQ ID NO 77
<211> LENGTH: 82
<212> TYPE: RNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(82)
<223> OTHER INFORMATION: all purines (A and G) are 2'-OH, all
      pyrimidines (C and U) are 2'-O-methyl

<400> SEQUENCE: 77
gggagaggag agaacguucu acuuauaccu gacggccgga ggcgcauagg ugcgcugucg    60
aucgaucgau cgaugaaggg cg                                             82

<210> SEQ ID NO 78
<211> LENGTH: 82
<212> TYPE: RNA
<213> ORGANISM: artificial
<220> FEATURE:
<223> OTHER INFORMATION: synthetic aptamer

```
<220> FEATURE:
<221> NAME/KEY: modified_base
<222> LOCATION: (1)..(82)
<223> OTHER INFORMATION: all purines (A and G) are 2'-OH, all
      pyrimidines (C and U) are 2'-O-methyl

<400> SEQUENCE: 78
gggagaggag agaacguucu acauggucgg augcugggga guaggcaagg uucgcugucg    60
aucgaucgau cgaugaaggg cg                                             82

<210> SEQ ID NO 79
<211> LENGTH: 82
<212> TYPE: RNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(82)
<223> OTHER INFORMATION: all purines (A and G) are 2'-OH, all
      pyrimidines (C and U) are 2'-O-methyl

<400> SEQUENCE: 79
gggagaggag agaacguucu acacgagagu acugaggcgc uugguacaga gucgcugucg    60
aucgaucgau cgaugaaggg cg                                             82

<210> SEQ ID NO 80
<211> LENGTH: 82
<212> TYPE: RNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(82)
<223> OTHER INFORMATION: all purines (A and G) are 2'-OH, all
      pyrimidines (C and U) are 2'-O-methyl

<400> SEQUENCE: 80
gggagaggag agaacguucu acagaaggua gaaaaaggau agcugugaga agcgcugucg    60
aucgaucgau cgaugaaggg cg                                             82

<210> SEQ ID NO 81
<211> LENGTH: 82
<212> TYPE: RNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(82)
<223> OTHER INFORMATION: all purines (A and G) are 2'-OH, all
      pyrimidines (C and U) are 2'-O-methyl

<400> SEQUENCE: 81
gggagaggag agaacguucu acugagggau aauacggguq ggauugucuu cccgcugucg    60
aucgaucgau cgaugaaggg cg                                             82

<210> SEQ ID NO 82
<211> LENGTH: 84
<212> TYPE: RNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(84)
```

<223> OTHER INFORMATION: all purines (A and G) are 2'-OH, all
      pyrimidines (C and U) are 2'-O-methyl

<400> SEQUENCE: 82
gggagaggag agaacguucu acauugagcg uugaaguugg ggaagcuccg aggccgcugu    60
cgaucgaucg aucgaugaag ggcg                                         84

<210> SEQ ID NO 83
<211> LENGTH: 82
<212> TYPE: RNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(82)
<223> OTHER INFORMATION: all purines (A and G) are 2'-OH, all
      pyrimidines (C and U) are 2'-O-methyl

<400> SEQUENCE: 83
gggagaggag agaacguucu acgcggagau auacagcgag guaauggaac gccgcugucg    60
aucgaucgau cgaugaaggg cg                                           82

<210> SEQ ID NO 84
<211> LENGTH: 82
<212> TYPE: RNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(82)
<223> OTHER INFORMATION: all purines (A and G) are 2'-OH, all
      pyrimidines (C and U) are 2'-O-methyl

<400> SEQUENCE: 84
gggagaggag agaacguucu acgaagacag cccaauagcg gcacggaacu ugcgcugucg    60
aucgaucgau cgaugaaggg cg                                           82

<210> SEQ ID NO 85
<211> LENGTH: 84
<212> TYPE: RNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(84)
<223> OTHER INFORMATION: all purines (A and G) are 2'-OH, all
      pyrimidines (C and U) are 2'-O-methyl

<400> SEQUENCE: 85
gggagaggag agaacguucu accgguugag ggcucgcgug gaagggccaa cacgcgcugu    60
cgaucgaucg aucgaugaag ggcg                                         84

<210> SEQ ID NO 86
<211> LENGTH: 82
<212> TYPE: RNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(82)
<223> OTHER INFORMATION: all purines (A and G) are 2'-OH, all
      pyrimidines (C and U) are 2'-O-methyl

<400> SEQUENCE: 86
gggagaggag agaacguucu acauaucaau agacucuuga cguuuggguu ugcgcugucg    60
aucgaucgau cgaugaaggg cg    82

<210> SEQ ID NO 87
<211> LENGTH: 79
<212> TYPE: RNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(79)
<223> OTHER INFORMATION: all purines (A and G) are 2'-OH, all
      pyrimidines (C and U) are 2'-O-methyl

<400> SEQUENCE: 87
gggagaggag agaacguucu acagugaagg aaaaguaagu gaaggugugc gcugucgauc    60
gaucgaucga ugaagggcg    79

<210> SEQ ID NO 88
<211> LENGTH: 82
<212> TYPE: RNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(82)
<223> OTHER INFORMATION: all purines (A and G) are 2'-OH, all
      pyrimidines (C and U) are 2'-O-methyl

<400> SEQUENCE: 88
gggagaggag agaacguucu acggaugaaa ugagugucug cgauagguua agcgcugucg    60
aucgaucgau cgaugaaggg cg    82

<210> SEQ ID NO 89
<211> LENGTH: 83
<212> TYPE: RNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(83)
<223> OTHER INFORMATION: all purines (A and G) are 2'-OH, all
      pyrimidines (C and U) are 2'-O-methyl

<400> SEQUENCE: 89
gggagaggag agaacguucu acggaaggaa augugugucu gcgauagguu aagcgcuguc    60
gaucgaucga ucgaugaagg gcg    83

<210> SEQ ID NO 90
<211> LENGTH: 49
<212> TYPE: RNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(49)
<223> OTHER INFORMATION: all purines (A and G) are 2'-OH, all
      pyrimidines (C and U) are 2'-fluoro

<400> SEQUENCE: 90
gggaaaagcg aaucauacac aagacgucgc cagauugagu gucgugguu    49

```
<210> SEQ ID NO 91
<211> LENGTH: 43
<212> TYPE: RNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(43)
<223> OTHER INFORMATION: all purines (A and G) are 2'-OH, all
      pyrimidines (C and U) are 2'-fluoro

<400> SEQUENCE: 91
ggaaucauac acaagacguc gccagauuga gugucguggu ucc                         43

<210> SEQ ID NO 92
<211> LENGTH: 41
<212> TYPE: RNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(41)
<223> OTHER INFORMATION: all purines (A and G) are 2'-OH, all
      pyrimidines (C and U) are 2'-fluoro

<400> SEQUENCE: 92
ggaaucauac acaagacguc gccagauuga gugucguggu u                           41

<210> SEQ ID NO 93
<211> LENGTH: 37
<212> TYPE: RNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(37)
<223> OTHER INFORMATION: all purines (A and G) are 2'-OH, all
      pyrimidines (C and U) are 2'-fluoro

<400> SEQUENCE: 93
ggagauccga ggugggcaau uaggcucaca agggu uu                               37

<210> SEQ ID NO 94
<211> LENGTH: 35
<212> TYPE: RNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(35)
<223> OTHER INFORMATION: all purines (A and G) are 2'-OH, all
      pyrimidines (C and U) are 2'-fluoro

<400> SEQUENCE: 94
ggauccgagg gugggcaaua ggcucacaag ggucc                                  35

<210> SEQ ID NO 95
<211> LENGTH: 43
<212> TYPE: RNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(43)
```

```
<223> OTHER INFORMATION: all purines (A and G) are 2'-OH, all
      pyrimidines (C and U) are 2'-fluoro

<400> SEQUENCE: 95
ggaaucauac acaagacguc aguaagauug aguguauggu ucc                    43

<210> SEQ ID NO 96
<211> LENGTH: 41
<212> TYPE: RNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(41)
<223> OTHER INFORMATION: all purines (A and G) are 2'-OH, all
      pyrimidines (C and U) are 2'-fluoro

<400> SEQUENCE: 96
ggaaucauac acaagacguc aguaagauug aguguauggu u                      41

<210> SEQ ID NO 97
<211> LENGTH: 21
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(21)
<223> OTHER INFORMATION: all purines (A and G) are deoxy, all
      pyrimidines (C and U) are 2'-O-methyl

<400> SEQUENCE: 97 uucugggac ccauggggga a                                             21

<210> SEQ ID NO 98
<211> LENGTH: 23
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(23)
<223> OTHER INFORMATION: all purines (A and G) are deoxy, all
      pyrimidines (C and U) are 2'-O-methyl

<400> SEQUENCE: 98
guucugggga cccaugggg aac                                           23

<210> SEQ ID NO 99
<211> LENGTH: 25
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(25)
<223> OTHER INFORMATION: all purines (A and G) are deoxy, all
      pyrimidines (C and U) are 2'-O-methyl

<400> SEQUENCE: 99
aguucugggg acccauggg gaacu                                         25

<210> SEQ ID NO 100
<211> LENGTH: 21
<212> TYPE: DNA
```

<213> ORGANISM: artificial
<220> FEATURE:
<223> OTHER INFORMATION: synthetic aptamer
<220> FEATURE:
<221> NAME/KEY: modified_base
<222> LOCATION: (1)..(21)
<223> OTHER INFORMATION: all purines (A and G) are deoxy, all
      pyrimidines (C and U) are 2'-O-methyl

<400> SEQUENCE: 100 gccugggac ccauggggg c                                              21

<210> SEQ ID NO 101
<211> LENGTH: 23
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(23)
<223> OTHER INFORMATION: all purines (A and G) are deoxy, all
      pyrimidines (C and U) are 2'-O-methyl

<400> SEQUENCE: 101
agccugggga cccauggggg gcu                                          23

<210> SEQ ID NO 102
<211> LENGTH: 25
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(25)
<223> OTHER INFORMATION: all purines (A and G) are deoxy, all
      pyrimidines (C and U) are 2'-O-methyl

<400> SEQUENCE: 102
uagccugggg acccaugggg ggcua                                        25

<210> SEQ ID NO 103
<211> LENGTH: 21
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(21)
<223> OTHER INFORMATION: all purines (A and G) are deoxy, all
      pyrimidines (C and U) are 2'-O-methyl

<400> SEQUENCE: 103 gccugggaa ccauggggg c                                              21

<210> SEQ ID NO 104
<211> LENGTH: 68
<212> TYPE: DNA
<213> ORGANISM: artificial
<220> FEATURE:
<223> OTHER INFORMATION: synthetic template

<400> SEQUENCE: 104
gggagaggag agaacgttct acagcctggg gacccatggg gggctggtcg atcgatcgat    60
catcgatg                                                             68

```
<210> SEQ ID NO 105
<211> LENGTH: 23
<212> TYPE: DNA
<213> ORGANISM: artificial
<220> FEATURE:
<223> OTHER INFORMATION: synthetic primer

<400> SEQUENCE: 105
catcgatgat cgatcgatcg acc                                              23

<210> SEQ ID NO 106
<211> LENGTH: 22
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(22)
<223> OTHER INFORMATION: all purines (A and G) are deoxy, all
      pyrimidines (C and U) are 2'-O-methyl

<400> SEQUENCE: 106
agccugggga cccauggggg cu                                               22

<210> SEQ ID NO 107
<211> LENGTH: 23
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(23)
<223> OTHER INFORMATION: all purines (A and G) are deoxy, all
      pyrimidines (C and U) are 2'-O-methyl

<400> SEQUENCE: 107
cgccugggga cccagggggg gcu                                              23

<210> SEQ ID NO 108
<211> LENGTH: 23
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(23)
<223> OTHER INFORMATION: all purines (A and G) are deoxy, all
      pyrimidines (C and U) are 2'-O-methyl

<400> SEQUENCE: 108
agccuggugg cccaugggu gcu                                               23

<210> SEQ ID NO 109
<211> LENGTH: 25
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(25)
<223> OTHER INFORMATION: all purines (A and G) are deoxy, all
      pyrimidines (C and U) are 2'-O-methyl

<400> SEQUENCE: 109
agccugggga cccauggggg guggu                                            25
```

```
<210> SEQ ID NO 110
<211> LENGTH: 23
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(23)
<223> OTHER INFORMATION: all purines (A and G) are deoxy, all
      pyrimidines (C and U) are 2'-O-methyl

<400> SEQUENCE: 110
agucugggga cagauggaug gcu                                              23

<210> SEQ ID NO 111
<211> LENGTH: 22
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(22)
<223> OTHER INFORMATION: all purines (A and G) are deoxy, all
      pyrimidines (C and U) are 2'-O-methyl

<400> SEQUENCE: 111
agcuguggag ucguguggggg cu                                              22

<210> SEQ ID NO 112
<211> LENGTH: 25
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(25)
<223> OTHER INFORMATION: all purines (A and G) are deoxy, all
      pyrimidines (C and U) are 2'-O-methyl

<400> SEQUENCE: 112
aagccugggg acccaugggg gggcu                                            25

<210> SEQ ID NO 113
<211> LENGTH: 37
<212> TYPE: DNA
<213> ORGANISM: artificial
<220> FEATURE:
<223> OTHER INFORMATION: synthetic aptamer

<400> SEQUENCE: 113
ggggcacgtt tatccgtccc tcctagtggc gtgcccc                               37

<210> SEQ ID NO 114
<211> LENGTH: 74
<212> TYPE: DNA
<213> ORGANISM: artificial
<220> FEATURE:
<223> OTHER INFORMATION: synthetic template

<400> SEQUENCE: 114
gatcccttgt tcagtccggg gcacgtttat ccgtccctcc tagtggcgtg ccccttaagc     60
cacaggactc caaa                                                        74

<210> SEQ ID NO 115
```

```
<211> LENGTH: 18
<212> TYPE: DNA
<213> ORGANISM: artificial
<220> FEATURE:
<223> OTHER INFORMATION: synthetic primer

<400> SEQUENCE: 115
gatcccttgt tcagtccg                                                 18

<210> SEQ ID NO 116
<211> LENGTH: 17
<212> TYPE: DNA
<213> ORGANISM: artificial
<220> FEATURE:
<223> OTHER INFORMATION: synthetic primer
<220> FEATURE:
<221> NAME/KEY: modified_base
<222> LOCATION: (17)..(17)
<223> OTHER INFORMATION: adenosine at position 17 is 2'-OH

<400> SEQUENCE: 116
ggagtcctgt ggcttaa                                                  17

<210> SEQ ID NO 117
<211> LENGTH: 20
<212> TYPE: DNA
<213> ORGANISM: artificial
<220> FEATURE:
<223> OTHER INFORMATION: synthetic primer
<220> FEATURE:
<221> NAME/KEY: misc_feature
<222> LOCATION: (1)..(3)
<223> OTHER INFORMATION: n at positions 1 to 3 is 5-biotin-T

<400> SEQUENCE: 117
nnnggagtcc tgtggcttaa                                               20

<210> SEQ ID NO 118
<211> LENGTH: 17
<212> TYPE: DNA
<213> ORGANISM: synthetic primer

<400> SEQUENCE: 118
ggagtcctgt ggcttaa                                                  17

<210> SEQ ID NO 119
<211> LENGTH: 37
<212> TYPE: DNA
<213> ORGANISM: artificial
<220> FEATURE:
<223> OTHER INFORMATION: synthetic aptamer

<400> SEQUENCE: 119
ggggcacatt tatccgtccc tcctagtggt gtgcccc                            37

<210> SEQ ID NO 120
<211> LENGTH: 37
<212> TYPE: DNA
<213> ORGANISM: artificial
<220> FEATURE:
<223> OTHER INFORMATION: synthetic aptamer

<400> SEQUENCE: 120
ggggtacctt tatccgtccc tcctagtggg gtgcccc                            37

<210> SEQ ID NO 121
<211> LENGTH: 37
```

```
<212> TYPE: DNA
<213> ORGANISM: artificial
<220> FEATURE:
<223> OTHER INFORMATION: synthetic aptamer

<400> SEQUENCE: 121
ggggtacctt tatccgtccc tcctagtggg gtacccc                              37

<210> SEQ ID NO 122
<211> LENGTH: 37
<212> TYPE: DNA
<213> ORGANISM: artificial
<220> FEATURE:
<223> OTHER INFORMATION: synthetic aptamer

<400> SEQUENCE: 122
ggggcaaatt tatccgtccc tcctagtggt ttgcccc                              37

<210> SEQ ID NO 123
<211> LENGTH: 37
<212> TYPE: DNA
<213> ORGANISM: artificial
<220> FEATURE:
<223> OTHER INFORMATION: synthetic aptamer

<400> SEQUENCE: 123
ggggcatatt tatccgtccc tcctagtggt atgcccc                              37

<210> SEQ ID NO 124
<211> LENGTH: 37
<212> TYPE: DNA
<213> ORGANISM: artificial
<220> FEATURE:
<223> OTHER INFORMATION: synthetic aptamer

<400> SEQUENCE: 124
ggggcacatt tatccgttcc tcctagtggt gtgcccc                              37

<210> SEQ ID NO 125
<211> LENGTH: 37
<212> TYPE: DNA
<213> ORGANISM: artificial
<220> FEATURE:
<223> OTHER INFORMATION: synthetic aptamer

<400> SEQUENCE: 125
ggggtacatt tatccgtccc tcctagtggc atgcccc                              37

<210> SEQ ID NO 126
<211> LENGTH: 37
<212> TYPE: DNA
<213> ORGANISM: artificial
<220> FEATURE:
<223> OTHER INFORMATION: synthetic aptamer

<400> SEQUENCE: 126
ggggcatgtt tatccgtccc tcctagtggc atgcccc                              37

<210> SEQ ID NO 127
<211> LENGTH: 36
<212> TYPE: DNA
<213> ORGANISM: artificial
<220> FEATURE:
<223> OTHER INFORMATION: synthetic aptamer

<400> SEQUENCE: 127
```

| | |
|---|---|
| ggggcaactt tatccgttcc tcctagtggg ttgccc | 36 |

<210> SEQ ID NO 128
<211> LENGTH: 37
<212> TYPE: DNA
<213> ORGANISM: artificial
<220> FEATURE:
<223> OTHER INFORMATION: synthetic aptamer

<400> SEQUENCE: 128

| | |
|---|---|
| ggggcacatt catccgtccc tcctagtggt gtgctcc | 37 |

<210> SEQ ID NO 129
<211> LENGTH: 37
<212> TYPE: DNA
<213> ORGANISM: artificial
<220> FEATURE:
<223> OTHER INFORMATION: synthetic aptamer

<400> SEQUENCE: 129

| | |
|---|---|
| ggggtaccttt gatccgtccc tcctagtggg gtgcccc | 37 |

<210> SEQ ID NO 130
<211> LENGTH: 37
<212> TYPE: DNA
<213> ORGANISM: artificial
<220> FEATURE:
<223> OTHER INFORMATION: synthetic aptamer

<400> SEQUENCE: 130

| | |
|---|---|
| ggggcatgtt tatccgttcc tcctagtggc atgcccc | 37 |

<210> SEQ ID NO 131
<211> LENGTH: 37
<212> TYPE: DNA
<213> ORGANISM: artificial
<220> FEATURE:
<223> OTHER INFORMATION: synthetic aptamer

<400> SEQUENCE: 131

| | |
|---|---|
| ggggcagctt tatccgttcc tcctagtggg ctgcctc | 37 |

<210> SEQ ID NO 132
<211> LENGTH: 37
<212> TYPE: DNA
<213> ORGANISM: artificial
<220> FEATURE:
<223> OTHER INFORMATION: synthetic aptamer

<400> SEQUENCE: 132

| | |
|---|---|
| ggggtacctt tatccgtttc tcctagtggg gtgcccc | 37 |

<210> SEQ ID NO 133
<211> LENGTH: 37
<212> TYPE: DNA
<213> ORGANISM: artificial
<220> FEATURE:
<223> OTHER INFORMATION: synthetic aptamer

<400> SEQUENCE: 133

| | |
|---|---|
| ggggtatgtt gatccgtccc tcctagtggc atgcccc | 37 |

<210> SEQ ID NO 134
<211> LENGTH: 37
<212> TYPE: DNA
<213> ORGANISM: artificial

```
<220> FEATURE:
<223> OTHER INFORMATION: synthetic aptamer

<400> SEQUENCE: 134
ggggcatgtt catccgttcc tcctagtggc gtgcccc                              37

<210> SEQ ID NO 135
<211> LENGTH: 37
<212> TYPE: DNA
<213> ORGANISM: artificial
<220> FEATURE:
<223> OTHER INFORMATION: synthetic aptamer

<400> SEQUENCE: 135
gggacacatt tatccgttac tcttagtggt gtgcccc                              37

<210> SEQ ID NO 136
<211> LENGTH: 37
<212> TYPE: DNA
<213> ORGANISM: artificial
<220> FEATURE:
<223> OTHER INFORMATION: synthetic aptamer

<400> SEQUENCE: 136
ggggcacatt tatccgttac tcttagtggt gtgcccc                              37

<210> SEQ ID NO 137
<211> LENGTH: 34
<212> TYPE: DNA
<213> ORGANISM: artificial
<220> FEATURE:
<223> OTHER INFORMATION: synthetic aptamer

<400> SEQUENCE: 137
ggggcacgtt tacagtccct ccttatcgcc tccc                                 34

<210> SEQ ID NO 138
<211> LENGTH: 34
<212> TYPE: DNA
<213> ORGANISM: artificial
<220> FEATURE:
<223> OTHER INFORMATION: synthetic aptamer

<400> SEQUENCE: 138
ggggcacgtt tacagtccct ccttatcgcc tccc                                 34

<210> SEQ ID NO 139
<211> LENGTH: 36
<212> TYPE: DNA
<213> ORGANISM: artificial
<220> FEATURE:
<223> OTHER INFORMATION: synthetic aptamer

<400> SEQUENCE: 139
gggcaacttt atccgttcct cttagtgggt tgcccc                               36

<210> SEQ ID NO 140
<211> LENGTH: 36
<212> TYPE: DNA
<213> ORGANISM: artificial
<220> FEATURE:
<223> OTHER INFORMATION: synthetic aptamer

<400> SEQUENCE: 140
gggctacttt atccgtccct cctagtgggt agcccc                               36
```

<210> SEQ ID NO 141
<211> LENGTH: 35
<212> TYPE: DNA
<213> ORGANISM: artificial
<220> FEATURE:
<223> OTHER INFORMATION: synthetic aptamer

<400> SEQUENCE: 141
ggcaccttta tccgtccctc ctagtggggt gcccc                                35

<210> SEQ ID NO 142
<211> LENGTH: 37
<212> TYPE: DNA
<213> ORGANISM: artificial
<220> FEATURE:
<223> OTHER INFORMATION: synthetic aptamer

<400> SEQUENCE: 142
ggggcacctt tatccgtccc tcctagtggg gtgcccc                              37

<210> SEQ ID NO 143
<211> LENGTH: 36
<212> TYPE: DNA
<213> ORGANISM: artificial
<220> FEATURE:
<223> OTHER INFORMATION: synthetic aptamer

<400> SEQUENCE: 143
gggcacattc atccgttcct cctagtggtg tgcccc                               36

<210> SEQ ID NO 144
<211> LENGTH: 34
<212> TYPE: DNA
<213> ORGANISM: artificial
<220> FEATURE:
<223> OTHER INFORMATION: synthetic aptamer

<400> SEQUENCE: 144
ggcaccttta tccgttcctt ctagtggggt gccc                                 34

<210> SEQ ID NO 145
<211> LENGTH: 36
<212> TYPE: DNA
<213> ORGANISM: artificial
<220> FEATURE:
<223> OTHER INFORMATION: synthetic aptamer
<220> FEATURE:
<221> NAME/KEY: misc_feature
<222> LOCATION: (28)..(28)
<223> OTHER INFORMATION: n at position 28 is a, t, c, or g

<400> SEQUENCE: 145
cggcaccttt atccgttact cttagtgngg tgcccc                               36

<210> SEQ ID NO 146
<211> LENGTH: 35
<212> TYPE: DNA
<213> ORGANISM: artificial
<220> FEATURE:
<223> OTHER INFORMATION: synthetic aptamer

<400> SEQUENCE: 146
ggcaccttga tccgttcctc ctagtggggt gcccc                                35

<210> SEQ ID NO 147
<211> LENGTH: 37

```
<212> TYPE: DNA
<213> ORGANISM: artificial
<220> FEATURE:
<223> OTHER INFORMATION: synthetic aptamer

<400> SEQUENCE: 147
gcgggcaaat tcatccgtcc ctcctagtgg tttgccc                         37

<210> SEQ ID NO 148
<211> LENGTH: 34
<212> TYPE: DNA
<213> ORGANISM: artificial
<220> FEATURE:
<223> OTHER INFORMATION: synthetic aptamer

<400> SEQUENCE: 148
gggcacttta tccgttcctt ctagtgggtg tccc                            34

<210> SEQ ID NO 149
<211> LENGTH: 38
<212> TYPE: DNA
<213> ORGANISM: artificial
<220> FEATURE:
<223> OTHER INFORMATION: synthetic aptamer

<400> SEQUENCE: 149
ggcggcagct ttatccgtac ctcccagtgg gctgctcc                        38

<210> SEQ ID NO 150
<211> LENGTH: 37
<212> TYPE: DNA
<213> ORGANISM: artificial
<220> FEATURE:
<223> OTHER INFORMATION: synthetic aptamer

<400> SEQUENCE: 150
ggggcagctt tatccgtacc tcccagtggg ctgcccc                         37

<210> SEQ ID NO 151
<211> LENGTH: 37
<212> TYPE: DNA
<213> ORGANISM: artificial
<220> FEATURE:
<223> OTHER INFORMATION: synthetic aptamer

<400> SEQUENCE: 151
ggggctactt tatccgtccc tcctagtggg tagcccc                         37

<210> SEQ ID NO 152
<211> LENGTH: 37
<212> TYPE: DNA
<213> ORGANISM: artificial
<220> FEATURE:
<223> OTHER INFORMATION: synthetic aptamer

<400> SEQUENCE: 152
ggggctactt tatccgtacc tcccagtggg tagcccc                         37

<210> SEQ ID NO 153
<211> LENGTH: 37
<212> TYPE: DNA
<213> ORGANISM: artificial
<220> FEATURE:
<223> OTHER INFORMATION: synthetic aptamer

<400> SEQUENCE: 153
```

```
gggctactt gatccgtccc tcctagtggg tagcccc                    37
```

<210> SEQ ID NO 154
<211> LENGTH: 37
<212> TYPE: DNA
<213> ORGANISM: artificial
<220> FEATURE:
<223> OTHER INFORMATION: synthetic aptamer

<400> SEQUENCE: 154

```
ggggctactt catccgtccc tcctagtggg tagcccc                   37
```

<210> SEQ ID NO 155
<211> LENGTH: 37
<212> TYPE: DNA
<213> ORGANISM: artificial
<220> FEATURE:
<223> OTHER INFORMATION: synthetic aptamer

<400> SEQUENCE: 155

```
ggggctactt tatccgttcc tcttagtggg tagcccc                   37
```

<210> SEQ ID NO 156
<211> LENGTH: 37
<212> TYPE: DNA
<213> ORGANISM: artificial
<220> FEATURE:
<223> OTHER INFORMATION: synthetic aptamer

<400> SEQUENCE: 156

```
ggggctactt tatccgttcc tcctagtggg tagcccc                   37
```

<210> SEQ ID NO 157
<211> LENGTH: 38
<212> TYPE: DNA
<213> ORGANISM: artificial
<220> FEATURE:
<223> OTHER INFORMATION: synthetic aptamer
<220> FEATURE:
<221> NAME/KEY: misc_feature
<222> LOCATION: (38)..(38)
<223> OTHER INFORMATION: n at position 38 is an inverted deoxy thymidine
     (3'-3' linked)

<400> SEQUENCE: 157

```
ggggctactt tatccgttcc tcctagtggg tagccccn                  38
```

<210> SEQ ID NO 158
<211> LENGTH: 24
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(23)
<223> OTHER INFORMATION: all purines (A and G) are deoxy, except
     adenosine at position 1 is 2'-O-methyl; all pyrimidines (C and U)
     are 2'-O-methyl
<220> FEATURE:
<221> NAME/KEY: misc_feature
<222> LOCATION: (24)..(24)
<223> OTHER INFORMATION: n at position 24 is an inverted deoxy thymidine
     (3'-3' linked)

<400> SEQUENCE: 158

```
agccugggga cccauggggg gcun                                 24
```

```
<210> SEQ ID NO 159
<211> LENGTH: 24
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(23)
<223> OTHER INFORMATION: all purines (A and G) are deoxy, except
      guanosine at position 2 is 2'-O-methyl;  all pyrimidines (C and U)
      are 2'-O-methyl
<220> FEATURE:
<221> NAME/KEY: misc_feature
<222> LOCATION: (24)..(24)
<223> OTHER INFORMATION: n at position 24 is an inverted deoxy thymidine
      (3'-3' linked)

<400> SEQUENCE: 159
agccugggga cccauggggg gcun                                              24

<210> SEQ ID NO 160
<211> LENGTH: 24
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(23)
<223> OTHER INFORMATION: all purines (A and G) are deoxy, except
      guanosine at position 6 is 2'-O-methyl;  all pyrimidines (C and U)
      are 2'-O-methyl
<220> FEATURE:
<221> NAME/KEY: misc_feature
<222> LOCATION: (24)..(24)
<223> OTHER INFORMATION: n at position 24 is an inverted deoxy thymidine
      (3'-3' linked)

<400> SEQUENCE: 160
agccugggga cccauggggg gcun                                              24

<210> SEQ ID NO 161
<211> LENGTH: 24
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(23)
<223> OTHER INFORMATION: all purines (A and G) are deoxy, except
      guanosine at position 7 is 2'-O-methyl; all pyrimidines (C and U)
      are 2'-O-methyl
<220> FEATURE:
<221> NAME/KEY: misc_feature
<222> LOCATION: (24)..(24)
<223> OTHER INFORMATION: n at position 24 is an inverted deoxy thymidine
      (3'-3' linked)

<400> SEQUENCE: 161
agccugggga cccauggggg gcun                                              24

<210> SEQ ID NO 162
<211> LENGTH: 24
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(23)
<223> OTHER INFORMATION: all purines (A and G) are deoxy, except
``` guanosine at position 8 is 2'-O-methyl; all pyrimidines (C and U)
        are 2'-O-methyl
<220> FEATURE:
<221> NAME/KEY: misc_feature
<222> LOCATION: (24)..(24)
<223> OTHER INFORMATION: n at position 24 is an inverted deoxy thymidine
        (3'-3' linked)

<400> SEQUENCE: 162
agccugggga cccauggggg gcun                                              24

<210> SEQ ID NO 163
<211> LENGTH: 24
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(23)
<223> OTHER INFORMATION: all purines (A and G) are deoxy, except
        guanosine at position 9 is 2'-O-methyl; all pyrimidines (C and U)
        are 2'-O-methyl
<220> FEATURE:
<221> NAME/KEY: misc_feature
<222> LOCATION: (24)..(24)
<223> OTHER INFORMATION: n at position 24 is an inverted deoxy thymidine
        (3'-3' linked)

<400> SEQUENCE: 163
agccugggga cccauggggg gcun                                              24

<210> SEQ ID NO 164
<211> LENGTH: 24
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(23)
<223> OTHER INFORMATION: all purines (A and G) are deoxy, except
        adenosine at position 10
        is 2'-O-methyl; all pyrimidines (C and U) are 2'-O-methyl
<220> FEATURE:
<221> NAME/KEY: misc_feature
<222> LOCATION: (24)..(24)
<223> OTHER INFORMATION: n at position 24 is an inverted deoxy thymidine
        (3'-3' linked)

<400> SEQUENCE: 164
agccugggga cccauggggg gcun                                              24

<210> SEQ ID NO 165
<211> LENGTH: 24
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(23)
<223> OTHER INFORMATION: all purines (A and G) are deoxy, except
        adenosine at position 14 is 2'-O-methyl; all pyrimidines (C and
        U) are 2'-O-methyl
<220> FEATURE:
<221> NAME/KEY: misc_feature
<222> LOCATION: (24)..(24)
<223> OTHER INFORMATION: n at position 24 is an inverted deoxy thymidine
        (3'-3' linked)

<400> SEQUENCE: 165
agccugggga cccauggggg gcun					24

<210> SEQ ID NO 166
<211> LENGTH: 24
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(23)
<223> OTHER INFORMATION: all purines (A and G) are deoxy, except
      guanosine at position 16 is 2'-O-methyl; all pyrimidines (C and U)
      are 2'-O-methyl
<220> FEATURE:
<221> NAME/KEY: misc_feature
<222> LOCATION: (24)..(24)
<223> OTHER INFORMATION: n at position 24 is an inverted deoxy thymidine
      (3'-3' linked)

<400> SEQUENCE: 166
agccugggga cccauggggg gcun					24

<210> SEQ ID NO 167
<211> LENGTH: 24
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(23)
<223> OTHER INFORMATION: all purines (A and G) are deoxy, except
      guanosine at position 17 is 2'-O-methyl; all pyrimidines (C and U)
      are 2'-O-methyl
<220> FEATURE:
<221> NAME/KEY: misc_feature
<222> LOCATION: (24)..(24)
<223> OTHER INFORMATION: n at position 24 is an inverted deoxy thymidine
      (3'-3' linked)

<400> SEQUENCE: 167
agccugggga cccauggggg gcun					24

<210> SEQ ID NO 168
<211> LENGTH: 24
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(23)
<223> OTHER INFORMATION: all purines (A and G) are deoxy, except
      guanosine at position 18
      is 2'-O-methyl;  all pyrimidines (C and U) are 2'-O-methyl
<220> FEATURE:
<221> NAME/KEY: misc_feature
<222> LOCATION: (24)..(24)
<223> OTHER INFORMATION: n at position 24 is an inverted deoxy thymidine
      (3'-3' linked)

<400> SEQUENCE: 168
agccugggga cccauggggg gcun					24

<210> SEQ ID NO 169
<211> LENGTH: 24
<212> TYPE: DNA
<213> ORGANISM: artificial
<220> FEATURE:
<223> OTHER INFORMATION: synthetic aptamer
<220> FEATURE:

```
<221> NAME/KEY: modified_base
<222> LOCATION: (1)..(23)
<223> OTHER INFORMATION: all purines (A and G) are deoxy, except
      guanosine at position 19 is 2'-O-methyl; all pyrimidines (C and U)
      are 2'-O-methyl
<220> FEATURE:
<221> NAME/KEY: misc_feature
<222> LOCATION: (24)..(24)
<223> OTHER INFORMATION: n at position 24 is an inverted deoxy thymidine
      (3'-3' linked)

<400> SEQUENCE: 169
agccugggga cccauggggg gcun                                            24

<210> SEQ ID NO 170
<211> LENGTH: 24
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(23)
<223> OTHER INFORMATION: all purines (A and G) are deoxy, except
      guanosine at position 20 is 2'-O-methyl; all pyrimidines (C and U)
      are 2'-O-methyl
<220> FEATURE:
<221> NAME/KEY: misc_feature
<222> LOCATION: (24)..(24)
<223> OTHER INFORMATION: n at position 24 is an inverted deoxy thymidine
      (3'-3' linked)

<400> SEQUENCE: 170
agccugggga cccauggggg gcun                                            24

<210> SEQ ID NO 171
<211> LENGTH: 24
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(23)
<223> OTHER INFORMATION: all purines (A and G) are deoxy, except
      guanosine at position 21 is 2'-O-methyl; all pyrimidines (C and U)
      are 2'-O-methyl
<220> FEATURE:
<221> NAME/KEY: misc_feature
<222> LOCATION: (24)..(24)
<223> OTHER INFORMATION: n at position 24 is an inverted deoxy thymidine
      (3'-3' linked)

<400> SEQUENCE: 171
agccugggga cccauggggg gcun                                            24

<210> SEQ ID NO 172
<211> LENGTH: 24
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(23)
<223> OTHER INFORMATION: all purines (A and G) are deoxy, except
      adenosine at position 1 is 2'-O-methyl, and guanosine at positions
      2, 20, and 21 are 2'-O-methyl; all pyrimidines (C and U) are
      2'-O-methyl
<220> FEATURE:
<221> NAME/KEY: misc_feature
<222> LOCATION: (24)..(24)
<223> OTHER INFORMATION: n at position 24 is an inverted deoxy thymidine
```

(3'-3' linked)

<400> SEQUENCE: 172
agccugggga cccauggggg gcun                                              24

<210> SEQ ID NO 173
<211> LENGTH: 24
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(23)
<223> OTHER INFORMATION: all purines (A and G) are deoxy, except
      guanosine at position 2 is 2'-O-methyl, and adenosine at positions
      10 and 14 are 2'-O-methyl; all pyrimidines (C and U) are
      2'-O-methyl
<220> FEATURE:
<221> NAME/KEY: misc_feature
<222> LOCATION: (24)..(24)
<223> OTHER INFORMATION: n at position 24 is an inverted deoxy thymidine
      (3'-3' linked)

<400> SEQUENCE: 173
agccugggga cccauggggg gcun                                              24

<210> SEQ ID NO 174
<211> LENGTH: 24
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(23)
<223> OTHER INFORMATION: all purines (A and G) are deoxy, except
      guanosine at positions 2, 7 and 17 are 2'-O-methyl; all
      pyrimidines (C and U) are 2'-O-methyl
<220> FEATURE:
<221> NAME/KEY: misc_feature
<222> LOCATION: (24)..(24)
<223> OTHER INFORMATION: n at position 24 is an inverted deoxy thymidine
      (3'-3' linked)

<400> SEQUENCE: 174
agccugggga cccauggggg gcun                                              24

<210> SEQ ID NO 175
<211> LENGTH: 24
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(23)
<223> OTHER INFORMATION: all purines (A and G) are deoxy, except
      guanosine at positions 2, 7 and 17 are 2'-O-methyl, and adenosine
      at positions 10 and 14 are 2'-O-methyl; all pyrimidines (C and U)
      are 2'-O-methyl
<220> FEATURE:
<221> NAME/KEY: misc_feature
<222> LOCATION: (24)..(24)
<223> OTHER INFORMATION: n at position 24 is an inverted deoxy thymidine
      (3'-3' linked)

<400> SEQUENCE: 175
agccugggga cccauggggg gcun                                              24

<210> SEQ ID NO 176

```
<211> LENGTH: 24
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(23)
<223> OTHER INFORMATION: all purines (A and G) are deoxy, except
      guanosine at positions 2, 7 and 17 are 2'-O-methyl, and adenosine
      at positions 1, 10 and 14 are 2'-O-methyl; all pyrimidines (C and
      U) are 2'-O-methyl
<220> FEATURE:
<221> NAME/KEY: misc_feature
<222> LOCATION: (24)..(24)
<223> OTHER INFORMATION: n at position 24 is an inverted deoxy thymidine
      (3'-3' linked)

<400> SEQUENCE: 176 agccuggga cccauggggg gcun                                             24

<210> SEQ ID NO 177
<211> LENGTH: 28
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(27)
<223> OTHER INFORMATION: all purines (A and G) are deoxy, except
      guanosine at positions 3, 8 and 20 are 2'-O-methyl, and adenosine
      at positions 11 and 15 are 2'-O-methyl; all pyrimidines (C and U)
      are 2'-O-methyl
<220> FEATURE:
<221> NAME/KEY: misc_feature
<222> LOCATION: (2)..(2)
<223> OTHER INFORMATION: n is a phosphorothioate internucleotide linkage
<220> FEATURE:
<221> NAME/KEY: misc_feature
<222> LOCATION: (17)..(17)
<223> OTHER INFORMATION: n is a phosphorothioate internucleotide linkage
<220> FEATURE:
<221> NAME/KEY: misc_feature
<222> LOCATION: (19)..(19)
<223> OTHER INFORMATION: n  is a phosphorothioate internucleotide
      linkage
<220> FEATURE:
<221> NAME/KEY: misc_feature
<222> LOCATION: (24)..(24)
<223> OTHER INFORMATION: n  is a phosphorothioate internucleotide
      linkage
<220> FEATURE:
<221> NAME/KEY: misc_feature
<222> LOCATION: (28)..(28)
<223> OTHER INFORMATION: n  is an inverted deoxy thymidine (3'-3'
      linked)

<400> SEQUENCE: 177
angccugggg acccaungng gggngcun                                        28

<210> SEQ ID NO 178
<211> LENGTH: 30
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(29)
<223> OTHER INFORMATION: all purines (A and G) are deoxy, except
      guanosine at positions 3, 8 and 21 are 2'-O-methyl, and adenosine
      at positions 12 and 16 are 2'-O-methyl; all pyrimidines (C and U)
      are 2'-O-methyl
<220> FEATURE:
```

```
<221> NAME/KEY: misc_feature
<222> LOCATION: (2)..(2)
<223> OTHER INFORMATION: n is a phosphorothioate internucleotide linkage
<220> FEATURE:
<221> NAME/KEY: misc_feature
<222> LOCATION: (11)..(11)
<223> OTHER INFORMATION: n is a phosphorothioate internucleotide linkage
<220> FEATURE:
<221> NAME/KEY: misc_feature
<222> LOCATION: (18)..(18)
<223> OTHER INFORMATION: n is a phosphorothioate internucleotide linkage
<220> FEATURE:
<221> NAME/KEY: misc_feature
<222> LOCATION: (20)..(20)
<223> OTHER INFORMATION: n is a phosphorothioate internucleotide linkage
<220> FEATURE:
<221> NAME/KEY: misc_feature
<222> LOCATION: (23)..(23)
<223> OTHER INFORMATION: n is a phosphorothioate internucleotide linkage
<220> FEATURE:
<221> NAME/KEY: misc_feature
<222> LOCATION: (26)..(26)
<223> OTHER INFORMATION: n  is a phosphorothioate internucleotide
      linkage
<220> FEATURE:
<221> NAME/KEY: misc_feature
<222> LOCATION: (30)..(30)
<223> OTHER INFORMATION: n is an inverted deoxy thymidine (3'-3' linked)

<400> SEQUENCE: 178 angccuggggg nacccaungn ggnggngcun                                          30

<210> SEQ ID NO 179
<211> LENGTH: 27
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(26)
<223> OTHER INFORMATION: all purines (A and G) are deoxy, except
      guanosine at positions 2, 7 and 18 are 2'-O-methyl, and adenosine
      at positions 1, 11 and 15 are 2'-O-methyl; all pyrimidines (C and
      U) are 2'-O-methyl
<220> FEATURE:
<221> NAME/KEY: misc_feature
<222> LOCATION: (9)..(9)
<223> OTHER INFORMATION: n is a phosphorothioate internucleotide linkage
<220> FEATURE:
<221> NAME/KEY: misc_feature
<222> LOCATION: (20)..(20)
<223> OTHER INFORMATION: n  is a phosphorothioate internucleotide
      linkage
<220> FEATURE:
<221> NAME/KEY: misc_feature
<222> LOCATION: (23)..(23)
<223> OTHER INFORMATION: n is a phosphorothioate internucleotide linkage
<220> FEATURE:
<221> NAME/KEY: misc_feature
<222> LOCATION: (27)..(27)
<223> OTHER INFORMATION: n is an inverted deoxy thymidine (3'-3' linked)

<400> SEQUENCE: 179
agccugggng acccaugggn ggngcun                                              27

<210> SEQ ID NO 180
<211> LENGTH: 28
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(27)
```

```
<223> OTHER INFORMATION: all purines (A and G) are deoxy, except
      guanosine at positions 2, 7 and 19 are 2'-O-methyl, and adenosine
      at positions 1, 11 and 15 are 2'-O-methyl; all pyrimidines (C and
      U) are 2'-O-methyl
<220> FEATURE:
<221> NAME/KEY: misc_feature
<222> LOCATION: (9)..(9)
<223> OTHER INFORMATION: n is a phosphorothioate internucleotide linkage
<220> FEATURE:
<221> NAME/KEY: misc_feature
<222> LOCATION: (17)..(17)
<223> OTHER INFORMATION: n is a phosphorothioate internucleotide linkage
<220> FEATURE:
<221> NAME/KEY: misc_feature
<222> LOCATION: (21)..(21)
<223> OTHER INFORMATION: n is a phosphorothioate internucleotide linkage
<220> FEATURE:
<221> NAME/KEY: misc_feature
<222> LOCATION: (24)..(24)
<223> OTHER INFORMATION: n is a phosphorothioate internucleotide linkage
<220> FEATURE:
<221> NAME/KEY: misc_feature
<222> LOCATION: (28)..(28)
<223> OTHER INFORMATION: n is an inverted deoxy thymidine (3'-3' linked)

<400> SEQUENCE: 180
agccugggng acccaunggg nggngcun                                        28

<210> SEQ ID NO 181
<211> LENGTH: 29
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(28)
<223> OTHER INFORMATION: all purines (A and G) are deoxy, except
      guanosine at positions 2, 7 and 20 are 2'-O-methyl, and adenosine
      at positions 1, 11 and 15 are 2'-O-methyl; all pyrimidines (C and
      U) are 2'-O-methyl
<220> FEATURE:
<221> NAME/KEY: misc_feature
<222> LOCATION: (9)..(9)
<223> OTHER INFORMATION: n is a phosphorothioate internucleotide linkage
<220> FEATURE:
<221> NAME/KEY: misc_feature
<222> LOCATION: (17)..(17)
<223> OTHER INFORMATION: n is a phosphorothioate internucleotide linkage
<220> FEATURE:
<221> NAME/KEY: misc_feature
<222> LOCATION: (19)..(19)
<223> OTHER INFORMATION: n is a phosphorothioate internucleotide linkage
<220> FEATURE:
<221> NAME/KEY: misc_feature
<222> LOCATION: (22)..(22)
<223> OTHER INFORMATION: n is a phosphorothioate internucleotide linkage
<220> FEATURE:
<221> NAME/KEY: misc_feature
<222> LOCATION: (25)..(25)
<223> OTHER INFORMATION: n is a phosphorothioate internucleotide linkage
<220> FEATURE:
<221> NAME/KEY: misc_feature
<222> LOCATION: (29)..(29)
<223> OTHER INFORMATION: n is an inverted deoxy thymidine (3'-3' linked)

<400> SEQUENCE: 181
agccugggng acccaungng gnggngcun                                       29

<210> SEQ ID NO 182
<211> LENGTH: 32
<212> TYPE: DNA
<213> ORGANISM: artificial
<220> FEATURE:
<223> OTHER INFORMATION: synthetic aptamer
```

<220> FEATURE:
<221> NAME/KEY: modified_base
<222> LOCATION: (1)..(31)
<223> OTHER INFORMATION: all purines (A and G) are deoxy, except
      guanosine at positions 2, 8 and 21 are 2'-O-methyl, and adenosine
      at positions 1, 13 and 17 are 2'-O-methyl; all pyrimidines (C and
      U) are 2'-O-methyl
<220> FEATURE:
<221> NAME/KEY: misc_feature
<222> LOCATION: (6)..(6)
<223> OTHER INFORMATION: n is a phosphorothioate internucleotide linkage
<220> FEATURE:
<221> NAME/KEY: misc_feature
<222> LOCATION: (9)..(9)
<223> OTHER INFORMATION: n is a phosphorothioate internucleotide linkage
<220> FEATURE:
<221> NAME/KEY: misc_feature
<222> LOCATION: (11)..(11)
<223> OTHER INFORMATION: n is a phosphorothioate internucleotide linkage
<220> FEATURE:
<221> NAME/KEY: misc_feature
<222> LOCATION: (19)..(19)
<223> OTHER INFORMATION: n is a phosphorothioate internucleotide linkage
<220> FEATURE:
<221> NAME/KEY: misc_feature
<222> LOCATION: (22)..(22)
<223> OTHER INFORMATION: n is a phosphorothioate internucleotide linkage
<220> FEATURE:
<221> NAME/KEY: misc_feature
<222> LOCATION: (24)..(24)
<223> OTHER INFORMATION: n is a phosphorothioate internucleotide linkage
<220> FEATURE:
<221> NAME/KEY: misc_feature
<222> LOCATION: (26)..(26)
<223> OTHER INFORMATION: n is a phosphorothioate internucleotide linkage
<220> FEATURE:
<221> NAME/KEY: misc_feature
<222> LOCATION: (28)..(28)
<223> OTHER INFORMATION: n is a phosphorothioate internucleotide linkage
<220> FEATURE:
<221> NAME/KEY: misc_feature
<222> LOCATION: (32)..(32)
<223> OTHER INFORMATION: n is an inverted deoxy thymidine (3'-3' linked)

<400> SEQUENCE: 182
agccunggng ngacccaung gngngngngc un                                    32

<210> SEQ ID NO 183
<211> LENGTH: 35
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(34)
<223> OTHER INFORMATION: all purines (A and G) are deoxy, except
      guanosine at positions 2, 9 and 23 are 2'-O-methyl, and adenosine
      at positions 1, 14 and 18 are 2'-O-methyl; all pyrimidines (C and
      U) are 2'-O-methyl
<220> FEATURE:
<221> NAME/KEY: misc_feature
<222> LOCATION: (6)..(6)
<223> OTHER INFORMATION: n is a phosphorothioate internucleotide linkage
<220> FEATURE:
<221> NAME/KEY: misc_feature
<222> LOCATION: (8)..(8)
<223> OTHER INFORMATION: n is a phosphorothioate internucleotide linkage
<220> FEATURE:
<221> NAME/KEY: misc_feature
<222> LOCATION: (10)..(10)
<223> OTHER INFORMATION: n is a phosphorothioate internucleotide linkage
<220> FEATURE:
<221> NAME/KEY: misc_feature
<222> LOCATION: (12)..(12)
<223> OTHER INFORMATION: n is a phosphorothioate internucleotide linkage
<220> FEATURE:

```
<221> NAME/KEY: misc_feature
<222> LOCATION: (20)..(20)
<223> OTHER INFORMATION: n is a phosphorothioate internucleotide linkage
<220> FEATURE:
<221> NAME/KEY: misc_feature
<222> LOCATION: (22)..(22)
<223> OTHER INFORMATION: n is a phosphorothioate internucleotide linkage
<220> FEATURE:
<221> NAME/KEY: misc_feature
<222> LOCATION: (24)..(24)
<223> OTHER INFORMATION: n is a phosphorothioate internucleotide linkage
<220> FEATURE:
<221> NAME/KEY: misc_feature
<222> LOCATION: (26)..(26)
<223> OTHER INFORMATION: n is a phosphorothioate internucleotide linkage
<220> FEATURE:
<221> NAME/KEY: misc_feature
<222> LOCATION: (28)..(28)
<223> OTHER INFORMATION: n is a phosphorothioate internucleotide linkage
<220> FEATURE:
<221> NAME/KEY: misc_feature
<222> LOCATION: (30)..(30)
<223> OTHER INFORMATION: n is a phosphorothioate internucleotide linkage
<220> FEATURE:
<221> NAME/KEY: misc_feature
<222> LOCATION: (32)..(32)
<223> OTHER INFORMATION: n is a phosphorothioate internucleotide linkage
<220> FEATURE:
<221> NAME/KEY: misc_feature
<222> LOCATION: (35)..(35)
<223> OTHER INFORMATION: n is an inverted deoxy thymidine (3'-3' linked)

<400> SEQUENCE: 183
agccungngn gngacccaun gngngngngn gncun                                35

<210> SEQ ID NO 184
<211> LENGTH: 23
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(23)
<223> OTHER INFORMATION: all purines (A and G) are deoxy;  all
      pyrimidines (C and U) are 2'-O-methyl
<220> FEATURE:
<221> NAME/KEY: misc_feature
<222> LOCATION: (2)..(2)
<223> OTHER INFORMATION: n is deoxy 7- deaza guanosine

<400> SEQUENCE: 184
anccugggga cccauggggg gcu                                             23

<210> SEQ ID NO 185
<211> LENGTH: 23
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(23)
<223> OTHER INFORMATION: all purines (A and G) are deoxy;  all
      pyrimidines (C and U) are 2'-O-methyl
<220> FEATURE:
<221> NAME/KEY: misc_feature
<222> LOCATION: (6)..(6)
<223> OTHER INFORMATION: n is deoxy 7-deaza guanosine

<400> SEQUENCE: 185 agccungggga cccauggggg gcu                                            23
```

```
<210> SEQ ID NO 186
<211> LENGTH: 23
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(23)
<223> OTHER INFORMATION: all purines (A and G) are deoxy; all
      pyrimidines (C and U) are 2'-O-methyl
<220> FEATURE:
<221> NAME/KEY: misc_feature
<222> LOCATION: (7)..(7)
<223> OTHER INFORMATION: n is deoxy 7-deaza guanosine

<400> SEQUENCE: 186
agccugngga cccauggggg gcu                                              23

<210> SEQ ID NO 187
<211> LENGTH: 23
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(23)
<223> OTHER INFORMATION: all purines (A and G) are deoxy; all
      pyrimidines (C and U) are 2'-O-methyl
<220> FEATURE:
<221> NAME/KEY: misc_feature
<222> LOCATION: (8)..(8)
<223> OTHER INFORMATION: n is deoxy 7-deaza guanosine

<400> SEQUENCE: 187
agccuggnga cccauggggg gcu                                              23

<210> SEQ ID NO 188
<211> LENGTH: 23
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(23)
<223> OTHER INFORMATION: all purines (A and G) are deoxy; all
      pyrimidines (C and U) are 2'-O-methyl
<220> FEATURE:
<221> NAME/KEY: misc_feature
<222> LOCATION: (9)..(9)
<223> OTHER INFORMATION: n is deoxy 7-deaza guanosine

<400> SEQUENCE: 188
agccugggna cccauggggg gcu                                              23

<210> SEQ ID NO 189
<211> LENGTH: 23
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(23)
<223> OTHER INFORMATION: all purines (A and G) are deoxy; all
      pyrimidines (C and U) are 2'-O-methyl
<220> FEATURE:
<221> NAME/KEY: misc_feature
<222> LOCATION: (16)..(16)
<223> OTHER INFORMATION: n is deoxy 7-deaza guanosine
```

```
<400> SEQUENCE: 189
agccugggga cccaungggg gcu                                              23

<210> SEQ ID NO 190
<211> LENGTH: 23
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(23)
<223> OTHER INFORMATION: all purines (A and G) are deoxy;  all
      pyrimidines (C and U) are 2'-O-methyl
<220> FEATURE:
<221> NAME/KEY: misc_feature
<222> LOCATION: (17)..(17)
<223> OTHER INFORMATION: n is deoxy 7-deaza guanosine

<400> SEQUENCE: 190
agccugggga cccaugnggg gcu                                              23

<210> SEQ ID NO 191
<211> LENGTH: 23
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(23)
<223> OTHER INFORMATION: all purines (A and G) are deoxy;  all
      pyrimidines (C and U) ar 2'-O-methyl
<220> FEATURE:
<221> NAME/KEY: misc_feature
<222> LOCATION: (18)..(18)
<223> OTHER INFORMATION: n is deoxy 7- deaza guanosine

<400> SEQUENCE: 191
agccugggga cccauggngg gcu                                              23

<210> SEQ ID NO 192
<211> LENGTH: 23
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(23)
<223> OTHER INFORMATION: all purines (A and G) are deoxy;  all
      pyrimidines (C and U) are 2'-O-methyl
<220> FEATURE:
<221> NAME/KEY: misc_feature
<222> LOCATION: (19)..(19)
<223> OTHER INFORMATION: n is deoxy 7-deaza guanosine

<400> SEQUENCE: 192
agccugggga cccaugggng gcu                                              23

<210> SEQ ID NO 193
<211> LENGTH: 23
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(23)
<223> OTHER INFORMATION: all purines (A and G) are deoxy;  all
      pyrimidines (C and U) are 2'-O-methyl
```

```
<220> FEATURE:
<221> NAME/KEY: misc_feature
<222> LOCATION: (20)..(20)
<223> OTHER INFORMATION: n is deoxy 7-deaza guanosine

<400> SEQUENCE: 193
agccugggga cccaugggggn gcu                                              23

<210> SEQ ID NO 194
<211> LENGTH: 23
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(23)
<223> OTHER INFORMATION: all purines (A and G) are deoxy;  all
      pyrimidines (C and U) are 2'-O-methyl
<220> FEATURE:
<221> NAME/KEY: misc_feature
<222> LOCATION: (21)..(21)
<223> OTHER INFORMATION: n is deoxy 7-deaza guanosine

<400> SEQUENCE: 194
agccugggga cccauggggg ncu                                               23

<210> SEQ ID NO 195
<211> LENGTH: 23
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(23)
<223> OTHER INFORMATION: all purines (A and G) are deoxy, all
      pyrimidines (C and U) are 2'-O-methyl

<400> SEQUENCE: 195
aggcugggga cccauggggg ccu                                               23

<210> SEQ ID NO 196
<211> LENGTH: 23
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(23)
<223> OTHER INFORMATION: all purines (A and G) are deoxy, except
      guanosine at position 3 is 2'-O-methyl; all pyrimidines are
      2'-O-methyl

<400> SEQUENCE: 196
aggcugggga cccauggggg ccu                                               23

<210> SEQ ID NO 197
<211> LENGTH: 23
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(23)
<223> OTHER INFORMATION: all purines (A and G) are deoxy;  all
      pyrimidines (C and U) are 2'-O-methyl

<400> SEQUENCE: 197
```

-continued agucugggga cccauggggg acu                                           23

<210> SEQ ID NO 198
<211> LENGTH: 23
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(23)
<223> OTHER INFORMATION: all purines (A and G) are deoxy, except
      adenosine at position 21 is 2'-O-methyl;  all pyrimidines are
      2'-O-methyl

<400> SEQUENCE: 198
agucugggga cccauggggg acu                                           23

<210> SEQ ID NO 199
<211> LENGTH: 23
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(23)
<223> OTHER INFORMATION: all purines (A and G) are deoxy;  all
      pyrimidines (C and U) are 2'-O-methyl

<400> SEQUENCE: 199
agacugggga cccauggggg ucu                                           23

<210> SEQ ID NO 200
<211> LENGTH: 23
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(23)
<223> OTHER INFORMATION: all purines (A and G) are deoxy, except
      adenosine at position 3 is 2'-O-methyl; all pyrimidines are
      2'-O-methyl

<400> SEQUENCE: 200
agacugggga cccauggggg ucu                                           23

<210> SEQ ID NO 201
<211> LENGTH: 24
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(23)
<223> OTHER INFORMATION: all purines (A and G) are deoxy, except
      guanosine at positions 7 and 17 are 2'-O-methyl, and adenosine at
      positions 1, 10 and 14 are 2'-O-methyl
<220> FEATURE:
<221> NAME/KEY: modified_base
<222> LOCATION: (1)..(23)
<223> OTHER INFORMATION: all pyrimidines (C and U) are 2'O-methyl
<220> FEATURE:
<221> NAME/KEY: misc_feature
<222> LOCATION: (2)..(2)
<223> OTHER INFORMATION: n at position 2 is deoxy inosine
<220> FEATURE:
<221> NAME/KEY: misc_feature

```
<222> LOCATION: (24)..(24)
<223> OTHER INFORMATION: n is an inverted deoxy thymidine (3'-3' linked)

<400> SEQUENCE: 201
anccugggga cccauggggg gcun                                              24

<210> SEQ ID NO 202
<211> LENGTH: 24
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(23)
<223> OTHER INFORMATION: all purines (A and G) are deoxy, except
      guanosine at positions 2, 7 and 17 are 2'-O-methyl, and adenosine
      at positions 1, 10, 14 are 2'-O-methyl
<220> FEATURE:
<221> NAME/KEY: modified_base
<222> LOCATION: (1)..(23)
<223> OTHER INFORMATION: all pyrimidines (C and U) are 2'-O-methyl
<220> FEATURE:
<221> NAME/KEY: misc_feature
<222> LOCATION: (6)..(6)
<223> OTHER INFORMATION: n is a deoxy inosine
<220> FEATURE:
<221> NAME/KEY: misc_feature
<222> LOCATION: (24)..(24)
<223> OTHER INFORMATION: n is an inverted deoxy thymidine (3'-3' linked)

<400> SEQUENCE: 202
agccunggga cccauggggg gcun                                              24

<210> SEQ ID NO 203
<211> LENGTH: 24
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(23)
<223> OTHER INFORMATION: all purines (A and G) are deoxy, except
      guanosine at positions 2, and 17 are 2'-O-methyl, and adenosine at
      positions 1, 10, 14 are 2'-O-methyl
<220> FEATURE:
<221> NAME/KEY: modified_base
<222> LOCATION: (1)..(23)
<223> OTHER INFORMATION: all pyrimidines (C and U) are 2'-O-methyl
<220> FEATURE:
<221> NAME/KEY: misc_feature
<222> LOCATION: (7)..(7)
<223> OTHER INFORMATION: n is a deoxy inosine
<220> FEATURE:
<221> NAME/KEY: misc_feature
<222> LOCATION: (24)..(24)
<223> OTHER INFORMATION: n is an inverted deoxy thymidine (3'-3' linked)

<400> SEQUENCE: 203
agccugngga cccauggggg gcun                                              24

<210> SEQ ID NO 204
<211> LENGTH: 24
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(23)
<223> OTHER INFORMATION: all purines (A and G) are deoxy, except
      guanosine at positions 2, and 7 are 2'-O-methyl, and adenosine at
```

```
                positions 1, 10, 14 are 2'-O-methyl
<220> FEATURE:
<221> NAME/KEY: modified_base
<222> LOCATION: (1)..(23)
<223> OTHER INFORMATION: all pyrimidines (C and U) are 2'-O-methyl
<220> FEATURE:
<221> NAME/KEY: misc_feature
<222> LOCATION: (8)..(8)
<223> OTHER INFORMATION: n is a deoxy inosine
<220> FEATURE:
<221> NAME/KEY: misc_feature
<222> LOCATION: (24)..(24)
<223> OTHER INFORMATION: n is an inverted deoxy thymidine (3'-3' linked)

<400> SEQUENCE: 204
agccuggnga cccauggggg gcun                                              24

<210> SEQ ID NO 205
<211> LENGTH: 24
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(23)
<223> OTHER INFORMATION: all purines (A and G) are deoxy, except
      guanosine at positions 2, 7 and 17 are 2'-O-methyl, and adenosine
      at positions 1, 10, 14 are 2'-O-methyl
<220> FEATURE:
<221> NAME/KEY: modified_base
<222> LOCATION: (1)..(23)
<223> OTHER INFORMATION: all pyrimidines (C and U) are 2'-O-methyl
<220> FEATURE:
<221> NAME/KEY: misc_feature
<222> LOCATION: (9)..(9)
<223> OTHER INFORMATION: n is a deoxy inosine
<220> FEATURE:
<221> NAME/KEY: misc_feature
<222> LOCATION: (24)..(24)
<223> OTHER INFORMATION: n is an inverted deoxy thymidine (3'-3' linked)

<400> SEQUENCE: 205
agccugggna cccauggggg gcun                                              24

<210> SEQ ID NO 206
<211> LENGTH: 24
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(23)
<223> OTHER INFORMATION: all purines (A and G) are deoxy, except
      guanosine at positions 2, 7 and 17 are 2'-O-methyl, and adenosine
      at positions 1, 10, 14 are 2'-O-methyl
<220> FEATURE:
<221> NAME/KEY: modified_base
<222> LOCATION: (1)..(23)
<223> OTHER INFORMATION: all pyrimidines (C and U) are 2'-O-methyl
<220> FEATURE:
<221> NAME/KEY: misc_feature
<222> LOCATION: (16)..(16)
<223> OTHER INFORMATION: n is a deoxy inosine
<220> FEATURE:
<221> NAME/KEY: misc_feature
<222> LOCATION: (24)..(24)
<223> OTHER INFORMATION: n is an inverted deoxy thymidine (3'-3' linked)

<400> SEQUENCE: 206
agccugggga cccaungggg gcun                                              24
```

```
<210> SEQ ID NO 207
<211> LENGTH: 24
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(23)
<223> OTHER INFORMATION: all purines (A and G) are deoxy, except
      guanosine at positions 2, and 7 are 2'-O-methyl, and adenosine at
      positions 1, 10, 14 are 2'-O-methyl
<220> FEATURE:
<221> NAME/KEY: modified_base
<222> LOCATION: (1)..(23)
<223> OTHER INFORMATION: all pyrimidines (C and U) are 2'-O-methyl
<220> FEATURE:
<221> NAME/KEY: misc_feature
<222> LOCATION: (17)..(17)
<223> OTHER INFORMATION: n is deoxy inosine
<220> FEATURE:
<221> NAME/KEY: misc_feature
<222> LOCATION: (24)..(24)
<223> OTHER INFORMATION: n is an inverted deoxy thymidine (3'-3' linked)

<400> SEQUENCE: 207
agccugggga cccaugnggg gcun                                            24

<210> SEQ ID NO 208
<211> LENGTH: 24
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(23)
<223> OTHER INFORMATION: all purines (A and G) are deoxy, except
      guanosine at positions 2, 7 and 17 are 2'-O-methyl, and adenosine
      at positions 1, 10, 14 are 2'-O-methyl
<220> FEATURE:
<221> NAME/KEY: modified_base
<222> LOCATION: (1)..(23)
<223> OTHER INFORMATION: all pyrimidines (C and U) are 2'-O-methyl
<220> FEATURE:
<221> NAME/KEY: misc_feature
<222> LOCATION: (18)..(18)
<223> OTHER INFORMATION: n is deoxy inosine
<220> FEATURE:
<221> NAME/KEY: misc_feature
<222> LOCATION: (24)..(24)
<223> OTHER INFORMATION: n is an inverted deoxy thymidine

<400> SEQUENCE: 208
agccugggga cccauggngg gcun                                            24

<210> SEQ ID NO 209
<211> LENGTH: 24
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(23)
<223> OTHER INFORMATION: all purines (A and G) are deoxy, except
      guanosine at positions 2, 7 and 17 are 2'-O-methyl, and adenosine
      at positions 1, 10, 14 are 2'-O-methyl
<220> FEATURE:
<221> NAME/KEY: modified_base
<222> LOCATION: (1)..(23)
<223> OTHER INFORMATION: all pyrimidines (C and U) are 2'-O-methyl
<220> FEATURE:
<221> NAME/KEY: misc_feature
<222> LOCATION: (19)..(19)
```

```
<223> OTHER INFORMATION: n is deoxy inosine
<220> FEATURE:
<221> NAME/KEY: misc_feature
<222> LOCATION: (24)..(24)
<223> OTHER INFORMATION: n is an inverted deoxy thymidine (3'-3' linked)

<400> SEQUENCE: 209
agccugggga cccaugggng gcun                                              24

<210> SEQ ID NO 210
<211> LENGTH: 24
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(23)
<223> OTHER INFORMATION: all purines (A and G) are deoxy, except
      guanosine at positions 2, 7 and 17 are 2'-O-methyl, and adenosine
      at positions 1, 10, 14 are 2'-O-methyl
<220> FEATURE:
<221> NAME/KEY: modified_base
<222> LOCATION: (1)..(23)
<223> OTHER INFORMATION: all pyrimidines (C and U) are 2'-O-methyl
<220> FEATURE:
<221> NAME/KEY: misc_feature
<222> LOCATION: (20)..(20)
<223> OTHER INFORMATION: n is a deoxy inosine
<220> FEATURE:
<221> NAME/KEY: misc_feature
<222> LOCATION: (24)..(24)
<223> OTHER INFORMATION: n is an inverted deoxy thymidine (3'-3' linked)

<400> SEQUENCE: 210
agccugggga cccauggggn gcun                                              24

<210> SEQ ID NO 211
<211> LENGTH: 24
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(23)
<223> OTHER INFORMATION: all purines (A and G) are deoxy, except
      guanosine at positions 2, 7 and 17 are 2'-O-methyl, and adenosine
      at positions 1, 10, 14 are 2'-O-methyl
<220> FEATURE:
<221> NAME/KEY: modified_base
<222> LOCATION: (1)..(23)
<223> OTHER INFORMATION: all pyrimidines (C and U) are 2'-O-methyl
<220> FEATURE:
<221> NAME/KEY: misc_feature
<222> LOCATION: (21)..(21)
<223> OTHER INFORMATION: n is a deoxy inosine
<220> FEATURE:
<221> NAME/KEY: misc_feature
<222> LOCATION: (24)..(24)
<223> OTHER INFORMATION: n is an inverted deoxy thymidine (3'-3' linked)

<400> SEQUENCE: 211
agccugggga cccaugggggg ncun                                             24

<210> SEQ ID NO 212
<211> LENGTH: 29
<212> TYPE: DNA
<213> ORGANISM: artificial
<220> FEATURE:
<223> OTHER INFORMATION: synthetic aptamer
<220> FEATURE:
<221> NAME/KEY: modified_base
```

```
<222> LOCATION: (1)..(28)
<223> OTHER INFORMATION: all purines (A and G) are deoxy, except
      guanosine at positions 2, 7 and 20 are 2'-O-methyl, and adenosine
      at positions 1, 11, 15 are 2'-O-methyl
<220> FEATURE:
<221> NAME/KEY: modified_base
<222> LOCATION: (1)..(28)
<223> OTHER INFORMATION: alll pyrimidines (C and U) are 2'-O-methyl
<220> FEATURE:
<221> NAME/KEY: misc_feature
<222> LOCATION: (9)..(9)
<223> OTHER INFORMATION: n is a phosphorothioate internucleotide linkage
<220> FEATURE:
<221> NAME/KEY: misc_feature
<222> LOCATION: (17)..(17)
<223> OTHER INFORMATION: n is a phosphorothioate internucleotide linkage
<220> FEATURE:
<221> NAME/KEY: misc_feature
<222> LOCATION: (19)..(19)
<223> OTHER INFORMATION: n is a phosphorothioate internucleotide linkage
<220> FEATURE:
<221> NAME/KEY: misc_feature
<222> LOCATION: (22)..(22)
<223> OTHER INFORMATION: n is a phosphorothioate internucleotide linkage
<220> FEATURE:
<221> NAME/KEY: misc_feature
<222> LOCATION: (24)..(24)
<223> OTHER INFORMATION: n is a deoxy inosine
<220> FEATURE:
<221> NAME/KEY: misc_feature
<222> LOCATION: (25)..(25)
<223> OTHER INFORMATION: n is a phosphorothioate internucleotide linkage
<220> FEATURE:
<221> NAME/KEY: misc_feature
<222> LOCATION: (29)..(29)
<223> OTHER INFORMATION: n is an inverted deoxy thymidine (3'-3' linked)

<400> SEQUENCE: 212
agccugggng acccaungng gngnngcun                                            29

<210> SEQ ID NO 213
<211> LENGTH: 29
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(28)
<223> OTHER INFORMATION: all purines (A and G) are deoxy, except
      guanosine at positions 2, 7 and 20 are 2'-O-methyl, and adenosine
      at positions 1, 11, 15 are 2'-O-methyl
<220> FEATURE:
<221> NAME/KEY: modified_base
<222> LOCATION: (1)..(28)
<223> OTHER INFORMATION: all pyrimidines (C and U) are 2-O-methyl
<220> FEATURE:
<221> NAME/KEY: misc_feature
<222> LOCATION: (9)..(9)
<223> OTHER INFORMATION: n is a phosphorothioate internucleotide linkage
<220> FEATURE:
<221> NAME/KEY: misc_feature
<222> LOCATION: (17)..(17)
<223> OTHER INFORMATION: n is a phosphorothioate internucleotide linkage
<220> FEATURE:
<221> NAME/KEY: misc_feature
<222> LOCATION: (18)..(18)
<223> OTHER INFORMATION: n is deoxy inosine
<220> FEATURE:
<221> NAME/KEY: misc_feature
<222> LOCATION: (19)..(19)
<223> OTHER INFORMATION: n is a phosphorothioate internucleotide linkage
<220> FEATURE:
<221> NAME/KEY: misc_feature
<222> LOCATION: (22)..(22)
<223> OTHER INFORMATION: n is a phosphorothioate internucleotide linkage
<220> FEATURE:
```

```
<221> NAME/KEY: misc_feature
<222> LOCATION: (24)..(24)
<223> OTHER INFORMATION: n is deoxy inosine
<220> FEATURE:
<221> NAME/KEY: misc_feature
<222> LOCATION: (25)..(25)
<223> OTHER INFORMATION: n is a phosphorothioate internucleotide linkage
<220> FEATURE:
<221> NAME/KEY: misc_feature
<222> LOCATION: (29)..(29)
<223> OTHER INFORMATION: n is an inverted deoxy thymidine (3'-3' linked)

<400> SEQUENCE: 213
agccugggng acccaunnng gngnngcun                                              29

<210> SEQ ID NO 214
<211> LENGTH: 32
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(31)
<223> OTHER INFORMATION: all purines (A and G) are deoxy, except
      guanosine at positions 2, 8 and 21 are 2'-O-methyl, and adenosine
      at positions 1, 13, 17 are 2'-O-methyl
<220> FEATURE:
<221> NAME/KEY: modified_base
<222> LOCATION: (1)..(31)
<223> OTHER INFORMATION: all pyrimidines (C and U) are 2'-O-methyl
<220> FEATURE:
<221> NAME/KEY: misc_feature
<222> LOCATION: (6)..(6)
<223> OTHER INFORMATION: n is a phosphorothioate internucleotide linkage
<220> FEATURE:
<221> NAME/KEY: misc_feature
<222> LOCATION: (9)..(9)
<223> OTHER INFORMATION: n is a phosphorothioate internucleotide linkage
<220> FEATURE:
<221> NAME/KEY: misc_feature
<222> LOCATION: (11)..(11)
<223> OTHER INFORMATION: n is a phosphorothioate internucleotide linkage
<220> FEATURE:
<221> NAME/KEY: misc_feature
<222> LOCATION: (19)..(19)
<223> OTHER INFORMATION: n is a phosphorothioate internucleotide linkage
<220> FEATURE:
<221> NAME/KEY: misc_feature
<222> LOCATION: (22)..(22)
<223> OTHER INFORMATION: n is a phosphorothioate internucleotide linkage
<220> FEATURE:
<221> NAME/KEY: misc_feature
<222> LOCATION: (24)..(24)
<223> OTHER INFORMATION: n is a phosphorothioate internucleotide linkage
<220> FEATURE:
<221> NAME/KEY: misc_feature
<222> LOCATION: (26)..(26)
<223> OTHER INFORMATION: n is a phosphorothioate internucleotide linkage
<220> FEATURE:
<221> NAME/KEY: misc_feature
<222> LOCATION: (27)..(27)
<223> OTHER INFORMATION: n is a deoxy inosine
<220> FEATURE:
<221> NAME/KEY: misc_feature
<222> LOCATION: (28)..(28)
<223> OTHER INFORMATION: n is a phosphorothioate internucleotide linkage
<220> FEATURE:
<221> NAME/KEY: misc_feature
<222> LOCATION: (32)..(32)
<223> OTHER INFORMATION: n is an inverted deoxy thymidine (3'-3' linked)

<400> SEQUENCE: 214
agccunggng ngacccaung gngngnnngc un                                          32
```

```
<210> SEQ ID NO 215
<211> LENGTH: 32
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(31)
<223> OTHER INFORMATION: all purines (A and G) are deoxy, except
      guanosine at positions 2, 8 and 21 are 2'-O-methyl, and adenosine
      at positions 1, 13, 17 are 2'-O-methyl
<220> FEATURE:
<221> NAME/KEY: modified_base
<222> LOCATION: (1)..(31)
<223> OTHER INFORMATION: all pyrimidines (C and U) are 2'-O-methyl
<220> FEATURE:
<221> NAME/KEY: misc_feature
<222> LOCATION: (6)..(6)
<223> OTHER INFORMATION: n is a phosphorothioate internucleotide linkage
<220> FEATURE:
<221> NAME/KEY: misc_feature
<222> LOCATION: (9)..(9)
<223> OTHER INFORMATION: n is a phosphorothioate internucleotide linkage
<220> FEATURE:
<221> NAME/KEY: misc_feature
<222> LOCATION: (11)..(11)
<223> OTHER INFORMATION: n is a phosphorothioate internucleotide linkage
<220> FEATURE:
<221> NAME/KEY: misc_feature
<222> LOCATION: (19)..(19)
<223> OTHER INFORMATION: n is a phosphorothioate internucleotide linkage
<220> FEATURE:
<221> NAME/KEY: misc_feature
<222> LOCATION: (20)..(20)
<223> OTHER INFORMATION: n is a deoxy inosine
<220> FEATURE:
<221> NAME/KEY: misc_feature
<222> LOCATION: (22)..(22)
<223> OTHER INFORMATION: n is a phosphorothioate internucleotide linkage
<220> FEATURE:
<221> NAME/KEY: misc_feature
<222> LOCATION: (24)..(24)
<223> OTHER INFORMATION: n is a phosphorothioate internucleotide linkage
<220> FEATURE:
<221> NAME/KEY: misc_feature
<222> LOCATION: (26)..(26)
<223> OTHER INFORMATION: n is a phosphorothioate internucleotide linkage
<220> FEATURE:
<221> NAME/KEY: misc_feature
<222> LOCATION: (27)..(27)
<223> OTHER INFORMATION: n is a deoxy inosine
<220> FEATURE:
<221> NAME/KEY: misc_feature
<222> LOCATION: (28)..(28)
<223> OTHER INFORMATION: n is a phosphorothioate internucleotide linkage
<220> FEATURE:
<221> NAME/KEY: misc_feature
<222> LOCATION: (32)..(32)
<223> OTHER INFORMATION: n is an inverted deoxy thymidine (3'-3' linked)

<400> SEQUENCE: 215
agccunggng ngacccaunn gngngnnngc un                                      32

<210> SEQ ID NO 216
<211> LENGTH: 29
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(28)
<223> OTHER INFORMATION: all purines (A and G) are deoxy, except
      guanosine at positions 2, 7 and 20 are 2'-O-methyl, and adenosine
      at positions 1, 11, 15 are 2'-O-methyl
<220> FEATURE:
```

```
<221> NAME/KEY: modified_base
<222> LOCATION: (1)..(28)
<223> OTHER INFORMATION: all pyrimidines (C and U) are 2'-O-methyl
<220> FEATURE:
<221> NAME/KEY: misc_feature
<222> LOCATION: (9)..(9)
<223> OTHER INFORMATION: n is a phosphorothioate internucleotide linkage
<220> FEATURE:
<221> NAME/KEY: misc_feature
<222> LOCATION: (17)..(17)
<223> OTHER INFORMATION: n is a phosphorothioate internucleotide linkage
<220> FEATURE:
<221> NAME/KEY: misc_feature
<222> LOCATION: (18)..(18)
<223> OTHER INFORMATION: n is a deoxy inosine
<220> FEATURE:
<221> NAME/KEY: misc_feature
<222> LOCATION: (19)..(19)
<223> OTHER INFORMATION: n is a phosphorothioate internucleotide linkage
<220> FEATURE:
<221> NAME/KEY: misc_feature
<222> LOCATION: (21)..(21)
<223> OTHER INFORMATION: n is a deoxy inosine
<220> FEATURE:
<221> NAME/KEY: misc_feature
<222> LOCATION: (22)..(22)
<223> OTHER INFORMATION: n is a phosphorothioate internucleotide linkage
<220> FEATURE:
<221> NAME/KEY: misc_feature
<222> LOCATION: (24)..(24)
<223> OTHER INFORMATION: n is a deoxy inosine
<220> FEATURE:
<221> NAME/KEY: misc_feature
<222> LOCATION: (25)..(25)
<223> OTHER INFORMATION: n is a phosphorothioate internucleotide linkage
<220> FEATURE:
<221> NAME/KEY: misc_feature
<222> LOCATION: (29)..(29)
<223> OTHER INFORMATION: n is an inverted deoxy thymidine (3'-3' linked)

<400> SEQUENCE: 216
agccugggng acccaunnng nngnngcun                                       29

<210> SEQ ID NO 217
<211> LENGTH: 29
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(28)
<223> OTHER INFORMATION: all purines (A and G) are deoxy, except
      guanosine at positions 2, 7 and 20 are 2'-O-methyl, and adenosine
      at positions 1, 11, 15 are 2'-O-methyl
<220> FEATURE:
<221> NAME/KEY: modified_base
<222> LOCATION: (1)..(28)
<223> OTHER INFORMATION: all pyrimidines (C and U) are 2'-O-methyl
<220> FEATURE:
<221> NAME/KEY: misc_feature
<222> LOCATION: (9)..(9)
<223> OTHER INFORMATION: n is a phosphorothioate internucleotide linkage
<220> FEATURE:
<221> NAME/KEY: misc_feature
<222> LOCATION: (17)..(17)
<223> OTHER INFORMATION: n is a phosphorothioate internucleotide linkage
<220> FEATURE:
<221> NAME/KEY: misc_feature
<222> LOCATION: (19)..(19)
<223> OTHER INFORMATION: n is a phosphorothioate internucleotide linkage
<220> FEATURE:
<221> NAME/KEY: misc_feature
<222> LOCATION: (21)..(21)
<223> OTHER INFORMATION: n is deoxy inosine
<220> FEATURE:
<221> NAME/KEY: misc_feature
```

<222> LOCATION: (22)..(22)
<223> OTHER INFORMATION: n is a phosphorothioate internucleotide linkage
<220> FEATURE:
<221> NAME/KEY: misc_feature
<222> LOCATION: (24)..(24)
<223> OTHER INFORMATION: n is deoxy inosine
<220> FEATURE:
<221> NAME/KEY: misc_feature
<222> LOCATION: (25)..(25)
<223> OTHER INFORMATION: n is a phosphorothioate internucleotide linkage
<220> FEATURE:
<221> NAME/KEY: misc_feature
<222> LOCATION: (29)..(29)
<223> OTHER INFORMATION: n is an inverted deoxy thymidine (3'-3' linked)

<400> SEQUENCE: 217
agccugggng acccaungng nngnngcun                                              29

<210> SEQ ID NO 218
<211> LENGTH: 32
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(31)
<223> OTHER INFORMATION: all purines (A and G) are deoxy, except
      guanosine at positions 2, 8 and 21 are 2'-O-methyl, and adenosine
      at positions 1, 13, 17 are 2'-O-methyl
<220> FEATURE:
<221> NAME/KEY: modified_base
<222> LOCATION: (1)..(31)
<223> OTHER INFORMATION: all pyrimidines (C and U) are 2'-O-methyl
<220> FEATURE:
<221> NAME/KEY: misc_feature
<222> LOCATION: (6)..(6)
<223> OTHER INFORMATION: n is a phosphorothioate internucleotide linkage
<220> FEATURE:
<221> NAME/KEY: misc_feature
<222> LOCATION: (9)..(9)
<223> OTHER INFORMATION: n is a phosphorothioate internucleotide linkage
<220> FEATURE:
<221> NAME/KEY: misc_feature
<222> LOCATION: (11)..(11)
<223> OTHER INFORMATION: n is a phosphorothioate internucleotide linkage
<220> FEATURE:
<221> NAME/KEY: misc_feature
<222> LOCATION: (19)..(19)
<223> OTHER INFORMATION: n is a phosphorothioate internucleotide linkage
<220> FEATURE:
<221> NAME/KEY: misc_feature
<222> LOCATION: (22)..(22)
<223> OTHER INFORMATION: n is a phosphorothioate internucleotide linkage
<220> FEATURE:
<221> NAME/KEY: misc_feature
<222> LOCATION: (23)..(23)
<223> OTHER INFORMATION: n is deoxy inosine
<220> FEATURE:
<221> NAME/KEY: misc_feature
<222> LOCATION: (24)..(24)
<223> OTHER INFORMATION: n is a phosphorothioate internucleotide linkage
<220> FEATURE:
<221> NAME/KEY: misc_feature
<222> LOCATION: (26)..(26)
<223> OTHER INFORMATION: n is a phosphorothioate internucleotide linkage
<220> FEATURE:
<221> NAME/KEY: misc_feature
<222> LOCATION: (27)..(27)
<223> OTHER INFORMATION: n is deoxy inosine
<220> FEATURE:
<221> NAME/KEY: misc_feature
<222> LOCATION: (28)..(28)
<223> OTHER INFORMATION: n is a phosphorothioate internucleotide linkage
<220> FEATURE:
<221> NAME/KEY: misc_feature
<222> LOCATION: (32)..(32)

```
<223> OTHER INFORMATION: n is an inverted deoxy thymidine (3'-3' linked)

<400> SEQUENCE: 218
agccunggng ngacccaung gnnngnnngc un                                    32

<210> SEQ ID NO 219
<211> LENGTH: 32
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(31)
<223> OTHER INFORMATION: all purines (A and G) are deoxy, except
      guanosine at positions 2, 8 and 21 are 2'-O-methyl, and adenosine
      at positions 1, 13, 17 are 2'-O-methyl
<220> FEATURE:
<221> NAME/KEY: modified_base
<222> LOCATION: (1)..(31)
<223> OTHER INFORMATION: all pyrimidines (C and U) are 2'O-methyl
<220> FEATURE:
<221> NAME/KEY: misc_feature
<222> LOCATION: (6)..(6)
<223> OTHER INFORMATION: n is a phosphorothioate internucleotide linkage
<220> FEATURE:
<221> NAME/KEY: misc_feature
<222> LOCATION: (9)..(9)
<223> OTHER INFORMATION: n is a phosphorothioate internucleotide linkage
<220> FEATURE:
<221> NAME/KEY: misc_feature
<222> LOCATION: (11)..(11)
<223> OTHER INFORMATION: n is a phosphorothioate internucleotide linkage
<220> FEATURE:
<221> NAME/KEY: misc_feature
<222> LOCATION: (19)..(19)
<223> OTHER INFORMATION: n is a phosphorothioate internucleotide linkage
<220> FEATURE:
<221> NAME/KEY: misc_feature
<222> LOCATION: (20)..(20)
<223> OTHER INFORMATION: n is deoxy inosine
<220> FEATURE:
<221> NAME/KEY: misc_feature
<222> LOCATION: (22)..(22)
<223> OTHER INFORMATION: n is a phosphorothioate internucleotide linkage
<220> FEATURE:
<221> NAME/KEY: misc_feature
<222> LOCATION: (23)..(23)
<223> OTHER INFORMATION: n is deoxy inosine
<220> FEATURE:
<221> NAME/KEY: misc_feature
<222> LOCATION: (24)..(24)
<223> OTHER INFORMATION: n is a phosphorothioate internucleotide linkage
<220> FEATURE:
<221> NAME/KEY: misc_feature
<222> LOCATION: (26)..(26)
<223> OTHER INFORMATION: n is a phosphorothioate internucleotide linkage
<220> FEATURE:
<221> NAME/KEY: misc_feature
<222> LOCATION: (27)..(27)
<223> OTHER INFORMATION: n is deoxy inosine
<220> FEATURE:
<221> NAME/KEY: misc_feature
<222> LOCATION: (28)..(28)
<223> OTHER INFORMATION: n is a phosphorothioate internucleotide linkage
<220> FEATURE:
<221> NAME/KEY: misc_feature
<222> LOCATION: (32)..(32)
<223> OTHER INFORMATION: n is an inverted deoxy thymidine (3'-3' linked)

<400> SEQUENCE: 219
agccunggng ngacccaunn gnnngnnngc un                                    32

<210> SEQ ID NO 220
<211> LENGTH: 38
```

```
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(37)
<223> OTHER INFORMATION: all purines (A and G) and all pyrimidines (C
      and T) are deoxy, except guanosine at position 1 is 2'-O-methyl
<220> FEATURE:
<221> NAME/KEY: misc_feature
<222> LOCATION: (38)..(38)
<223> OTHER INFORMATION: n is an inverted deoxy thymidine (3'-3' linked)

<400> SEQUENCE: 220
ggggctactt tatccgttcc tcctagtggg tagcccen                              38

<210> SEQ ID NO 221
<211> LENGTH: 38
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(37)
<223> OTHER INFORMATION: all purines (A and G) and all pyrimidines (C
      and T) are deoxy, except guanosine at position 2 is 2'-O-methyl
<220> FEATURE:
<221> NAME/KEY: misc_feature
<222> LOCATION: (38)..(38)
<223> OTHER INFORMATION: n is an inverted deoxy thymidine (3'-3' linked)

<400> SEQUENCE: 221
ggggctactt tatccgttcc tcctagtggg tagcccen                              38

<210> SEQ ID NO 222
<211> LENGTH: 38
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(37)
<223> OTHER INFORMATION: all purines (A and G) and all pyrimidines (C
      and T) are deoxy, except guanosine at position 3 is 2'-O-methyl
<220> FEATURE:
<221> NAME/KEY: misc_feature
<222> LOCATION: (38)..(38)
<223> OTHER INFORMATION: n is an inverted deoxy thymidine (3'-3' linked)

<400> SEQUENCE: 222
ggggctactt tatccgttcc tcctagtggg tagcccen                              38

<210> SEQ ID NO 223
<211> LENGTH: 38
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(37)
<223> OTHER INFORMATION: all purines (A and G) and all pyrimidines (C
      and T) are deoxy, except guanosine at position 4 is 2'-O-methyl
<220> FEATURE:
<221> NAME/KEY: misc_feature
<222> LOCATION: (38)..(38)
<223> OTHER INFORMATION: n is an inverted deoxy thymidine (3'-3' linked)

<400> SEQUENCE: 223
```
ggggctactt tatccgttcc tcctagtggg tagccccn                    38

<210> SEQ ID NO 224
<211> LENGTH: 38
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(37)
<223> OTHER INFORMATION: all purines (A and G) and all pyrimidines (C
      and T) are deoxy, except cytidine at position 5 is 2'-O-methyl
<220> FEATURE:
<221> NAME/KEY: misc_feature
<222> LOCATION: (38)..(38)
<223> OTHER INFORMATION: n is an inverted deoxy thymidine (3'-3' linked)

<400> SEQUENCE: 224
ggggctactt tatccgttcc tcctagtggg tagccccn                    38

<210> SEQ ID NO 225
<211> LENGTH: 38
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(37)
<223> OTHER INFORMATION: all purines (A and G) and all pyrimidines (C
      and T) are deoxy, except uridine at position 6 is 2'-O-methyl
<220> FEATURE:
<221> NAME/KEY: misc_feature
<222> LOCATION: (38)..(38)
<223> OTHER INFORMATION: n is an inverted deoxy thymidine (3'-3' linked)

<400> SEQUENCE: 225
ggggcuactt tatccgttcc tcctagtggg tagccccn                    38

<210> SEQ ID NO 226
<211> LENGTH: 38
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(37)
<223> OTHER INFORMATION: all purines (A and G) and all pyrimidines (C
      and T) are deoxy, except adenosine at position 7 is 2'-O-methyl
<220> FEATURE:
<221> NAME/KEY: misc_feature
<222> LOCATION: (38)..(38)
<223> OTHER INFORMATION: n is an inverted deoxy thymidine (3'-3' linked)

<400> SEQUENCE: 226
ggggctactt tatccgttcc tcctagtggg tagccccn                    38

<210> SEQ ID NO 227
<211> LENGTH: 38
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(37)
<223> OTHER INFORMATION: all purines (A and G) and all pyrimidines (C
      and T) are deoxy, except cytidine at position 8 is 2'-O-methyl
<220> FEATURE:
<221> NAME/KEY: misc_feature
<222> LOCATION: (38)..(38)
<223> OTHER INFORMATION: n is an inverted deoxy thymidine (3'-3' linked)

<400> SEQUENCE: 227
ggggctactt tatccgttcc tctagtggg tagccccn                    38

<210> SEQ ID NO 228
<211> LENGTH: 38
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(37)
<223> OTHER INFORMATION: all purines (A and G) and all pyrimidines (C
      and T) are deoxy, except uridine  at position 9 is 2'-O-methyl
<220> FEATURE:
<221> NAME/KEY: misc_feature
<222> LOCATION: (38)..(38)
<223> OTHER INFORMATION: n is an inverted deoxy thymidine (3'-3' linked)

<400> SEQUENCE: 228
ggggctacut tatccgttcc tctagtggg tagccccn                    38

<210> SEQ ID NO 229
<211> LENGTH: 38
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(37)
<223> OTHER INFORMATION: all purines (A and G) and all pyrimidines (C
      and T) are deoxy, except uridine  at position 10 is 2'-O-methyl
<220> FEATURE:
<221> NAME/KEY: misc_feature
<222> LOCATION: (38)..(38)
<223> OTHER INFORMATION: n is an inverted deoxy thymidine (3'-3' linked)

<400> SEQUENCE: 229
ggggctactu tatccgttcc tctagtggg tagccccn                    38

<210> SEQ ID NO 230
<211> LENGTH: 38
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(37)
<223> OTHER INFORMATION: all purines (A and G) and all pyrimidines (C
      and T) are deoxy, except uridine  at position 11 is 2'-O-methyl
<220> FEATURE:
<221> NAME/KEY: misc_feature
<222> LOCATION: (38)..(38)
<223> OTHER INFORMATION: n is an inverted deoxy thymidine (3'-3' linked)

<400> SEQUENCE: 230
ggggctactt uatccgttcc tctagtggg tagccccn                    38

<210> SEQ ID NO 231
<211> LENGTH: 38
<212> TYPE: DNA
<213> ORGANISM: artificial
<220> FEATURE:
<223> OTHER INFORMATION: synthetic aptamer
<220> FEATURE:
<221> NAME/KEY: modified_base

```
<222> LOCATION: (1)..(37)
<223> OTHER INFORMATION: all purines (A and G) and all pyrimidines (C
      and T) are deoxy, except adenosine at position 12 is 2'-O-methyl
<220> FEATURE:
<221> NAME/KEY: misc_feature
<222> LOCATION: (38)..(38)
<223> OTHER INFORMATION: n is an inverted deoxy thymidine (3'-3' linked)

<400> SEQUENCE: 231
ggggctactt tatccgttcc tcctagtggg tagccccn                              38

<210> SEQ ID NO 232
<211> LENGTH: 38
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(37)
<223> OTHER INFORMATION: all purines (A and G) and all pyrimidines (C
      and T) are deoxy, except uridine at position 13 is 2'-O-methyl
<220> FEATURE:
<221> NAME/KEY: misc_feature
<222> LOCATION: (38)..(38)
<223> OTHER INFORMATION: n is an inverted deoxy thymidine (3'-3' linked)

<400> SEQUENCE: 232
ggggctactt tauccgttcc tcctagtggg tagccccn                              38

<210> SEQ ID NO 233
<211> LENGTH: 38
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(37)
<223> OTHER INFORMATION: all purines (A and G) and all pyrimidines (C
      and T) are deoxy, except cytidine at position 14 is 2'-O-methyl
<220> FEATURE:
<221> NAME/KEY: misc_feature
<222> LOCATION: (38)..(38)
<223> OTHER INFORMATION: n is an inverted deoxy thymidine (3'-3' linked)

<400> SEQUENCE: 233
ggggctactt tatccgttcc tcctagtggg tagccccn                              38

<210> SEQ ID NO 234
<211> LENGTH: 38
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(37)
<223> OTHER INFORMATION: all purines (A and G) and all pyrimidines (C
      and T) are deoxy, except cytidine at position 15 is 2'-O-methyl
<220> FEATURE:
<221> NAME/KEY: misc_feature
<222> LOCATION: (38)..(38)
<223> OTHER INFORMATION: n is an inverted deoxy thymidine (3'-3' linked)

<400> SEQUENCE: 234
ggggctactt tatccgttcc tcctagtggg tagccccn                              38

<210> SEQ ID NO 235
<211> LENGTH: 38
<212> TYPE: DNA
```

<213> ORGANISM: artificial
<220> FEATURE:
<223> OTHER INFORMATION: synthetic aptamer
<220> FEATURE:
<221> NAME/KEY: modified_base
<222> LOCATION: (1)..(37)
<223> OTHER INFORMATION: all purines (A and G) and all pyrimidines (C
      and T) are deoxy, except guanosine at position 16 is 2'-O-methyl
<220> FEATURE:
<221> NAME/KEY: misc_feature
<222> LOCATION: (38)..(38)
<223> OTHER INFORMATION: n is an inverted deoxy thymidine (3'-3' linked)

<400> SEQUENCE: 235
ggggctactt tatccgttcc tcctagtggg tagccccn                                38

<210> SEQ ID NO 236
<211> LENGTH: 38
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(37)
<223> OTHER INFORMATION: all purines (A and G) and all pyrimidines (C
      and T) are deoxy, except uridine at position 17 is 2'-O-methyl
<220> FEATURE:
<221> NAME/KEY: misc_feature
<222> LOCATION: (38)..(38)
<223> OTHER INFORMATION: n is an inverted deoxy thymidine (3'-3' linked)

<400> SEQUENCE: 236
ggggctactt tatccgutcc tcctagtggg tagccccn                                38

<210> SEQ ID NO 237
<211> LENGTH: 38
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(37)
<223> OTHER INFORMATION: all purines (A and G) and all pyrimidines (C
      and T) are deoxy, except uridine at position 18 is 2'-O-methyl
<220> FEATURE:
<221> NAME/KEY: misc_feature
<222> LOCATION: (38)..(38)
<223> OTHER INFORMATION: n is an inverted deoxy thymidine (3'-3' linked)

<400> SEQUENCE: 237
ggggctactt tatccgtucc tcctagtggg tagccccn                                38

<210> SEQ ID NO 238
<211> LENGTH: 38
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(37)
<223> OTHER INFORMATION: all purines (A and G) and all pyrimidines (C
      and T) are deoxy, except cytidine at position 19 is 2'-O-methyl
<220> FEATURE:
<221> NAME/KEY: misc_feature
<222> LOCATION: (38)..(38)
<223> OTHER INFORMATION: n is an inverted deoxy thymidine (3'-3' linked)

<400> SEQUENCE: 238
ggggctactt tatccgttcc tcctagtggg tagccccn                                38

<210> SEQ ID NO 239
<211> LENGTH: 38
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(37)
<223> OTHER INFORMATION: all purines (A and G) and all pyrimidines (C and T) are deoxy, except cytidine at position 20 is 2'-O-methyl
<220> FEATURE:
<221> NAME/KEY: misc_feature
<222> LOCATION: (38)..(38)
<223> OTHER INFORMATION: n is an inverted deoxy thymidine (3'-3' linked)

<400> SEQUENCE: 239
ggggctactt tatccgttcc tcctagtggg tagccccn            38

<210> SEQ ID NO 240
<211> LENGTH: 38
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(37)
<223> OTHER INFORMATION: all purines (A and G) and all pyrimidines (C and T) are deoxy, except uridine at position 21 is 2'-O-methyl
<220> FEATURE:
<221> NAME/KEY: misc_feature
<222> LOCATION: (38)..(38)
<223> OTHER INFORMATION: n is an inverted deoxy thymidine (3'-3' linked)

<400> SEQUENCE: 240
ggggctactt tatccgttcc ucctagtggg tagccccn            38

<210> SEQ ID NO 241
<211> LENGTH: 38
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(37)
<223> OTHER INFORMATION: all purines (A and G) and all pyrimidines (C and T) are deoxy, except cytidine at position 22 is 2'-O-methyl
<220> FEATURE:
<221> NAME/KEY: misc_feature
<222> LOCATION: (38)..(38)
<223> OTHER INFORMATION: n is an inverted deoxy thymidine (3'-3' linked)

<400> SEQUENCE: 241
ggggctactt tatccgttcc tcctagtggg tagccccn            38

<210> SEQ ID NO 242
<211> LENGTH: 38
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(37)
<223> OTHER INFORMATION: all purines (A and G) and all pyrimidines (C and T) are deoxy, except cytidine at position 23 is 2'-O-methyl
<220> FEATURE:
<221> NAME/KEY: misc_feature
<222> LOCATION: (38)..(38)

```
<223> OTHER INFORMATION: n is an inverted deoxy thymidine (3'-3' linked)

<400> SEQUENCE: 242
ggggctactt tatccgttcc tcctagtggg tagccccn                               38

<210> SEQ ID NO 243
<211> LENGTH: 38
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(37)
<223> OTHER INFORMATION: all purines (A and G) and all pyrimidines (C
      and T) are deoxy, except uridine at position 24 is 2'-O-methyl
<220> FEATURE:
<221> NAME/KEY: misc_feature
<222> LOCATION: (38)..(38)
<223> OTHER INFORMATION: n is an inverted deoxy thymidine (3'-3' linked)

<400> SEQUENCE: 243
ggggctactt tatccgttcc tccuagtggg tagccccn                               38

<210> SEQ ID NO 244
<211> LENGTH: 38
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(37)
<223> OTHER INFORMATION: all purines (A and G) and all pyrimidines (C
      and T) are deoxy, except adenosine at position 25 is 2'-O-methyl
<220> FEATURE:
<221> NAME/KEY: misc_feature
<222> LOCATION: (38)..(38)
<223> OTHER INFORMATION: n is an inverted deoxy thymidine (3'-3' linked)

<400> SEQUENCE: 244
ggggctactt tatccgttcc tcctagtggg tagccccn                               38

<210> SEQ ID NO 245
<211> LENGTH: 38
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(37)
<223> OTHER INFORMATION: all purines (A and G) and all pyrimidines (C
      and T) are deoxy, except guanosine at position 26 is 2'-O-methyl
<220> FEATURE:
<221> NAME/KEY: misc_feature
<222> LOCATION: (38)..(38)
<223> OTHER INFORMATION: n is an inverted deoxy thymidine (3'-3' linked)

<400> SEQUENCE: 245
ggggctactt tatccgttcc tcctagtggg tagccccn                               38

<210> SEQ ID NO 246
<211> LENGTH: 38
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(37)
```

```
<223> OTHER INFORMATION: all purines (A and G) and all pyrimidines (C
      and T) are deoxy, except uridine at position 27 is 2'-O-methyl
<220> FEATURE:
<221> NAME/KEY: misc_feature
<222> LOCATION: (38)..(38)
<223> OTHER INFORMATION: n is an inverted deoxy thymidine (3'-3' linked)

<400> SEQUENCE: 246
ggggctactt tatccgttcc tctaguggg tagccccn                                 38

<210> SEQ ID NO 247
<211> LENGTH: 38
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(37)
<223> OTHER INFORMATION: all purines (A and G) and all pyrimidines (C
      and T) are deoxy, except guanosine at position 28 is 2'-O-methyl
<220> FEATURE:
<221> NAME/KEY: misc_feature
<222> LOCATION: (38)..(38)
<223> OTHER INFORMATION: n is an inverted deoxy thymidine (3'-3' linked)

<400> SEQUENCE: 247
ggggctactt tatccgttcc tctagtggg tagccccn                                 38

<210> SEQ ID NO 248
<211> LENGTH: 38
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(37)
<223> OTHER INFORMATION: all purines (A and G) and all pyrimidines (C
      and T) are deoxy, except guanosine at position 29 is 2'-O-methyl
<220> FEATURE:
<221> NAME/KEY: misc_feature
<222> LOCATION: (38)..(38)
<223> OTHER INFORMATION: n is an inverted deoxy thymidine (3'-3' linked)

<400> SEQUENCE: 248
ggggctactt tatccgttcc tctagtggg tagccccn                                 38

<210> SEQ ID NO 249
<211> LENGTH: 38
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(37)
<223> OTHER INFORMATION: all purines (A and G) and all pyrimidines (C
      and T) are deoxy, except guanosine at position 30 is 2'-O-methyl
<220> FEATURE:
<221> NAME/KEY: misc_feature
<222> LOCATION: (38)..(38)
<223> OTHER INFORMATION: n is an inverted deoxy thymidine (3'-3' linked)

<400> SEQUENCE: 249
ggggctactt tatccgttcc tctagtggg tagccccn                                 38

<210> SEQ ID NO 250
<211> LENGTH: 38
<212> TYPE: DNA
<213> ORGANISM: artificial
```

```
<220> FEATURE:
<223> OTHER INFORMATION: synthetic aptamer
<220> FEATURE:
<221> NAME/KEY: modified_base
<222> LOCATION: (1)..(37)
<223> OTHER INFORMATION: all purines (A and G) and all pyrimidines (C
      and T) are deoxy, except uridine at position 31 is 2'-O-methyl
<220> FEATURE:
<221> NAME/KEY: misc_feature
<222> LOCATION: (38)..(38)
<223> OTHER INFORMATION: n is an inverted deoxy thymidine (3'-3' linked)

<400> SEQUENCE: 250
ggggctactt tatccgttcc tcctagtggg uagccccn                              38

<210> SEQ ID NO 251
<211> LENGTH: 38
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(37)
<223> OTHER INFORMATION: all purines (A and G) and all pyrimidines (C
      and T) are deoxy, except adenosine at position 32 is 2'-O-methyl
<220> FEATURE:
<221> NAME/KEY: misc_feature
<222> LOCATION: (38)..(38)
<223> OTHER INFORMATION: n is an inverted deoxy thymidine (3'-3' linked)

<400> SEQUENCE: 251
ggggctactt tatccgttcc tcctagtggg tagccccn                              38

<210> SEQ ID NO 252
<211> LENGTH: 38
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(37)
<223> OTHER INFORMATION: all purines (A and G) and all pyrimidines (C
      and T) are deoxy, except guanosine at position 33 is 2'-O-methyl
<220> FEATURE:
<221> NAME/KEY: misc_feature
<222> LOCATION: (38)..(38)
<223> OTHER INFORMATION: n is an inverted deoxy thymidine (3'-3' linked)

<400> SEQUENCE: 252
ggggctactt tatccgttcc tcctagtggg tagccccn                              38

<210> SEQ ID NO 253
<211> LENGTH: 38
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(37)
<223> OTHER INFORMATION: all purines (A and G) and all pyrimidines (C
      and T) are deoxy, except cytidine at position 34 is 2'-O-methyl
<220> FEATURE:
<221> NAME/KEY: misc_feature
<222> LOCATION: (38)..(38)
<223> OTHER INFORMATION: n is an inverted deoxy thymidine (3'-3' linked)

<400> SEQUENCE: 253
ggggctactt tatccgttcc tcctagtggg tagccccn                              38
```

<210> SEQ ID NO 254
<211> LENGTH: 38
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(37)
<223> OTHER INFORMATION: all purines (A and G) and all pyrimidines (C
and T) are deoxy, except cytidine at position 35 is 2'-O-methyl
<220> FEATURE:
<221> NAME/KEY: misc_feature
<222> LOCATION: (38)..(38)
<223> OTHER INFORMATION: n is an inverted deoxy thymidine (3'-3' linked)

<400> SEQUENCE: 254
ggggctactt tatccgttcc tcctagtggg tagccccn                          38

<210> SEQ ID NO 255
<211> LENGTH: 38
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(37)
<223> OTHER INFORMATION: all purines (A and G) and all pyrimidines (C
and T) are deoxy, except cytidine at position 36 is 2'-O-methyl
<220> FEATURE:
<221> NAME/KEY: misc_feature
<222> LOCATION: (38)..(38)
<223> OTHER INFORMATION: n is an inverted deoxy thymidine (3'-3' linked)

<400> SEQUENCE: 255
ggggctactt tatccgttcc tcctagtggg tagccccn                          38

<210> SEQ ID NO 256
<211> LENGTH: 38
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(37)
<223> OTHER INFORMATION: all purines (A and G) and all pyrimidines (C
and T) are deoxy, except cytidine at position 37 is 2'-O-methyl
<220> FEATURE:
<221> NAME/KEY: misc_feature
<222> LOCATION: (38)..(38)
<223> OTHER INFORMATION: n is an inverted deoxy thymidine (3'-3' linked)

<400> SEQUENCE: 256
ggggctactt tatccgttcc tcctagtggg tagccccn                          38

<210> SEQ ID NO 257
<211> LENGTH: 38
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(37)
<223> OTHER INFORMATION: all purines (A and G) are deoxy, except
guanosine at positions 1, 2, 3, 4, 30 and 33 are 2'-O-methyl, and
adenosine at positions 7 and 32 are 2'-O-methyl
<220> FEATURE:
<221> NAME/KEY: modified_base
<222> LOCATION: (1)..(37)

<223> OTHER INFORMATION: all pyrimidines (C and T) are deoxy
<220> FEATURE:
<221> NAME/KEY: misc_feature
<222> LOCATION: (38)..(38)
<223> OTHER INFORMATION: n is an inverted deoxy thymidine (3'-3' linked)

<400> SEQUENCE: 257
ggggctactt tatccgttcc tcctagtggg tagccccn         38

<210> SEQ ID NO 258
<211> LENGTH: 38
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(37)
<223> OTHER INFORMATION: all purines (A and G) are deoxy
<220> FEATURE:
<221> NAME/KEY: modified_base
<222> LOCATION: (1)..(37)
<223> OTHER INFORMATION: all pyrimidines (C and T) are deoxy, except
      cytidine at positions 5, 8, 34, 35, 36, and 37 are 2'-O-methyl,
      and uridine at positions 6 and 31 are 2'-O-methyl
<220> FEATURE:
<221> NAME/KEY: misc_feature
<222> LOCATION: (38)..(38)
<223> OTHER INFORMATION: n is an inverted deoxy thymidine (3'-3' linked)

<400> SEQUENCE: 258
ggggcuactt tatccgttcc tcctagtggg uagccccn         38

<210> SEQ ID NO 259
<211> LENGTH: 38
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(37)
<223> OTHER INFORMATION: all purines (A and G) are deoxy, except
      guanosine at positions 1, 2, 3, and 4 are 2'-O-methyl
<220> FEATURE:
<221> NAME/KEY: modified_base
<222> LOCATION: (1)..(37)
<223> OTHER INFORMATION: all pyrimdines (C and T) are deoxy, except
      cytidine at positions 34, 35, 36, and 37 are 2'-O-methyl
<220> FEATURE:
<221> NAME/KEY: misc_feature
<222> LOCATION: (38)..(38)
<223> OTHER INFORMATION: n is an inverted deoxy thymidine (3'-3' linked)

<400> SEQUENCE: 259
ggggctactt tatccgttcc tcctagtggg tagccccn         38

<210> SEQ ID NO 260
<211> LENGTH: 38
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(37)
<223> OTHER INFORMATION: all purines (A and G) are deoxy, except
      guanosine at positions 1, 2, 3, 4 and 33 are 2'-O-methyl
<220> FEATURE:
<221> NAME/KEY: modified_base
<222> LOCATION: (1)..(37)
<223> OTHER INFORMATION: all pyrimdines (C and T) are deoxy, except
      cytidine at positions 5, 34, 35, 36, and 37 are 2'-O-methyl

```
<220> FEATURE:
<221> NAME/KEY: misc_feature
<222> LOCATION: (38)..(38)
<223> OTHER INFORMATION: n is an inverted deoxy thymidine (3'- 3'
      linked)

<400> SEQUENCE: 260
ggggctactt tatccgttcc tcctagtggg tagccccn                                38

<210> SEQ ID NO 261
<211> LENGTH: 36
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(35)
<223> OTHER INFORMATION: all purines (A and G) are deoxy, except
      guanosine at positions 1, 2, 3,  and 32 are 2'-O-methyl
<220> FEATURE:
<221> NAME/KEY: modified_base
<222> LOCATION: (1)..(35)
<223> OTHER INFORMATION: all pyrimdines (C and T) are deoxy, except
      cytidine at positions 4, 33, 34, and 35 are 2'-O-methyl
<220> FEATURE:
<221> NAME/KEY: misc_feature
<222> LOCATION: (36)..(36)
<223> OTHER INFORMATION: n is an inverted deoxy thymidine (3'- 3'
      linked)

<400> SEQUENCE: 261 gggctactt atccgttcct cctagtgggt agcccn                                  36

<210> SEQ ID NO 262
<211> LENGTH: 38
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(37)
<223> OTHER INFORMATION: all purines (A and G) are deoxy, except
      guanosine at positions 1, 2, 3, 4 and 33 are 2'-O-methyl, and
      adenosine at position 7 is 2'-O-methyl
<220> FEATURE:
<221> NAME/KEY: modified_base
<222> LOCATION: (1)..(37)
<223> OTHER INFORMATION: all pyrimdines (C and T) are deoxy, except
      cytidine at positions 34, 35, 36, and 37 are 2'-O-methyl
<220> FEATURE:
<221> NAME/KEY: misc_feature
<222> LOCATION: (38)..(38)
<223> OTHER INFORMATION: n is an inverted deoxy thymidine (3'- 3'
      linked)

<400> SEQUENCE: 262
ggggctactt tatccgttcc tcctagtggg tagccccn                                38

<210> SEQ ID NO 263
<211> LENGTH: 38
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(37)
<223> OTHER INFORMATION: all purines (A and G) are deoxy, except
      guanosine at positions 1, 2, 3, 4 and 33 are 2'-O-methyl, and
      adenosine at position 7 is 2'-O-methyl
<220> FEATURE:
```

```
<221> NAME/KEY: modified_base
<222> LOCATION: (1)..(37)
<223> OTHER INFORMATION: all pyrimdines (C and T) are deoxy, except
      cytidine at positions 5, 8, 34,  35, 36, and 37 are 2'-O-methyl,
      and uridine at position 6 is 2'-O-methyl
<220> FEATURE:
<221> NAME/KEY: misc_feature
<222> LOCATION: (38)..(38)
<223> OTHER INFORMATION: n is an inverted deoxy thymidine (3'- 3'
      linked)

<400> SEQUENCE: 263
ggggcuactt tatccgttcc tcctagtggg tagccccn                            38

<210> SEQ ID NO 264
<211> LENGTH: 38
<212> TYPE: DNA
<213> ORGANISM: artificial
<220> FEATURE:
<223> OTHER INFORMATION: syjnthetic aptamer
<220> FEATURE:
<221> NAME/KEY: modified_base
<222> LOCATION: (1)..(37)
<223> OTHER INFORMATION: all purines (A and G) are deoxy, except
      guanosine at positions 1, 2, 3, 4 and 33 are 2'-O-methyl, and
      adenosine at position 7 is 2'-O-methyl
<220> FEATURE:
<221> NAME/KEY: modified_base
<222> LOCATION: (1)..(37)
<223> OTHER INFORMATION: all pyrimdines (C and T) are deoxy, except
      cytidine at positions 20, 34,  35, 36, and 37 are 2'-O-methyl,
      and uridine at positions 11, 17, and 18 are  2'-O-methyl
<220> FEATURE:
<221> NAME/KEY: misc_feature
<222> LOCATION: (38)..(38)
<223> OTHER INFORMATION: n is an inverted deoxy thymidine (3'- 3'
      linked)

<400> SEQUENCE: 264
ggggctactt uatccguucc tcctagtggg tagccccn                            38

<210> SEQ ID NO 265
<211> LENGTH: 38
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(37)
<223> OTHER INFORMATION: all purines (A and G) are deoxy, except
      guanosine at positions 1, 2, 3, 4 and 33 are 2'-O-methyl, and
      adenosine at position 7 is 2'-O-methyl
<220> FEATURE:
<221> NAME/KEY: modified_base
<222> LOCATION: (1)..(37)
<223> OTHER INFORMATION: all pyrimdines (C and, T) are deoxy, except
      cytidine at positions 5, 8, 20, 34,  35, 36, and 37 are 2'-O-
      methyl,  and uridine at positions 6, 11, 17, and 18 are  2'-O-
      methyl
<220> FEATURE:
<221> NAME/KEY: misc_feature
<222> LOCATION: (38)..(38)
<223> OTHER INFORMATION: n is an inverted deoxy thymidine (3'- 3'
      linked)

<400> SEQUENCE: 265
ggggcuactt uatccguucc tcctagtggg tagccccn                            38

<210> SEQ ID NO 266
<211> LENGTH: 39
<212> TYPE: DNA
<213> ORGANISM: artificial
```

```
<220> FEATURE:
<223> OTHER INFORMATION: synthetic aptamer
<220> FEATURE:
<221> NAME/KEY: modified_base
<222> LOCATION: (1)..(38)
<223> OTHER INFORMATION: all purines (A and G) are deoxy, except
      guanosine at positions 1, 2, 3, 4 and 34 are 2'-O-methyl, and
      adenosine at position 7 is 2'-O-methyl
<220> FEATURE:
<221> NAME/KEY: modified_base
<222> LOCATION: (1)..(38)
<223> OTHER INFORMATION: all pyrimidines (C and T) are deoxy,
      except cytidine at positions 35, 36, 37, and 38, are 2'-O-methyl
<220> FEATURE:
<221> NAME/KEY: misc_feature
<222> LOCATION: (9)..(9)
<223> OTHER INFORMATION: n is a phosphorothioate internucleotide linkage
<220> FEATURE:
<221> NAME/KEY: misc_feature
<222> LOCATION: (39)..(39)
<223> OTHER INFORMATION: n is an inverted deoxy thymidine (3'-3' linked)

<400> SEQUENCE: 266
ggggctacnt ttatccgttc ctcctagtgg gtagccccn                              39

<210> SEQ ID NO 267
<211> LENGTH: 39
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(38)
<223> OTHER INFORMATION: all purines (A and G) are deoxy, except
      guanosine at positions 1, 2, 3, 4 and 34 are 2'-O-methyl, and
      adenosine at position 7 is 2'-O-methyl
<220> FEATURE:
<221> NAME/KEY: modified_base
<222> LOCATION: (1)..(38)
<223> OTHER INFORMATION: all pyrimidines (C and T) are deoxy, except
      cytidine at positions 35, 36, 37, and 38 are 2'-O-methyl
<220> FEATURE:
<221> NAME/KEY: misc_feature
<222> LOCATION: (10)..(10)
<223> OTHER INFORMATION: n is a phosphorothioate internucleotide linkage
<220> FEATURE:
<221> NAME/KEY: misc_feature
<222> LOCATION: (39)..(39)
<223> OTHER INFORMATION: n is an inverted deoxy thymidine (3'-3' linked)

<400> SEQUENCE: 267
ggggctactn ttatccgttc ctcctagtgg gtagccccn                              39

<210> SEQ ID NO 268
<211> LENGTH: 39
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(38)
<223> OTHER INFORMATION: all purines (A and G) are deoxy, except
      guanosine at positions 1, 2, 3, 4 and 34 are 2'-O-methyl, and
      adenosine at position 7 is 2'-O-methyl
<220> FEATURE:
<221> NAME/KEY: modified_base
<222> LOCATION: (1)..(38)
<223> OTHER INFORMATION: all pyrimdines (C and T) are deoxy, except
      cytidine at positions 35, 36, 37 and 38 are 2'-O-methyl
<220> FEATURE:
<221> NAME/KEY: misc_feature
<222> LOCATION: (11)..(11)
<223> OTHER INFORMATION: n is a phosphorothioate internucleotide linkage
```

```
<220> FEATURE:
<221> NAME/KEY: misc_feature
<222> LOCATION: (39)..(39)
<223> OTHER INFORMATION: n is an inverted deoxy thymidine (3'-3' linked)

<400> SEQUENCE: 268
ggggctactt ntatccgttc ctcctagtgg gtagccccn                              39

<210> SEQ ID NO 269
<211> LENGTH: 39
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(38)
<223> OTHER INFORMATION: all purines (A and G) are deoxy, except
      guanosine at positions 1, 2, 3, 4 and 34 are 2'-O-methyl, and
      adenosine at position 7 is 2'-O-methyl
<220> FEATURE:
<221> NAME/KEY: modified_base
<222> LOCATION: (1)..(38)
<223> OTHER INFORMATION: all pyrimidines (C and T) are deoxy, except
      cytidine at positions 35, 36, 37, and 38 are 2'-O-methyl
<220> FEATURE:
<221> NAME/KEY: misc_feature
<222> LOCATION: (12)..(12)
<223> OTHER INFORMATION: n is a phosphorothioate internucleotide linkage
<220> FEATURE:
<221> NAME/KEY: misc_feature
<222> LOCATION: (39)..(39)
<223> OTHER INFORMATION: n is an inverted deoxy thymidine (3'-3' linked)

<400> SEQUENCE: 269
ggggctactt tnatccgttc ctcctagtgg gtagccccn                              39

<210> SEQ ID NO 270
<211> LENGTH: 39
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(38)
<223> OTHER INFORMATION: all purines (A and G) are deoxy, except
      guanosine at positions 1, 2, 3, 4 and 34 are 2'-O-methyl, and
      adenosine at position 7 is 2'-O-methyl
<220> FEATURE:
<221> NAME/KEY: modified_base
<222> LOCATION: (1)..(38)
<223> OTHER INFORMATION: all pyrimidines (C and T) are deoxy, except
      cytidine at positions 35, 36, 37, and 38 are 2'O-methyl
<220> FEATURE:
<221> NAME/KEY: misc_feature
<222> LOCATION: (13)..(13)
<223> OTHER INFORMATION: n is a phosphorothioate internucleotide linkage
<220> FEATURE:
<221> NAME/KEY: misc_feature
<222> LOCATION: (39)..(39)
<223> OTHER INFORMATION: n is an inverted deoxy thymidine (3'-3' linked)

<400> SEQUENCE: 270
ggggctactt tantccgttc ctcctagtgg gtagccccn                              39

<210> SEQ ID NO 271
<211> LENGTH: 39
<212> TYPE: DNA
<213> ORGANISM: artificial
<220> FEATURE:
<223> OTHER INFORMATION: synthetic aptamer
<220> FEATURE:
```

```
<221> NAME/KEY: modified_base
<222> LOCATION: (1)..(38)
<223> OTHER INFORMATION: all purines (A and G) are deoxy, except
      guanosine at positions 1, 2, 3, 4 and 34 are 2'-O-methyl, and
      adenosine at position 7 is 2'-O-methyl
<220> FEATURE:
<221> NAME/KEY: modified_base
<222> LOCATION: (1)..(38)
<223> OTHER INFORMATION: all pyrimidines (C and T) are deoxy, except
      cytidine at positions 35, 36, 37, and 38 are 2'-O-methyl
<220> FEATURE:
<221> NAME/KEY: misc_feature
<222> LOCATION: (14)..(14)
<223> OTHER INFORMATION: n is a phosphorothioate internucleotide linkage
<220> FEATURE:
<221> NAME/KEY: misc_feature
<222> LOCATION: (39)..(39)
<223> OTHER INFORMATION: n is an inverted deoxy thymidine (3'-3' linked)

<400> SEQUENCE: 271
ggggctactt tatnccgttc ctcctagtgg gtagccccn                             39

<210> SEQ ID NO 272
<211> LENGTH: 39
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(38)
<223> OTHER INFORMATION: all purines (A and G) are deoxy, except
      guanosine at positions 1, 2, 3, 4 and 34 are 2'-O-methyl, and
      adenosine at position 7 is 2'-O-methyl
<220> FEATURE:
<221> NAME/KEY: modified_base
<222> LOCATION: (1)..(38)
<223> OTHER INFORMATION: all pyrimidines (C and T) are deoxy, except
      cytidine at positions 35, 36, 37, and 38 are 2'-O-methyl
<220> FEATURE:
<221> NAME/KEY: misc_feature
<222> LOCATION: (15)..(15)
<223> OTHER INFORMATION: n is a phosphorothiaote internucleotide linkage
<220> FEATURE:
<221> NAME/KEY: misc_feature
<222> LOCATION: (39)..(39)
<223> OTHER INFORMATION: n is an inverted deoxy thymidine (3'-3' linked)

<400> SEQUENCE: 272
ggggctactt tatcncgttc ctcctagtgg gtagccccn                             39

<210> SEQ ID NO 273
<211> LENGTH: 39
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(38)
<223> OTHER INFORMATION: all purines (A and G) are deoxy, except
      guanosine at positions 1, 2, 3, 4 and 34 are 2'-O-methyl, and
      adenosine at position 7 is 2'-O-methyl
<220> FEATURE:
<221> NAME/KEY: modified_base
<222> LOCATION: (1)..(38)
<223> OTHER INFORMATION: all pyrimidines (C and T) are deoxy, except
      cytidine at positions 35, 36, 37 and 38 are 2'-O-methyl
<220> FEATURE:
<221> NAME/KEY: misc_feature
<222> LOCATION: (16)..(16)
<223> OTHER INFORMATION: n is a phosphorothioate internucleotide linkage
<220> FEATURE:
<221> NAME/KEY: misc_feature
<222> LOCATION: (39)..(39)
```

<223> OTHER INFORMATION: n is an inverted deoxy thymidine (3'-3' linked)

<400> SEQUENCE: 273
ggggctactt tatccngttc ctcctagtgg gtagccccn					39

<210> SEQ ID NO 274
<211> LENGTH: 39
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(38)
<223> OTHER INFORMATION: all purines (A and G) are deoxy, except
      guanosine at positions 1, 2, 3, 4 and 34 are 2'-O-methyl, and
      adenosine at position 7 is 2'-O-methyl
<220> FEATURE:
<221> NAME/KEY: modified_base
<222> LOCATION: (1)..(38)
<223> OTHER INFORMATION: all pyrimidines (C and T) are deoxy, except
      cytidine at positions 35, 36, 37, and 38 are 2'-O-methyl
<220> FEATURE:
<221> NAME/KEY: misc_feature
<222> LOCATION: (17)..(17)
<223> OTHER INFORMATION: n is a phosphorothioate internucleotide linkage
<220> FEATURE:
<221> NAME/KEY: misc_feature
<222> LOCATION: (39)..(39)
<223> OTHER INFORMATION: n is an inverted deoxy thymidine (3'-3' linked)

<400> SEQUENCE: 274
ggggctactt tatccgnttc ctcctagtgg gtagccccn					39

<210> SEQ ID NO 275
<211> LENGTH: 39
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(38)
<223> OTHER INFORMATION: all purines (A and G) are deoxy, except
      guanosine at positions 1, 2, 3, 4 and 34 are 2'-O-methyl, and
      adenosine at position 7 is 2'-O-methyl
<220> FEATURE:
<221> NAME/KEY: modified_base
<222> LOCATION: (1)..(38)
<223> OTHER INFORMATION: all pyrimidines (C and T) are deoxy, except
      cytidine at positions 35, 36, 37, and 38 are 2'-O-methyl
<220> FEATURE:
<221> NAME/KEY: misc_feature
<222> LOCATION: (18)..(18)
<223> OTHER INFORMATION: n is a phosphorothioate internucleotide linkage
<220> FEATURE:
<221> NAME/KEY: misc_feature
<222> LOCATION: (39)..(39)
<223> OTHER INFORMATION: n is an inverted deoxy thymidine (3'-3' linked)

<400> SEQUENCE: 275
ggggctactt tatccgtntc ctcctagtgg gtagccccn					39

<210> SEQ ID NO 276
<211> LENGTH: 39
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(38)
<223> OTHER INFORMATION: all purines (A and G) are deoxy, except guanosine at positions 1, 2, 3, 4 and 34 are 2'-O-methyl, and
       adenosine at position 7 is 2'-O-methyl
<220> FEATURE:
<221> NAME/KEY: modified_base
<222> LOCATION: (1)..(38)
<223> OTHER INFORMATION: all pyrimidines (C and T) are deoxy, except
       cytidine at positions 35, 36, 37, and 38 are 2'-O-methyl
<220> FEATURE:
<221> NAME/KEY: misc_feature
<222> LOCATION: (19)..(19)
<223> OTHER INFORMATION: n is a phosphorothioate internucleotide linkage
<220> FEATURE:
<221> NAME/KEY: misc_feature
<222> LOCATION: (39)..(39)
<223> OTHER INFORMATION: n is an inverted deoxy thymidine (3'-3' linked)

<400> SEQUENCE: 276
ggggctactt tatccgttnc ctcctagtgg gtagccccn                    39

<210> SEQ ID NO 277
<211> LENGTH: 39
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(38)
<223> OTHER INFORMATION: all purines (A and G) are deoxy, except
       guanosine at positions 1, 2, 3, 4 and 34 are 2'-O-methyl, and
       adenosine at position 7 is 2'-O-methyl
<220> FEATURE:
<221> NAME/KEY: modified_base
<222> LOCATION: (1)..(38)
<223> OTHER INFORMATION: all pyrimidines (C and T) are deoxy, except
       cytidine at positions 35, 36, 37, and 38 are 2'-O-methyl
<220> FEATURE:
<221> NAME/KEY: misc_feature
<222> LOCATION: (20)..(20)
<223> OTHER INFORMATION: n is a phosphorothioate internucleotide linkage
<220> FEATURE:
<221> NAME/KEY: misc_feature
<222> LOCATION: (39)..(39)
<223> OTHER INFORMATION: n is an inverted deoxy thymidine (3'-3' linked)

<400> SEQUENCE: 277
ggggctactt tatccgttcn ctcctagtgg gtagccccn                    39

<210> SEQ ID NO 278
<211> LENGTH: 39
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(38)
<223> OTHER INFORMATION: all purines (A and G) are deoxy, except
       guanosine at positions 1, 2, 3, 4 and 34 are 2'-O-methyl, and
       adenosine at position 7 is 2'-O-methyl
<220> FEATURE:
<221> NAME/KEY: modified_base
<222> LOCATION: (1)..(38)
<223> OTHER INFORMATION: all pyrimidines (C and T) are deoxy, except
       cytidine at positions 35, 36, 37, and 38 are 2'-O-methyl
<220> FEATURE:
<221> NAME/KEY: misc_feature
<222> LOCATION: (21)..(21)
<223> OTHER INFORMATION: n is a phosphorothioate internucleotide linkage
<220> FEATURE:
<221> NAME/KEY: misc_feature
<222> LOCATION: (39)..(39)
<223> OTHER INFORMATION: n is an inverted deoxy thymidine (3'-3' linked)

<400> SEQUENCE: 278

```
ggggctactt tatccgttcc ntcctagtgg gtagccccn                                    39
```

<210> SEQ ID NO 279
<211> LENGTH: 39
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(38)
<223> OTHER INFORMATION: all purines (A and G) are deoxy, except
      guanosine at positions 1, 2, 3, 4 and 34 are 2'-O-methyl, and
      adenosine at position 7 is 2'-O-methyl
<220> FEATURE:
<221> NAME/KEY: modified_base
<222> LOCATION: (1)..(38)
<223> OTHER INFORMATION: all pyrimidines (C and T) are deoxy, except
      cytidine at positions 35, 36, 37 and 38 are 2'-O-methyl
<220> FEATURE:
<221> NAME/KEY: misc_feature
<222> LOCATION: (22)..(22)
<223> OTHER INFORMATION: n is a phosphorothioate internucleotide linkage
<220> FEATURE:
<221> NAME/KEY: misc_feature
<222> LOCATION: (39)..(39)
<223> OTHER INFORMATION: n is an inverted deoxy thymidine

<400> SEQUENCE: 279

```
ggggctactt tatccgttcc tncctagtgg gtagccccn                                    39
```

<210> SEQ ID NO 280
<211> LENGTH: 39
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(38)
<223> OTHER INFORMATION: all purines (A and G) are deoxy, except
      guanosine at positions 1, 2, 3, 4 and 34 are 2'-O-methyl, and
      adenosine at position 7 is 2'-O-methyl
<220> FEATURE:
<221> NAME/KEY: modified_base
<222> LOCATION: (1)..(38)
<223> OTHER INFORMATION: all pyrimidines (C and T) are deoxy, except
      cytidine at positions 35, 36, 37 and 38 are 2'-O-methyl
<220> FEATURE:
<221> NAME/KEY: misc_feature
<222> LOCATION: (23)..(23)
<223> OTHER INFORMATION: n is a phosphothioate internucleotide linkage
<220> FEATURE:
<221> NAME/KEY: misc_feature
<222> LOCATION: (39)..(39)
<223> OTHER INFORMATION: n is an inverted deoxy thymidine (3'-3' linked)

<400> SEQUENCE: 280

```
ggggctactt tatccgttcc tcnctagtgg gtagccccn                                    39
```

<210> SEQ ID NO 281
<211> LENGTH: 39
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(38)
<223> OTHER INFORMATION: all purines (A and G) are deoxy, except
      guanosine at positions 1, 2, 3, 4 and 34 are 2'-O-methyl, and
      adenosine at position 7 is 2'-O-methyl
<220> FEATURE:

```
<221> NAME/KEY: modified_base
<222> LOCATION: (1)..(38)
<223> OTHER INFORMATION: all pyrimidines (C and T) are deoxy, except
      cytidine at positions 35, 36, 37 and 38 are 2'-O-methyl
<220> FEATURE:
<221> NAME/KEY: misc_feature
<222> LOCATION: (24)..(24)
<223> OTHER INFORMATION: n is a phosphorothioate internucleotide linkage
<220> FEATURE:
<221> NAME/KEY: misc_feature
<222> LOCATION: (39)..(39)
<223> OTHER INFORMATION: n is an inverted deoxy thymidine (3'-3' linked)

<400> SEQUENCE: 281
ggggctactt tatccgttcc tccntagtgg gtagccccn                              39

<210> SEQ ID NO 282
<211> LENGTH: 39
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(38)
<223> OTHER INFORMATION: all purines (A and G) are deoxy, except
      guanosine at positions 1, 2, 3, 4 and 34 are 2'-O-methyl, and
      adenosine at position 7 is 2'-O-methyl
<220> FEATURE:
<221> NAME/KEY: modified_base
<222> LOCATION: (1)..(38)
<223> OTHER INFORMATION: all pyrimidines (C and T) are deoxy, except
      cytidine at positions 35, 36, 37, and 38 are 2'-O-methyl
<220> FEATURE:
<221> NAME/KEY: misc_feature
<222> LOCATION: (25)..(25)
<223> OTHER INFORMATION: n is a phosphorothioate internucleotide linkage
<220> FEATURE:
<221> NAME/KEY: misc_feature
<222> LOCATION: (39)..(39)
<223> OTHER INFORMATION: n is an inverted deoxy thymidine (3'-3' linked)

<400> SEQUENCE: 282
ggggctactt tatccgttcc tcctnagtgg gtagccccn                              39

<210> SEQ ID NO 283
<211> LENGTH: 39
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(38)
<223> OTHER INFORMATION: all purines (A and G) are deoxy, except
      guanosine at positions 1, 2, 3, 4 and 34 are 2'-O-methyl, and
      adenosine at position 7 is 2'-O-methyl
<220> FEATURE:
<221> NAME/KEY: modified_base
<222> LOCATION: (1)..(38)
<223> OTHER INFORMATION: all pyrimidines (C and T) are deoxy, except
      cytidine at positions 35, 36, 37 and 38 are 2'-O-methyl
<220> FEATURE:
<221> NAME/KEY: misc_feature
<222> LOCATION: (26)..(26)
<223> OTHER INFORMATION: n is a phosphorothioate internucleotide linkage
<220> FEATURE:
<221> NAME/KEY: misc_feature
<222> LOCATION: (39)..(39)
<223> OTHER INFORMATION: n is an inverted deoxy thymidine (3'-3' linked)

<400> SEQUENCE: 283
ggggctactt tatccgttcc tcctangtgg gtagccccn                              39
```

<210> SEQ ID NO 284
<211> LENGTH: 39
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(38)
<223> OTHER INFORMATION: all purines (A and G) are deoxy, except
      guanosine at positions 1, 2, 3, 4 and 34 are 2'-O-methyl, and
      adenosine at position 7 is 2'-O-methyl
<220> FEATURE:
<221> NAME/KEY: modified_base
<222> LOCATION: (1)..(38)
<223> OTHER INFORMATION: all pyrimidines (C and T) are deoxy, except
      cytidine at positions 35, 36, 37, and 38 are 2'O-methyl
<220> FEATURE:
<221> NAME/KEY: misc_feature
<222> LOCATION: (27)..(27)
<223> OTHER INFORMATION: n is a phosphorothioate internucleotide linkage
<220> FEATURE:
<221> NAME/KEY: misc_feature
<222> LOCATION: (39)..(39)
<223> OTHER INFORMATION: n is an inverted deoxy thymidine (3'-3' linked)

<400> SEQUENCE: 284
ggggctactt tatccgttcc tcctagntgg gtagccccn                            39

<210> SEQ ID NO 285
<211> LENGTH: 39
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(38)
<223> OTHER INFORMATION: all purines (A and G) are deoxy, except
      guanosine at positions 1, 2, 3, 4 and 34 are 2'-O-methyl, and
      adenosine at position 7 is 2'-O-methyl
<220> FEATURE:
<221> NAME/KEY: modified_base
<222> LOCATION: (1)..(38)
<223> OTHER INFORMATION: all pyrimidines (C and T) are deoxy, except
      cytidine at positions 35, 36, 37, and 38 are 2'-O-methyl
<220> FEATURE:
<221> NAME/KEY: misc_feature
<222> LOCATION: (28)..(28)
<223> OTHER INFORMATION: n is a phosphorothioate internucleotide linkage
<220> FEATURE:
<221> NAME/KEY: misc_feature
<222> LOCATION: (39)..(39)
<223> OTHER INFORMATION: n is an inverted deoxy thymidine (3'-3' linked)

<400> SEQUENCE: 285
ggggctactt tatccgttcc tcctagtngg gtagccccn                            39

<210> SEQ ID NO 286
<211> LENGTH: 39
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(38)
<223> OTHER INFORMATION: all purines (A and G) are deoxy, except
      guanosine at positions 1, 2, 3, 4 and 34 are 2'-O-methyl, and
      adenosine at position 7 is 2'-O-methyl
<220> FEATURE:
<221> NAME/KEY: modified_base
<222> LOCATION: (1)..(38)
<223> OTHER INFORMATION: all pyrimidines (C and T) are deoxy, except cytidine at positions 35, 36, 37, and 38 are 2'-O-methyl
<220> FEATURE:
<221> NAME/KEY: misc_feature
<222> LOCATION: (29)..(29)
<223> OTHER INFORMATION: n is a phosphorothioate internucleotide linkage
<220> FEATURE:
<221> NAME/KEY: misc_feature
<222> LOCATION: (39)..(39)
<223> OTHER INFORMATION: n is an inverted deoxy thymidine (3'-3' linked)

<400> SEQUENCE: 286
ggggctactt tatccgttcc tcctagtgng gtagccccn                                  39

<210> SEQ ID NO 287
<211> LENGTH: 39
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(38)
<223> OTHER INFORMATION: all purines (A and G) are deoxy, except
      guanosine at positions 1, 2, 3, 4 and 34 are 2'-O-methyl, and
      adenosine at position 7 is 2'-O-methyl
<220> FEATURE:
<221> NAME/KEY: modified_base
<222> LOCATION: (1)..(38)
<223> OTHER INFORMATION: all pyrimidines (C and T) are deoxy, except
      cytidine at positions 35, 36, 37, and 38 are 2'-O-methyl
<220> FEATURE:
<221> NAME/KEY: misc_feature
<222> LOCATION: (30)..(30)
<223> OTHER INFORMATION: n is a phosphorothioate internucleotide linkage
<220> FEATURE:
<221> NAME/KEY: misc_feature
<222> LOCATION: (39)..(39)
<223> OTHER INFORMATION: n is an inverted deoxy thymidine (3'-3' linked)

<400> SEQUENCE: 287
ggggctactt tatccgttcc tcctagtggn gtagccccn                                  39

<210> SEQ ID NO 288
<211> LENGTH: 39
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(38)
<223> OTHER INFORMATION: all purines (A and G) are deoxy, except
      guanosine at positions 1, 2, 3, 4 and 34 are 2'-O-methyl, and
      adenosine at position 7 is 2'-O-methyl
<220> FEATURE:
<221> NAME/KEY: modified_base
<222> LOCATION: (1)..(38)
<223> OTHER INFORMATION: all pyrimidines (C and T) are deoxy, except
      cytidine at positions 35, 36, 37, and 38 are 2'-O-methyl
<220> FEATURE:
<221> NAME/KEY: misc_feature
<222> LOCATION: (31)..(31)
<223> OTHER INFORMATION: n is a phosphorothioate internucleotide linkage
<220> FEATURE:
<221> NAME/KEY: misc_feature
<222> LOCATION: (39)..(39)
<223> OTHER INFORMATION: n is an inverted deoxy thymidine (3'-3' linked)

<400> SEQUENCE: 288
ggggctactt tatccgttcc tcctagtggg ntagccccn                                  39

<210> SEQ ID NO 289
<211> LENGTH: 39

```
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(38)
<223> OTHER INFORMATION: all purines (A and G) are deoxy, except
      guanosine at positions 1, 2, 3, 4 and 34 are 2'-O-methyl, and
      adenosine at position 7 is 2'-O-methyl
<220> FEATURE:
<221> NAME/KEY: modified_base
<222> LOCATION: (1)..(38)
<223> OTHER INFORMATION: all pyrimidines (C and T) are deoxy, except
      cytidine at positions 35, 36, 37 and 38 are 2'O-methyl
<220> FEATURE:
<221> NAME/KEY: misc_feature
<222> LOCATION: (32)..(32)
<223> OTHER INFORMATION: n is a phosphorothioate internucleotide linkage
<220> FEATURE:
<221> NAME/KEY: misc_feature
<222> LOCATION: (39)..(39)
<223> OTHER INFORMATION: n is an inverted deoxy thymidine (3'-3' linked)

<400> SEQUENCE: 289
ggggctactt tatccgttcc tcctagtggg tnagccccn                            39

<210> SEQ ID NO 290
<211> LENGTH: 46
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(45)
<223> OTHER INFORMATION: all purines (A and G) are deoxy, except
      guanosine at positions 1, 2, 3, 4 and 41 are 2'-O-methyl, and
      adenosine at position 7 is 2'-O-methyl
<220> FEATURE:
<221> NAME/KEY: modified_base
<222> LOCATION: (1)..(45)
<223> OTHER INFORMATION: all pyrimidines (C and T) are deoxy, except
      cytidine at positions 42, 43, 44 and 45 are 2'-O-methyl
<220> FEATURE:
<221> NAME/KEY: misc_feature
<222> LOCATION: (10)..(10)
<223> OTHER INFORMATION: n is a phosphorothioate internucleotide linkage
<220> FEATURE:
<221> NAME/KEY: misc_feature
<222> LOCATION: (14)..(14)
<223> OTHER INFORMATION: n is a phosphorothioate internucleotide linkage
<220> FEATURE:
<221> NAME/KEY: misc_feature
<222> LOCATION: (17)..(17)
<223> OTHER INFORMATION: n is a phosphorothioate internucleotide linkage
<220> FEATURE:
<221> NAME/KEY: misc_feature
<222> LOCATION: (22)..(22)
<223> OTHER INFORMATION: n is a phosphorothioate internucleotide linkage
<220> FEATURE:
<221> NAME/KEY: misc_feature
<222> LOCATION: (26)..(26)
<223> OTHER INFORMATION: n is a phosphorothioate internucleotide linkage
<220> FEATURE:
<221> NAME/KEY: misc_feature
<222> LOCATION: (30)..(30)
<223> OTHER INFORMATION: n is a phosphorothioate internucleotide linkage
<220> FEATURE:
<221> NAME/KEY: misc_feature
<222> LOCATION: (34)..(34)
<223> OTHER INFORMATION: n is a phosphorothioate internucleotide linkage
<220> FEATURE:
<221> NAME/KEY: misc_feature
<222> LOCATION: (38)..(38)
<223> OTHER INFORMATION: n is a phosphorothioate internucleotide linkage
<220> FEATURE:
```

<221> NAME/KEY: misc_feature
<222> LOCATION: (46)..(46)
<223> OTHER INFORMATION: n is an inverted deoxy thymidine (3'-3' linked)

<400> SEQUENCE: 290
ggggctactn ttantcncgt tncctncctn agtngggnta gccccn           46

<210> SEQ ID NO 291
<211> LENGTH: 46
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(45)
<223> OTHER INFORMATION: all purines (A and G) are deoxy, except
      guanosine at positions 1, 2, 3, 4 and 41 are 2'-O-methyl, and
      adenosine at position 7 is 2'-O-methyl
<220> FEATURE:
<221> NAME/KEY: modified_base
<222> LOCATION: (1)..(45)
<223> OTHER INFORMATION: all pyrimidines (C and T) are deoxy, except
      cytidine at positions 5, 8, 42, 43, 44, and 45 are 2'-O-methyl
<220> FEATURE:
<221> NAME/KEY: misc_feature
<222> LOCATION: (10)..(10)
<223> OTHER INFORMATION: n is a phosphorothioate internucleotide linkage
<220> FEATURE:
<221> NAME/KEY: misc_feature
<222> LOCATION: (14)..(14)
<223> OTHER INFORMATION: n is a phosphorothioate internucleotide linkage
<220> FEATURE:
<221> NAME/KEY: misc_feature
<222> LOCATION: (17)..(17)
<223> OTHER INFORMATION: n is a phosphorothioate internucleotide linkage
<220> FEATURE:
<221> NAME/KEY: misc_feature
<222> LOCATION: (22)..(22)
<223> OTHER INFORMATION: n is a phosphorothioate internucleotide linkage
<220> FEATURE:
<221> NAME/KEY: misc_feature
<222> LOCATION: (26)..(26)
<223> OTHER INFORMATION: n is a phosphorothioate internucleotide linkage
<220> FEATURE:
<221> NAME/KEY: misc_feature
<222> LOCATION: (30)..(30)
<223> OTHER INFORMATION: n is a phosphorothioate internucleotide linkage
<220> FEATURE:
<221> NAME/KEY: misc_feature
<222> LOCATION: (34)..(34)
<223> OTHER INFORMATION: n is a phosphorothioate internucleotide linkage
<220> FEATURE:
<221> NAME/KEY: misc_feature
<222> LOCATION: (38)..(38)
<223> OTHER INFORMATION: n is a phosphorothioate internucleotide linkage
<220> FEATURE:
<221> NAME/KEY: misc_feature
<222> LOCATION: (46)..(46)
<223> OTHER INFORMATION: n is an inverted deoxy thymidine (3'-3' linked)

<400> SEQUENCE: 291
ggggcuactn ttantcncgt tncctncctn agtngggnta gccccn           46

<210> SEQ ID NO 292
<211> LENGTH: 45
<212> TYPE: DNA
<213> ORGANISM: artificial
<220> FEATURE:
<223> OTHER INFORMATION: synthetic aptamer
<220> FEATURE:
<221> NAME/KEY: modified_base
<222> LOCATION: (1)..(44)
<223> OTHER INFORMATION: all purines (A and G) are deoxy, except
      guanosine at positions 1, 2, 3, 4 and 40 are 2'-O-methyl, and

```
      adenosine at position 7 is 2'-O-methyl
<220> FEATURE:
<221> NAME/KEY: modified_base
<222> LOCATION: (1)..(44)
<223> OTHER INFORMATION: all pyrimidines (C and T) are deoxy, except
      cytidine at positions 5, 8, 23, 41, 42, 43 and 44 are 2'-O-methyl
<220> FEATURE:
<221> NAME/KEY: misc_feature
<222> LOCATION: (10)..(10)
<223> OTHER INFORMATION: n is a phosphorothioate internucleotide linkage
<220> FEATURE:
<221> NAME/KEY: misc_feature
<222> LOCATION: (14)..(14)
<223> OTHER INFORMATION: n is a phosphorothioate internucleotide linkage
<220> FEATURE:
<221> NAME/KEY: misc_feature
<222> LOCATION: (17)..(17)
<223> OTHER INFORMATION: n is a phosphorothioate internucleotide linkage
<220> FEATURE:
<221> NAME/KEY: misc_feature
<222> LOCATION: (25)..(25)
<223> OTHER INFORMATION: n is a phosphorothioate internucleotide linkage
<220> FEATURE:
<221> NAME/KEY: misc_feature
<222> LOCATION: (29)..(29)
<223> OTHER INFORMATION: n is a phosphorothioate internucleotide linkage
<220> FEATURE:
<221> NAME/KEY: misc_feature
<222> LOCATION: (33)..(33)
<223> OTHER INFORMATION: n is a phosphorothioate internucleotide linkage
<220> FEATURE:
<221> NAME/KEY: misc_feature
<222> LOCATION: (37)..(37)
<223> OTHER INFORMATION: n is a phosphorothioate internucleotide linkage
<220> FEATURE:
<221> NAME/KEY: misc_feature
<222> LOCATION: (45)..(45)
<223> OTHER INFORMATION: n is an inverted deoxy thymidine (3'-3' linked)

<400> SEQUENCE: 292
ggggcuactn tuantcncgu ucctncctna gtngggntag ccccn              45

<210> SEQ ID NO 293
<211> LENGTH: 31
<212> TYPE: DNA
<213> ORGANISM: artificial
<220> FEATURE:
<223> OTHER INFORMATION: synthetic aptamer
<220> FEATURE:
<221> NAME/KEY: misc_feature
<222> LOCATION: (1)..(1)
<223> OTHER INFORMATION: n is a branched 40 kDa PEG
<220> FEATURE:
<221> NAME/KEY: misc_feature
<222> LOCATION: (2)..(2)
<223> OTHER INFORMATION: n is an amine group
<220> FEATURE:
<221> NAME/KEY: modified_base
<222> LOCATION: (3)..(30)
<223> OTHER INFORMATION: all purines are deoxy, except guanosine at
      positions 4, 9, and 22 are 2'-O-methyl, and adenosine at positions
      3, 13, and 17 are 2'-O-methyl
<220> FEATURE:
<221> NAME/KEY: modified_base
<222> LOCATION: (3)..(30)
<223> OTHER INFORMATION: all pyrimidines are 2'-O-methyl
<220> FEATURE:
<221> NAME/KEY: misc_feature
<222> LOCATION: (11)..(11)
<223> OTHER INFORMATION: n is a phosphorothioate internucleotide linkage
<220> FEATURE:
<221> NAME/KEY: misc_feature
<222> LOCATION: (19)..(19)
<223> OTHER INFORMATION: n is a phosphorothioate internucleotide linkage
<220> FEATURE:
<221> NAME/KEY: misc_feature
<222> LOCATION: (20)..(20)
```

-continued

```
<223> OTHER INFORMATION: n is deoxy inosine
<220> FEATURE:
<221> NAME/KEY: misc_feature
<222> LOCATION: (21)..(21)
<223> OTHER INFORMATION: n is a phosphorothioate internucleotide linkage
<220> FEATURE:
<221> NAME/KEY: misc_feature
<222> LOCATION: (23)..(23)
<223> OTHER INFORMATION: n is deoxy inosine
<220> FEATURE:
<221> NAME/KEY: misc_feature
<222> LOCATION: (24)..(24)
<223> OTHER INFORMATION: n is a phosphorothioate internucleotide linkage
<220> FEATURE:
<221> NAME/KEY: misc_feature
<222> LOCATION: (26)..(26)
<223> OTHER INFORMATION: n is deoxy inosine
<220> FEATURE:
<221> NAME/KEY: misc_feature
<222> LOCATION: (27)..(27)
<223> OTHER INFORMATION: n is a phosphorothioate internucleotide linkage
<220> FEATURE:
<221> NAME/KEY: misc_feature
<222> LOCATION: (31)..(31)
<223> OTHER INFORMATION: n is an inverted deoxy thymidine (3'-3' linked)

<400> SEQUENCE: 293
nnagccuggg ngacccaunn ngnngnngcu n                                         31

<210> SEQ ID NO 294
<211> LENGTH: 31
<212> TYPE: DNA
<213> ORGANISM: artificial
<220> FEATURE:
<223> OTHER INFORMATION: synthetic aptamer
<220> FEATURE:
<221> NAME/KEY: misc_feature
<222> LOCATION: (1)..(1)
<223> OTHER INFORMATION: n is a branched 60 kDa PEG
<220> FEATURE:
<221> NAME/KEY: misc_feature
<222> LOCATION: (2)..(2)
<223> OTHER INFORMATION: n is a n amine group
<220> FEATURE:
<221> NAME/KEY: modified_base
<222> LOCATION: (3)..(30)
<223> OTHER INFORMATION: all purines are deoxy, except guanosine at
      positions 4, 9, and 22 are 2'-O-methyl, and adenosine at positions
      3, 13, and 17 are 2'-O-methyl
<220> FEATURE:
<221> NAME/KEY: modified_base
<222> LOCATION: (3)..(30)
<223> OTHER INFORMATION: all pyrimidines are 2'-O-methyl
<220> FEATURE:
<221> NAME/KEY: misc_feature
<222> LOCATION: (11)..(11)
<223> OTHER INFORMATION: n is a phosphorothioate internucleotide linkage
<220> FEATURE:
<221> NAME/KEY: misc_feature
<222> LOCATION: (19)..(19)
<223> OTHER INFORMATION: n is a phosphorothioate internucleotide linkage
<220> FEATURE:
<221> NAME/KEY: misc_feature
<222> LOCATION: (20)..(20)
<223> OTHER INFORMATION: n is deoxy inosine
<220> FEATURE:
<221> NAME/KEY: misc_feature
<222> LOCATION: (21)..(21)
<223> OTHER INFORMATION: n is a phosphorothioate internucleotide linkage
<220> FEATURE:
<221> NAME/KEY: misc_feature
<222> LOCATION: (23)..(23)
<223> OTHER INFORMATION: n is deoxy inosine
<220> FEATURE:
<221> NAME/KEY: misc_feature
<222> LOCATION: (24)..(24)
<223> OTHER INFORMATION: n is a phosphorothioate internucleotide linkage
```

```
<220> FEATURE:
<221> NAME/KEY: misc_feature
<222> LOCATION: (26)..(26)
<223> OTHER INFORMATION: n is deoxy inosine
<220> FEATURE:
<221> NAME/KEY: misc_feature
<222> LOCATION: (27)..(27)
<223> OTHER INFORMATION: n is a phosphorothioate internucleotide linkage
<220> FEATURE:
<221> NAME/KEY: misc_feature
<222> LOCATION: (31)..(31)
<223> OTHER INFORMATION: n is an inverted deoxy thymidine (3'-3' linked)

<400> SEQUENCE: 294
nnagccuggg ngacccaunn ngnngnngcu n                                        31

<210> SEQ ID NO 295
<211> LENGTH: 32
<212> TYPE: DNA
<213> ORGANISM: artificial
<220> FEATURE:
<223> OTHER INFORMATION: synthetic aptamer
<220> FEATURE:
<221> NAME/KEY: misc_feature
<222> LOCATION: (1)..(1)
<223> OTHER INFORMATION: n is 20 kDa PEG
<220> FEATURE:
<221> NAME/KEY: misc_feature
<222> LOCATION: (2)..(2)
<223> OTHER INFORMATION: n is an amine group
<220> FEATURE:
<221> NAME/KEY: modified_base
<222> LOCATION: (3)..(30)
<223> OTHER INFORMATION: all purines are deoxy, except guanosine at
      positions 4, 9, and 22 are 2'-O-methyl, and adenosine at positions
      3, 13, and 17 are 2'-O-methyl
<220> FEATURE:
<221> NAME/KEY: modified_base
<222> LOCATION: (3)..(30)
<223> OTHER INFORMATION: all pyrimidines are 2'-O-methyl
<220> FEATURE:
<221> NAME/KEY: misc_feature
<222> LOCATION: (11)..(11)
<223> OTHER INFORMATION: n is a phosphorothioate internucleotide linkage
<220> FEATURE:
<221> NAME/KEY: misc_feature
<222> LOCATION: (19)..(19)
<223> OTHER INFORMATION: n is a phosphorothioate internucleotide linkage
<220> FEATURE:
<221> NAME/KEY: misc_feature
<222> LOCATION: (20)..(20)
<223> OTHER INFORMATION: n is deoxy inosine
<220> FEATURE:
<221> NAME/KEY: misc_feature
<222> LOCATION: (21)..(21)
<223> OTHER INFORMATION: n is a phosphorothioate internucleotide linkage
<220> FEATURE:
<221> NAME/KEY: misc_feature
<222> LOCATION: (23)..(23)
<223> OTHER INFORMATION: n is deoxy inosine
<220> FEATURE:
<221> NAME/KEY: misc_feature
<222> LOCATION: (24)..(24)
<223> OTHER INFORMATION: n is a phosphorothioate internucleotide linkage
<220> FEATURE:
<221> NAME/KEY: misc_feature
<222> LOCATION: (26)..(26)
<223> OTHER INFORMATION: n is deoxy inosine
<220> FEATURE:
<221> NAME/KEY: misc_feature
<222> LOCATION: (27)..(27)
<223> OTHER INFORMATION: n is a phosphorothioate internucleotide linkage
<220> FEATURE:
<221> NAME/KEY: misc_feature
<222> LOCATION: (31)..(31)
<223> OTHER INFORMATION: n is an amine group
<220> FEATURE:
```

```
<221> NAME/KEY: misc_feature
<222> LOCATION: (32)..(32)
<223> OTHER INFORMATION: n is a 20 kDa PEG

<400> SEQUENCE: 295
nnagccuggg ngacccaunn ngnngnngcu nn                                       32

<210> SEQ ID NO 296
<211> LENGTH: 32
<212> TYPE: DNA
<213> ORGANISM: artificial
<220> FEATURE:
<223> OTHER INFORMATION: synthetic aptamer
<220> FEATURE:
<221> NAME/KEY: misc_feature
<222> LOCATION: (1)..(1)
<223> OTHER INFORMATION: n is a 30 kDa PEG
<220> FEATURE:
<221> NAME/KEY: misc_feature
<222> LOCATION: (2)..(2)
<223> OTHER INFORMATION: n is an amine group
<220> FEATURE:
<221> NAME/KEY: modified_base
<222> LOCATION: (3)..(30)
<223> OTHER INFORMATION: all purines are deoxy, except guanosine at
      positions 4, 9, and 22 are 2'-O-methyl, and adenosine at positions
      3, 13, and 17 are 2'-O-methyl
<220> FEATURE:
<221> NAME/KEY: modified_base
<222> LOCATION: (3)..(30)
<223> OTHER INFORMATION: all pyrimidines are 2'-O-methyl
<220> FEATURE:
<221> NAME/KEY: misc_feature
<222> LOCATION: (11)..(11)
<223> OTHER INFORMATION: n is a phosphorothioate internucleotide linkage
<220> FEATURE:
<221> NAME/KEY: misc_feature
<222> LOCATION: (19)..(19)
<223> OTHER INFORMATION: n is a phosphorothioate internucleotide linkage
<220> FEATURE:
<221> NAME/KEY: misc_feature
<222> LOCATION: (20)..(20)
<223> OTHER INFORMATION: n is deoxy inosine
<220> FEATURE:
<221> NAME/KEY: misc_feature
<222> LOCATION: (21)..(21)
<223> OTHER INFORMATION: n is a phosphorothioate internucleotide linkage
<220> FEATURE:
<221> NAME/KEY: misc_feature
<222> LOCATION: (23)..(23)
<223> OTHER INFORMATION: n is deoxy inosine
<220> FEATURE:
<221> NAME/KEY: misc_feature
<222> LOCATION: (24)..(24)
<223> OTHER INFORMATION: n is a phosphorothioate internucleotide linkage
<220> FEATURE:
<221> NAME/KEY: misc_feature
<222> LOCATION: (26)..(26)
<223> OTHER INFORMATION: n is deoxy inosine
<220> FEATURE:
<221> NAME/KEY: misc_feature
<222> LOCATION: (27)..(27)
<223> OTHER INFORMATION: n is a phosphorothioate internucleotide linkage
<220> FEATURE:
<221> NAME/KEY: misc_feature
<222> LOCATION: (31)..(31)
```

```
<223> OTHER INFORMATION: n is an amine group
<220> FEATURE:
<221> NAME/KEY: misc_feature
<222> LOCATION: (32)..(32)
<223> OTHER INFORMATION: n is a 30 kDa PEG

<400> SEQUENCE: 296
nnagccuggg ngacccaunn ngnngnngcu nn                                    32

<210> SEQ ID NO 297
<211> LENGTH: 30
<212> TYPE: DNA
<213> ORGANISM: artificial
<220> FEATURE:
<223> OTHER INFORMATION: synthetic aptamer
<220> FEATURE:
<221> NAME/KEY: misc_feature
<222> LOCATION: (1)..(1)
<223> OTHER INFORMATION: n is an amine group
<220> FEATURE:
<221> NAME/KEY: modified_base
<222> LOCATION: (2)..(29)
<223> OTHER INFORMATION: all purines are deoxy, except guanosine at
      positions 3, 8 and 21 are 2'-O-methyl, and adenosine at positions
      2, 12, and 16 are 2'-O-methyl
<220> FEATURE:
<221> NAME/KEY: modified_base
<222> LOCATION: (2)..(29)
<223> OTHER INFORMATION: all pyridmidines are 2'-O-methyl
<220> FEATURE:
<221> NAME/KEY: misc_feature
<222> LOCATION: (10)..(10)
<223> OTHER INFORMATION: n is a phosphorothioate internucleotide linkage
<220> FEATURE:
<221> NAME/KEY: misc_feature
<222> LOCATION: (18)..(18)
<223> OTHER INFORMATION: n is a phosphorothioate internucleotide linkage
<220> FEATURE:
<221> NAME/KEY: misc_feature
<222> LOCATION: (19)..(19)
<223> OTHER INFORMATION: n is deoxy inosine
<220> FEATURE:
<221> NAME/KEY: misc_feature
<222> LOCATION: (20)..(20)
<223> OTHER INFORMATION: n is a phosphorothioate internucleotide linkage
<220> FEATURE:
<221> NAME/KEY: misc_feature
<222> LOCATION: (22)..(22)
<223> OTHER INFORMATION: n is deoxy inosine
<220> FEATURE:
<221> NAME/KEY: misc_feature
<222> LOCATION: (23)..(23)
<223> OTHER INFORMATION: n is a phosphorothioate internucleotide linkage
<220> FEATURE:
<221> NAME/KEY: misc_feature
<222> LOCATION: (25)..(25)
<223> OTHER INFORMATION: n is deoxy inosine
<220> FEATURE:
<221> NAME/KEY: misc_feature
<222> LOCATION: (26)..(26)
<223> OTHER INFORMATION: n is a phosphorothioate internucleotide linkage
<220> FEATURE:
<221> NAME/KEY: misc_feature
<222> LOCATION: (30)..(30)
<223> OTHER INFORMATION: n is an amine group

<400> SEQUENCE: 297
nagccugggn gacccaunnn gnngnngcun                                       30

<210> SEQ ID NO 298
<211> LENGTH: 28
<212> TYPE: DNA
<213> ORGANISM: artificial
<220> FEATURE:
<223> OTHER INFORMATION: synthetic aptamer
```

```
<220> FEATURE:
<221> NAME/KEY: modified_base
<222> LOCATION: (1)..(28)
<223> OTHER INFORMATION: all purines (A and G) are deoxy, except
      guanosine at positions 2, 7, and 20 are 2'-O-methyl, and adenosine
      at positions 1, 11 and 15 are 2'-O-methyl
<220> FEATURE:
<221> NAME/KEY: modified_base
<222> LOCATION: (1)..(28)
<223> OTHER INFORMATION: all pyrimidines (C and U) are 2'-O-methyl
<220> FEATURE:
<221> NAME/KEY: misc_feature
<222> LOCATION: (9)..(9)
<223> OTHER INFORMATION: n is a phosphorothioate internucleotide linkage
<220> FEATURE:
<221> NAME/KEY: misc_feature
<222> LOCATION: (17)..(17)
<223> OTHER INFORMATION: n is a phosphorothioate internucleotide linkage
<220> FEATURE:
<221> NAME/KEY: misc_feature
<222> LOCATION: (18)..(18)
<223> OTHER INFORMATION: n is a deoxy inosine
<220> FEATURE:
<221> NAME/KEY: misc_feature
<222> LOCATION: (19)..(19)
<223> OTHER INFORMATION: n is a phosphorothioate internucleotide linkage
<220> FEATURE:
<221> NAME/KEY: misc_feature
<222> LOCATION: (21)..(21)
<223> OTHER INFORMATION: n is deoxy inosine
<220> FEATURE:
<221> NAME/KEY: misc_feature
<222> LOCATION: (22)..(22)
<223> OTHER INFORMATION: n is a phosphorothioate internucleotide linkage
<220> FEATURE:
<221> NAME/KEY: misc_feature
<222> LOCATION: (24)..(24)
<223> OTHER INFORMATION: n is deoxy inosine
<220> FEATURE:
<221> NAME/KEY: misc_feature
<222> LOCATION: (25)..(25)
<223> OTHER INFORMATION: n is a phosphorothioate internucleotide linkage

<400> SEQUENCE: 298
agccugggng acccaunnng nngnngcu                                          28
```